US008569302B2

(12) United States Patent
Canales et al.

(10) Patent No.: US 8,569,302 B2
(45) Date of Patent: Oct. 29, 2013

(54) INHIBITORS OF FLAVIVIRIDAE VIRUSES

(75) Inventors: Eda Canales, San Mateo, CA (US); Lee S. Chong, Newark, CA (US); Michael O'Neil Hanrahan Clarke, Redwood City, CA (US); Edward Doerffler, Union City, CA (US); Scott E. Lazerwith, San Francisco, CA (US); Willard Lew, San Mateo, CA (US); Qi Liu, Foster City, CA (US); Michael Mertzman, Belmont, CA (US); Philip A. Morganelli, Oakland, CA (US); William J. Watkins, Saratoga, CA (US); Hong Ye, Richmond, CA (US)

(73) Assignee: Gilead Sciences, Inc., Foster City, CA (US)

( * ) Notice: Subject to any disclaimer, the term of this patent is extended or adjusted under 35 U.S.C. 154(b) by 81 days.

(21) Appl. No.: 12/838,684

(22) Filed: Jul. 19, 2010

(65) Prior Publication Data
US 2011/0020278 A1 Jan. 27, 2011

Related U.S. Application Data

(60) Provisional application No. 61/227,367, filed on Jul. 21, 2009, provisional application No. 61/240,911, filed on Sep. 9, 2009, provisional application No. 61/359,466, filed on Jun. 29, 2010.

(51) Int. Cl.
*A61K 31/4965* (2006.01)
*A61K 31/535* (2006.01)
*A61K 31/505* (2006.01)
*A61K 31/44* (2006.01)
*A61K 31/425* (2006.01)
*A61K 31/41* (2006.01)
*A61K 31/38* (2006.01)
*C07D 409/14* (2006.01)
*C07D 239/02* (2006.01)
*C07D 413/14* (2006.01)
*C07D 419/14* (2006.01)
*C07D 257/04* (2006.01)

(52) U.S. Cl.
USPC .......... 514/252.01; 514/255.05; 514/231.5; 514/274; 514/210.18; 514/336; 514/369; 514/382; 514/444; 514/131; 514/238; 514/316; 514/405; 546/280; 548/187; 548/251; 549/60

(58) Field of Classification Search
USPC ............. 514/252.01, 252.05, 274, 336, 369, 514/444, 210.18, 231.5; 544/131, 238, 316, 544/405; 546/280; 549/60
See application file for complete search history.

(56) References Cited

U.S. PATENT DOCUMENTS

| | | | |
|---|---|---|---|
| 5,861,421 A | 1/1999 | Christensen, IV et al. | |
| 6,881,741 B2 | 4/2005 | Chan Chun Kong et al. | |
| 6,887,877 B2 | 5/2005 | Chan Chun Kong et al. | |
| 7,402,608 B2 | 7/2008 | Chan Chun Kong et al. | |
| 7,521,473 B2 | 4/2009 | Lee et al. | |
| 7,569,600 B2 | 8/2009 | Denis et al. | |
| 2002/0002199 A1 | 1/2002 | Jeppesen et al. | |
| 2003/0229053 A1 | 12/2003 | Chan Chun Kong et al. | |
| 2004/0116509 A1 | 6/2004 | Chan Chun Kong et al. | |
| 2005/0119332 A1 | 6/2005 | Jeppesen et al. | |
| 2006/0142347 A1 | 6/2006 | Chan Chun Kong et al. | |
| 2006/0276533 A1 | 12/2006 | Denis et al. | |
| 2007/0099929 A1 | 5/2007 | Thede et al. | |
| 2008/0299080 A1 | 12/2008 | Chan Chun Kong et al. | |
| 2009/0274655 A1 | 11/2009 | Grimes et al. | |
| 2011/0178058 A1 | 7/2011 | Canales et al. | |
| 2011/0178129 A1* | 7/2011 | Canales et al. | 514/336 |
| 2012/0156166 A1 | 6/2012 | Cho et al. | |

FOREIGN PATENT DOCUMENTS

| | | |
|---|---|---|
| WO | WO-2002100846 A1 | 12/2002 |
| WO | WO-2002100851 A2 | 12/2002 |
| WO | WO-2004/052885 | 6/2004 |
| WO | WO-2005/095386 A1 | 10/2005 |
| WO | WO-2006/072347 | 7/2006 |
| WO | WO-2006/072348 | 7/2006 |
| WO | WO-2007/093365 A2 | 8/2007 |
| WO | WO-2008058393 A1 | 5/2008 |

(Continued)

OTHER PUBLICATIONS

Boyer, N. et al. (2000) "Pathogenesis, diagnosis and management of hepatitis C," *Journal of Hepatology* 32 (suppl 1):98-112.
Calisher, C. et al. (1989) "Antigenic Relationships between Flaviviruses as Determined by Cross-neutralization Tests with Polyclonal Antisera," *J.gen. Virol.* 70:37-43.
Di Besceglie, A. et al. (1999) "Some 1.8 percent of the U.S. adult population are infected with the hepatitis C virus, most without knowing it" *Scientific American* October pp. 80-85.
Domingo, E. et al. (1985) "The quasispecies (extremely heterogeneous) nature of viral RNA genome populations: biological relevance—a review" *Gene* 40:1-8.

(Continued)

*Primary Examiner* — James O Wilson
*Assistant Examiner* — Ebenezer O Sackey
(74) *Attorney, Agent, or Firm* — Kilpatrick Townsend & Stockton LLP

(57) ABSTRACT

Provided are compounds of Formula I:

Formula (I)

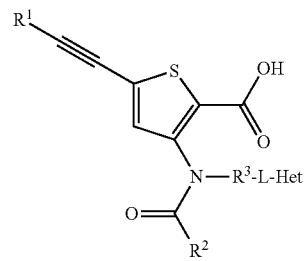

and pharmaceutically acceptable salts and esters thereof. The compounds, compositions, and methods provided are useful for the treatment of Flaviviridae virus infections, particularly hepatitis C infections.

20 Claims, No Drawings

(56) References Cited

FOREIGN PATENT DOCUMENTS

| WO | WO-2010/065668 | 6/2010 |
| WO | WO-2011/031669 | 3/2011 |
| WO | WO-2011/068715 | 6/2011 |
| WO | WO-2011/088345 | 7/2011 |
| WO | WO-2012/006055 | 1/2012 |

OTHER PUBLICATIONS

Dymock, B. et al. (2000) "Novel approaches to the treatment of hepatitis C virus infection," *Antiviral Chemistry & Chemotherapy* 11(2):79-86.

Fukumoto, T. et al. (1996) "Viral Dynamics of Hepatitis C Early After Orthotopic Liver Transplantation: Evidence for Rapid Turnover of Serum Virions," *Hepatology* 24:1351-1354.

Gordon, C. et al. (2005) "Control of Hepatitis C: A Medicinal Chemistry Perspective," *Journal of Medicinal Chemistry* 48(1):1-20.

Herlihy, K. et al. (2008) "Development of Intergenotypic Chimeric Replicons to Determine the Broad-Spectrum Antiviral Activities of Hepatitis C Virus Polymerase Inhibitors," *Antimicrobial Agents and Chemotherapy* 52(10):3523-3534.

International Search Report for PCTUS/2010/042394, mailed Sep. 29, 2010.

Maradpour, D. et al. (2007) "Replication of Hepatitis C Virus," *Nature Reviews/Microbiolory* 596):453-463.

Martell, M. et al. (1992) "Hepatitis C Virus (HCV) Circulates as a Population of Different but Closely Related Genomes: Quasispecies Nature of HCV Genome Distribution," *Journal of Virology* 66(5):3225-3229.

Moennig, V. et al. (1992) "The Pestiviruses," *Advances in Virus Research* 41:53-98.

Neumann, A. (1998) "Hepatitis C Viral Dynamics in Vivo and the Antiviral Efficacy of Interferon-α Therapy," *Science* 282:103-107.

Schul, W. (2007) "A Dengue Fever Viremia Model in Mice Shows Reduction in Viral Replication and Suppression of the Inflammatory Response after Treatment with Antiviral Drugs," *J. Infectious Disease* 195:665-674.

Scott, L. et al. (2002) "Interferon-α-2b Plus Ribavirin," *Drugs* 2:507-556.

Written Opinion for PCT/US2010/042394 mailed Sep. 29, 2010.

U.S. Appl. No. 13/801,011, filed Mar. 13, 2013, Watkins et al.

U.S. Appl. No. 13/801,039, filed Mar. 13, 2013, Evans et al.

U.S. Appl. No. 13/800,991, filed Mar. 13, 2013, Hashash et al.

International Search Report and Written Opinion for PCT/US2010/047983 mailed Nov. 15, 2010.

International Search Report and Written Opinion for PCT/US2012/046741 mailed Aug. 22, 2012.

Office Communications for U.S. Appl. No. 13/392,467.

Office Communications for U.S. Appl. No. 13/006,761.

Office Communications for U.S. Appl. No. 13/007,150.

U.S. Appl. No. 13/549,130, filed Jul. 13, 2012, Watkins et al.

U.S. Appl. No. 61/684,507, filed Aug. 17, 2012, Watkins et al.

U.S. Appl. No. 61/684,543, filed Aug. 17, 2012, Evans et al.

International Search Report for Application No. PCT/US2011/021279, mailed May 2, 2011.

International Search Report for Application No. PCT/US2011/021335, mailed Feb. 22, 2011.

Notice of Allowance for U.S. Appl. No. 13/392,467, mailed Sep. 21, 2012.

Notice of Allowance for U.S. Appl. No. 13/006,761, mailed Oct. 3, 2012.

Office Action for U.S. Appl. No. 13/007,150, mailed Oct. 3, 2012.

\* cited by examiner

INHIBITORS OF FLAVIVIRIDAE VIRUSES

This application is filed under 35 U.S.C. 111(a) claiming the benefit under 35 U.S.C. 119(e) of U.S. provisional applications 61/227,367 filed Jul. 21, 2009, 61/240,911 filed Sep. 9, 2009 and 61/359,466 filed Jun. 29, 2010; each of which is herein incorporated by reference its entirety for all purposes.

FIELD OF THE INVENTION

The present application includes novel inhibitors of Flaviviridae viruses, compositions containing such compounds, therapeutic methods that include the administration of such compounds.

BACKGROUND OF THE INVENTION

Viruses comprising the Flaviviridae family include at least three distinguishable genera including pestiviruses, flaviviruses, and hepaciviruses (Calisher, et al., J. Gen. Viral., 1993, 70, 37-43). While pestiviruses cause many economically important animal diseases such as bovine viral diarrhea virus (BVDV), classical swine fever virus (CSFV, hog cholera) and border disease of sheep (BDV), their importance in human disease is less well characterized (Moennig, V., et al., Adv. Vir. Res. 1992, 48, 53-98). Flaviviruses are responsible for important human diseases such as dengue fever and yellow fever while hepaciviruses cause hepatitis C virus infections in humans. Other important viral infections caused by the Flaviviridae family include West Nile virus (WNV) Japanese encephalitis virus (JEV), tick-borne encephalitis virus, Junjin virus, Murray Valley encephalitis, St Louis enchaplitis, Omsk hemorrhagic fever virus and Ma virus.

The hepatitis C virus (HCV) is the leading cause of chronic liver disease worldwide (Boyer, N. et al. J Hepatol. 32:98-112, 2000) so a significant focus of current antiviral research is directed toward the development of improved methods of treatment of chronic HCV infections in humans (Di Besceglie, A. M. and Bacon, B. R., Scientific American, October: 80-85, (1999); Gordon, C. P., et al., J. Med. Chem. 2005, 48, 1-20; Maradpour, D.; et al., Nat. Rev. Micro. 2007, 5(6), 453-463). A number of HCV treatments are reviewed by Dymock et al. in Antiviral Chemistry & Chemotherapy, 11:2; 79-95 (2000). Virologic cures of patients with chronic HCV infection are difficult to achieve because of the prodigious amount of daily virus production in chronically infected patients and the high spontaneous mutability of HCV virus (Neumann, et al., Science 1998, 282, 103-7; Fukimoto, et al., Hepatology, 1996, 24, 1351-4; Domingo, et al., Gene, 1985, 40, 1-8; Martell, et al., J. Virol. 1992, 66, 3225-9).

Currently, there are primarily two antiviral compounds, ribavirin, a nucleoside analog, and interferon-alpha (α) (IFN), that are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. Drugs 2002, 62, 507-556) but less than half the patients given this treatment show a persistent benefit.

Combined, infections from the Flaviviridae virus family cause significant mortality, morbidity and economic losses throughout the world. Alkynyl substituted thiophenes with anti-Flaviviridae virus activity have been disclosed by Chan, et al., WO 2008058393; Wunberg, et al., WO 2006072347; and Chan, et al., WO 2002100851; but none of these are currently clinically approved antiviral therapeutics. Therefore, there remains a need to develop effective treatments for Flaviviridae virus infections.

SUMMARY OF THE INVENTION

Provided are compounds of Formula I:

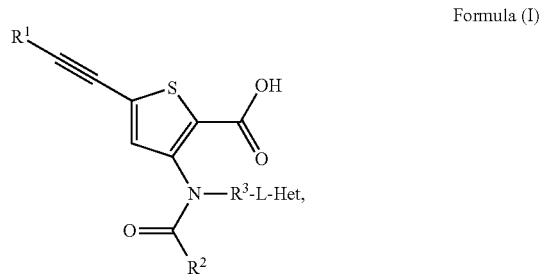

Formula (I)

or a pharmaceutically acceptable salt or ester thereof, wherein:

$R^1$ is selected from the group consisting of optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted 3-18 membered heterocyclylalkyl and optionally substituted $C_{6-18}$ arylalkyl, wherein, each substituted $R^1$ is substituted with one or more $Q^1$;

each $Q^1$ is independently selected from the group consisting of halogen, oxo, oxide, —$NO_2$, —N(=O), —$SR^{10}$, —S(O)$R^{10}$, —S(O)$_2R^{10}$, —S(O)$_2NR^{10}R^{11}$, —$NR^{10}$C(O)$R^{11}$, —$NR^{10}$C(O)$NR^{11}R^{12}$, —$NR^{10}$S(O)$R^{11}$, —$NR^{10}$S(O)$_2R^{11}$, —OP(O)$R^{11}R^{12}$, —P(O)$R^{11}R^{12}$, —P(O)$OR^{11}R^{12}$, —P(O)(OR$^{11}$)OR$^{12}$, —C(O)NR$^{11}R^{12}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)$C_{1-6}$ alkyl, optionally substituted —C(O)$C_{2-6}$ alkenyl, optionally substituted —C(O)$C_{2-6}$ alkynyl, optionally substituted —C(O)$C_{3-6}$ cycloalkyl, optionally substituted —C(O)$C_{6-12}$ aryl, optionally substituted —C(O)-3-14 membered heteroaryl, optionally substituted —C(O)$C_{6-12}$ arylalkyl, optionally substituted-3-10 membered heterocyclyl, —OH, —NR$^{11}R^{12}$, —C(O)OR$^{10}$, —CN, —$N_3$, —C(=NR$^{13}$)NR$^{11}R^{12}$, —C(=NR$^{13}$)OR$^{10}$, —$NR^{10}$C(=NR$^{13}$)NR$^{11}R^{12}$, —NR$^{11}$C(O)OR$^{10}$, and —OC(O)NR$^{11}R^{12}$;

each $R^{10}$, $R^{11}$, and $R^{12}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

or $R^{11}$ and $R^{12}$ taken together with the atoms to which they are attached form a 3 to 10 membered heterocyclyl;

each $R^{13}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, —CN, —C(O)$R^{14}$, —CHO and —S(O)$_2R^{14}$;

each $R^{14}$, independently, is optionally substituted $C_{1-12}$ alkyl;

wherein, each substituted $Q^1$, substituted $R^{10}$, substituted $R^{11}$, substituted $R^{12}$, substituted $R^{13}$, or substituted $R^{14}$ is independently substituted with one or more $Q^6$;

$R^2$ is selected from the group consisting of optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

wherein, each substituted $R^2$ is substituted with one or more $Q^2$;

each $Q^2$, independently, is selected from the group consisting of halogen, oxo, oxide, —NO$_2$, —N(=O), —SR$^{20}$, —S(O)$_2R^{20}$, —S(O)$_2NR^{20}R^{21}$, —NR$^{20}$C(O)R$^{21}$, —NR$^{20}$C(O)NR$^{21}R^{22}$, —NR$^{20}$S(O)R$^{21}$, —NR$^{20}$S(O)$_2R^{21}$, —OP(O)R$^{21}R^{22}$, —P(O)R$^{21}R^{22}$, —P(O)OR$^{21}R^{22}$, —P(O)(OR$^{21}$)OR$^{22}R^{22}$, —C(O)NR$^{21}R^{22}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)$C_{1-6}$ alkyl, optionally substituted —C(O)$C_{2-6}$ alkenyl, optionally substituted —C(O)$C_{2-6}$ alkynyl, optionally substituted —C(O)$C_{3-6}$ cycloalkyl, optionally substituted —C(O)$C_{6-12}$ aryl, optionally substituted —C(O)-3-14 membered heteroaryl, optionally substituted —C(O)$C_{6-12}$ arylalkyl, optionally substituted 3-10 membered heterocyclyl, —OH, —NR$^{21}R^{22}$, —C(O)OR$^{20}$, —CN, —N$_3$, —C(=NR$^{23}$)NR$^{21}R^{22}$, —C(=NR$^{23}$)OR$^{20}$, —NR$^{20}$C(=NR$^{23}$)NR$^{21}R^{22}$, —NR$^{21}$C(O)OR$^{20}$, and —OC(O)NR$^{21}R^{22}$;

each $R^{20}$, $R^{21}$, and $R^{22}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-2}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-16}$ arylalkyl;

or $R^{21}$ and $R^{22}$ taken together with the atoms to which they are attached form a 3 to 10 membered heterocyclyl;

each $R^{23}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, —CN, —C(O)R$^{24}$, —CHO and —S(O)$_2R^{24}$;

each $R^{24}$ individually is optionally substituted $C_{1-12}$ alkyl;

wherein, each substituted $Q^2$, substituted $R^{20}$, substituted $R^{21}$, substituted $R^{22}$, substituted $R^{23}$, or substituted $R^{24}$ is independently substituted with one or more $Q^6$;

$R^3$ is selected from the group consisting of optionally substituted $C_{1-12}$ alkylene, $C_{2-12}$ alkenylene, substituted $C_{2-12}$ alkenylene, $C_{2-12}$ alkynylene, substituted $C_{2-12}$ alkynylene, $C_{3-12}$ cycloalkylene, substituted $C_{3-12}$ cycloalkylene, optionally substituted $C_{6-14}$ arylene, optionally substituted 3-14 membered heteroarylene, optionally substituted 3-12 membered heterocyclylene, optionally substituted 3-18 membered heteroarylalkylene, and optionally substituted $C_{6-16}$ arylalkylene;

wherein each substituted $R^3$ is substituted with one or more $Q^3$;

each $Q^3$, independently, is selected from the group consisting of halogen, oxo, oxide, —NO$_2$, —N(=O), —SR$^{30}$, —S(O)R$^{30}$, —S(O)$_2R^{30}$, —S(O)$_4NR^{30}R^{31}$, —NR$^{30}$C(O)R$^{31}$, —NR$^{30}$C(O)NR$^{31}R^{32}$, —NR$^{30}$S(O)R$^{31}$, —NR$^{30}$S(O)$_1R^{31}$, —OP(O)R$^{31}R^{32}$, —P(O)R$^{31}R^{32}$, —P(O)OR$^{31}R^{32}$, —P(O)(OR$^{31}$)OR$^{32}$, —C(O)NR$^{31}R^{32}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)$C_{1-6}$ alkyl, optionally substituted —C(O)$C_{2-6}$ alkenyl, optionally substituted —C(O)$C_{2-6}$ alkynyl, optionally substituted —C(O)$C_{3-6}$ cycloalkyl, optionally substituted —C(O)$C_{6-12}$ aryl, optionally substituted —C(O)-3-14 membered heteroaryl, optionally substituted —C(O)$C_{6-12}$ arylalkyl, optionally substituted 3-10 membered heterocyclyl, —OH, —NR$^{31}R^{32}$, —C(O)OR$^{30}$, —CN, —N$_3$, —C(=NR$^{33}$)NR$^{31}R^{32}$, —C(=NR$^{33}$)OR$^{30}$, —NR$^{30}$C(=NR$^{33}$)NR$^{31}R^{32}$, —NR$^{31}$C(O)OR$^{30}$, and —OC(O)NR$^{31}R^{32}$;

each $R^{30}$, $R^{31}$, and $R^{32}$, independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

or $R^{31}$ and $R^{32}$ taken together with the atoms to which they are attached form a 3 to 10 membered heterocyclyl;

each $R^{33}$ independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, —CN, —C(O)R$^{34}$, —CHO and —S(O)$_2R^{34}$;

each $R^{34}$ individually is optionally substituted $C_{1-12}$ alkyl;

wherein, each substituted $Q^3$, substituted $R^{30}$, substituted $R^{31}$, substituted $R^{32}$, substituted $R^{33}$, or substituted $R^{34}$ is independently substituted with one or more $Q^6$;

L is selected from the group consisting of —O—, —S—, —S(O)—, and —S(O)$_2$—;

Het is an optionally substituted 3-12 membered heterocyclyl or optionally substituted 3-14 membered heteroaryl;

wherein, each substituted Het is substituted with one or more $Q^4$;

each $Q^4$, independently, is selected from the group consisting of halogen, oxo, oxide, —NO$_2$, —N(=O), —SR$^{40}$, —S(O)R$^{40}$, —S(O)$_2$R$^{40}$, —S(O)$_2$NR$^{40}$R$^{41}$, —NR$^{40}$C(O)R$^{41}$, —NR$^{40}$C(O)NR$^{41}$R$^{42}$, —NR$^{40}$S(O)R$^{41}$, —NR$^{40}$S(O)$_2$R$^{41}$, —OP(O)R$^{41}$R$^{42}$, —P(O)R$^{41}$R$^{42}$, —P(O)OR$^{41}$R$^{42}$, —P(O)(OR$^{41}$)OR$^{42}$, —C(O)NR$^{41}$R$^{42}$, optionally substituted C$_{1-6}$ alkyl, optionally substituted C$_{2-6}$ alkenyl, optionally substituted C$_{2-6}$ alkynyl, optionally substituted C$_{3-6}$ cycloalkyl, optionally substituted C$_{6-12}$ arylalkyl, optionally substituted C$_{6-12}$ aryl, optionally substituted 3-14 membered heteroaryl, optionally substituted C$_{1-6}$alkyloxy, optionally substituted C$_{2-6}$ alkenyloxy, optionally substituted C$_{2-6}$ alkynyloxy, optionally substituted C$_{3-6}$ cycloalkyloxy, optionally substituted C$_{6-12}$ aryloxy, optionally substituted 3-14 membered heteroaryloxy, optionally substituted 4-12 membered heterocyclyloxy, optionally substituted —C(O)C$_{1-6}$ alkyl, optionally substituted —C(O)C$_{2-6}$ alkenyl, optionally substituted —C(O)C$_{2-6}$ alkynyl, optionally substituted —C(O)C$_{3-6}$ cycloalkyl, optionally substituted —C(O)C$_{6-12}$ aryl, optionally substituted —C(O)-3-14 membered heteroaryl, optionally substituted —C(O)C$_{6-12}$ arylalkyl, optionally substituted 3-10 membered heterocyclyl, —OH, —NR$^{41}$R$^{42}$, —C(O)OR$^{40}$, —CN, —N$_3$, —C(=NR$^{43}$)NR$^{41}$R$^{42}$, —C(=NR$^{43}$)OR$^{40}$, —NR$^{40}$C(=NR$^{43}$)NR$^{41}$R$^{42}$, —NR$^{41}$C(O)OR$^{40}$, and —OC(O)NR$^{41}$R$^{42}$;

each $R^{40}$, $R^{41}$, and $R^{42}$, independently is selected from the group consisting of H, optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, and optionally substituted C$_{6-18}$ arylalkyl;

or $R^{41}$ and $R^{42}$ taken together with the atoms to which they are attached form a 3 to 10 membered heterocyclyl;

each $R^{43}$, independently, is selected from the group consisting of H, optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, optionally substituted C$_{6-18}$ arylalkyl, —CN, —C(O)R$^{44}$, —CHO and —S(O)$_2$R$^{44}$;

each $R^{44}$ individually is optionally substituted C$_{1-12}$ alkyl;

wherein, each substituted $Q^4$, substituted $R^{40}$, substituted $R^{41}$, substituted $R^{42}$, substituted $R^{43}$, or substituted $R^{44}$ is independently substituted with one or more $Q^5$;

each $Q^5$, individually, is selected from the group consisting of halogen, oxo, oxide, —NO$_2$, —N(=O), —SR$^{50}$, —S(O)R$^{50}$, —S(O)$_2$R$^{50}$, —S(O)$_2$NR$^{50}$R$^{51}$, —NR$^{50}$C(O)R$^{51}$, —NR$^{50}$C(O)NR$^{51}$R$^{52}$, —NR$^{50}$S(O)R$^{51}$, —NR$^{50}$S(O)$_2$R$^{51}$, —OP(O)R$^{51}$R$^{52}$, —P(O)R$^{51}$R$^{52}$, —P(O)OR$^{51}$R$^{52}$, —P(O)(OR$^{51}$)OR$^{52}$, —C(O)NR$^{51}$R$^{52}$, optionally substituted C$_{1-6}$ alkyl, optionally substituted C$_{2-6}$ alkenyl, optionally substituted C$_{2-6}$ alkynyl, optionally substituted C$_{3-6}$ cycloalkyl, optionally substituted C$_{6-12}$ arylalkyl, optionally substituted C$_{6-12}$ aryl, optionally substituted 3-14 membered heteroaryl, optionally substituted C$_{1-6}$ alkyloxy, optionally substituted C$_{2-6}$ alkenyloxy, optionally substituted C$_{2-6}$ alkynyloxy, optionally substituted C$_{3-6}$ cycloalkyloxy, optionally substituted C$_{6-12}$ aryloxy, optionally substituted 3-14 membered heteroaryloxy, optionally substituted 4-12 membered heterocyclyloxy, optionally substituted —C(O)C$_{1-6}$ alkyl, optionally substituted —C(O)C$_{2-6}$ alkenyl, optionally substituted —C(O)C$_{2-6}$ alkynyl, optionally substituted —C(O)C$_{3-6}$ cycloalkyl, optionally substituted —C(O)C$_{6-12}$ aryl, optionally substituted —C(O)-3-14 membered heteroaryl, optionally substituted —C(O)C$_{6-12}$ arylalkyl, optionally substituted 3-10 membered heterocyclyl, —OH, —NR$^{51}$R$^{52}$, —O(O)OR$^{50}$, —CN, —N$_3$, —C(=NR$^{53}$)NR$^{51}$R$^{52}$, —C(=NR$^{53}$)OR$^{50}$, —NR$^{50}$C(=NR$^{53}$)NR$^{51}$R$^{52}$, —NR$^{51}$C(O)OR$^{50}$, and —OC(O)NR$^{51}$R$^{52}$;

each $R^{50}$, $R^{51}$, and $R^{52}$, independently is selected from the group consisting of H, optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, and optionally substituted C$_{6-18}$ arylalkyl;

or $R^{51}$ and $R^{52}$ taken together with the atoms to which they are attached form a 3 to 10 membered heterocyclyl;

each $R^{53}$, independently, is selected from the group consisting of H, optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, optionally substituted C$_{6-18}$ arylalkyl, —CN, —C(O)R$^{54}$, —CHO and —S(O)$_2$R$^{54}$;

each $R^{54}$, independently, is optionally substituted C$_{1-12}$ alkyl;

wherein, each substituted $Q^5$, substituted $R^{50}$, substituted $R^{51}$, substituted $R^{52}$, substituted $R^{50}$, or substituted $R^{54}$ is independently substituted with one or more $Q^6$;

each $Q^6$, independently, is selected from the group consisting of halogen, oxo, oxide, —NO$_2$, —N(=O), —SR$^{60}$, —S(O)R$^{60}$, —S(O)$_2$R$^{60}$, —S(O)$_2$NR$^{60}$R$^{61}$, —NR$^{60}$C(O)R$^{61}$, —NR$^{60}$C(O)NR$^{61}$R$^{62}$, —NR$^{60}$S(O)R$^{61}$, —NR$^{60}$S(O)$_2$R$^{61}$, —OP(O)R$^{61}$R$^{62}$, —P(O)R$^{61}$R$^{62}$, —P(O)OR$^{61}$R$^{62}$, —P(O)(OR$^{61}$)OR$^{62}$, —C(O)NR$^{61}$R$^{62}$, C$_{1-6}$ alkyl, C$_{2-6}$ alkenyl, C$_{2-6}$ alkynyl, C$_{3-6}$ cycloalkyl, C$_{6-12}$ arylalkyl, C$_{6-12}$ aryl, 3-14 membered heteroaryl, C$_{1-6}$ alkyloxy, C$_{2-6}$ alkenyloxy, C$_{2-6}$ alkynyloxy, C$_{3-6}$ cycloalkyloxy, C$_{6-12}$ aryloxy, 3-14 membered heteroaryloxy, 4-12 membered heterocyclyloxy, —C(O)C$_{1-6}$ alkyl, —C(O)C$_{2-6}$ alkenyl, —C(O)C$_{2-6}$ alkynyl, —C(O)C$_{3-6}$ cycloalkyl, —C(O)C$_{1-6}$ haloalkyl, —C(O)C$_{6-12}$ aryl, —C(O)-3-14 membered heteroaryl, —C(O)C$_{6-12}$ arylalkyl, 3-10 membered heterocyclyl, —OH, —NR$^{61}$R$^{62}$, —C(O)OR$^{60}$, —CN, —N$_3$, —C(=NR$^{63}$)NR$^{61}$R$^{62}$, —C(=NR$^{63}$)NR$^{60}$, —NR$^{60}$C(=NR$^{63}$)NR$^{61}$R$^{62}$, —NR$^{61}$C(O)OR$^{60}$, and —OC(O)NR$^{61}$R$^{62}$;

each $R^{60}$, $R^{61}$, and $R^{62}$, independently, is selected from the group consisting of H, C$_{1-12}$ alkyl, C$_{2-12}$ alkenyl, C$_{2-12}$ alkynyl, C$_{3-12}$ cycloalkyl, C$_{1-12}$ haloalkyl, C$_{6-14}$ aryl, 3-14 membered heteroaryl, 3-12 membered heterocyclyl, 3-18 membered heteroarylalkyl, and C$_{6-18}$ arylalkyl;

or $R^{61}$ and $R^{62}$ taken together with the atoms to which they are attached form a 3 to 10 membered heterocyclyl;

each $R^{63}$ independently is selected from the group consisting of H, C$_{1-12}$ alkyl, C$_{2-12}$ alkenyl, C$_{2-12}$ alkynyl, C$_{3-12}$ cycloalkyl, C$_{6-14}$ aryl, 3-14 membered heteroaryl, 3-12 membered heterocyclyl, 3-18 membered heteroarylalkyl, C$_{6-18}$ arylalkyl, —CN, —C(O)R$^{64}$, —CHO and —S(O)$_2$R$^{64}$; and each $R^{64}$ individually is C$_{1-12}$ alkyl.

In another aspect, a method for treating Flaviviridae viral infections is provided comprising administering a therapeutically effective amount of a compound of Formula I to a mammal in need thereof. The compound of Formula I is administered to a human subject in need thereof, such as a human being who is infected with viruses of the Flaviviridae family. In another embodiment, the compound of Formula I is administered to a human subject in need thereof, such as a human being who is infected with a HCV virus. In one embodiment, the treatment results in the reduction of one or more of the viral loads or clearance of viral RNA in a patient.

In another embodiment, provided is a method of treating and/or preventing a disease caused by a viral infection wherein the viral infection is caused by a virus selected from the group consisting of dengue virus, yellow fever virus, West Nile virus, Japanese encephalitis virus, tick-borne encephalitis virus, Junjin virus, Murray Valley encephalitis virus, St Louis encephalitis virus, Omsk hemorrhagic fever virus, bovine viral disarrhea virus, Zika virus and Hepatitis C virus; by administering to a subject in need thereof a therapeutically effective amount of a compound of Formula I, or a pharmaceutically acceptable salt or ester thereof.

In another aspect, provided is the use of a compound of Formula I for the manufacture of a medicament for the treatment of Flaviviridae viral infections. In another aspect, provided is a compound of Formula I for use in treating a Flaviviridae viral infection. In one embodiment, the Flaviviridae viral infection is acute or chronic HCV infection. In one embodiment of each aspect of use and compound, the treatment results in the reduction of one or more of the viral loads or clearance of RNA in the patient.

In another aspect, provided is a method for treating or preventing HCV comprising administering an effective amount of a compound of Formula I to a patient in need thereof. In another aspect, provided is the use of a compound of the present invention for the manufacture of a medicament for the treatment or prevention of HCV.

In another aspect, provided is a pharmaceutical composition comprising a compound of Formula I or a pharmaceutically acceptable salt or ester thereof and one or more pharmaceutically acceptable carriers or excipients. The pharmaceutical composition of Formula I may further comprise one or more additional therapeutic agents. The one or more additional therapeutic agent may be, without limitation, selected from: interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, endothelin antagonists, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers and other drugs for treating HCV; or mixtures thereof.

In another aspect, provided is a method for the treatment or prevention of the symptoms or effects of an HCV infection in an infected animal which comprises administering to, i.e. treating, said animal with a pharmaceutical combination composition or formulation comprising an effective amount of a Formula I compound, and a second compound having anti-HCV properties.

In another embodiment, provided are compounds of Formula I and pharmaceutically acceptable salts and esters thereof and all racemates, enantiomers, diastereomers, tautomers, polymorphs, pseudopolymorphs and amorphous forms thereof.

In another aspect, provided are processes and novel intermediates disclosed herein which are useful for preparing Formula I compounds.

In other aspects, novel methods for synthesis, analysis, separation, isolation, purification, characterization, and testing of the compounds of Formula I are provided.

The present invention includes combinations of aspects and embodiments, as well as preferences, as herein described throughout the present specification.

DETAILED DESCRIPTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined herein.

Each document referenced herein is incorporated by reference in its entirety for all purposes.

In one embodiment of Formula I, $R^1$ is optionally substituted $C_{1-12}$ alkyl, optionally substituted $C_{2-12}$ alkenyl, optionally substituted $C_{2-12}$ alkynyl, or optionally substituted $C_{3-12}$ cycloalkyl. In another aspect of this embodiment, $R^1$ is optionally substituted $C_1$-$C_{12}$ alkyl. In another aspect of this embodiment, $R^1$ is optionally substituted $C_3$-$C_7$ secondary or tertiary alkyl. In another aspect of this embodiment, $R^1$ is optionally substituted $C_3$-$C_5$ cycloalkyl. In another aspect of this embodiment, $R^1$ is prop-2-yl (isopropyl) or 2-methylprop-2-yl (t-butyl).

In another embodiment of Formula I, $R^2$ is optionally substituted $C_{1-12}$ alkyl, optionally substituted $C_{2-12}$ alkenyl, optionally substituted $C_{2-12}$ alkynyl, optionally substituted $C_{3-12}$ cycloalkyl, or optionally substituted $C_{6-18}$ arylalkyl. In another aspect of this embodiment, $R^2$ is optionally substituted $C_{3-12}$ cycloalkyl. In another aspect of this embodiment, $R^2$ is optionally substituted methylcyclohexyl. In another aspect of this embodiment, $R^2$ is optionally substituted methylcyclohexenyl. In another aspect of this embodiment, $R^2$ is optionally substituted 4-methylcyclohexyl. In a preferred aspect of this embodiment, $R^2$ is

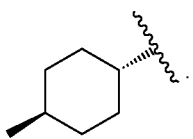

In another preferred aspect of this embodiment, $R^2$ is

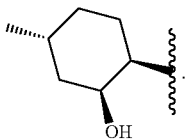 [SMILES: *[C@@H]1CC[C@@H](C)C[C@@H]1O]

In another preferred aspect of this embodiment, $R^2$ is

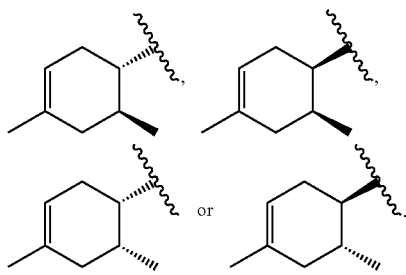

In another preferred aspect of this embodiment, $R^2$ is

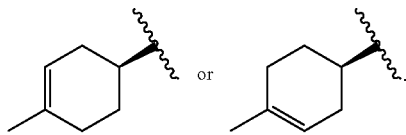

In another embodiment of Formula I, $R^3$ is optionally substituted $C_{1-12}$ alkylene, $C_{3-12}$ cycloalkylene, substituted $C_{3-12}$ cycloalkylene, optionally substituted $C_{6-14}$ arylene or optionally substituted 3-12 membered heterocyclylene. In another aspect of this embodiment, $R^3$ is optionally substituted $C_2$-$C_6$ alkylene. In another aspect of this embodiment, $R^3$ is optionally substituted $C_3$-$C_6$ cycloalkylene. In another aspect of this embodiment, $R^3$ is optionally substituted 4-6 membered heterocyclylene. In another aspect of this embodiment, $R^3$ is an optionally substituted 4-6 membered nitrogen-containing heterocyclylene.

In one embodiment of Formula I, L is —O—. In another embodiment of Formula I, L is —S—. In another embodiment of Formula I, L is —S(O)—. In another embodiment of Formula I, L is —S(O)$_2$—.

In another embodiment of Formula I, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is an optionally substituted 3-12 membered heterocyclyl comprising one or two heteroatoms selected from O, S, or N. In another aspect of this embodiment, Het is an optionally substituted 5-10 membered heteroaryl comprising one to four heteroatoms selected from O, S, or N. In another aspect of this embodiment, Het is optionally substituted pyridinyl. In another aspect of this embodiment, Het is optionally substituted pyridazinyl. In another aspect of this embodiment, Het is optionally substituted tetrahydro-2H-pyranyl. In another aspect of this embodiment, Het is optionally substituted piperidinyl. In another aspect of this embodiment, Het is optionally substituted pyrrolidinyl. In another aspect of this embodiment, Het is optionally substituted tetrahydrothiophenyl. In another aspect of this embodiment, Het is optionally substituted pyrazinyl. In another aspect of this embodiment, Het is optionally substituted 1H-tetrazolyl. In another aspect of this embodiment, Het is optionally substituted azetidinyl. In another aspect of this embodiment, Het is optionally substituted tetrahydrofuranyl. In another aspect of this embodiment, Het is optionally substituted tetrahydro-2H-furo[2,3-b]furanyl. In another aspect of this embodiment, Het is optionally substituted thiazoyl. In another aspect of this embodiment, Het is optionally substituted 1H-imidazolyl. In another aspect of this embodiment, Het is optionally substituted 4H-1,2,4-triazolyl. In another aspect of this embodiment, Het is optionally substituted 1H-pyrazolyl. In another aspect of this embodiment, Het is optionally substituted 1,3,4-thiadiazolyl. In another aspect of this embodiment, Het is optionally substituted quinolinyl. In another aspect of this embodiment, Het is optionally substituted [1,2,4]triazolo[4,3-a]pyridinyl. In another aspect of this embodiment, Het is optionally substituted thiophenyl. In another aspect of this embodiment, Het is optionally substituted 1,2,4-thiadiazolyl. In another aspect of this embodiment, Het is optionally substituted pyrimidinyl. In another aspect of this embodiment, Het is optionally substituted 1H-1,2,3-triazolyl. In another aspect of this embodiment, Het is optionally substituted 1,3,4-oxadiazolyl. In another aspect of this embodiment, Het is optionally substituted imidazo[1,2-b]pyridazinyl.

In another embodiment of Formula I, $R^1$ is optionally substituted $C_1$-$C_{12}$ alkyl. In another aspect of this embodiment, $R^2$ is optionally substituted methylcyclohexyl or optionally substituted methylcyclohexenyl. In another aspect of this embodiment, $R^3$ is optionally substituted $C_{1-12}$ alkylene, $C_{3-12}$ cycloalkylene, substituted $C_{3-12}$ cycloalkylene, optionally substituted $C_{6-14}$ arylene or optionally substituted 3-12 membered heterocyclylene. In another aspect of this embodiment, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is optionally substituted pyridinyl, optionally substituted pyridazinyl, optionally substituted tetrahydro-2H-pyranyl, optionally substituted piperidinyl, optionally substituted pyrrolidinyl, optionally substituted tetrahydrothiophenyl, optionally substituted pyrazinyl, optionally substituted 1H-tetrazolyl, optionally substituted azetidinyl, optionally substituted tetrahydrofuranyl, optionally substituted tetrahydro-2H-furo[2,3-b]furanyl, optionally substituted thiazoyl, optionally substituted 1H-imidazolyl, optionally substituted 4H-1,2,4-triazolyl, optionally substituted 1H-pyrazolyl, optionally substituted 1,3,4-thiadiazolyl, optionally substituted quinolinyl, optionally substituted [1,2,4]triazolo[4,3-a]pyridinyl, optionally substituted thiophenyl, optionally substituted 1,2,4-thiadiazolyl, optionally substituted pyrimidinyl, optionally substituted 1H-1,2,3-triazolyl, optionally substituted 1,3,4-oxadiazolyl or optionally substituted imidazo[1,2-b]pyridazinyl. In another aspect of this embodiment, L is —O—. In another aspect of this embodiment, L is —S—. In another aspect of this embodiment, L is —S(O)—. In another aspect of this embodiment, L is —S(O)$_2$—.

In another embodiment of Formula I, $R^1$ is optionally substituted $C_{3-12}$ cycloalkyl. In another aspect of this embodiment, $R^2$ is optionally substituted methylcyclohexyl or optionally substituted methylcyclohexenyl. In another aspect of this embodiment, $R^3$ is optionally substituted $C_{1-12}$ alkylene, $C_{3-12}$ cycloalkylene, substituted $C_{3-12}$ cycloalkylene, optionally substituted $C_{6-14}$ arylene or optionally substituted 3-12 membered heterocyclylene. In another aspect of this embodiment, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is optionally substituted pyridinyl, optionally substituted pyridazinyl, optionally substituted tetrahydro-2H-pyranyl, optionally substituted piperidinyl, optionally substituted pyrrolidinyl, optionally substituted tetrahydrothiophenyl, optionally substituted pyrazinyl, optionally substituted 1H-tetrazolyl, optionally substituted azetidinyl, optionally substituted tetrahydrofuranyl, optionally substituted tetrahydro-2H-furo[2,3-b]furanyl, optionally substituted thiazoyl, optionally substituted 1H-imidazolyl, optionally substituted 4H-1,2,4-triazolyl, optionally substituted 1H-pyrazolyl, optionally substituted 1,3,4-thiadiazolyl, optionally substituted quinolinyl, optionally substituted [1,2,4]triazolo[4,3-a]pyridinyl, optionally substituted thiophenyl, optionally substituted 1,2,4-thiadiazolyl, optionally substituted pyrimidinyl, optionally substituted 1H-1,2,3-triazolyl, optionally substituted 1,3,4-oxadiazolyl or optionally substituted imidazo[1,2-b]pyridazinyl. In another aspect of this embodiment, L is —O—.

In another aspect of this embodiment, L is —S—. In another aspect of this embodiment, L is —S(O)—. In another aspect of this embodiment, L is —S(O)$_2$—.

In another embodiment of Formula I, $R^1$ is optionally substituted $C_1$-$C_{12}$ alkyl and $R^2$ is optionally substituted $C_{3-12}$ cycloalkyl. In another aspect of this embodiment, $R^2$ is optionally substituted methylcyclohexyl or optionally substituted methylcyclohexenyl. In another aspect of this embodiment, $R^3$ is optionally substituted $C_{1-12}$ alkylene, $C_{2-12}$ alkenylene, substituted $C_{2-12}$ alkenylene, $C_{2-12}$ alkynylene, substituted $C_{2-12}$ alkynylene, $C_{3-12}$ cycloalkylene, substituted $C_{3-12}$ cycloalkylene, optionally substituted $C_{6-14}$ arylene, optionally substituted 3-14 membered heteroarylene, optionally substituted 3-12 membered heterocyclylene, optionally substituted 3-18 membered heteroarylalkylene, or optionally substituted $C_{6-18}$ arylalkylene. In another aspect of this embodiment, $R^3$ is optionally substituted $C_{1-12}$ alkylene, $C_{3-12}$ cycloalkylene, substituted $C_{3-12}$ cycloalkylene, optionally substituted $C_{6-14}$ arylene, or optionally substituted 3-12 membered heterocyclylene. In another aspect of this embodiment, L is —O—, —S—, —S(O)— or —S(O)$_2$—. In another aspect of this embodiment, L is —O—. In another aspect of this embodiment, L is —S—. In another aspect of this embodiment, L is —S(O)—. In another aspect of this embodiment, L is —S(O)$_2$—.

In another embodiment of Formula I, $R^1$ is optionally substituted $C_3$-$C_{12}$ cycloalkyl and $R^2$ is optionally substituted $C_{3-12}$ cycloalkyl. In another aspect of this embodiment, $R^2$ is optionally substituted methylcyclohexyl or optionally substituted methylcyclohexenyl. In another aspect of this embodiment, $R^3$ is optionally substituted $C_{1-12}$ alkylene, $C_{2-12}$ alkenylene, substituted $C_{2-12}$ alkenylene, $C_{2-12}$ alkynylene, substituted $C_{2-12}$ alkynylene, $C_{3-12}$ cycloalkylene, substituted $C_{3-12}$ cycloalkylene, optionally substituted $C_{6-14}$ arylene, optionally substituted 3-14 membered heteroarylene, optionally substituted 3-12 membered heterocyclylene, optionally substituted 3-18 membered heteroarylalkylene, or optionally substituted $C_{6-18}$ arylalkylene. In another aspect of this embodiment, $R^3$ is optionally substituted $C_{1-12}$ alkylene, $C_{3-12}$ cycloalkylene, substituted $C_{3-12}$ cycloalkylene, optionally substituted $C_{6-14}$ arylene, or optionally substituted 3-12 membered heterocyclylene. In another aspect of this embodiment, L is —O—, —S—, —S(O)— or —S(O)$_2$—. In another aspect of this embodiment, L is —O—. In another aspect of this embodiment, L is —S—. In another aspect of this embodiment, L is —S(O)—. In another aspect of this embodiment, L is —S(O)$_2$—.

In another embodiment of Formula I, $R^1$ is optionally substituted $C_1$-$C_{12}$ alkyl, $R^2$ is optionally substituted $C_{3-12}$ cycloalkyl and $R^3$ is optionally substituted $C_{1-12}$ alkylene, $C_{3-12}$ cycloalkylene, substituted $C_{3-12}$ cycloalkylene, optionally substituted $C_{6-14}$ arylene, or optionally substituted 3-12 membered heterocyclylene. In another aspect of this embodiment, $R^3$ is optionally substituted $C_{1-6}$ alkylene. In another aspect of this embodiment, $R^3$ is $C_{4-6}$ cycloalkylene or substituted $C_{4-6}$ cycloalkylene. In another aspect of this embodiment, $R^3$ is an optionally substituted 5-6 membered heterocyclylene. In another aspect of this embodiment, L is —O—, —S—, —S(O)— or —S(O)$_2$—. In another aspect of this embodiment, L is —O—. In another aspect of this embodiment, L is —S—. In another aspect of this embodiment, L is —S(O)—. In another aspect of this embodiment, L is —S(O)$_2$—. In another aspect of this embodiment, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is an optionally substituted 3-12 membered heterocyclyl comprising one or two heteroatoms selected from O, S, or N. In another aspect of this embodiment, Het is an optionally substituted 5-10 membered heteroaryl comprising one to four heteroatoms selected from O, S, or N.

In another embodiment of Formula I, $R^1$ is optionally substituted $C_3$-$C_7$ secondary or tertiary alkyl and $R^2$ is optionally substituted methylcyclohexyl or optionally substituted methylcyclohexenyl. In another aspect of this embodiment, $R^1$ is prop-2-yl (isopropyl) or 2-methylprop-2-yl (t-butyl). In another aspect of this embodiment, $R^2$ is optionally substituted 4-methylcyclohexyl. In a preferred aspect of this embodiment, $R^2$ is

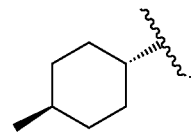 [SMILES: *[C@H]1CC[C@H](C)CC1]

In another preferred aspect of this embodiment, $R^2$ is

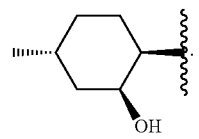 [SMILES: *[C@@H]1CC[C@@H](C)C[C@@H]1O]

In another preferred aspect of this embodiment, $R^2$ is

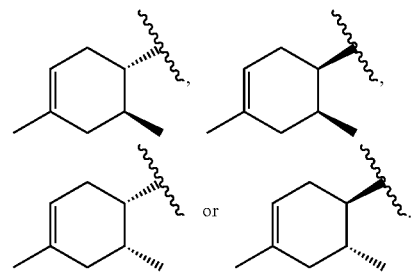

In another preferred aspect of this embodiment, $R^2$ is

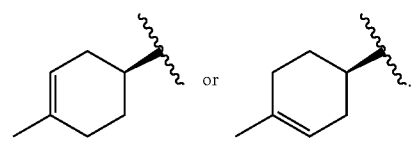

In another embodiment of Formula I, $R^1$ is optionally substituted $C_3$-$C_5$ cycloalkyl and $R^2$ is optionally substituted methylcyclohexyl or optionally substituted methylcyclohexenyl. In another aspect of this embodiment, $R^1$ is prop-2-yl (isopropyl) or 2-methylprop-2-yl (t-butyl). In another aspect of this embodiment, $R^2$ is optionally substituted 4-methylcyclohexyl. In a preferred aspect of this embodiment, $R^2$ is

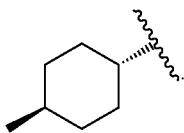 [SMILES: *[C@H]1CC[C@H](C)CC1]

In another preferred aspect of this embodiment, $R^2$ is

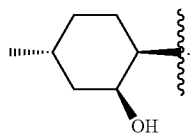 [SMILES: *[C@@H]1CC[C@@H](C)C[C@@H]1O]

In another preferred aspect of this embodiment, $R^2$ is

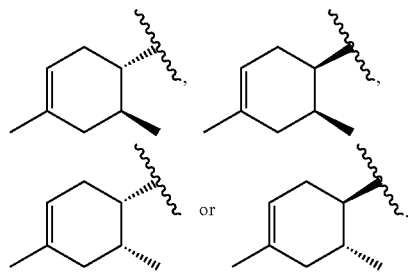

In another preferred aspect of this embodiment, $R^2$ is

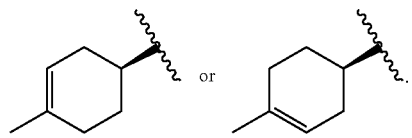

In another embodiment of Formula I, $R^1$ is optionally substituted $C_3$-$C_7$ secondary or tertiary alkyl and $R^2$ is optionally substituted methylcyclohexyl or optionally substituted methylcyclohexenyl. In another aspect of this embodiment, $R^3$ is optionally substituted $C_{1-6}$ alkylene. In another aspect of this embodiment, $R^3$ is $C_{4-6}$ cycloalkylene or substituted $C_{4-6}$ cycloalkylene. In another aspect of this embodiment, $R^3$ is an optionally substituted 4-6 membered nitrogen-containing heterocyclylene. In another aspect of this embodiment, L is —O—, —S—, —S(O)— or —S(O)$_2$—. In another aspect of this embodiment, L is —O—. In another aspect of this embodiment, L is —S—. In another aspect of this embodiment, L is —S(O)—. In another aspect of this embodiment, L is —S(O)$_2$—. In another aspect of this embodiment, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is an optionally substituted 3-12 membered heterocyclyl comprising one or two heteroatoms selected from O, S, or N. In aspect of this embodiment, Het is an optionally substituted 5-10 membered heteroaryl comprising one to four heteroatoms selected from O, S, or N.

In another embodiment of Formula I, L is —O—, $R^1$ is optionally substituted $C_3$-$C_7$ secondary or tertiary alkyl and $R^2$ is optionally substituted methylcyclohexyl or optionally substituted methylcyclohexenyl. In another aspect of this embodiment, $R^3$ is optionally substituted $C_{1-6}$ alkylene. In another aspect of this embodiment, $R^3$ is $C_{4-6}$ cycloalkylene or substituted $C_{4-6}$ cycloalkylene. In another aspect of this embodiment, $R^3$ is an optionally substituted 5-6 membered heterocyclylene. In another aspect of this embodiment, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is an optionally substituted 3-12 membered heterocyclyl comprising one or two heteroatoms selected from O, S, or N. In aspect of this embodiment, Het is an optionally substituted 5-10 membered heteroaryl comprising one to four heteroatoms selected from O, S, or N.

In another embodiment, compounds of Formula I are represented by compounds of Formula II:

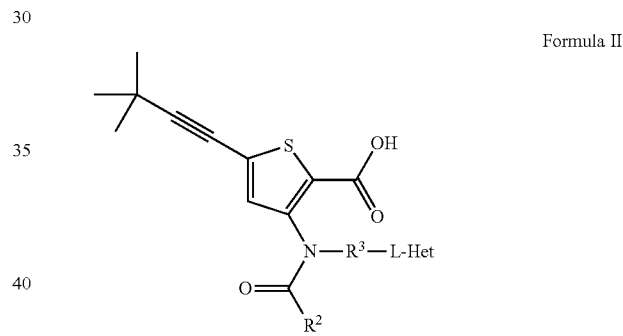

Formula II or pharmaceutically acceptable salts and esters thereof, wherein:
$R^2$ is optionally substituted 4-methylcyclohexyl or optionally substituted methylcyclohexenyl and the remaining variables are defined as for Formula I.

In one embodiment of Formula II, $R^2$ is:

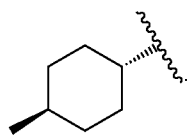 [SMILES: *[C@H]1CC[C@H](C)CC1]

In one embodiment of Formula II, $R^2$ is:

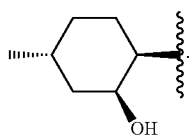 [SMILES: *[C@@H]1CC[C@@H](C)C[C@@H]1O]

In another embodiment of Formula II, R² is

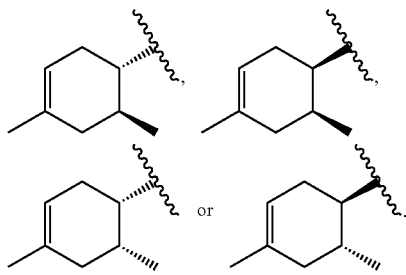

In another embodiment of Formula II, R² is

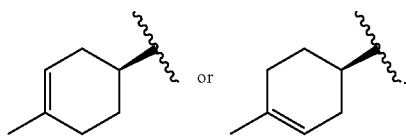

In one embodiment of Formula II, R³ is optionally substituted $C_{1-6}$ alkylene. In another embodiment of Formula II, R³ is $C_{4-6}$ cycloalkylene or substituted $C_{4-6}$ cycloalkylene. In one embodiment of Formula II, R³ is an optionally substituted 5-6 membered heterocyclylene. In another embodiment of Formula II, L is —O—, —S—, —S(O)— or —S(O)$_2$—. In another embodiment of Formula II, L is —O—. In another embodiment of Formula II, L is —S—. In another embodiment of Formula II, L is —S(O)—. In another embodiment of Formula II, L is —S(O)$_2$—. In another embodiment of Formula II, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another embodiment of Formula II, Het is an optionally substituted 3-12 membered heterocyclyl comprising one or two heteroatoms selected from O, S, or N. In another embodiment of Formula II, Het is an optionally substituted 5-10 membered heteroaryl comprising one to four heteroatoms selected from O, S, or N.

In another embodiment of Formula II, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is optionally substituted pyridinyl. In another aspect of this embodiment, Het is optionally substituted pyridine-2-yl. In another aspect of this embodiment, Het is optionally substituted pyridazinyl. In another aspect of this embodiment, Het is optionally substituted tetrahydro-2H-pyranyl. In another aspect of this embodiment, Het is optionally substituted piperidinyl. In another aspect of this embodiment, Het is optionally substituted pyrrolidinyl. In another aspect of this embodiment, Het is optionally substituted tetrahydrothiophenyl. In another aspect of this embodiment, Het is optionally substituted pyrazinyl. In another aspect of this embodiment, Het is optionally substituted 1H-tetrazolyl. In another aspect of this embodiment, Het is optionally substituted azetidinyl. In another aspect of this embodiment, Het is optionally substituted tetrahydrofuranyl. In another aspect of this embodiment, Het is optionally substituted tetrahydrofuran-3-yl. In another aspect of this embodiment, Het is optionally substituted tetrahydro-2H-furo[2,3-b]furanyl. In another aspect of this embodiment, Het is optionally substituted thiazoyl. In another aspect of this embodiment, Het is optionally substituted 1H-imidazolyl. In another aspect of this embodiment, Het is optionally substituted 4H-1,2,4-triazolyl. In another aspect of this embodiment, Het is optionally substituted 1H-pyrazolyl. In another aspect of this embodiment, Het is optionally substituted 1,3,4-thiadiazolyl. In another aspect of this embodiment, Het is optionally substituted quinolinyl. In another aspect of this embodiment, Het is optionally substituted [1,2,4]triazolo[4,3-a]pyridinyl. In another aspect of this embodiment, Het is optionally substituted thiophenyl. In another aspect of this embodiment, Het is optionally substituted 1,2,4-thiadiazolyl. In another aspect of this embodiment, Het is optionally substituted pyrimidinyl. In another aspect of this embodiment, Het is optionally substituted 1H-1,2,3-triazolyl. In another aspect of this embodiment, Het is optionally substituted 1,3,4-oxadiazolyl. In another aspect of this embodiment, Het is optionally substituted imidazo[1,2-b]pyridazinyl. In another aspect of this embodiment, L is —O—. In another aspect of this embodiment, L is —S—. In another aspect of this embodiment, L is —S(O)—. In another aspect of this embodiment, L is —S(O)$_2$—. In another aspect of this embodiment, R² is:

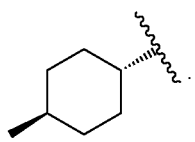

In another aspect of this embodiment, R² is:

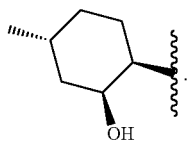 [SMILES: *[C@@H]1CC[C@@H](C)C[C@@H]1O]

In another preferred aspect of this embodiment, R² is

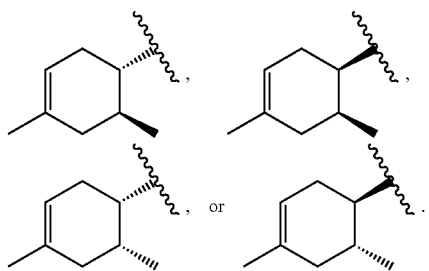

In another preferred aspect of this embodiment, R² is

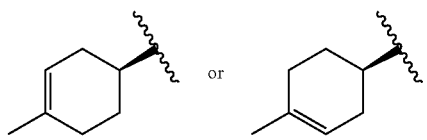

In one embodiment of Formula II, L is —O—. In another aspect of this embodiment, R³ is optionally substituted C$_{1-6}$ alkylene. In another aspect of this embodiment, R³ is C$_{4-6}$ cycloalkylene or substituted C$_{4-6}$ cycloalkylene. In another aspect of this embodiment, R³ is an optionally substituted 5-6 membered heterocyclylene. In another aspect of this embodiment, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is an optionally substituted 3-12 membered heterocyclyl comprising one or two heteroatoms selected from O, S, or N. In another aspect of this embodiment, Het is an optionally substituted 5-10 membered heteroaryl comprising one to four heteroatoms selected from O, S, or N. In another aspect of this embodiment, Het is optionally substituted pyridinyl. In another aspect of this embodiment, Het is optionally substituted pyridazinyl. In another aspect of this embodiment, Het is optionally substituted tetrahydro-2H-pyranyl. In another aspect of this embodiment, Het is optionally substituted piperidinyl. In another aspect of this embodiment, Het is optionally substituted pyrrolidinyl. In another aspect of this embodiment, Het is optionally substituted tetrahydrothiophenyl. In another aspect of this embodiment, Het is optionally substituted pyrazinyl. In another aspect of this embodiment, Het is optionally substituted 1H-tetrazolyl. In another aspect of this embodiment, Het is optionally substituted azetidinyl. In another aspect of this embodiment, Het is optionally substituted tetrahydrofuranyl. In another aspect of this embodiment, Het is optionally substituted tetrahydro-2H-furo[2,3-b]furanyl. In another aspect of this embodiment, Het is optionally substituted thiazoyl. In another aspect of this embodiment, Het is optionally substituted 1H-imidazolyl. In another aspect of this embodiment, Het is optionally substituted 4H-1,2,4-triazolyl. In another aspect of this embodiment, Net is optionally substituted 1H-pyrazolyl. In another aspect of this embodiment, Het is optionally substituted 1,3,4-thiadiazolyl. In another aspect of this embodiment, Net is optionally substituted quinolinyl. In another aspect of this embodiment, Het is optionally substituted [1,2,4]triazolo[4,3-a]pyridinyl. In another aspect of this embodiment, Net is optionally substituted thiophenyl. In another aspect of this embodiment, Net is optionally substituted 1,2,4-thiadiazolyl. In another aspect of this embodiment, Net is optionally substituted pyrimidinyl. In another aspect of this embodiment, Het is optionally substituted 1H-1,2,3-triazolyl. In another aspect of this embodiment, Het is optionally substituted 1,3,4-oxadiazolyl. In another aspect of this embodiment, Net is optionally substituted imidazo[1,2-b]pyridazinyl. In another aspect of this embodiment, R² is:

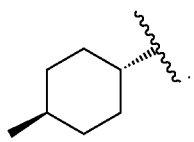 [SMILES: *[C@H]1CC[C@H](C)CC1]

In another aspect of this embodiment, R² is:

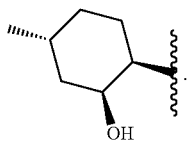 [SMILES: *[C@@H]1CC[C@@H](C)C[C@@H]1O]

In another preferred aspect of this embodiment, R² is

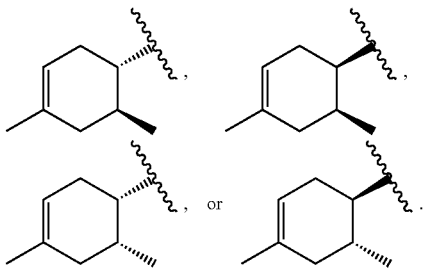

In another preferred aspect of this embodiment, R² is

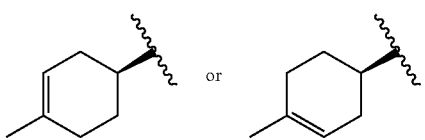

In one embodiment of Formula II, L is —O— and R³ is C$_{4-6}$ cycloalkylene or substituted C$_{4-6}$ cycloalkylene. In another aspect of this embodiment, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is an optionally substituted 3-12 membered heterocyclyl comprising one or two heteroatoms selected from O, S, or N. In another aspect of this embodiment, Het is an optionally substituted 5-10 membered heteroaryl comprising one to four heteroatoms selected from O, S, or N. In another aspect of this embodiment, Het is optionally substituted pyridinyl. In another aspect of this embodiment, Het is optionally substituted pyridazinyl. In another aspect of this embodiment, Het is optionally substituted tetrahydro-2H-pyranyl. In another aspect of this embodiment, Het is optionally substituted piperidinyl. In another aspect of this embodiment, Het is optionally substituted pyrrolidinyl. In another aspect of this embodiment, Het is optionally substituted tetrahydrothiophenyl. In another aspect of this embodiment, Het is optionally substituted pyrazinyl. In another aspect of this embodiment, Het is optionally substituted 1H-tetrazolyl. In another aspect of this embodiment, Het is optionally substituted azetidinyl. In another aspect of this embodiment, Het is optionally substituted tetrahydrofuranyl. In another aspect of this embodiment, Het is optionally substituted tetrahydro-2H-furo[2,3-b]furanyl. In another aspect of this embodiment, Het is optionally substituted thiazoyl. In another aspect of this embodiment, Het is optionally substituted 1H-imidazolyl. In another aspect of this embodiment, Het is optionally substituted 4H-1,2,4-triazolyl. In another aspect of this embodiment, Het is optionally substituted 1H-pyrazolyl. In another aspect of this embodiment, Het is optionally substituted 1,3,4-thiadiazolyl. In another aspect of this embodiment, Het is optionally substituted quinolinyl. In another aspect of this embodiment, Het is optionally substituted [1,2,4]triazolo[4,3-a]pyridinyl. In another aspect of this embodiment, Het is optionally substituted thiophenyl. In another aspect of this embodiment, Het is optionally substituted 1,2,4-thiadiazolyl. In another aspect of this embodiment, Het is optionally substituted pyrimidinyl. In another aspect of this embodiment, Het is optionally substituted 1H-1,2,3-triazolyl. In another aspect of this embodiment, Het is optionally substituted 1,3, 4-oxadiazolyl. In another aspect of this embodiment, Het is optionally substituted imidazo[1,2-b]pyridazinyl. In another aspect of this embodiment, R² is:

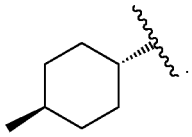 [SMILES: *[C@H]1CC[C@H](C)CC1]

In another aspect of this embodiment, R² is:

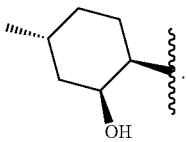 [SMILES: *[C@@H]1CC[C@@H](C)C[C@@H]1O]

In another preferred aspect of this embodiment, R² is

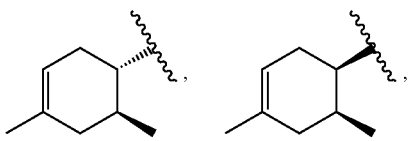

In another preferred aspect of this embodiment, R² is

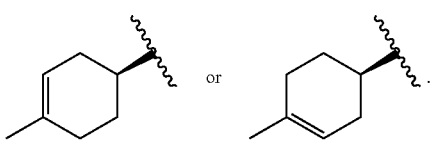

In one embodiment of Formula II, L is —O—, R³ is $C_{4-6}$ cycloalkylene or substituted $C_{4-6}$ cycloalkylene and R² is optionally substituted methylcyclohexyl optionally substituted methylcyclohexenyl. In another aspect of this embodiment, Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N. In another aspect of this embodiment, Het is an optionally substituted 3-12 membered heterocyclyl comprising one or two heteroatoms selected from O, S, or N. In another aspect of this embodiment, Het is an optionally substituted 5-10 membered heteroaryl comprising one to four heteroatoms selected from O, S, or N. In another aspect of this embodiment, Het is optionally substituted pyridinyl. In another aspect of this embodiment, Het is optionally substituted pyridazinyl. In another aspect of this embodiment, Het is optionally substituted tetrahydro-2H-pyranyl. In another aspect of this embodiment, Het is optionally substituted piperidinyl. In another aspect of this embodiment, Het is optionally substituted pyrrolidinyl. In another aspect of this embodiment, Het is optionally substituted tetrahydrothiophenyl. In another aspect of this embodiment, Het is optionally substituted pyrazinyl. In another aspect of this embodiment, Het is optionally substituted 1H-tetrazolyl. In another aspect of this embodiment, Het is optionally substituted azetidinyl. In another aspect of this embodiment, Het is optionally substituted tetrahydrofuranyl. In another aspect of this embodiment, Het is optionally substituted tetrahydro-2H-furo[2,3-b]furanyl. In another aspect of this embodiment, Het is optionally substituted thiazoyl. In another aspect of this embodiment, Het is optionally substituted 1H-imidazolyl. In another aspect of this embodiment, Het is optionally substituted 4H-1,2,4-triazolyl. In another aspect of this embodiment, Het is optionally substituted 1H-pyrazolyl. In another aspect of this embodiment, Het is optionally substituted 1,3,4-thiadiazolyl. In another aspect of this embodiment, Het is optionally substituted quinolinyl. In another aspect of this embodiment, Het is optionally substituted [1,2,4]triazolo[4,3-a]pyridinyl. In another aspect of this embodiment, Het is optionally substituted thiophenyl. In another aspect of this embodiment, Het is optionally substituted 1,2,4-thiadiazolyl. In another aspect of this embodiment, Net is optionally substituted pyrimidinyl. In another aspect of this embodiment, Net is optionally substituted 1H-1,2,3-triazolyl. In another aspect of this embodiment, Net is optionally substituted 1,3,4-oxadiazolyl. In another aspect of this embodiment, Net is optionally substituted imidazo[1,2-b]pyridazinyl. In another aspect of this embodiment, R² is:

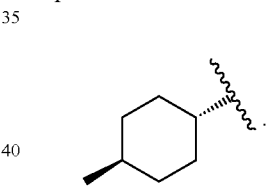

In another aspect of this embodiment, R² is:

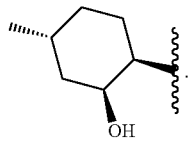 [SMILES: *[C@@H]1CC[C@@H](C)C[C@@H]1O]

In another preferred aspect of this embodiment, R² is

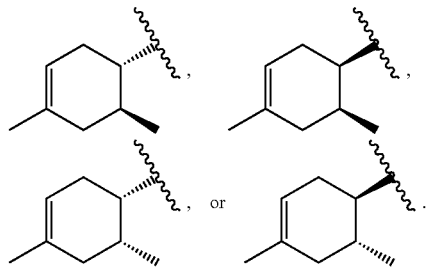

In another preferred aspect of this embodiment, $R^2$ is
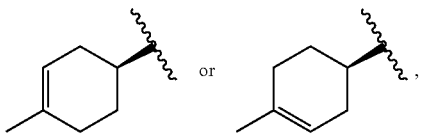 or ,
In another embodiment, the compound of Formula I or Formula II is
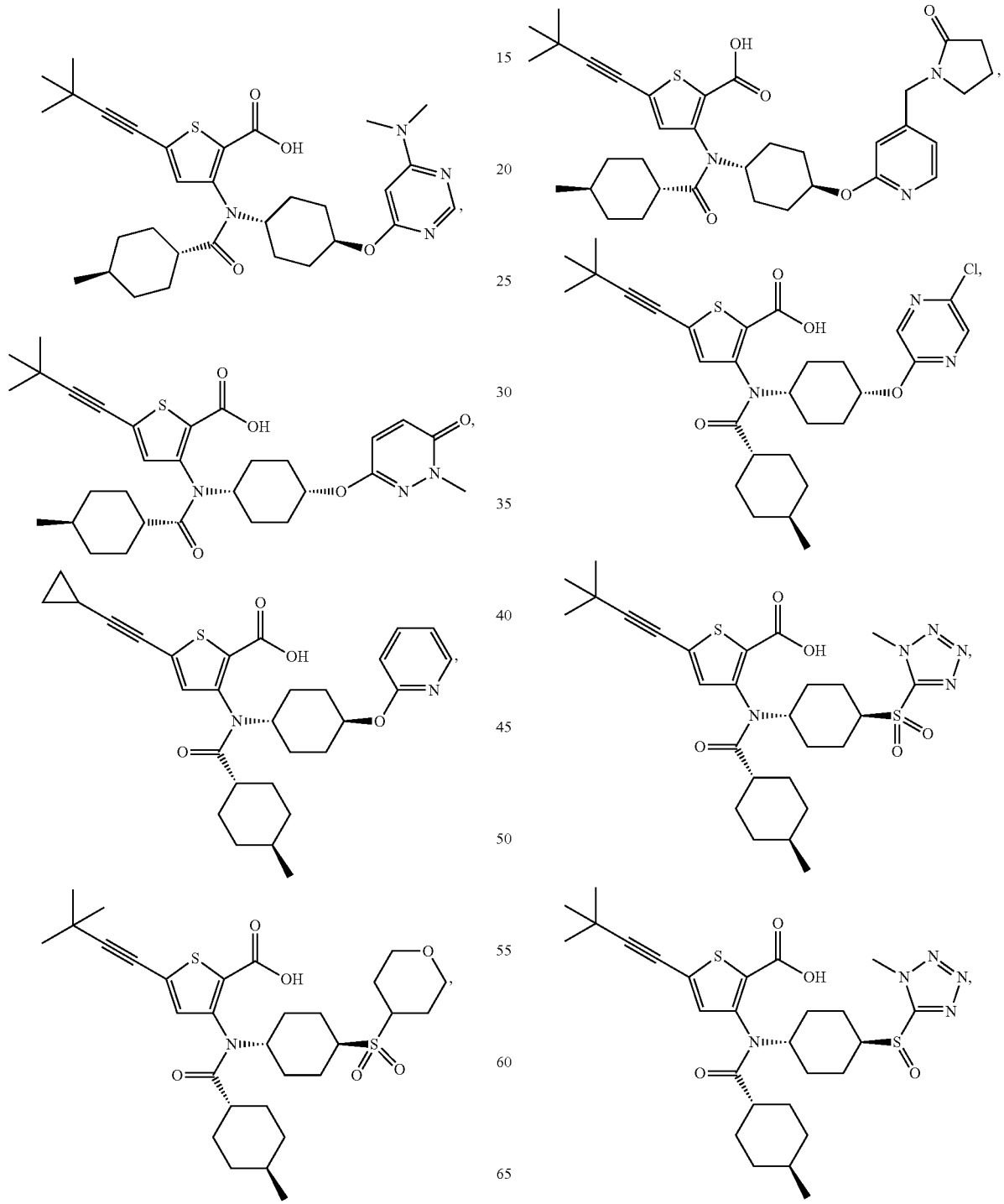
-continued
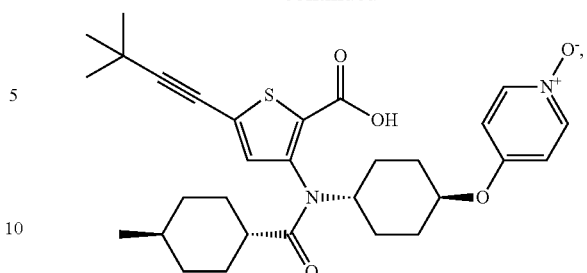

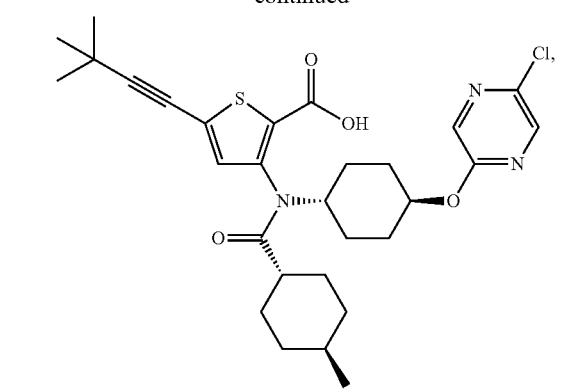
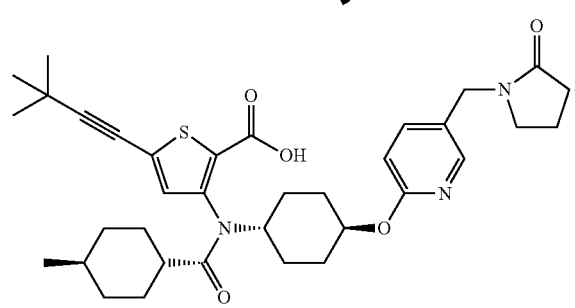
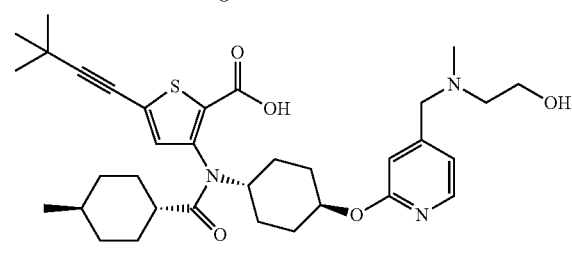
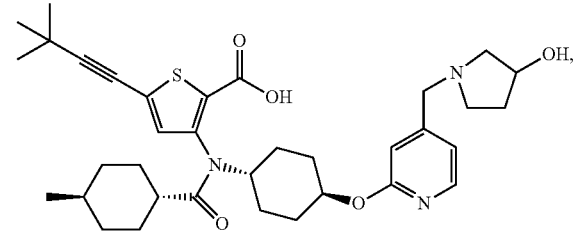
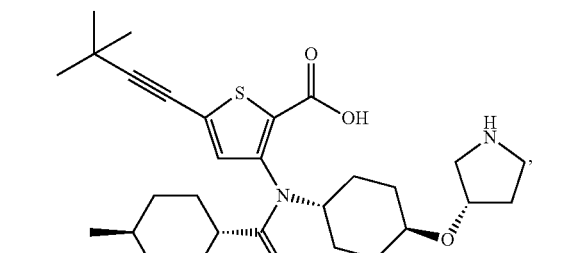
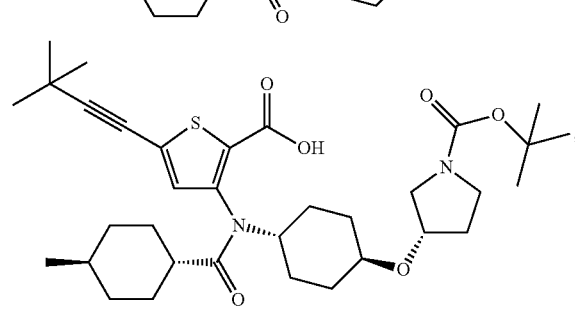
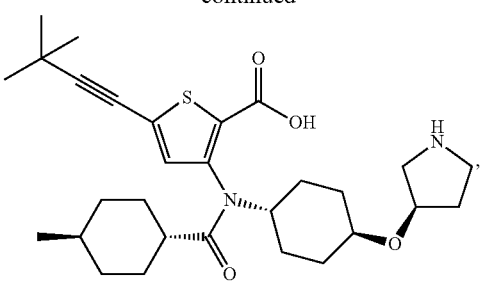
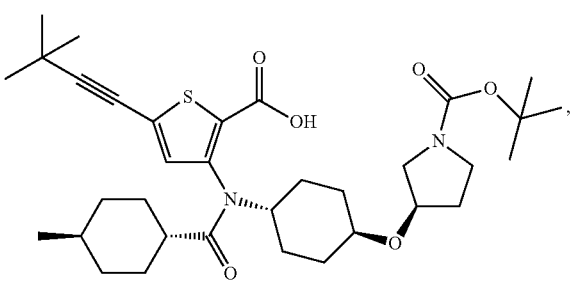
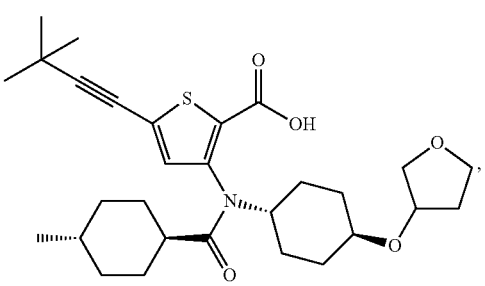
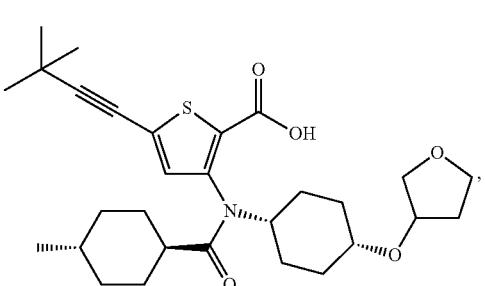
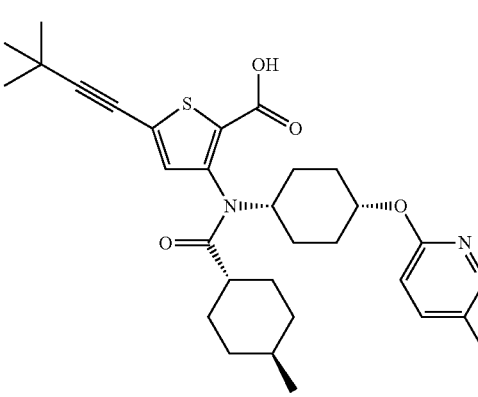

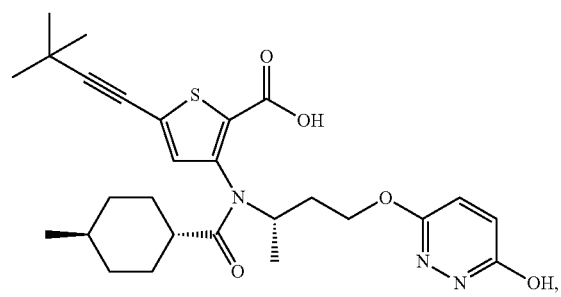
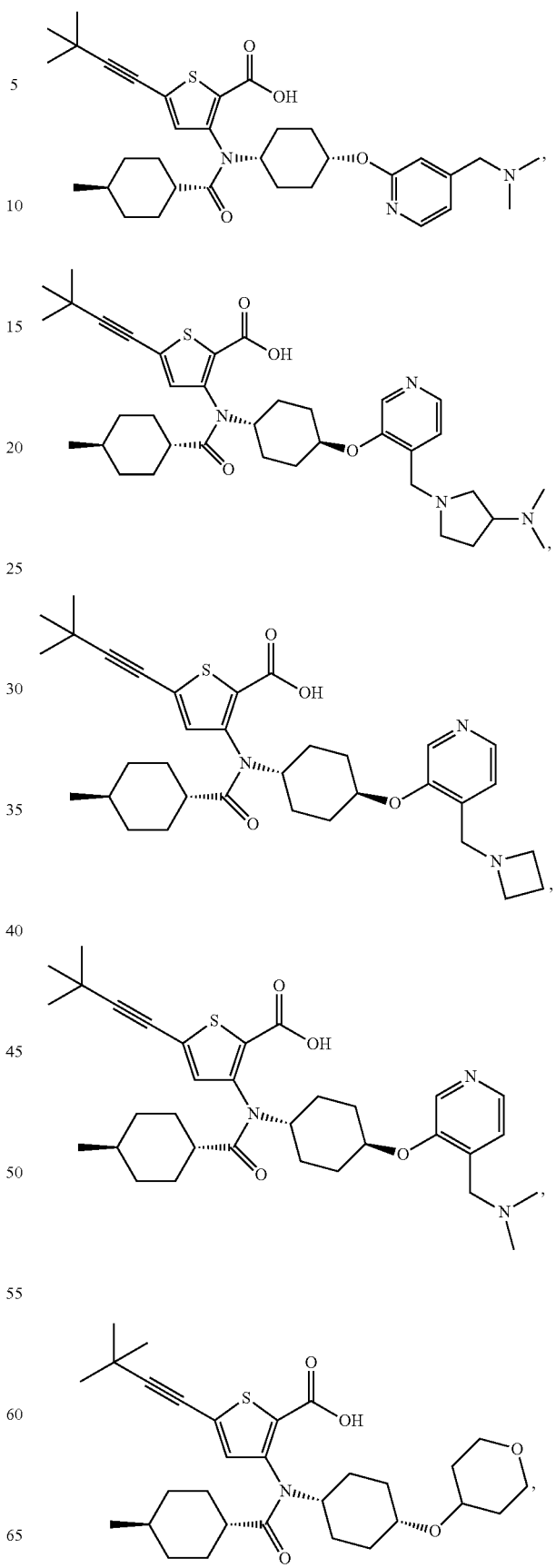

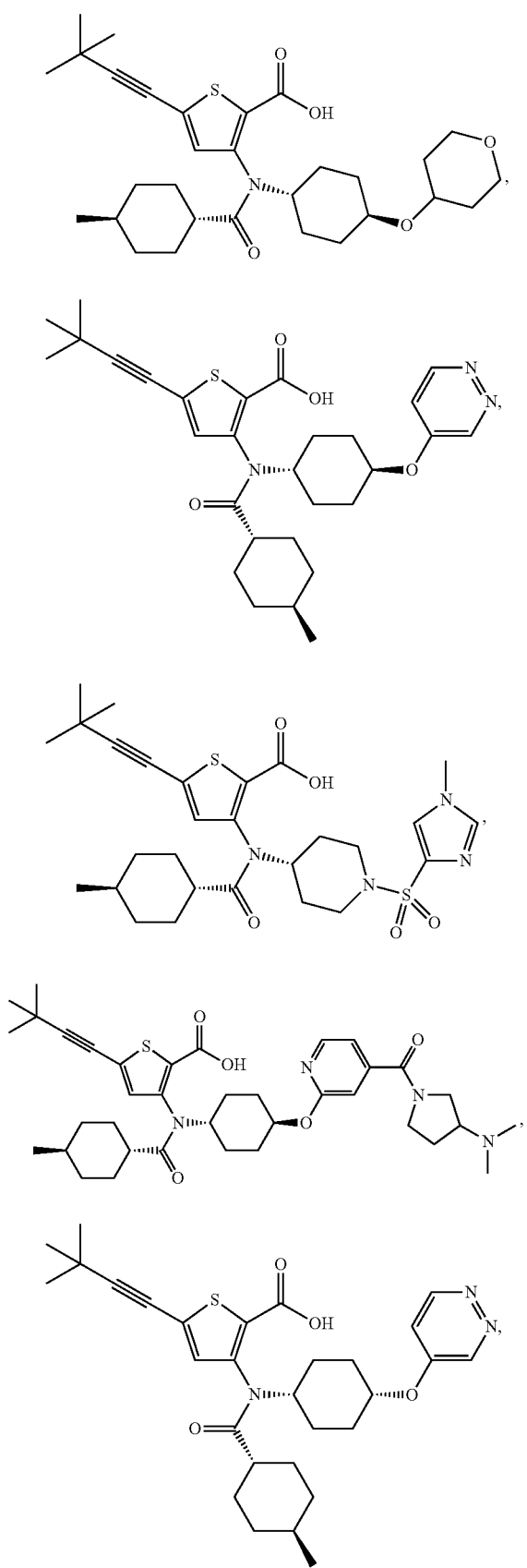
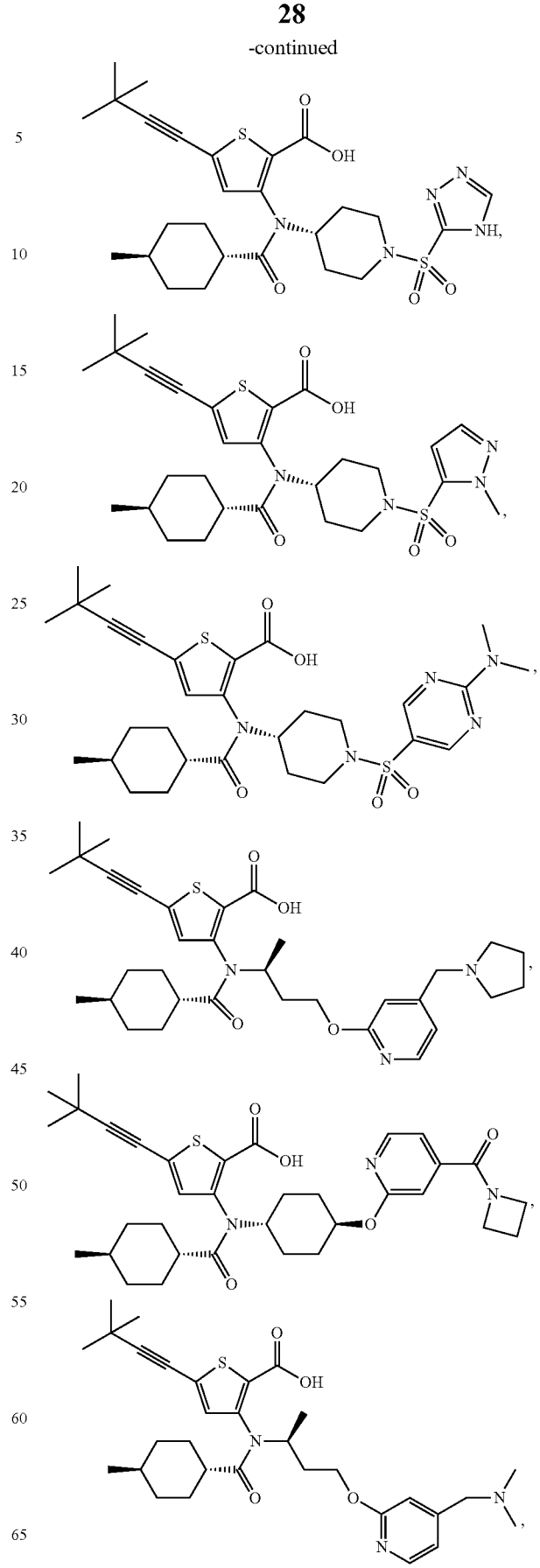

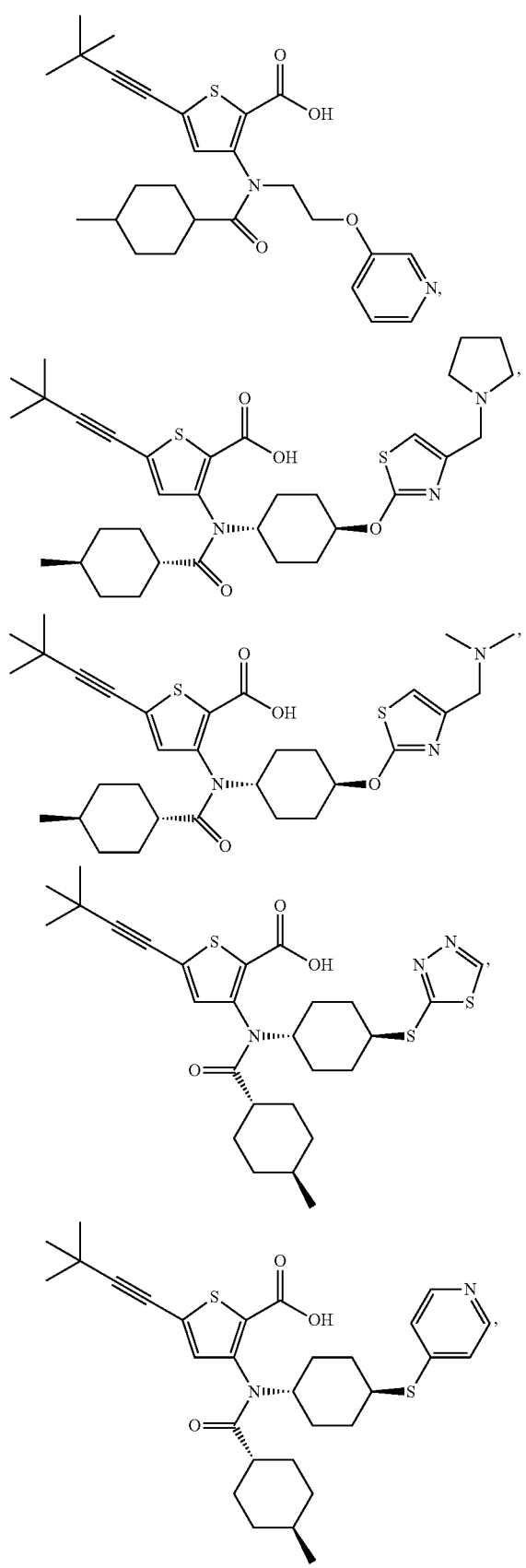
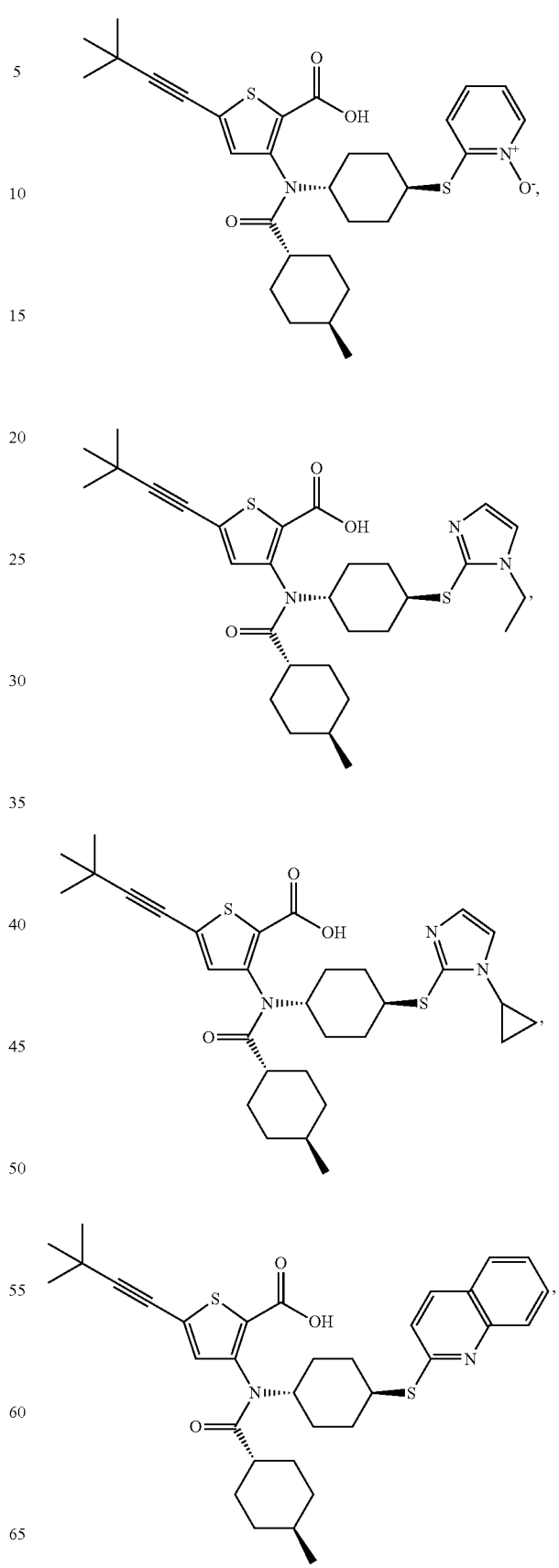

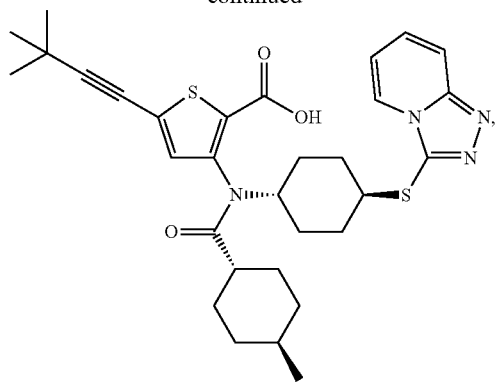
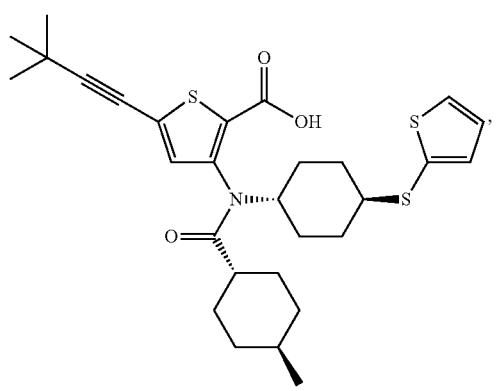
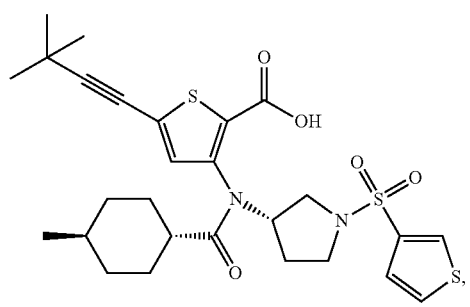
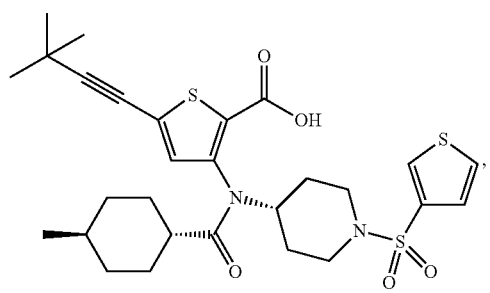
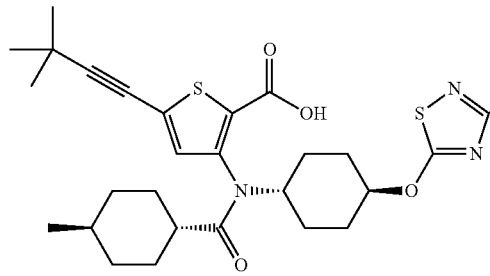
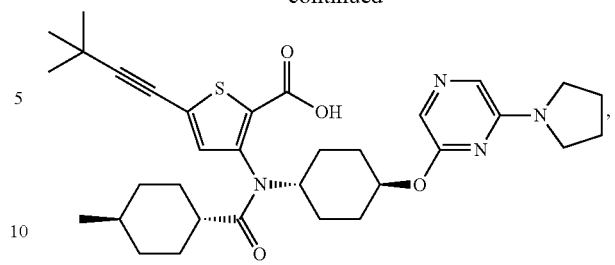
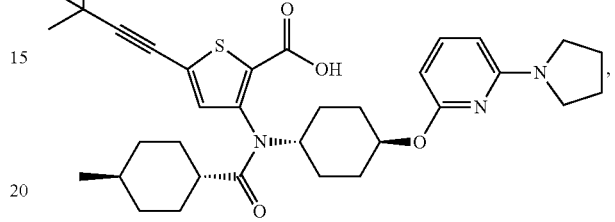
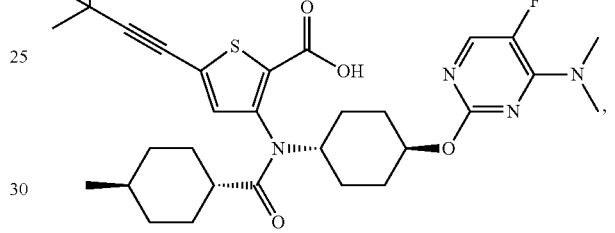
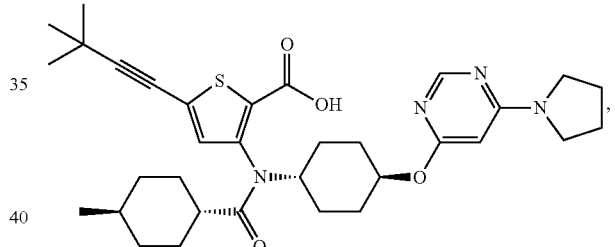
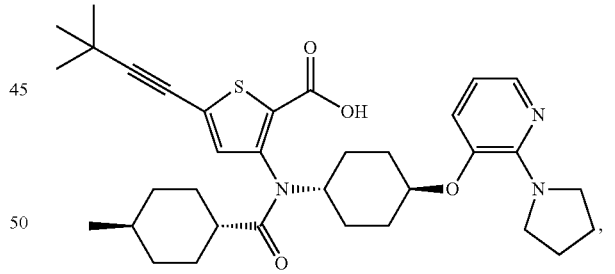
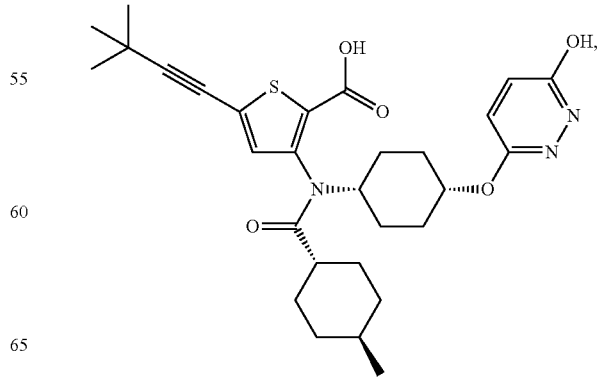

33
-continued
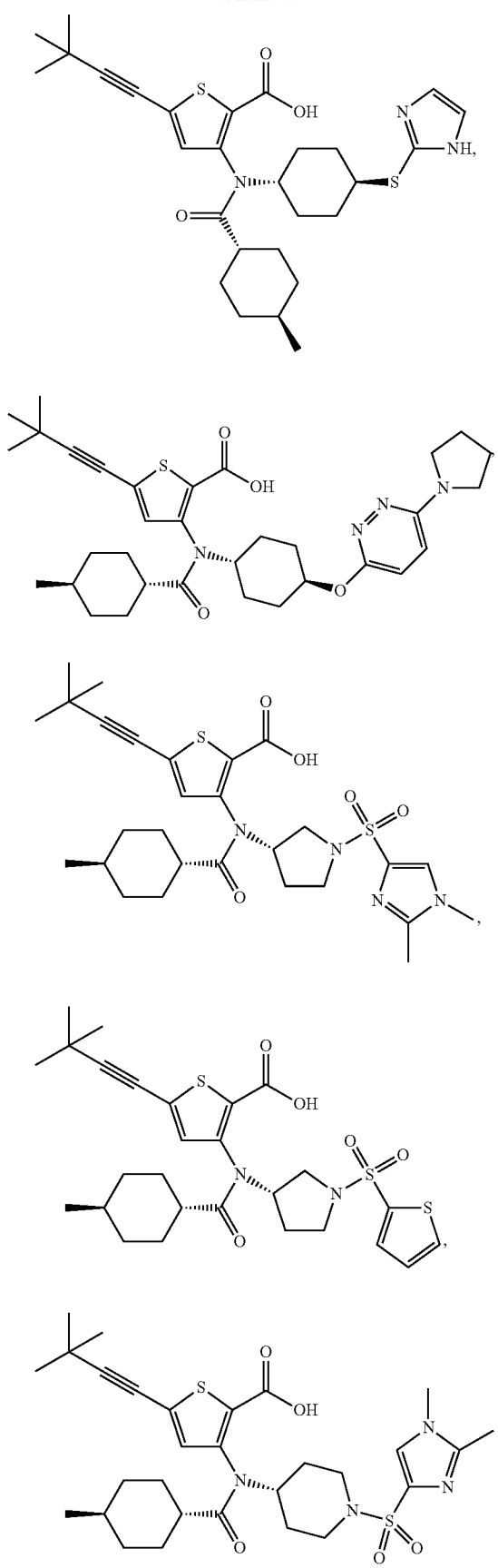
34
-continued
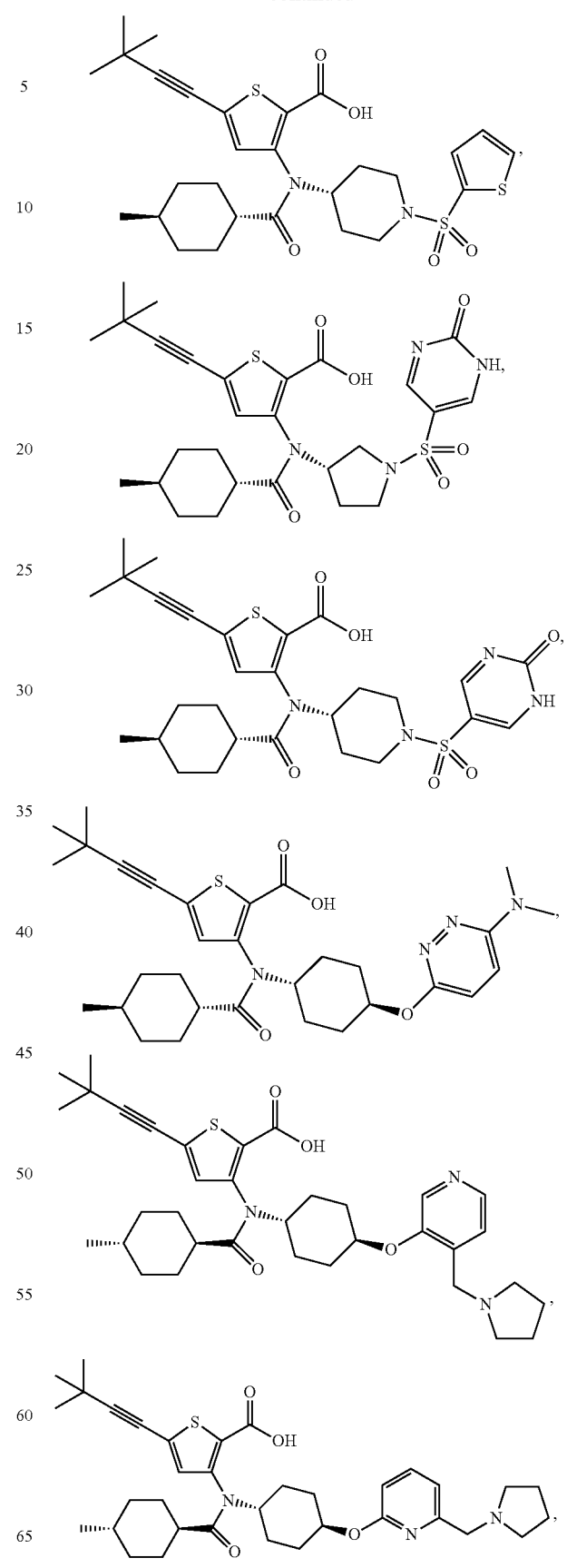

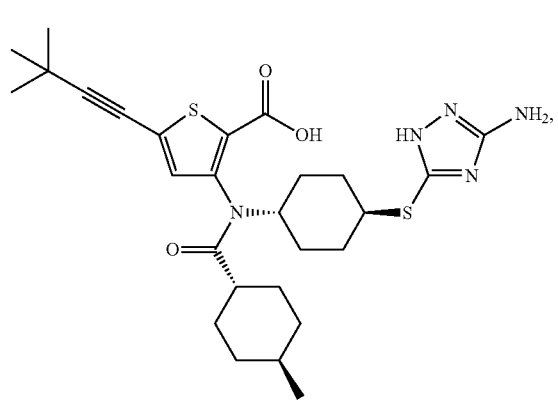
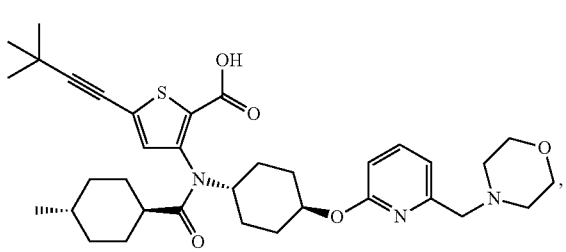
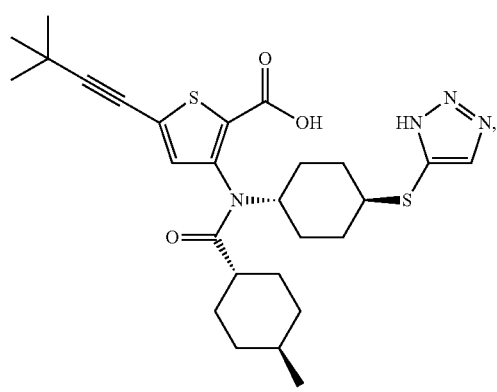
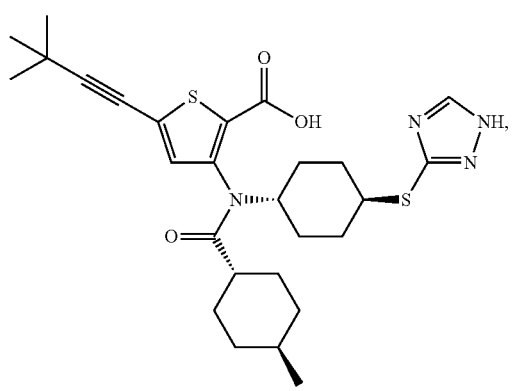
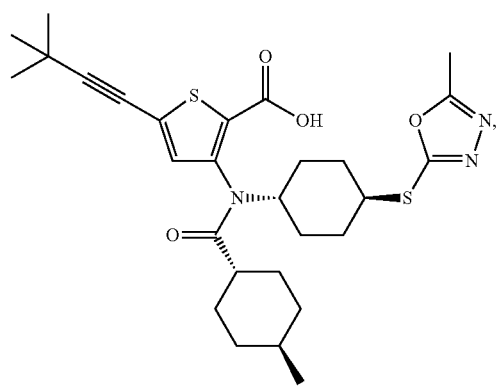
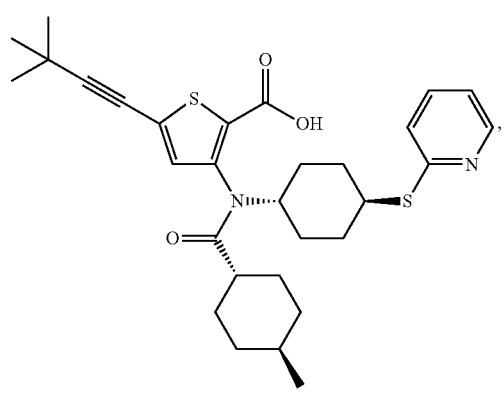
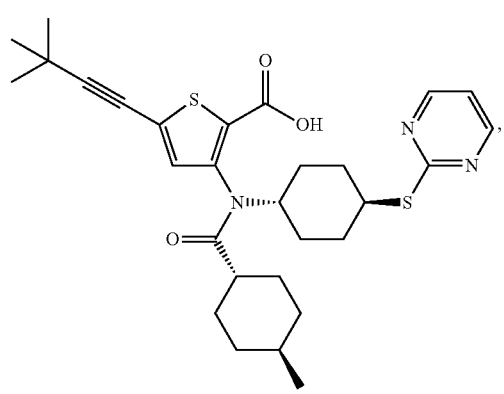
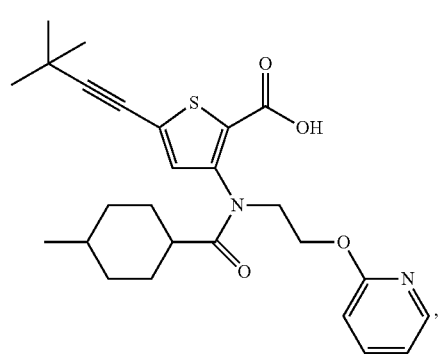

37
-continued
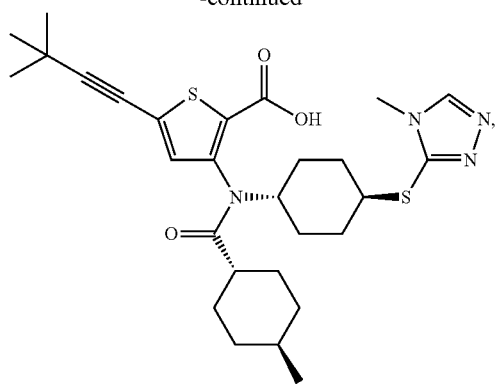
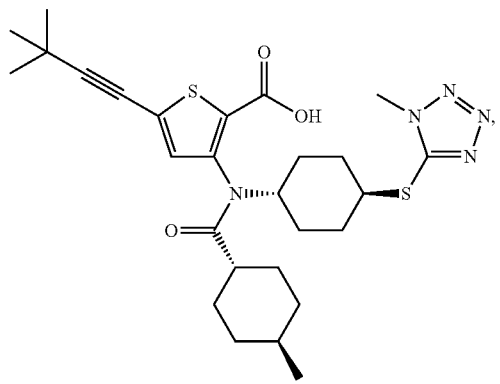
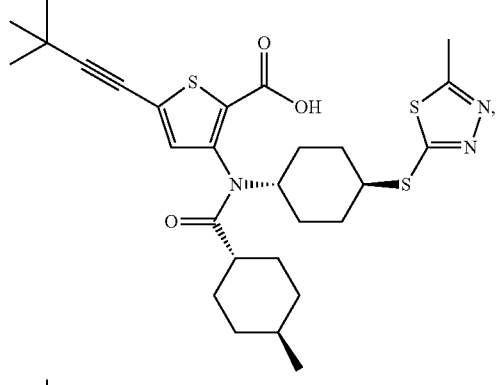
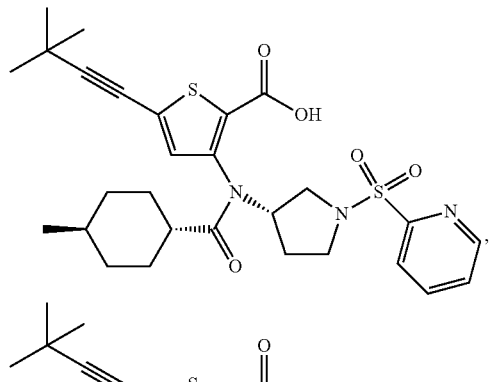
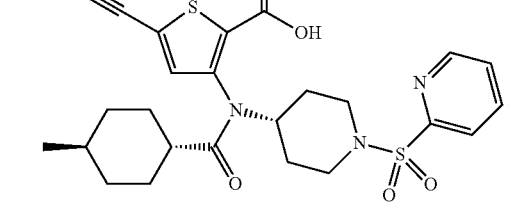
38
-continued
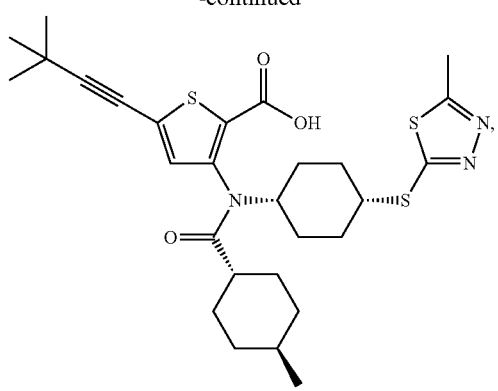
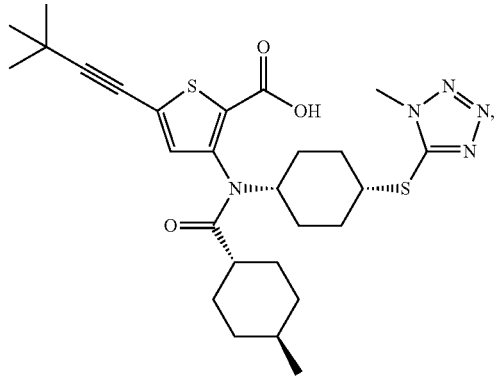
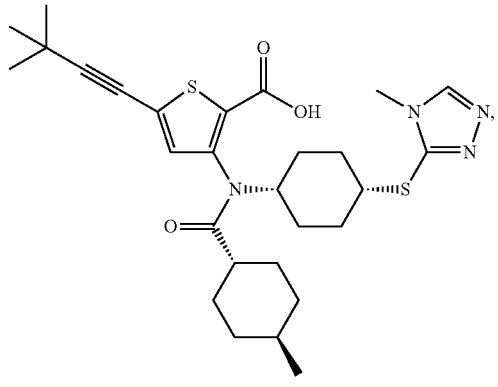
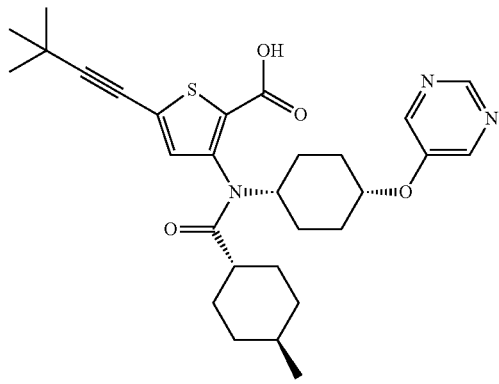

39
-continued
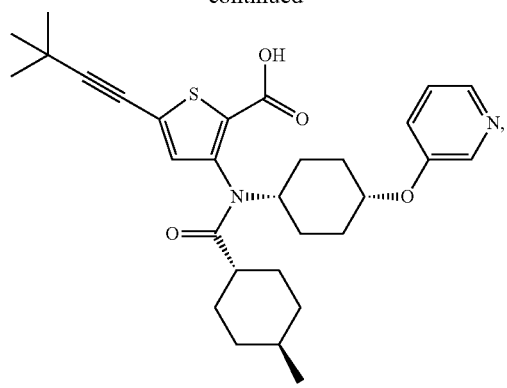
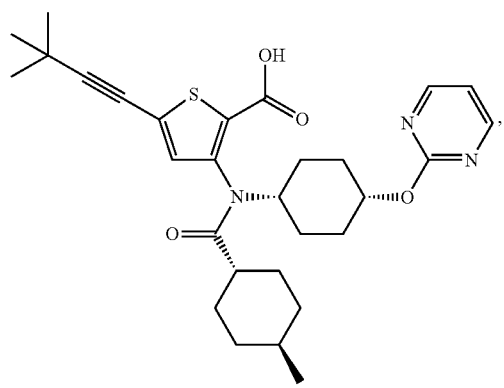
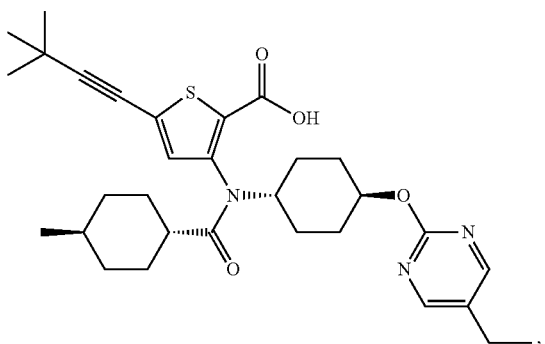
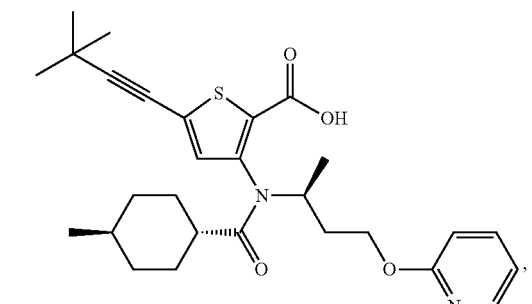
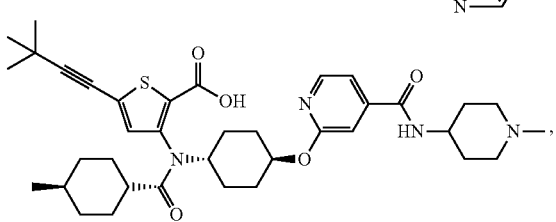
40
-continued
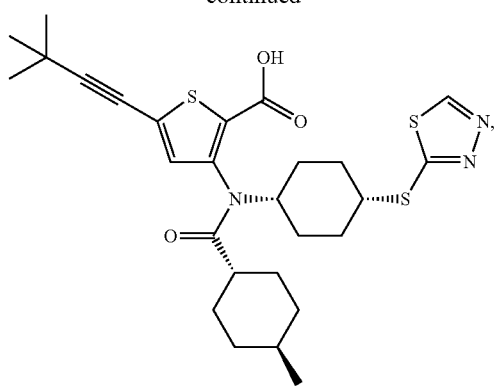
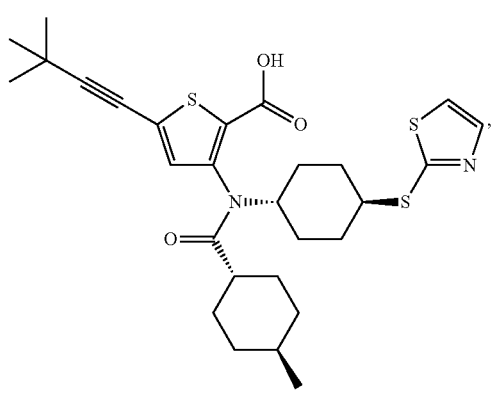
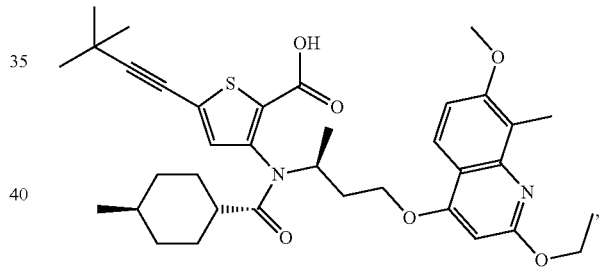
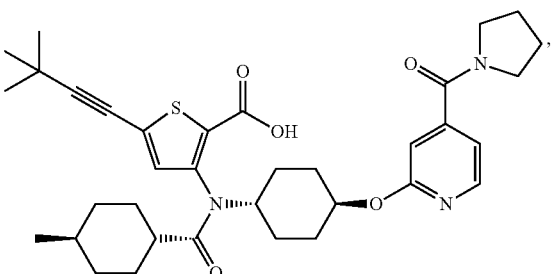
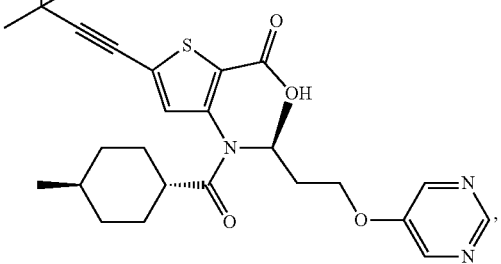

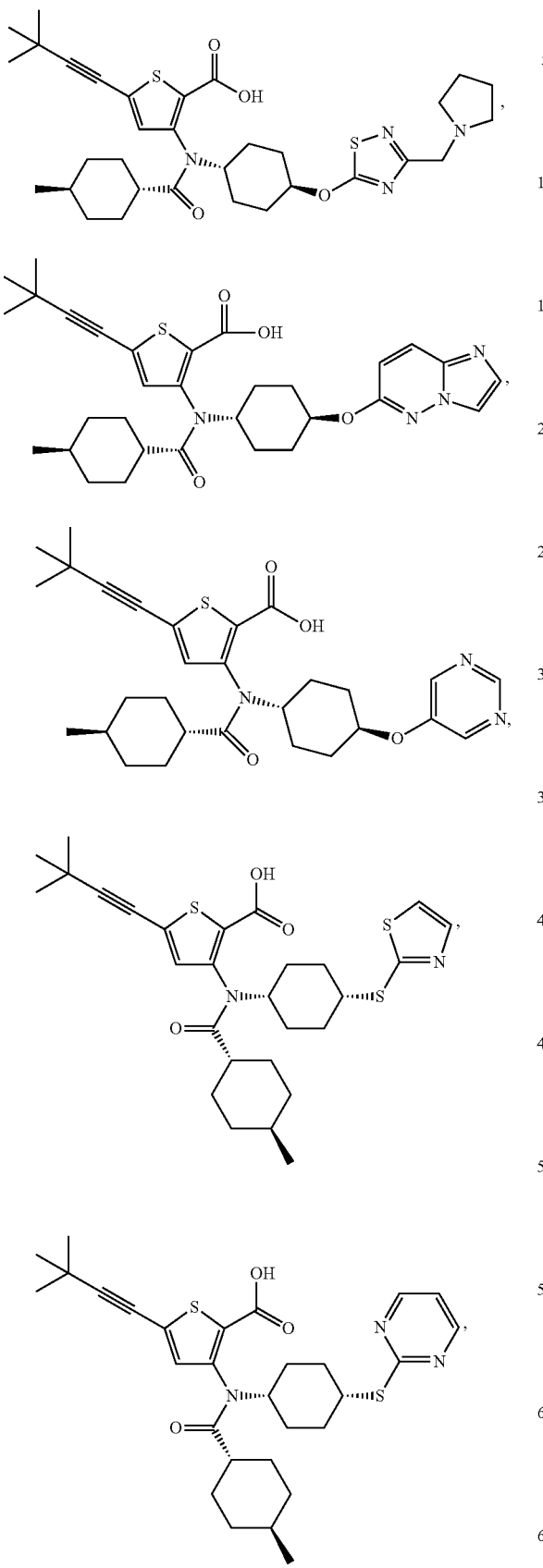
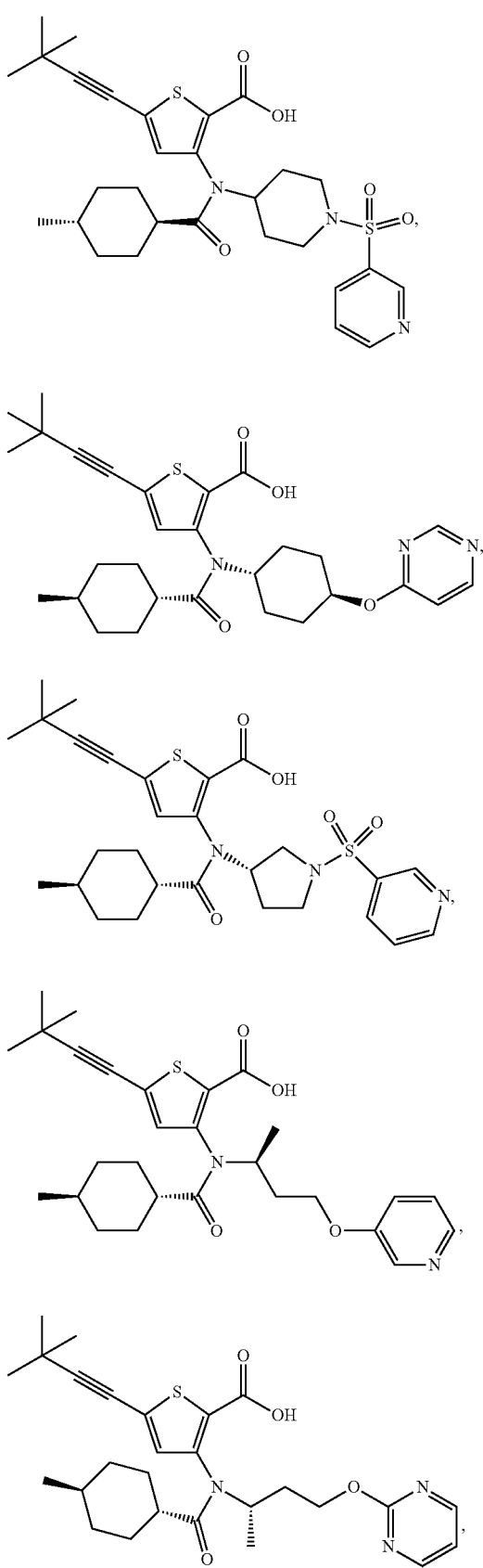

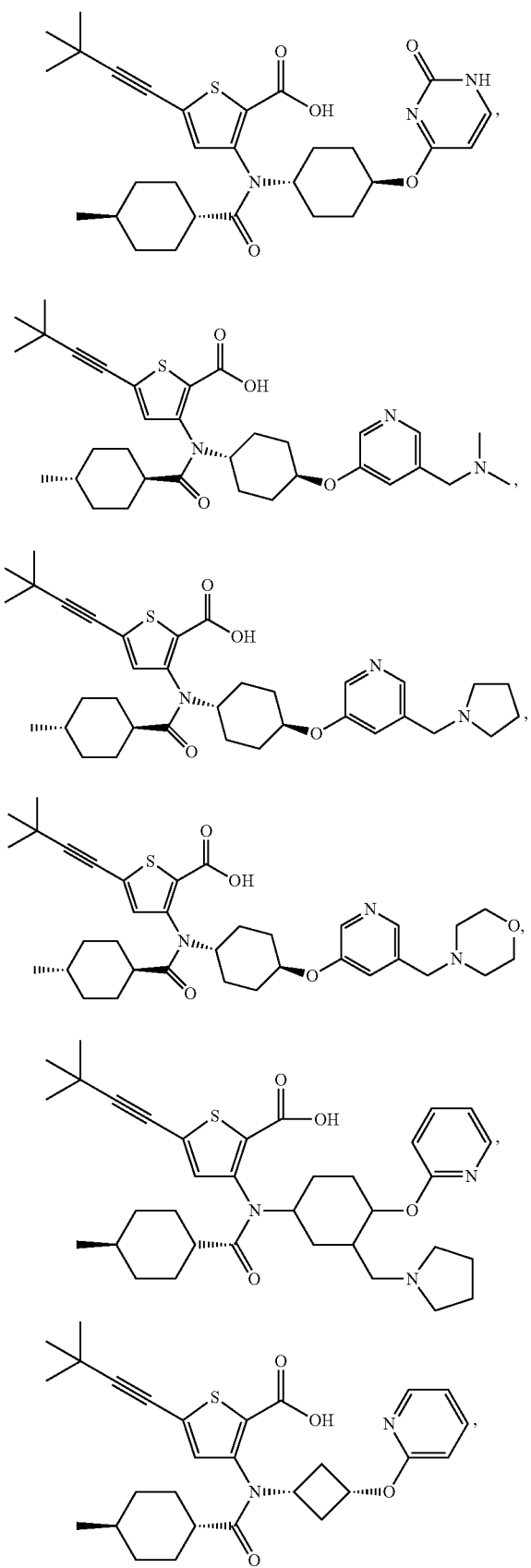
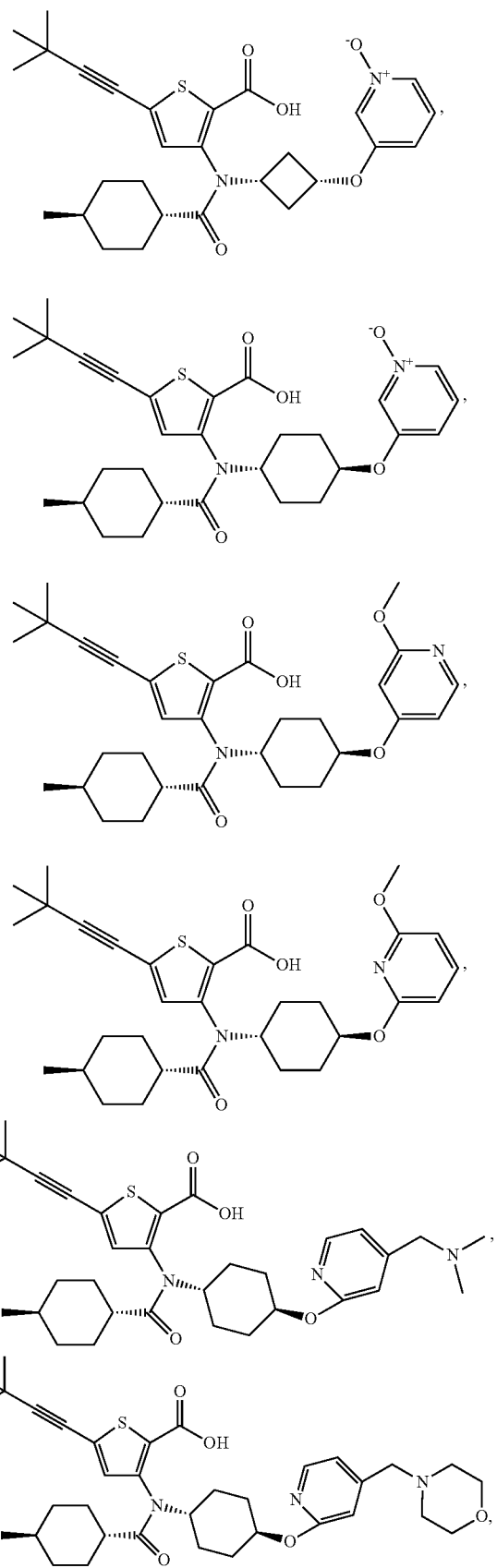

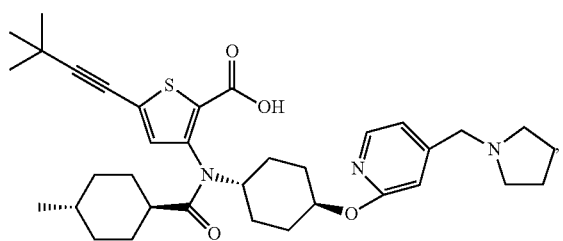
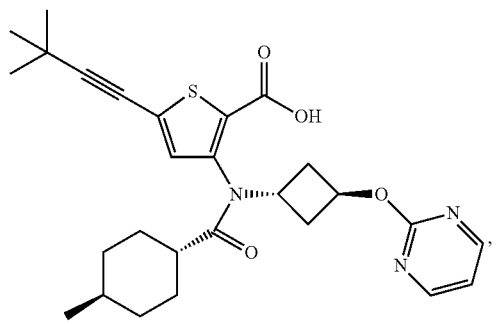
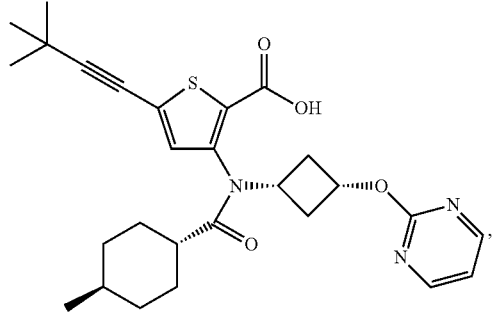
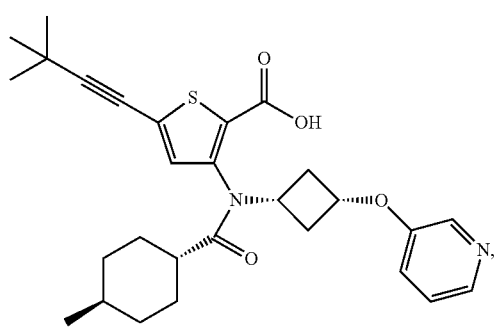
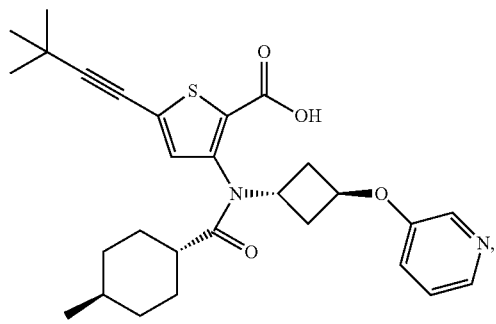
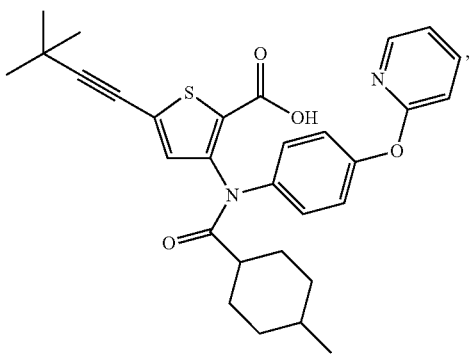
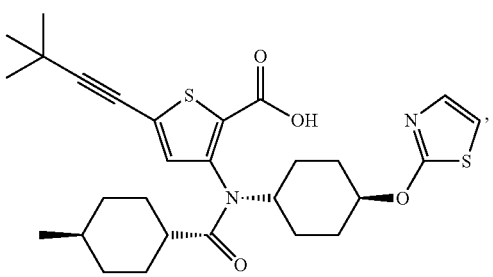
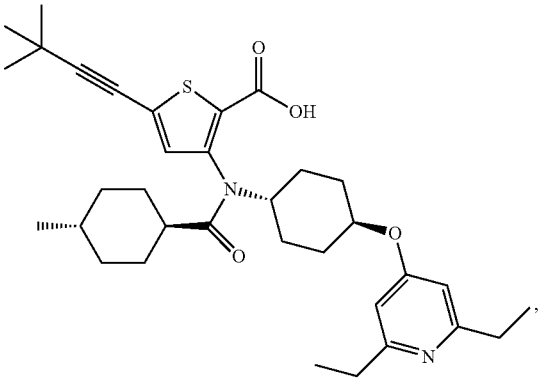
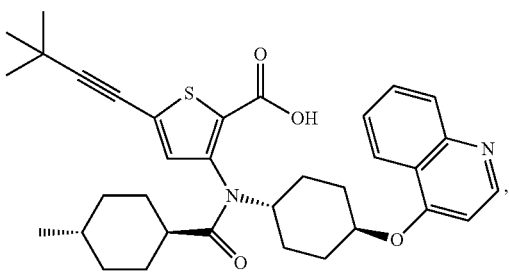
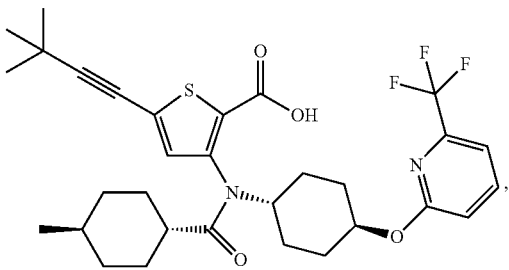

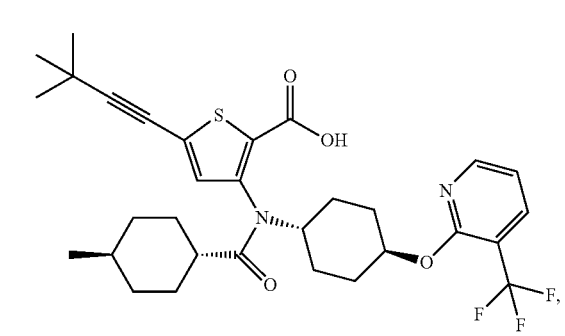
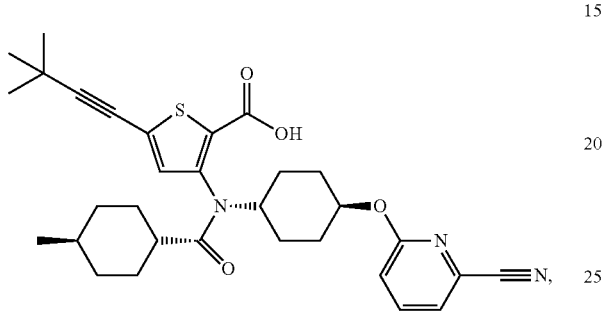
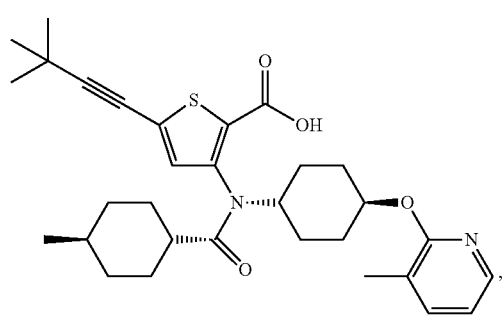
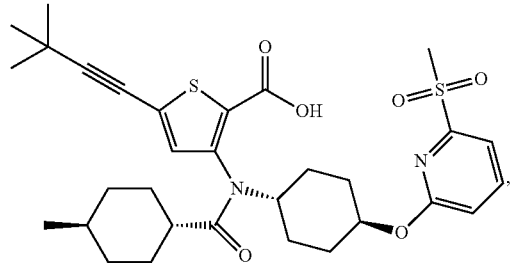
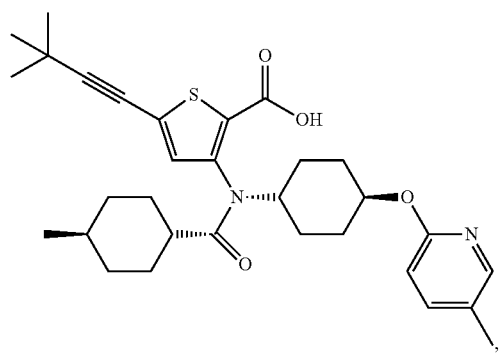
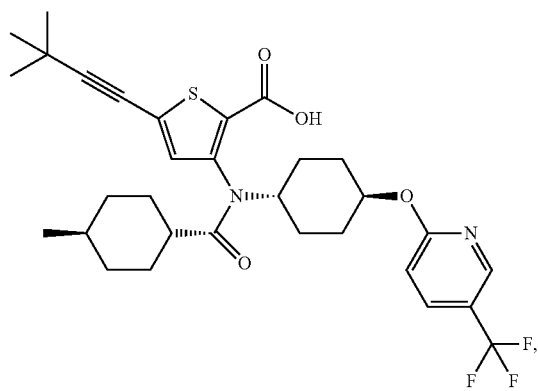
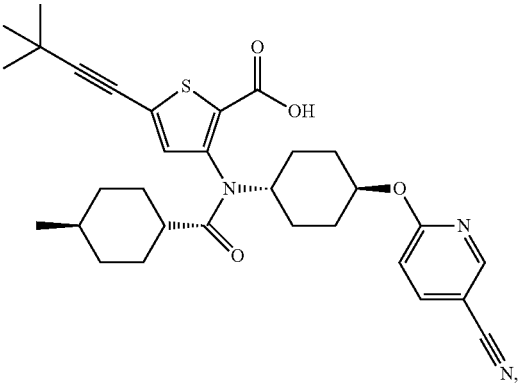
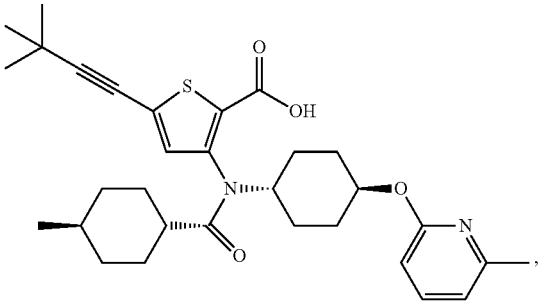
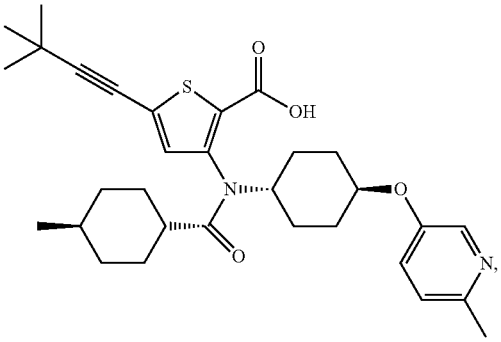
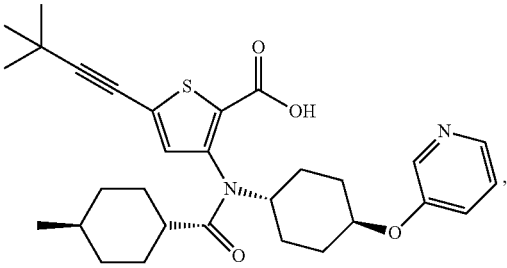

49
-continued
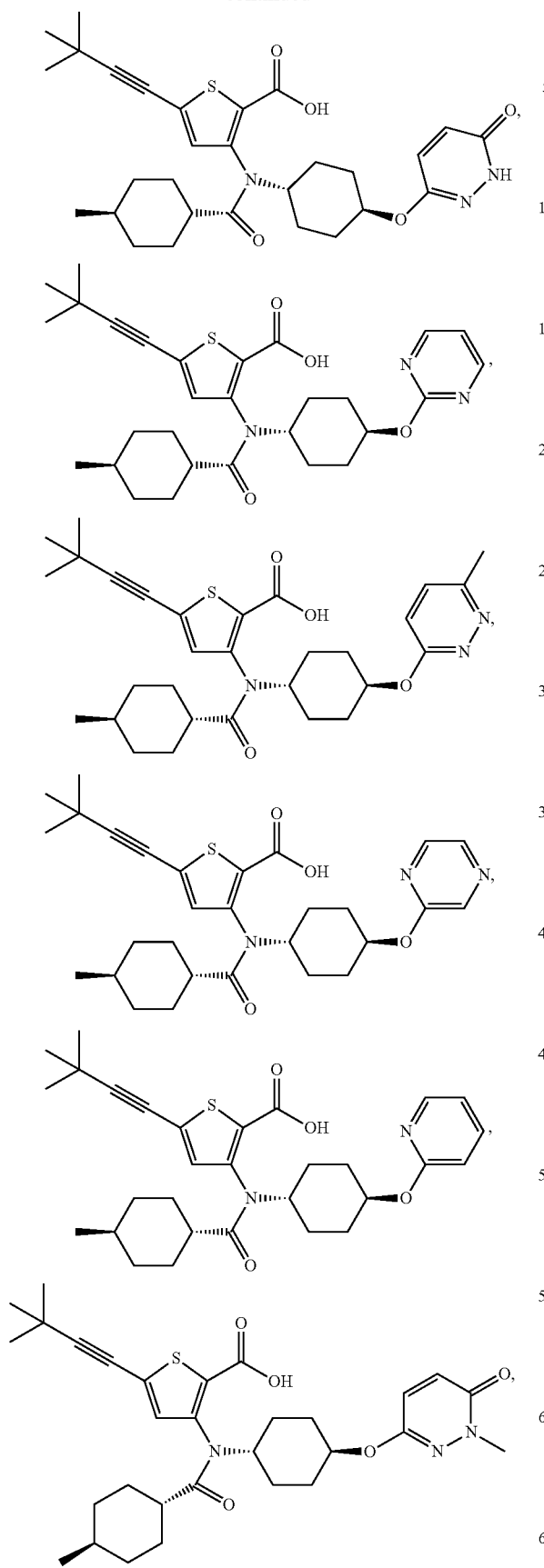
50
-continued
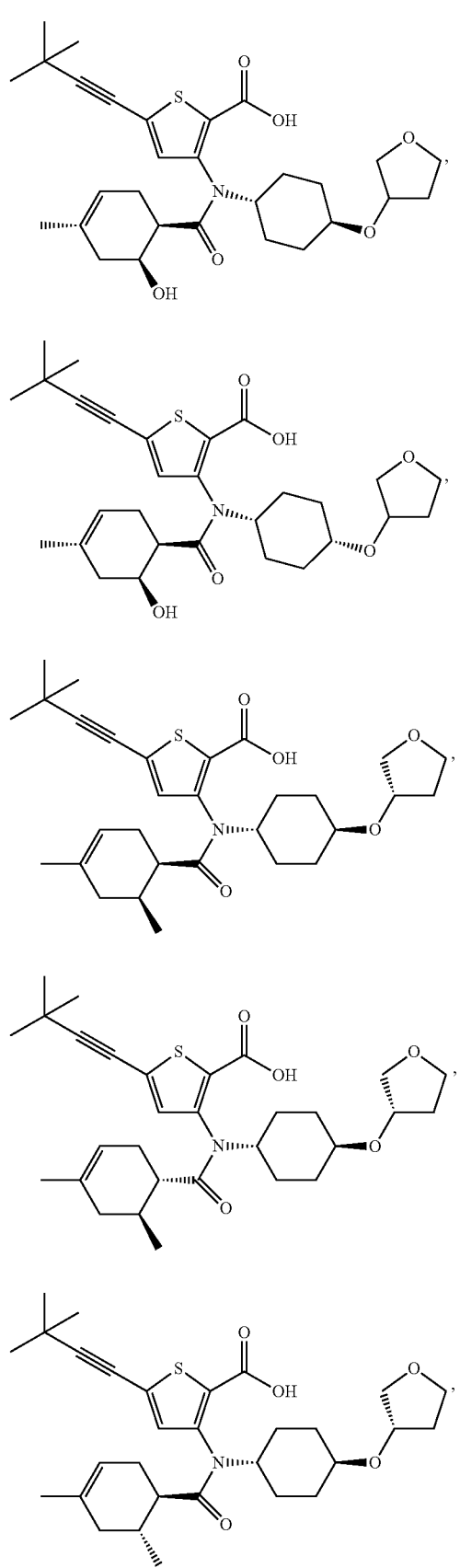

51
-continued
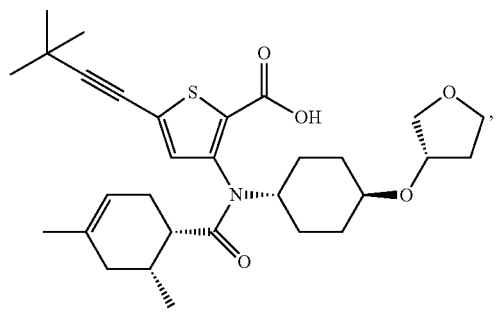
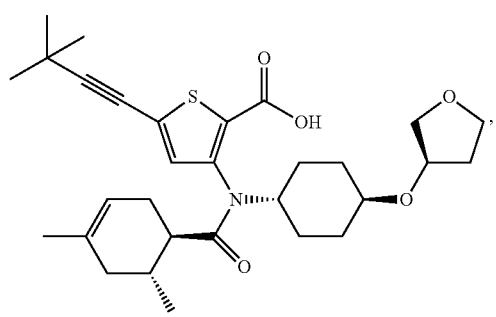
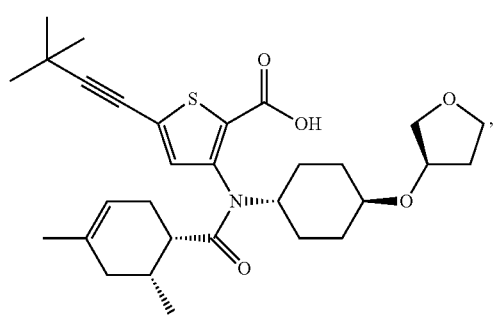
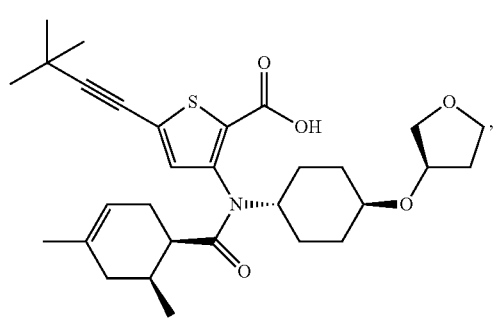
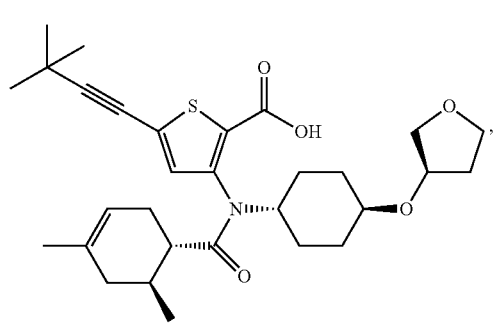
52
-continued
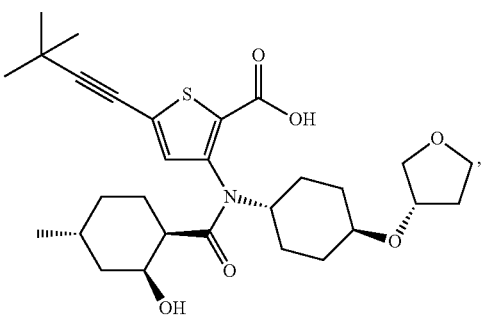
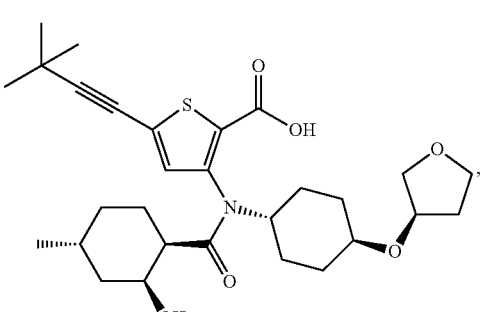
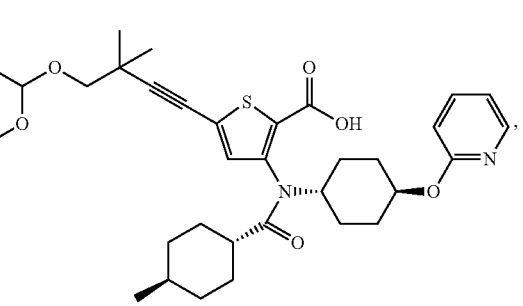
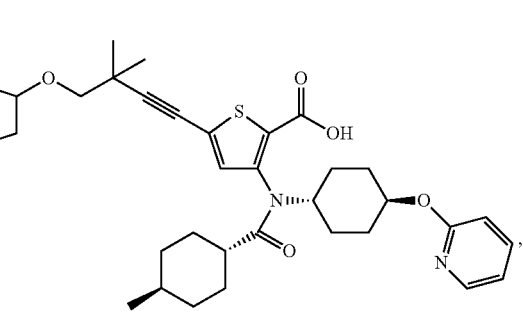
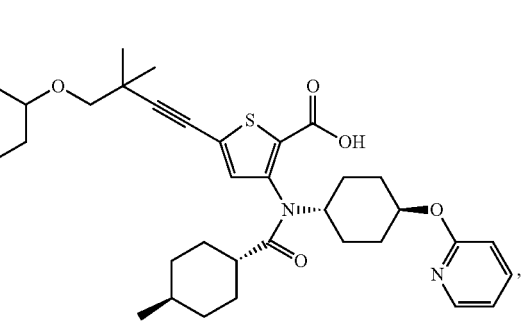

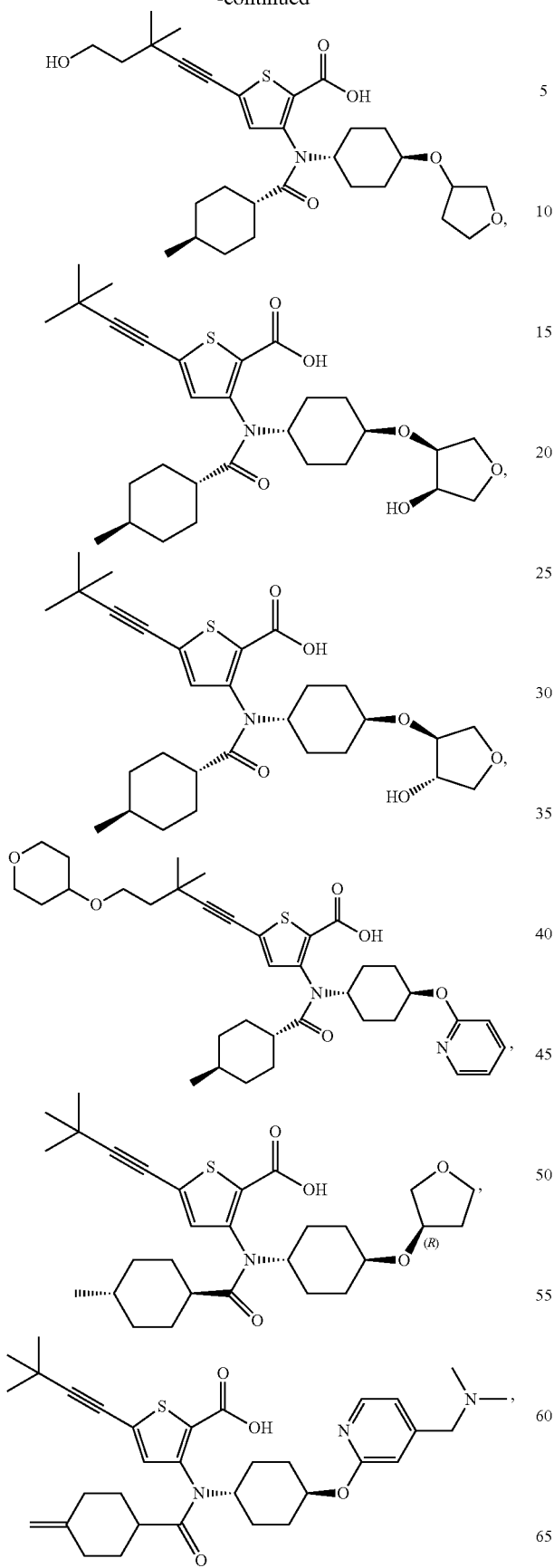
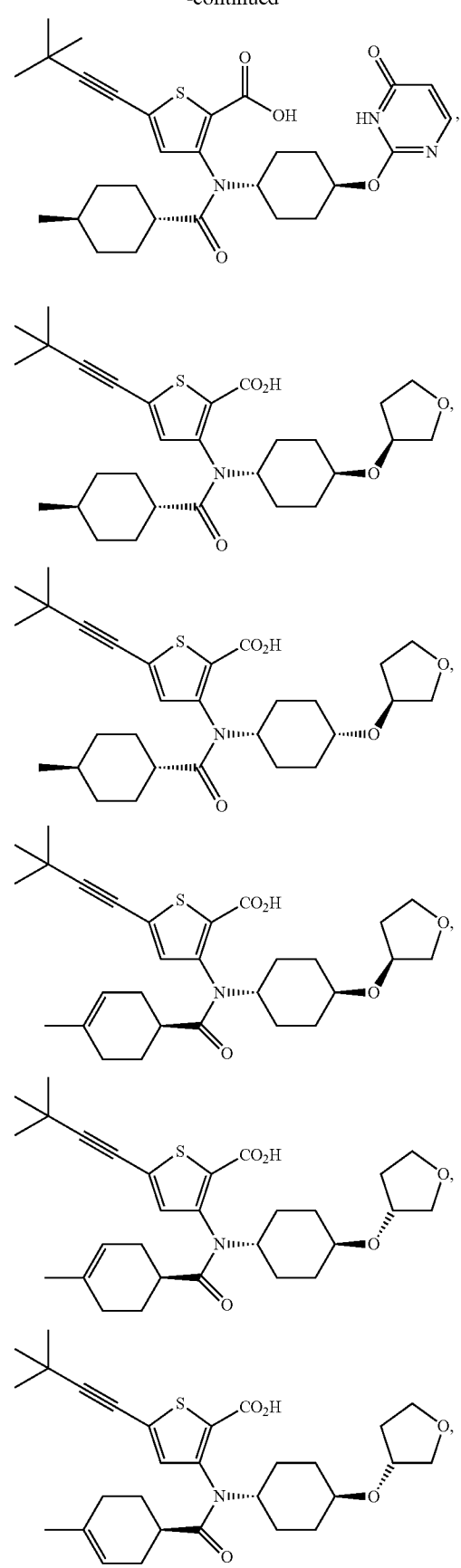

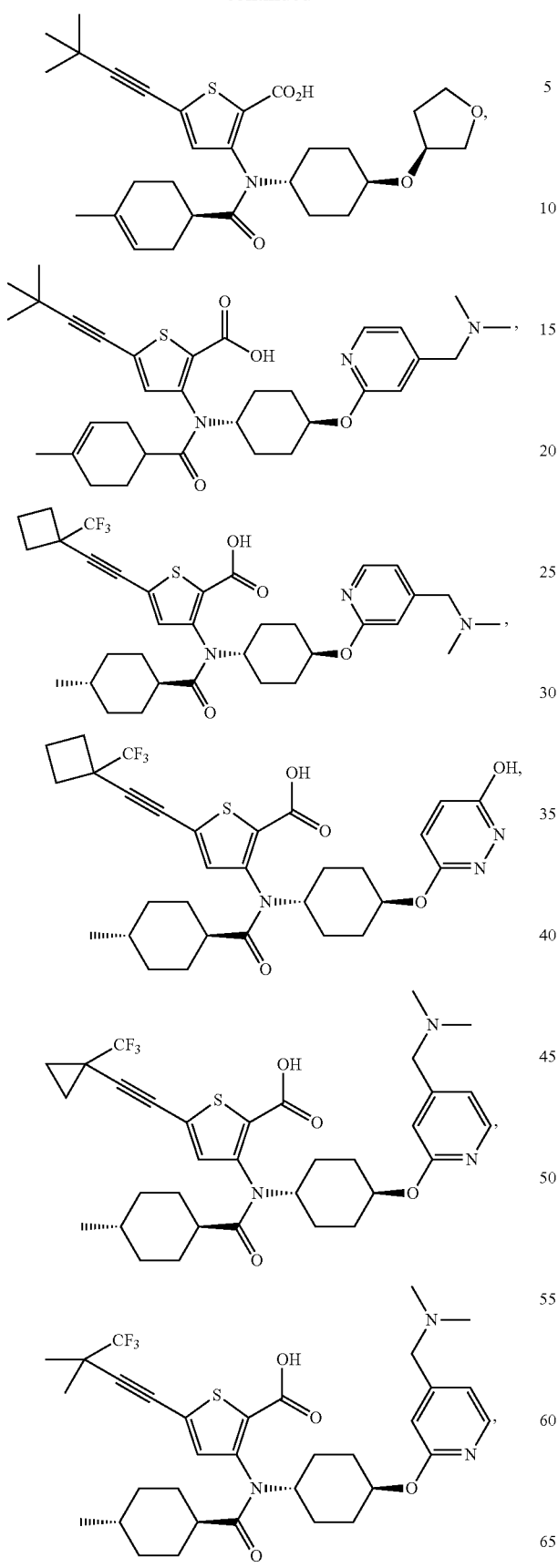
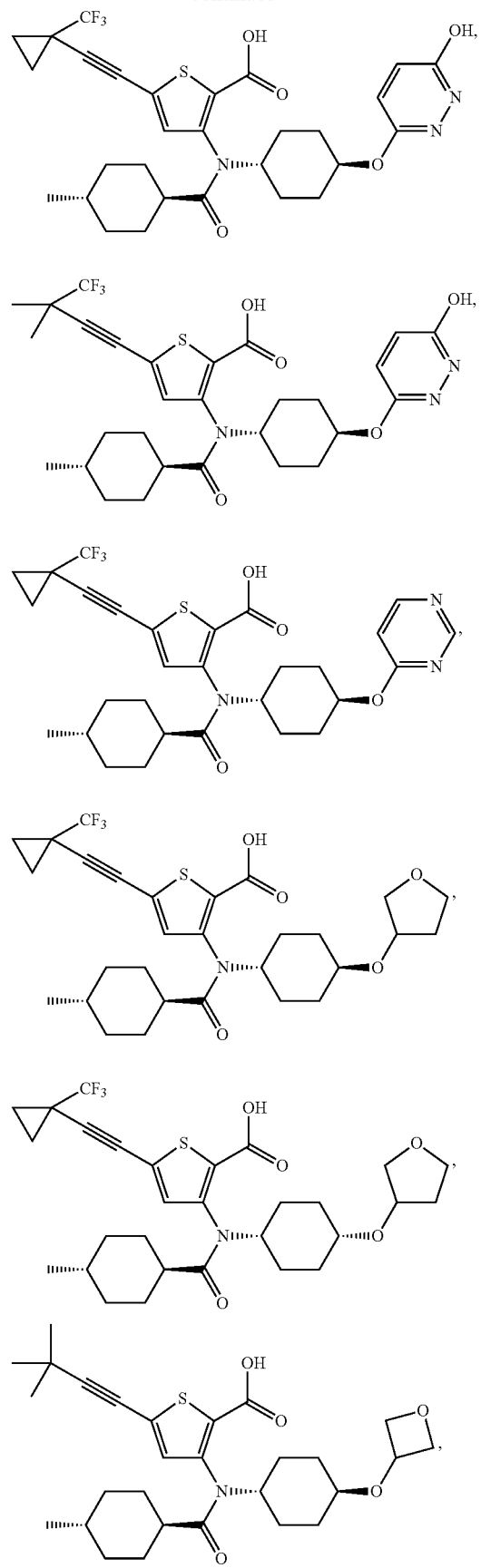

-continued

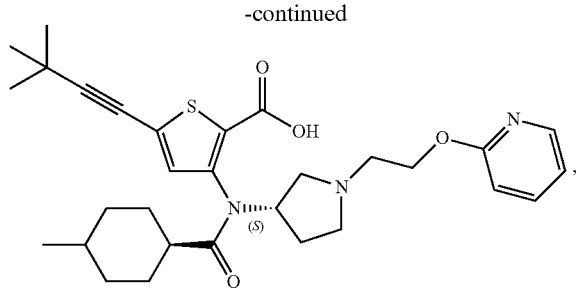

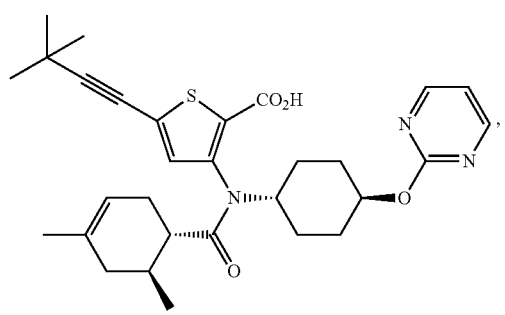

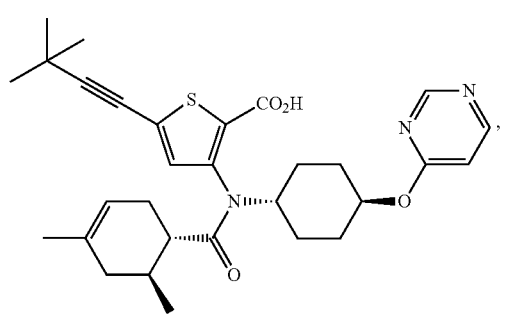

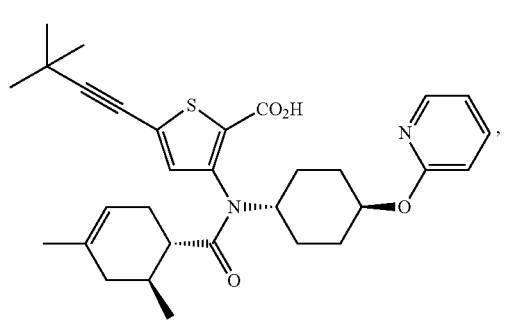

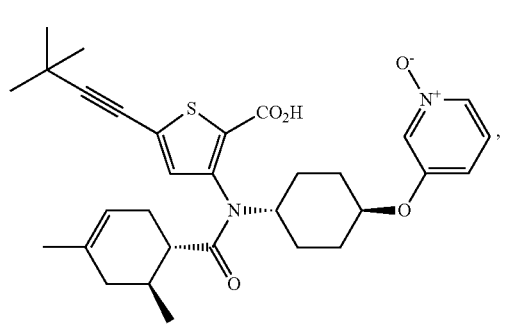

-continued

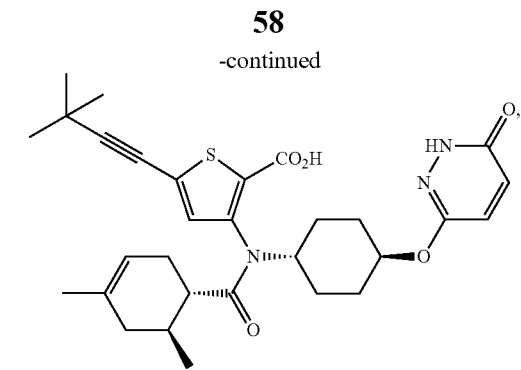

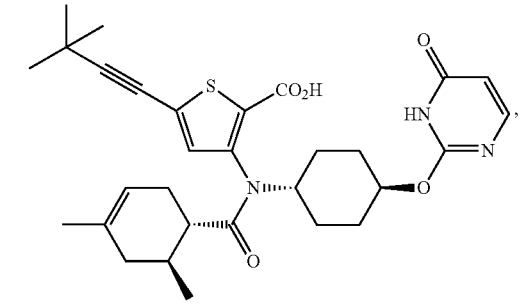

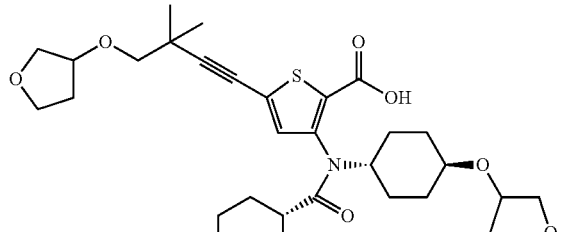

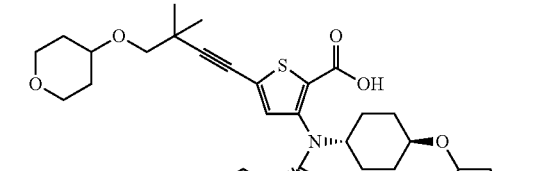

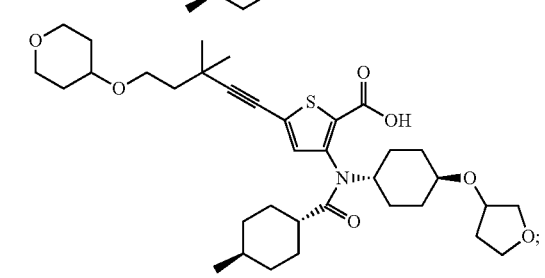

or a pharmaceutically acceptable salt or ester thereof.

Definitions

Unless stated otherwise, the following terms and phrases as used herein are intended to have the following meanings. The fact that a particular term or phrase is not specifically defined should not be correlated to indefiniteness or lacking clarity, but rather terms herein are used within their ordinary meaning. When trade names are used herein, applicants intend to independently include the tradename product and the active pharmaceutical ingredient(s) of the tradename product.

The term "treating", and grammatical equivalents thereof, when used in the context of treating a disease, means slowing or stopping the progression of a disease, or ameliorating at least one symptom of a disease, more preferably ameliorating more than one symptom of a disease. For example, treatment of a hepatitis C virus infection can include reducing the HCV viral load in an HCV infected human being, and/or reducing the severity of jaundice present in an HCV infected human being.

"Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, 1-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu), and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary, or cyclic carbon atoms with at least one site of unsaturation, i.e. a carbon-carbon, sp2 double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, vinyl (—$CH=CH_2$), allyl (—$CH_2CH=CH_2$), cyclopentenyl (—$C_5H_7$), and 5-hexenyl (—$CH_2CH_2CH_2CH_2CH=CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2C$≡CH), and the like.

"Alkylene" refers to a saturated, branched or straight chain radical or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethylene (—$CH(CH_3)$—), 1,2-ethylene (—$CH_2CH_2$—), 1,1-propylene (—$CH(CH_2CH_3)$—), 1,2-propylene (—$CH_2CH(CH_3)$—), 1,3-propylene (—$CH_2CH_2CH_2$—), 1,4-butylene (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—$CH_2C$≡C—), and 4-pentynyl (—$CH_2CH_2CH_2C$≡C—).

"Alkylyne" refers to a saturated, branched or straight chain radical having two radical centers derived by the removal of three hydrogen atoms from two carbon atoms of a parent alkane. For example, an alkylyne group can have 2 to 20 carbon atoms, 2 to 10 carbon atoms, or 2 to 6 carbon atoms. Typical alkylyne radicals include, but are not limited to, 1,2-ethylyne (—$CH_2CH$=), 1,2-propylyne (—$CH_2C(CH_3)$=), 1,3-propylyne (—$CH_2CH_2CH$=), 1,4-butylyne (—$CH_2CH_2CH_2CH$=), and the like.

"Aryl" means a monovalent aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylene" refers to an aryl as defined above having two monovalent radical centers derived by the removal of two hydrogen atoms from the same or two different carbon atoms of a parent aryl. Typical arylene radicals include, but are not limited to, phenylene.

"Arylalkyl" refers to an acyclic alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Cycloalkyl" refers to a saturated or partially unsaturated ring having 3 to 7 carbon atoms as a monocycle, 7 to 12 carbon atoms as a bicycle, and up to about 20 carbon atoms as a polycycle. Monocyclic cycloalkyl groups have 3 to 6 ring atoms, still more typically 5 or 6 ring atoms. Bicyclic cycloalkyl groups have 7 to 12 ring atoms, e.g., arranged as a bicyclo (4,5), (5,5), (5,6) or (6,6) system, or 9 or 10 ring atoms arranged as a bicyclo (5,6) or (6,6) system. Cycloalkyl groups include hydrocarbon mono-, bi-, and poly-cyclic rings, whether fused, bridged, or spiro. Non-limiting examples of monocyclic cycloalkyls include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl. Non-limiting examples of bicyclo cycloalkyls includes naphthyl, tetrahydronapthalene, decaline and bicyclo[3.1.0]hex-6-yl and the like.

"Cycloalkylene" refers to a cycloalkyl as defined above having two monovalent radical centers derived by the removal of two hydrogen atoms from the same or two different carbon atoms of a parent cycloalkyl. Typical cycloalkylene radicals include, but are not limited to, cyclopropylene, cyclobutylene, cyclopentylene and cyclohexylene.

"Halogen" refers to F, Cl, Br, or I.

As used herein the term "haloalkyl" refers to an alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as —CF$_3$.

As used herein, the term "haloalkoxy" refers to a group —OR$^a$, where R$^a$ is a haloalkyl group as herein defined. As non-limiting examples, haloalkoxy groups include —O(CH$_2$)F, —O(CH)F$_2$, and —OCF$_3$.

"Heterocycle" or "heterocyclyl" refers to a saturated or partially saturated cyclic group having from 1 to 14 carbon atoms and from 1 to 6 heteroatoms selected from N, S, P, or O, and includes single ring and multiple ring systems including, fused, bridged, and spiro ring systems. "Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and J. Am. Chem. Soc. (1960) 82:5566. In one embodiment, the carbon, nitrogen, phosphorous, or sulfur atom(s) of the heterocyclic group may be oxidized to provide for C(=O), N-oxide, phosphinane oxide, sulfinyl, or sulfonyl moieties.

As one example, substituted heterocyclyls include, for example, heterocyclic rings substituted with any of the substituents disclosed herein including oxo groups. A non-limiting example of a carbonyl substituted heterocyclyl is:

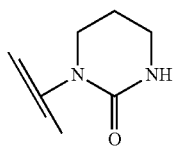

Examples of heterocycles include by way of example and not limitation dihydroypyridyl, tetrahydropyridyl (piperidyl), tetrahydrothiophenyl, sulfur oxidized tetrahydrothiophenyl, piperidinyl, 4-piperidonyl, pyrrolidinyl, azetidinyl, 2-pyrrolidonyl, tetrahydrofuranyl, decahydroquinolinyl, octahydroisoquinolinyl, pyranyl, morpholinyl, and bis-tetrahydrofuranyl:

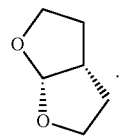

"Heterocyclene" or "heterocyclylene" refers to a "heterocycle" or "heterocyclyl" as defined above having two monovalent radical centers derived by the removal of two hydrogen atoms from the same or two different carbon atoms of a parent heterocycle, the removal of two hydrogen atoms from two nitrogen atoms of a parent heterocycle, or the removal of a hydrogen atom from a nitrogen and the removal of a hydrogen atom from a carbon atom of a parent heterocycle. Non-limiting examples of heterocyclene or heterocyclylenes are:

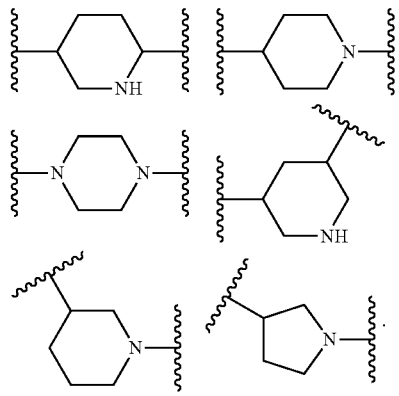

"Heteroaryl" refers to a monovalent aromatic heterocyclyl having at least one heteroatom in the ring. Thus, "heteroaryl" refers to an aromatic group of from 1 to 14 carbon atoms and 1 to 6 heteroatoms selected from oxygen, nitrogen, sulfur, or phosphorous. For multiple ring systems, by way of example, the term "heteroaryl" includes fused, bridged, and spiro ring systems having aromatic and non-aromatic rings. In one embodiment, the carbon, nitrogen, or sulfur ring atom(s) of the heteroaryl group may be oxidized to provide for C(=O), N-oxide, sulfinyl, or sulfonyl moieties.

Examples of heteroaryls include by way of example and not limitation pyridyl, thiazolyl, pyrimidinyl, furanyl, thienyl, pyrrolyl, pyrazolyl, imidazolyl, tetrazolyl, benzofuranyl, thianaphthalenyl, indolyl, quinolinyl, isoquinolinyl, benzimidazolyl, tetrahydroquinolinyl, tetrahydroisoquinolinyl, 6H-1,2,5-thiadiazinyl, 2H,6H-1,5,2-dithiazinyl, thienyl, thianthrenyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl. "Heterocyclylene" refers to a heterocyclyl, as defined herein, derived by replacing a hydrogen atom from a carbon atom or heteroatom of a heterocyclyl, with an open valence. Similarly, "heteroarylene" refers to an aromatic heterocyclylene.

"Heterocyclylalkyl" refers to an acyclic alkyl radical in which one of the hydrogen atoms bonded to a carbon atom, typically a terminal or sp3 carbon atom, is replaced with a heterocyclyl radical (i.e., a heterocyclyl-alkylene-moiety). Typical heterocyclyl alkyl groups include, but are not limited to heterocyclyl-CH$_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclylalkyl group comprises 2 to 20 carbon atoms and 1-6 heteroatoms, e.g., the alkyl portion of the heterocyclylalkyl group comprises 1 to 6 carbon atoms and the heterocyclyl moiety comprises 1 to 14 carbon atoms. Examples of heterocyclylalkyls include by way of example and not limitation 5-membered sulfur, oxygen, phosphorus, and/or nitrogen containing heterocycles such as pyrrolidiylmethyl, 2-tetrahydrofuranylylethan-1-yl, and the like, 6-membered sulfur, oxygen, and/or nitrogen containing heterocycles such as piperidinylmethyl, morpholinylmethyl, piperidinylethyl, teterahydropyranylethyl, and the like.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)— carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, and the like.

The term "heterocyclyloxy" represents a heterocyclyl group attached to the adjacent atom by an oxygen.

When there is a sulfur atom present, the sulfur atom can be at different oxidation levels, namely, S, SO, SO$_2$, or SO$_3$. All such oxidation levels are within the scope of the present invention.

When there is a phosphorous atom present, the phosphorous atom can be at different oxidation levels, namely, POR$^a$R$^b$R$^c$, PO$_2$R$^a$R$^b$, or PO$_3$R$^a$R$^b$, where R$^a$, R$^b$, and R$^c$ each independently is chosen from H, C$_{1-12}$ alkyl, C$_{2-12}$ alkenyl, C$_{2-12}$ alkynyl, C$_{6-14}$ aryl, 3-12 membered heterocycle, 3-18 membered heteroarylalkyl, C$_{6-18}$ arylalkyl; or two taken together (with or without oxygens) form a 5 to 10 membered heterocycle. All such oxidation levels are within the scope of the present invention The term "optionally substituted" in reference to a particular moiety of the compound of Formula I-II (e.g., an optionally substituted aryl group) refers to a moiety wherein all substituents are hydrogen or wherein one or more of the hydrogens of the moiety may be replaced by substituents such as those listed under the definition of "substituted" or as otherwise specified.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Divalent groups may also be similarly substituted. Unless otherwise indicated, typical substituents include, but are not limited to, —X, —R$^b$, —O$^-$, =O, —OR$^b$, —SR$^b$, —S$^-$, —NR$^b_2$, —N$^+$R$^b_3$, =NR$^b$, —CX$_3$, —CN, —OCN, —SCN, —N=C=O, —NCS, —NO, —NO$_2$, =N$_2$, —N$_3$, —NHC(=O)R$^b$, —OC(=O)R$^b$, —NHC(=O)NR$^b_2$, —S(=O)$_2$—, —S(=O)$_2$OH, —S(=O)$_2$R$^b$, —OS(=O)$_2$OR$^b$, —S(=O)$_2$NR$^b_2$, —S(=O)R$^b$, —OP(=O)(OR$^b$)$_2$, —P(=O)(OR$^b$)$_2$, —P(=O)(O$^-$)$_2$, —P(=O)(OH)$_2$, —P(O)(OR$^b$)(O$^-$), —C(=O)R$^b$, —C(=O)X, —C(S)R$^b$, —C(O)OR$^b$, —C(O)O$^-$, —C(S)OR$^b$, —C(O)SR$^b$, —C(S)SR$^b$, —C(O)NR$^b_2$, —C(S)NR$^b_2$, —C(=NR$^b$)NR$^b_2$, where each X is independently a halogen: F, Cl, Br, or I; and each R$^b$ is independently H, alkyl, aryl, arylalkyl, a heterocycle, or a protecting group or prodrug moiety. Alkylene, alkynylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

Those skilled in the art will recognize that when moieties such as "alkyl", "aryl", "heterocyclyl", etc. are substituted with one or more substituents, they could alternatively be referred to as "alkylene", "arylene", "heterocyclylene", etc. moieties (i.e., indicating that at least one of the hydrogen atoms of the parent "alkyl", "aryl", "heterocyclyl" moieties has been replaced with the indicated substituent(s)). When moieties such as "alkyl", "aryl", "heterocyclyl", etc. are referred to herein as "substituted" or are shown diagrammatically to be substituted (or optionally substituted, e.g., when the number of substituents ranges from zero to a positive integer), then the terms "alkyl", "aryl", "heterocyclyl", etc. are understood to be interchangeable with "alkylene", "arylene", "heterocyclylene", etc.

As will be appreciated by those skilled in the art, the compounds of the present invention may exist in solvated or hydrated form. The scope of the present invention includes such forms. Again, as will be appreciated by those skilled in the art, the compounds may be capable of esterification. The scope of the present invention includes esters and other physiologically functional derivatives. The scope of the present invention includes prodrug forms of the compound herein described.

"Ester" means any ester of a compound in which any of the —COOH functions of the molecule is replaced by a —C(O)OR function, or in which any of the —OH functions of the molecule are replaced with a —OC(O)R function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Non-limiting examples of prodrugs include ester moieties, quaternary ammonium moieties, glycol moieties, and the like.

One skilled in the art will recognize that substituents and other moieties of the compounds of Formula I or II should be selected in order to provide a compound which is sufficiently stable to provide a pharmaceutically useful compound which can be formulated into an acceptably stable pharmaceutical composition. Compounds of Formula I or II which have such stability are contemplated as falling within the scope of the present invention.

As will be appreciated by those skilled in the art, the compounds of the present invention may contain one or more chiral centers. The scope of the present invention includes such forms. Again, as will be appreciated by those skilled in the art, the compound is capable of esterification. The scope of the present invention includes esters and other physiologically functional derivatives. In addition, the scope of the present invention includes prodrug forms of the compound herein described.

A compound of Formula I-II and its pharmaceutically acceptable salts may exist as different polymorphs or pseudopolymorphs. As used herein, crystalline polymorphism means the ability of a crystalline compound to exist in different crystal structures. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I-II and their pharmaceutically acceptable salts.

A compound of Formula I-II and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I-II and their pharmaceutically acceptable salts.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by the formulae of the present invention, as well as any wholly or partially equilibrated mixtures thereof. The present invention also includes the individual isomers of the compounds represented by the formulas above as mixtures with isomers thereof in which one or more chiral centers are inverted.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to stereoisomers of a compound which are non-superimposable mirror images of one another.

"Atropisomers" refer to stereoisomers of a compound resulting from hindered rotation about single bonds where the steric strain barrier to rotation is high enough to allow for the isolation of the individual conformer. Atropisomers display axial chirality. Atropisomers may be equilibrated thermally and the interconversion barrier may be measured kinetically. Atropisomerism may occur apart from the presence of other forms of chiral isomerism. Thus, as illustrated, the depicted nitrogen atom is planar and compounds of Formula I are capable of existing as atropisomers:

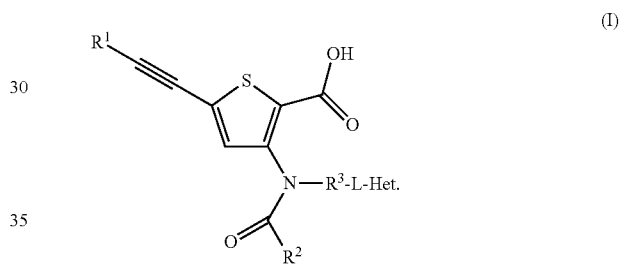

(I)

In one embodiment of the present invention, the compounds exist in a conformeric form of Formula Ia:

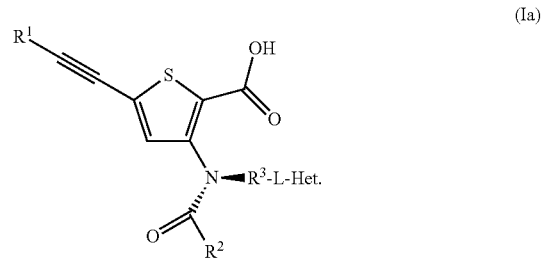

(Ia)

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The present invention includes a salt or solvate of the compounds herein described, including combinations thereof such as a solvate of a salt. The compounds of the present invention may exist in solvated, for example hydrated, as well as unsolvated forms, and the present invention encompasses all such forms.

Typically, but not absolutely, the salts of the present invention are pharmaceutically acceptable salts. Salts encompassed within the term "pharmaceutically acceptable salts" refer to non-toxic salts of the compounds of this invention.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

The modifier "about" used in connection with a quantity is inclusive of the stated value and has the meaning dictated by the context (e.g., includes the degree of error associated with measurement of the particular quantity).

Whenever a compound described herein is substituted with more than one of the same designated group, e.g., "R" or "R¹", then it will be understood that the groups may be the same or different, i.e., each group is independently selected. Wavy lines,

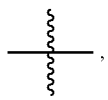

indicate the site of covalent bond attachments to the adjoining substructures, groups, moieties, or atoms.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Selected substituents comprising the compounds of Formula I-II may be present to a recursive degree. In this context, "recursive substituent" means that a substituent may recite another instance of itself. The multiple recitations may be direct or indirect through a sequence of other substituents. Because of the recursive nature of such substituents, theoretically, a large number of compounds may be present in any given embodiment. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis. Recursive substituents may be an intended aspect of the invention. One of ordinary skill in the art of medicinal chemistry understands the versatility of such substituents. To the degree that recursive substituents are present in an embodiment of the invention, they may recite another instance of themselves, 0, 1, 2, 3, or 4 times.

The compounds of Formula I-II also include molecules that incorporate isotopes of the atoms specified in the particular molecules. Non-limiting examples of these isotopes include D, T, $^{14}C$, $^{13}C$ and $^{15}N$.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphoric acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

The definitions and substituents for various genus and sub-genus of the present compounds are described and illustrated herein. It should be understood by one skilled in the art that any combination of the definitions and substituents described above should not result in an inoperable species or compound. "Inoperable species or compounds" means compound structures that violates relevant scientific principles (such as, for example, a carbon atom connecting to more than four covalent bonds) or compounds too unstable to permit isolation and formulation into pharmaceutically acceptable dosage forms.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 μm (including particle sizes in a range between 0.1 and 500 μm in increments such as 0.5 μm, 1 μm, 30 μm, 35 μm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can also be formulated to provide controlled release of the active ingredient to allow less frequent dosing or to improve the pharmacokinetic or toxicity profile of the active ingredient. Accordingly, the invention also provides compositions comprising one or more compounds of the invention formulated for sustained or controlled release.

The effective dose of an active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. The effective dose can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

In yet another embodiment, the present application discloses pharmaceutical compositions comprising a compound of Formula I or a pharmaceutically acceptable salt thereof, and a pharmaceutically acceptable carrier or excipient.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy, Including HCV Combination Therapy

In another embodiment, the compounds of the present invention may be combined with one or more active agent. Non-limiting examples of suitable combinations include combinations of one or more compounds of the present invention with one or more interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, endothelin antagonists, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers and other drugs for treating HCV; or mixtures thereof.

More specifically, one or more compounds of the present invention may be combined with one or more compounds selected from the group consisting of 1) interferons, e.g., pegylated rIFN-alpha 2b (PEG-Intron), pegylated rIFN-alpha 2a (Pegasys), rIFN-alpha 2b (IntronA), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon, 2) ribavirin and its analogs, e.g., ribavirin (Rebetol, Copegus), and taribavirin (Viramidine), 3) HCV NS3 protease inhibitors, e.g., boceprevir (SCH-503034, SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227), 4) alpha-glucosidase 1 inhibitors, e.g., celgosivir (MX-3253), Miglitol, and UT-231B, 5) hepatoprotectants, e.g., emericasan (IDN-6556), ME-3738, GS-9450 (LB-84451), silibilin, and MitoQ, 6) nucleoside or nucleotide inhibitors of HCV NS5B polymerase, e.g., R1626, R7128 (R4048), IDX184, IDX-102, P51-7851, BCX-4678, valopicitabine (NM-283), and MK-0608, 7) non-nucleoside inhibitors of HCV NS5B polymerase, e.g., filibuvir (PF-868554), ABT-333, ABT-072, B1-207127, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190, 8) HCV NS5A inhibitors, e.g., AZD-2836 (A-831), AZD-7295 (A-689), and BMS-790052, 9) TLR-7 agonists, imiquimod, 852A, GS-9524, ANA-773, ANA-975, AZD-8848 (DSP-3025), PF-04878691, and SM-360320, 10) cyclophillin inhibitors, e.g., DEBIO-025, SCY-635, and NIM811, 11) HCV IRES inhibitors, e.g., MCI-067, 12) pharmacokinetic enhancers, e.g., BAS-100, SPI-452, PF-419-4477, TMC-41629, GS-9350, GS-9585, and roxythromycin, 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, and VX-497 (merimepodib)

14) mevalonate decarboxylase antagonists, e.g., statins, HMGCoA synthase inhibitors (e.g., hymeglusin), squalene synthesis inhibitors (e.g., zaragozic acid);

15) angiotensin II receptor antagonists, e.g., losartan, irbesartan, olmesartan, candesartan, valsartan, telmisartan, eprosartan;

16) angiotensin-converting enzyme inhibitors, e.g., captopril, zofenopril, enalapril, ramipril, quinapril, perindopril, lisinopril, benazepril, fosinopril;

17) other anti-fibrotic agents, e.g., amiloride and 18) endothelin antagonists, e.g. bosentan and ambrisentan.

In yet another embodiment, the present application discloses pharmaceutical compositions comprising a compound of the present invention, or a pharmaceutically acceptable salt thereof, in combination with at least one additional active agent, and a pharmaceutically acceptable carrier or excipient. In yet another embodiment, the present application provides a combination pharmaceutical agent with two or more therapeutic agents in a unitary dosage form. Thus, it is also possible to combine any compound of the invention with one or more other active agents in a unitary dosage form.

The combination therapy may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active agents. In other cases, it may be desirable to administer a unit dose of one or more other active agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

As will be appreciated by those skilled in the art, when treating a viral infection such as HCV, such treatment may be characterized in a variety of ways and measured by a variety of endpoints. The scope of the present invention is intended to encompass all such characterizations.

SYNTHETIC EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
|---|---|
| $Ac_2O$ | acetic anhydride |
| AIBN | 2,2'-azobis(2-methylpropionitrile) |
| Bn | benzyl |
| BnBr | benzylbromide |
| BSA | bis(trimethylsilyl)acetamide |
| BzCl | benzoyl chloride |
| CDI | carbonyl diimidazole |
| DABCO | 1,4-diazabicyclo[2.2.2]octane |
| DBN | 1,5-diazabicyclo[4.3.0]non-5-ene |
| DDQ | 2,3-dichloro-5,6-dicyano-1,4-benzoquinone |
| DBU | 1,5-diazabicyclo[5.4.0]undec-5-ene |
| DCA | dichloroacetamide |

TABLE 1-continued

List of abbreviations and acronyms.

| Abbreviation | Meaning |
| --- | --- |
| DCC | dicyclohexylcarbodiimide |
| DCM | dichloromethane |
| DMAP | 4-dimethylaminopyridine |
| DME | 1,2-dimethoxyethane |
| DMTCl | dimethoxytrityl chloride |
| DMSO | dimethylsulfoxide |
| DMTr | 4,4'-dimethoxytrityl |
| DMF | dimethylformamide |
| EtOAc | ethyl acetate |
| ESI | electrospray ionization |
| HMDS | hexamethyldisilazane |
| HPLC | High pressure liquid chromatography |
| LDA | lithium diisopropylamide |
| LRMS | low resolution mass spectrum |
| MCPBA | meta-chloroperbenzoic acid |
| MeCN | acetonitrile |
| MeOH | methanol |
| MMTC | mono methoxytrityl chloride |
| m/z or m/e | mass to charge ratio |
| MH+ | mass plus 1 |
| MH− | mass minus 1 |
| MsOH | methanesulfonic acid |
| MS or ms | mass spectrum |
| NBS | N-bromosuccinimide |
| Ph | phenyl |
| rt or rt. | room temperature |
| TBAF | tetrabutylammonium fluoride |
| TMSCl | chlorotrimethylsilane |
| TMSBr | bromotrimethylsilane |
| TMSI | iodotrimethylsilane |
| TMSOTf | (trimethylsilyl)trifluoromethylsulfonate |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| Tr | triphenylmethyl |
| Tol | 4-methylbenzoyl |
| Turbo Grignard | 1:1 mixture of isopropylmagnesium chloride and lithium chloride |
| δ | parts per million down field from tetramethylsilane |

General Schemes

The compounds of this invention may be synthesized by several routes with key bond-forming steps as indicated in Schemes A-C, in which the carboxylate substituent R indicates either a protecting group such as an alkyl ester (where necessary), or the free acid itself. Alkyl ester protecting groups are conveniently removed by saponification with an alkali metal hydroxide in a protic solvent such as water or an alcohol, and may be facilitated by use of ethereal solvent mixtures and/or heating. Alternatively they may be removed by dealkylation through heating with an alkali metal halide in an aprotic solvent. As will be appreciated, substituents on Het may be modified subsequent to other bond-forming steps by, for example, N-oxidation with a typical oxidant such as metachloroperbenzoic acid in a solvent such as dichloromethane, O-dealkylation through treatment with a reagent such as boron tribromide in a solvent such as dichloromethane, or hydrolysis.

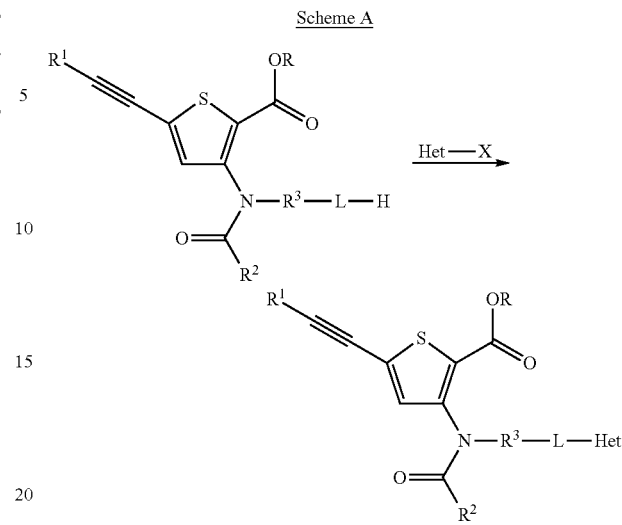

Scheme A

The bond between L and Het may be formed by displacement of X on Het, where X is a leaving group such as a halide, sulfinate, sulfonate or phosphate moiety. The reaction is conveniently performed by deprotonation of L-H with a base such as sodium hydride or potassium hexamethyldisilazide, or is facilitated by the presence of a tertiary amine; it can be carried out in a variety of solvents such as THF, dioxane, dichloromethane, NMP, DMF or DMSO and may be accelerated by heating.

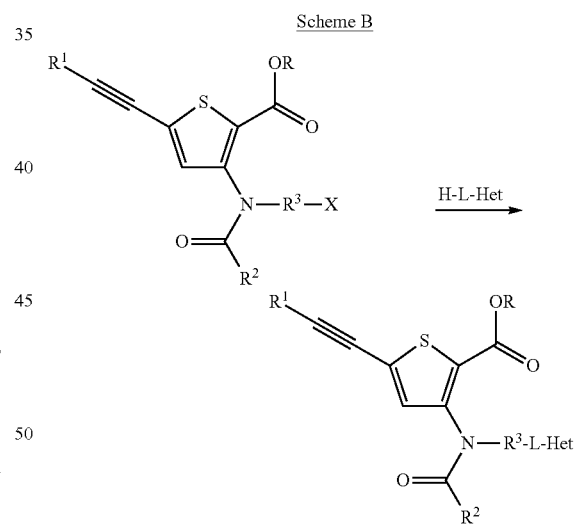

Scheme B

The bond between $R^3$ and L may be formed by nucleophilic displacement of a leaving group X on $R^3$. The leaving group may vary widely and includes, but is not limited to, halide, carboxylate, sulfinate, sultanate or phosphate moieties, and it may be generated from the corresponding alcohol in situ through treatment with reagents such as dialkyl azodicarboxylates. The reaction may also be facilitated by deprotonation of Het-L-H with a base such as sodium hydride or potassium hexamethyldisilazide, or is facilitated by the presence of a tertiary amine; it can be carried out in a variety of solvents such as THF, dioxane, dichloromethane, NMP, DMF or DMSO and may be accelerated by heating.

Scheme C

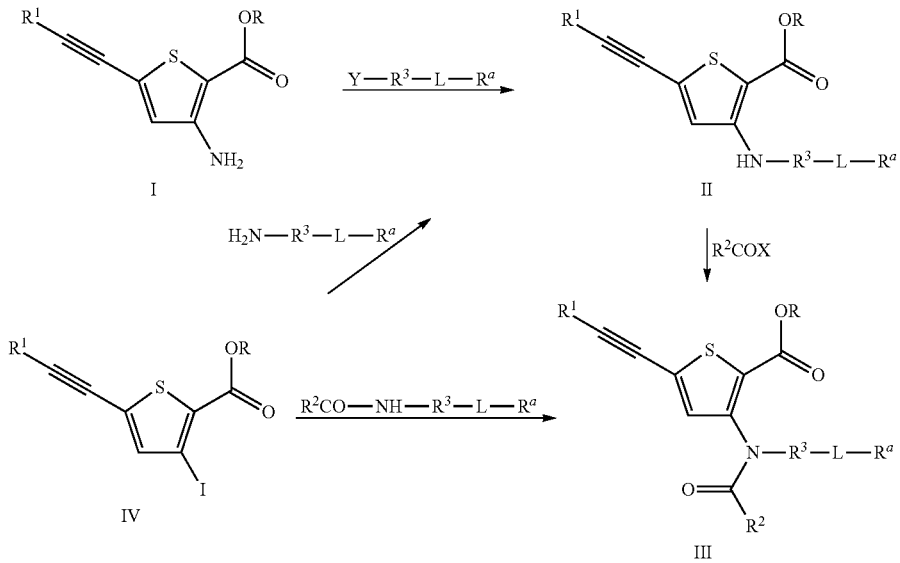

The starting material in Scheme A may be synthesized as depicted in Scheme C. Substituted 3-aminothiophenes II may be generated by reductive amination of $Y$—$R^3$-L-R (where Y indicates an aldehyde or ketone and R and $R^a$ depict optional protecting groups), or by direct alkylation (where Y indicates a leaving group such as a halide, sulfinate, sulfonate or phosphate moiety) of the 3-aminothiophene I (see patent application WO2008/58393). In the latter case the alkylation may be facilitated by deprotonation of the amine with a base such as sodium hydride or potassium hexamethyldisilazide, and can be carried out in a variety of solvents such as THF, dioxane, dichloromethane, NMP, DMF or DMSO and may be accelerated by heating. In cases where $R^3$ is aromatic, the reaction may be catalyzed by Pd (*J. Org. Chem.*, 2000, 65, 1158-1174). Alternatively II may be generated by coupling of an amine with a 3-iodothiophene IV catalyzed by Pd (*J. Org. Chem.*, 2000, 65, 1158-1174). The amine II is converted to the amide III by acylation with a carboxylic acid derivative such as an acyl chloride or anhydride in the presence of a base such as pyridine or a tertiary amine in an inert solvent such as dichloromethane. Alternatively IV may be converted to III directly by amidation catalyzed by Cu (*J. Am. Chem. Soc.*, 2002, 124, 7421-7428).

The starting material for Scheme B may be generated in an analogous fashion, with the leaving group X being generated in a final step by standard methods from the precursor alcohol.

The synthesis of iodothiophene IV is illustrated below for the case where $R^1$=tBu, and other variants may be synthesized in analogous fashion:

Scheme D

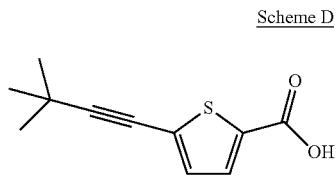

nBuLi (2.2 equiv)
THF, -78° C., 1 h
then $I_2$, THF
65%

-continued

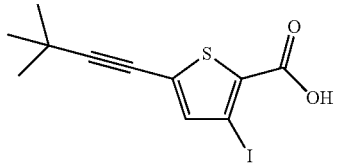

To a solution of 5-(3,3-Dimethyl-but-1-ynyl)-thiophene-2-carboxylic acid (6.2 g, 30 mmol; see patent application U.S. Pat. No. 5,861,421) in THF (100 mL) was added a solution of nBuLi (2.0 M in pentane, 33 mL, 66 mmol) via an addition funnel at −78° C. After addition, the reaction was stirred at −78° C. for 1 h. A solution of $I_2$ (7.7 g, 30 mmol) in THF (100 mL) was added slowly (ca. 15 min) to the flask. After a further 10 mins, the reaction was quenched with 1 N HCl (50 mL) and warmed to room temperature. The volatiles were removed in vacuo and the residue was dissolved in ether (500 mL). The organic solution was washed with 1 M $Na_2S_2O_3$ (100 mL×2), brine (100 mL) and dried over $Na_2SO_4$. After concentrated in vacuo, the residue was purified by silica gel chromatography (EtOAc/hexanes) to give 5-(3,3-Dimethyl-but-1-ynyl)-3-iodo-thiophene-2-carboxylic acid (5.9 g, 65%) as a white solid.

Scheme E

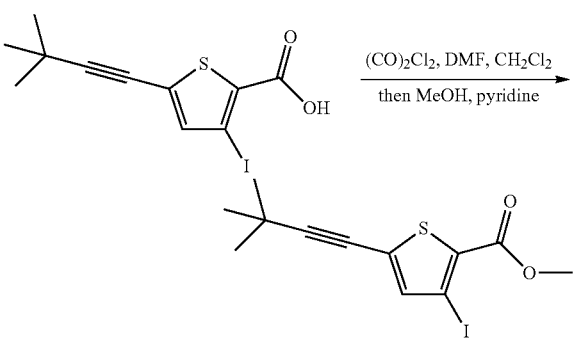

To a solution of 5-(3,3-Dimethyl-but-1-ynyl)-3-iodo-thiophene-2-carboxylic acid (1.0 g, 3.0 mmol) and DMF (20

μL) in dry dichloromethane (10 mL) was added oxalyl chloride (508 μL, 6.0 mmol) at room temperature. After stirring at room temperature for 90 min, the reaction was concentrated in vacuo to remove volatiles. The residue was dissolved in pyridine (5 mL) and methanol (5 mL) and stirred for 2 h. The volatiles were removed in vacuo and the residue was participated between ether (150 mL) and saturated NH₄Cl solution (50 mL). The organic layer was washed with saturated NH₄Cl solution (50 mL) and dried over Na₂SO₄. After concentration in vacuo, the residue was purified by silica gel chromatography (EtOAc/hexanes) to give the desired product (835 mg, 80%).

Experimentals

Example 1

Compound 1: 5-(3,3-Dimethyl-but-1-ynyl)-3-{(trans-4-methyl-cyclohexanecarbonyl)-[trans-4-(pyridin-2-yloxy)-cyclohexyl]-amino}-thiophene-2-carboxylic acid Scheme 1

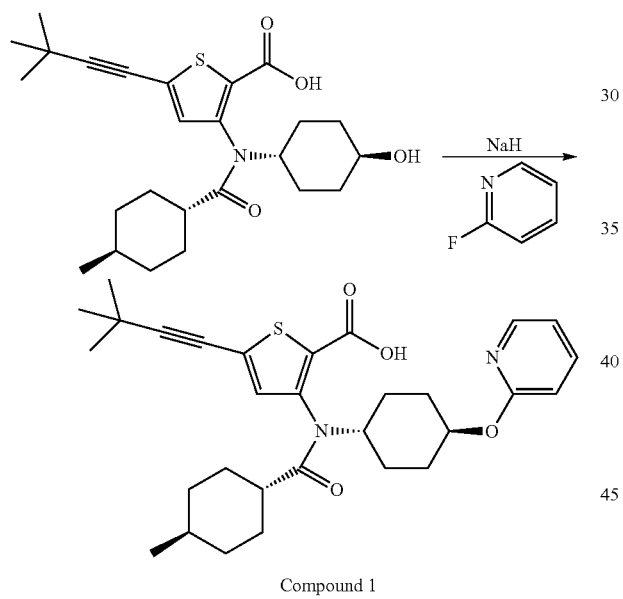

Compound 1

A mixture of 5-(3,3-Dimethyl-but-1-ynyl)-3-[(trans-4-hydroxy-cyclohexyl)-(trans-4-methyl-cyclohexanecarbonyl)-amino]-thiophene-2-carboxylic acid (78 mg, 0.175 mmol) and 2-fluoro-pyridine (145 μL, 1.68 mmol) in DMF (0.6 mL) was treated with sodium hydride (67 mg, 1.68 mmol, 60% oil dispersion) in two or three portions. The mixture was stirred until the bubbling slowed, and was sealed and heated by microwave at 100 deg C. for 30 min. After cooling, ethyl acetate (2-3 mL) was added and the mixture was carefully quenched with citric acid (10% aqueous solution, 2-3 mL). Water was added and the mixture was extracted with ethyl acetate (2×30 mL). The combined organic layers were dried over sodium sulfate, filtered and concentrated. The residue was purified by HPLC (Gemini column, 35% acetonitrile:water, 2 min, 35-50% acetonitrile:water, 2 min, 50-95% acetonitrile:water 13 min, both solvents containing 0.1% trifluoroacetic acid). This resulted in 65 mg (58% yield) of the title compound as a white powder (TFA salt): MS (m/z): 520.9 [M−H]⁻; HPLC retention time: 4.61 min (2-98% acetonitrile:water with 0.05% trifluoroacetic acid).

Example 2

Compound 2: 5-(3,3-Dimethyl-but-1-ynyl)-3-{(trans-4-methyl-cyclohexanecarbonyl)-[trans-4-(pyrazin-2-yloxy)-cyclohexyl]-amino}-thiophene-2-carboxylic acid

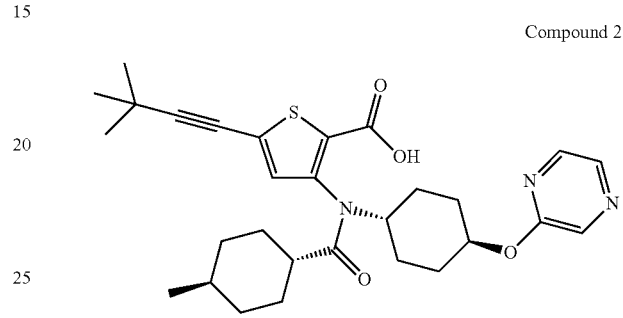

Compound 2

The title compound was synthesized in a manner analogous to Example 1, using 2-chloro-pyrazine in place of 2-fluoro-pyridine. Also, silica gel chromatography (1% EtOH:dichloromethane 2 min, 1-8% EtOH:dichloromethane, 12 min, 30 mL/min, 12 g silica column) was utilized instead of HPLC for purification: MS (m/z): 522.1 [M−H]⁻; HPLC retention time: 5.04 min (2-98% acetonitrile:water with 0.05% trifluoroacetic acid).

Example 3

Compound 3: 5-(3,3-Dimethyl-but-1-ynyl)-3-{(trans-4-methyl-cyclohexanecarbonyl)-[trans-4-(6-methyl-pyridazin-3-yloxy)-cyclohexyl]-amino}-thiophene-2-carboxylic acid

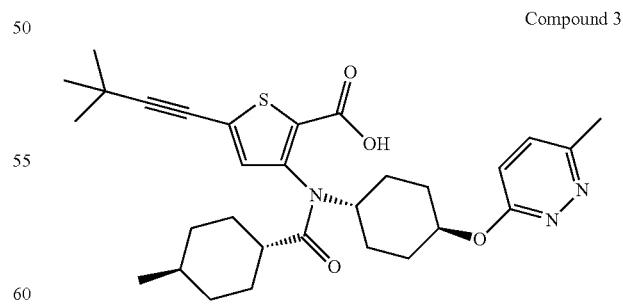

Compound 3

The title compound was synthesized in a manner analogous to Example 1, using 3-chloro-6-methyl-pyridazine in place of 2-fluoro-pyridine: MS (m/z): 536.1 [M−H]⁻; HPLC retention time: 3.73 min (2-98% acetonitrile:water with 0.05% trifluoroacetic acid).

Example 4

Compound 4: 5-(3,3-Dimethyl-but-1-ynyl)-3-{(trans-4-methyl-cyclohexanecarbonyl)-[trans-4-(pyrimidin-2-yloxy)-cyclohexyl]-amino}-thiophene-2-carboxylic acid Compound 4

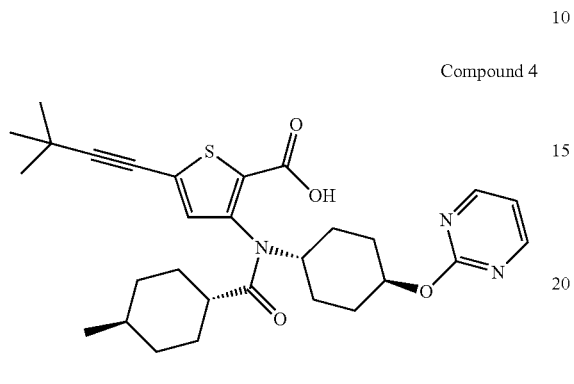

The title compound was synthesized in a manner analogous to Example 1, using 2-chloro-pyrimidine in place of 2-fluoro-pyridine: MS (m/z): 522.0 [M−H]$^-$; HPLC retention time: 4.82 min (2-98% acetonitrile:water with 0.05% trifluoroacetic acid).

Example 5

Compound 5: 5-(3,3-Dimethyl-but-1-ynyl)-3-{(trans-4-methyl-cyclohexanecarbonyl)-[trans-4-(pyridin-3-yloxy)-cyclohexyl]-amino}-thiophene-2-carboxylic acid Compound 5

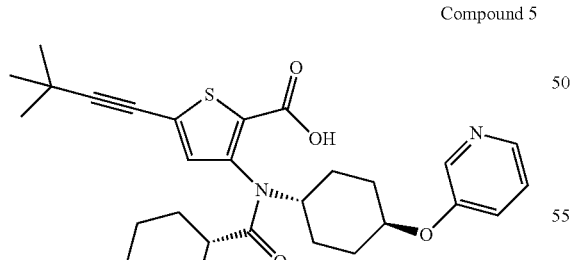

The title compound was synthesized in a manner analogous to Example 1, using 3-fluoro-pyridine in place of 2-fluoro-pyridine: MS (m/z): 520.9 [M−H]$^-$; HPLC retention time: 3.54 min (2-98% acetonitrile:water with 0.05% trifluoroacetic acid).

Example 6

Compound 6: 5-(3,3-Dimethyl-but-1-ynyl)-3-[[trans-4-(6-methanesulfonyl-pyridin-2-yloxy)-cyclohexyl]-(trans-4-methyl-cyclohexanecarbonyl)-amino]-thiophene-2-carboxylic acid Compound 6

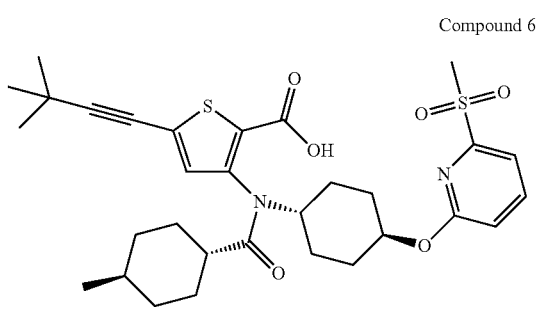 [SMILES: CC(C)(C)C#Cc1cc(N(C(=O)[C@H]2CC[C@H](C)CC2)[C@H]2CC[C@H](Oc3cccc(S(C)(=O)=O)n3)CC2)c(C(=O)O)s1]

The title compound was synthesized in a manner analogous to Example 1, using 2-chloro-6-methanesulfonyl-pyridine in place of 2-fluoro-pyridine: MS (m/z): 598.9 [M−H]$^-$; HPLC retention time: 4.79 min (2-98% acetonitrile:water with 0.05% trifluoroacetic acid).

Example 7

Compound 7: 5-(3,3-Dimethyl-but-1-ynyl)-3-{(trans-4-methyl-cyclohexanecarbonyl)-[trans-4-(6-methyl-pyridin-3-yloxy)-cyclohexyl]-amino}-thiophene-2-carboxylic acid Compound 7

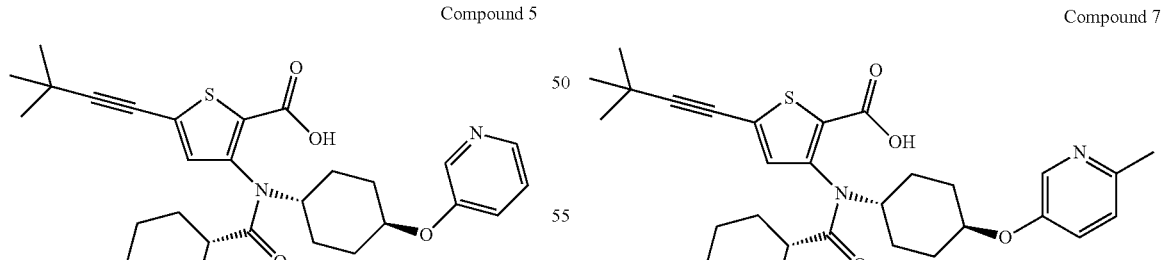

The title compound was synthesized in a manner analogous to Example 1, using 5-fluoro-2-methyl-pyridine in place of 2-fluoro-pyridine: MS (m/z): 534.9 [M−H]$^-$; HPLC retention time: 4.40 min (2-98% acetonitrile:water with 0.05% trifluoroacetic acid).

Example 8

Compound 8: 5-(3,3-Dimethyl-but-1-ynyl)-3-{(trans-4-methyl-cyclohexanecarbonyl)-[trans-4-(6-methyl-pyridin-2-yloxy)-cyclohexyl]-amino}-thiophene-2-carboxylic acid

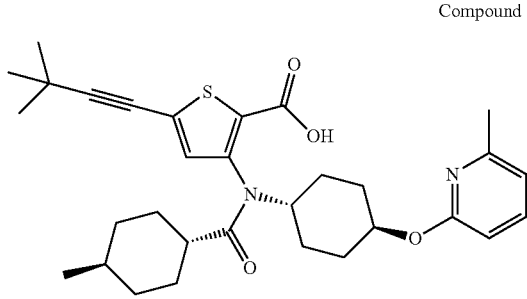

Compound 8

The title compound was synthesized in a manner analogous to Example 1, using 2-chloro-6-methyl-pyridine in place of 2-fluoro-pyridine: MS (m/z): 534.8 [M−H]⁻; HPLC retention time: 4.05 min (2-98% acetonitrile:water with 0.05% trifluoroacetic acid).

Example 9

Compound 9: 3-[[trans-4-(5-Cyano-pyridin-2-yloxy)-cyclohexyl]-(trans-4-methyl-cyclohexanecarbonyl)-amino]-5-(3,3-dimethyl-but-1-ynyl)-thiophene-2-carboxylic acid

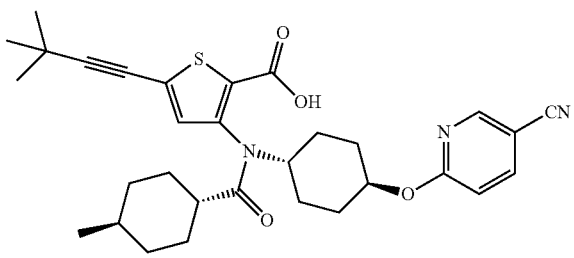

Compound 9

The title compound was synthesized in a manner analogous to Example 1, using 6-chloro-nicotinonitrile in place of 2-fluoro-pyridine: MS (m/z): 545.9 [M−H]⁻; HPLC retention time: 5.17 min (2-98% acetonitrile:water with 0.05% trifluoroacetic acid).

Example 10

Compound 10: 5-(3,3-Dimethyl-but-1-ynyl)-3-{(trans-4-methyl-cyclohexanecarbonyl)-[trans-4-(5-trifluoromethyl-pyridin-2-yloxy)-cyclohexyl]-amino}-thiophene-2-carboxylic acid

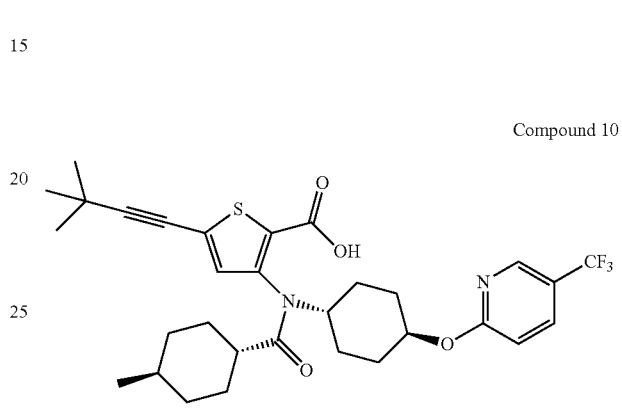

Compound 10

The title compound was synthesized in a manner analogous to Example 1, using 2-chloro-5-trifluoromethyl-pyridine in place of 2-fluoro-pyridine: MS (m/z): 588.8 [M−H]⁻; HPLC retention time: 5.55 min (2-98% acetonitrile:water with 0.05% trifluoroacetic acid).

Example 11

Compound 11: 5-(3,3-Dimethyl-but-1-ynyl)-3-{(trans-4-methyl-cyclohexanecarbonyl)-[trans-4-(5-methyl-pyridin-2-yloxy)-cyclohexyl]-amino}-thiophene-2-carboxylic acid

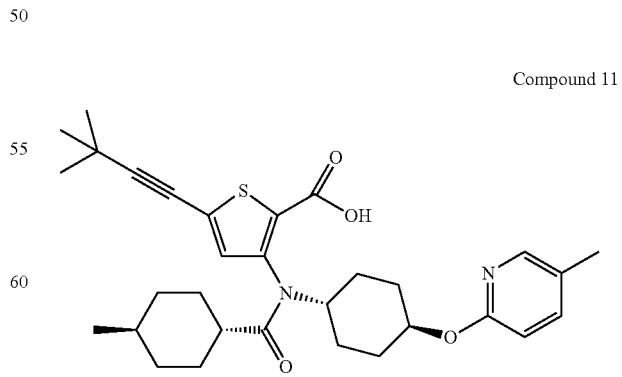

Compound 11

The title compound was synthesized in a manner analogous to Example 1, using 2-chloro-5-methyl-pyridine in place of 2-fluoro-pyridine: MS (m/z): 534.8 [M−H]⁻; HPLC retention time: 4.44 min (2-98% acetonitrile:water with 0.05% trifluoroacetic acid).

Example 12

Compound 12: 5-(3,3-Dimethyl-but-1-ynyl)-3-{(trans-4-methyl-cyclohexanecarbonyl)-[trans-4-(3-methyl-pyridin-2-yloxy)-cyclohexyl]-amino}-thiophene-2-carboxylic acid

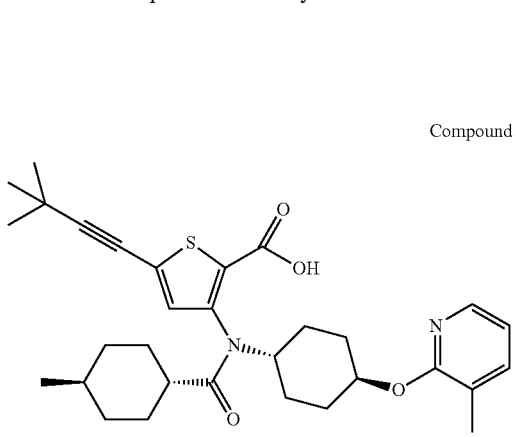

Compound 12

The title compound was synthesized in a manner analogous to Example 1, using 2-chloro-3-methyl-pyridine in place of 2-fluoro-pyridine: MS (m/z): 534.9 [M−H]⁻; HPLC retention time: 5.28 min (2-98% acetonitrile:water with 0.05% trifluoroacetic acid).

Example 13

Compound 13: 3-[[trans-4-(6-Cyano-pyridin-2-yloxy)-cyclohexyl]-(trans-4-methyl-cyclohexanecarbonyl)-amino]-5-(3,3-dimethyl-but-1-ynyl)-thiophene-2-carboxylic acid

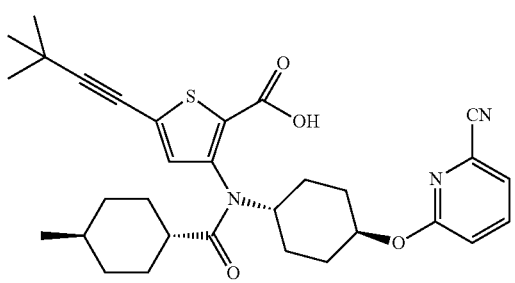

Compound 13

The title compound was synthesized in a manner analogous to Example 1, using 6-chloro-pyridine-2-carbonitrile in place of 2-fluoro-pyridine: MS (m/z): 545.9 [M−H]⁻; HPLC retention time: 5.17 min (2-98% acetonitrile:water with 0.05% trifluoroacetic acid).

Example 14

Compound 14: 5-(3,3-Dimethyl-but-1-ynyl)-3-{(trans-4-methyl-cyclohexanecarbonyl)-[trans-4-(6-oxo-1,6-dihydropyridazin-3-yloxy)-cyclohexyl]-amino}-thiophene-2-carboxylic acid

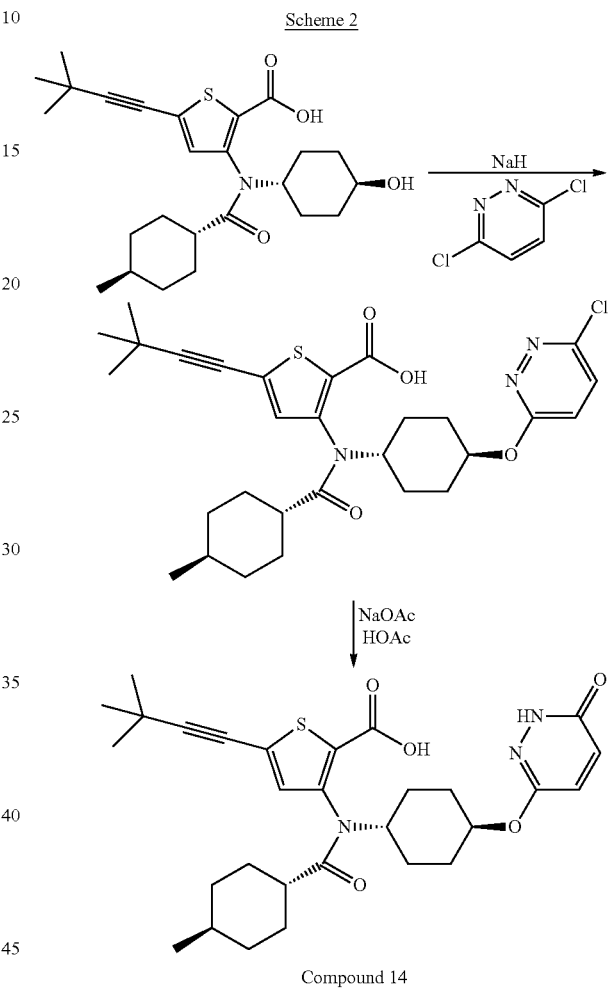

Scheme 2

Compound 14

A mixture of 5-(3,3-Dimethyl-but-1-ynyl)-3-[(trans-4-hydroxy-cyclohexyl)-(trans-4-methyl-cyclohexanecarbonyl)-amino]-thiophene-2-carboxylic acid (53 mg, 0.12 mmol) and 3,6-dichloropyridazine (86 mg, 0.58 mmol) in DMF (0.5 mL) was treated with sodium hydride (58 mg, 1.4 mmol, 60% oil dispersion) in two portions. The mixture was stirred until the bubbling slowed, and was sealed and heated by microwave at 100 deg C. for 30 min. After cooling, ethyl acetate (2-3 mL) was added and the mixture was carefully quenched with citric acid (10% aqueous solution, 2-3 mL). Water was added and the mixture was extracted with ethyl acetate (2×30 mL). The combined organic layers were dried over magnesium sulfate, filtered and concentrated. The residue was passed through a plug of silica (10% MeOH:DCM eluent) and concentrated to yield 69 mg of 5-(3,3-Dimethyl-but-1-ynyl)-3-{(trans-4-methyl-cyclohexanecarbonyl)-[trans-4-(6-chloro-pyridazin-3-yloxy)-cyclohexyl]-amino}-thiophene-2-carboxylic acid as a black oil which was carried on without further purification.

A crude sample of (3,3-Dimethyl-but-1-ynyl)-3-{(trans-4-methyl-cyclohexanecarbonyl)-[trans-4-(6-chloro-pyridazin-3-yloxy)-cyclohexyl]-amino}-thiophene-2-carboxylic acid (69 mg) was dissolved in acetic acid (1 mL) and treated with sodium acetate (36 mg). The mixture was heated at 100 deg C. for 4 hours and then partitioned between water and ethyl acetate. The aqueous phase was neutralized by addition of aqueous sodium hydroxide and extracted with ethyl acetate (3×30 mL). The combined organic layers were dried over magnesium sulfate, filtered and concentrated. The residue was purified by HPLC (Gemini column; 25% acetonitrile: water, 2 min; 25-100% acetonitrile:water, 16 min; 100% acetonitrile, 3 min; both solvents containing 0.1% trifluoroacetic acid). This resulted in 14 mg (19% yield over 2 steps) of the title compound as a white powder (TFA salt): MS (m/z): 537.9 [M−H]$^-$; HPLC retention time: 4.31 min (2-98% acetonitrile:water with 0.05% trifluoroacetic acid).

Example 15

Compound 15: 5-(3,3-Dimethyl-but-1-ynyl)-3-{(trans-4-methyl-cyclohexanecarbonyl)-[trans-4-(thiazol-2-yloxy)-cyclohexyl]-amino}-thiophene-2-carboxylic acid Compound 15

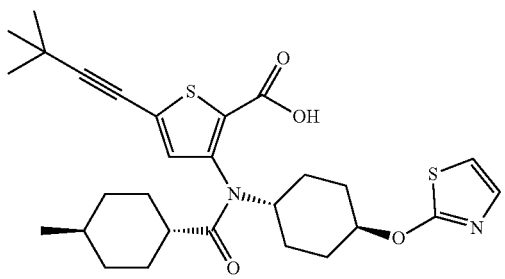

The title compound was synthesized in a manner analogous to Example 1, using 2-chloro-thiazole in place of 2-fluoro-pyridine: MS (m/z): 526.9 [M−H]$^-$; HPLC retention time: 5.08 min (2-98% acetonitrile:water with 0.05% trifluoroacetic acid).

Example 16

Compound 16: 5-(3,3-Dimethyl-but-1-ynyl)-3-{(trans-4-methyl-cyclohexanecarbonyl)-[trans-4-(3-trifluoromethyl-pyridin-2-yloxy)-cyclohexyl]-amino}-thiophene-2-carboxylic acid Compound 16

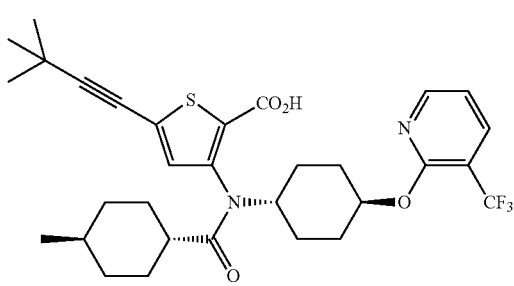

The title compound was synthesized in a manner analogous to Example 1, using 2-bromo-3-trifluoromethyl-pyridine in place of 2-fluoro-pyridine: MS (m/z): 588.8 [M−H]$^-$; HPLC retention time: 5.47 min (2-98% acetonitrile:water with 0.05% trifluoroacetic acid).

Example 17

Compound 17: 5-(3,3-Dimethyl-but-1-ynyl)-3-{(trans-4-methyl-cyclohexanecarbonyl)-[trans-4-(6-trifluoromethyl-pyridin-2-yloxy)-cyclohexyl]-amino}-thiophene-2-carboxylic acid Compound 17

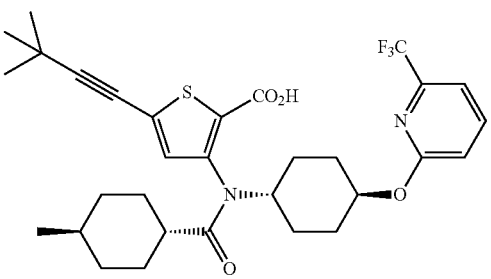

The title compound was synthesized in a manner analogous to Example 1, using 2-chloro-6-trifluoromethyl-pyridine in place of 2-fluoro-pyridine: MS (m/z): 588.9 [M−H]$^-$; HPLC retention time: 5.45 min (2-98% acetonitrile:water with 0.05% trifluoroacetic acid).

Example 18

Compound 18: 5-(3,3-Dimethyl-but-1-ynyl)-3-[[trans-4-(6-methoxy-pyridin-2-yloxy)-cyclohexyl]-(trans-4-methyl-cyclohexanecarbonyl)-amino]-thiophene-2-carboxylic acid Compound 18

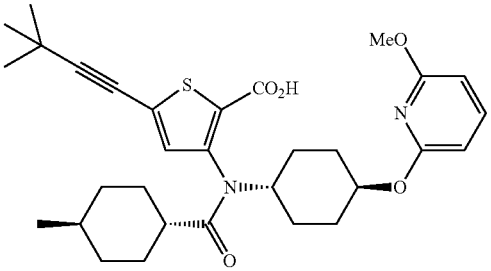

The title compound was synthesized in a manner analogous to Example 1, using 2-chloro-6-methoxy-pyridine in place of 2-fluoro-pyridine: MS (m/z): 550.9 [M−H]$^-$; HPLC retention time: 5.29 min (2-98% acetonitrile:water with 0.05% trifluoroacetic acid).

Example 19

Compound 19: 5-(3,3-Dimethyl-but-1-ynyl)-3-[[trans-4-(2-methoxy-pyridin-4-yloxy)-cyclohexyl]-(trans-4-methyl-cyclohexanecarbonyl)-amino]-thiophene-2-carboxylic acid Compound 19

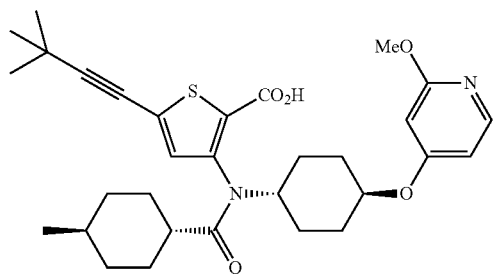

The title compound was synthesized in a manner analogous to Example 1, using 4-chloro-2-methoxy-pyridine in place of 2-fluoro-pyridine: MS (m/z): 550.9 [M−H]−; HPLC retention time: 3.75 min (2-98% acetonitrile:water with 0.05% trifluoroacetic acid).

Example 20

Compound 20: 5-(3,3-Dimethyl-but-1-ynyl)-3-{(trans-4-methyl-cyclohexanecarbonyl)-[cis-3-(pyridin-3-yloxy)-cyclobutyl]-amino}-thiophene-2-carboxylic acid Compound 20

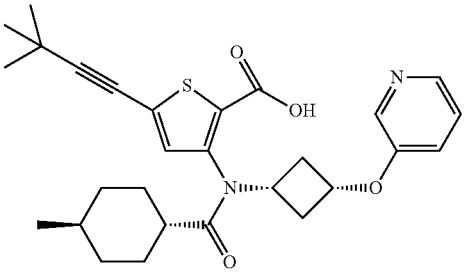

Scheme 3

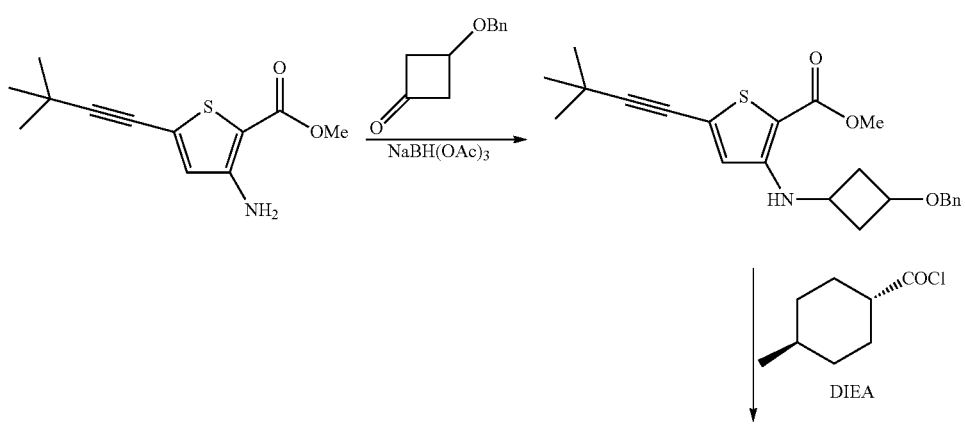

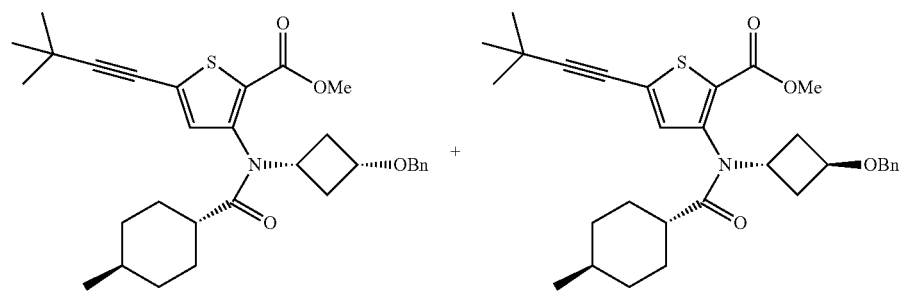

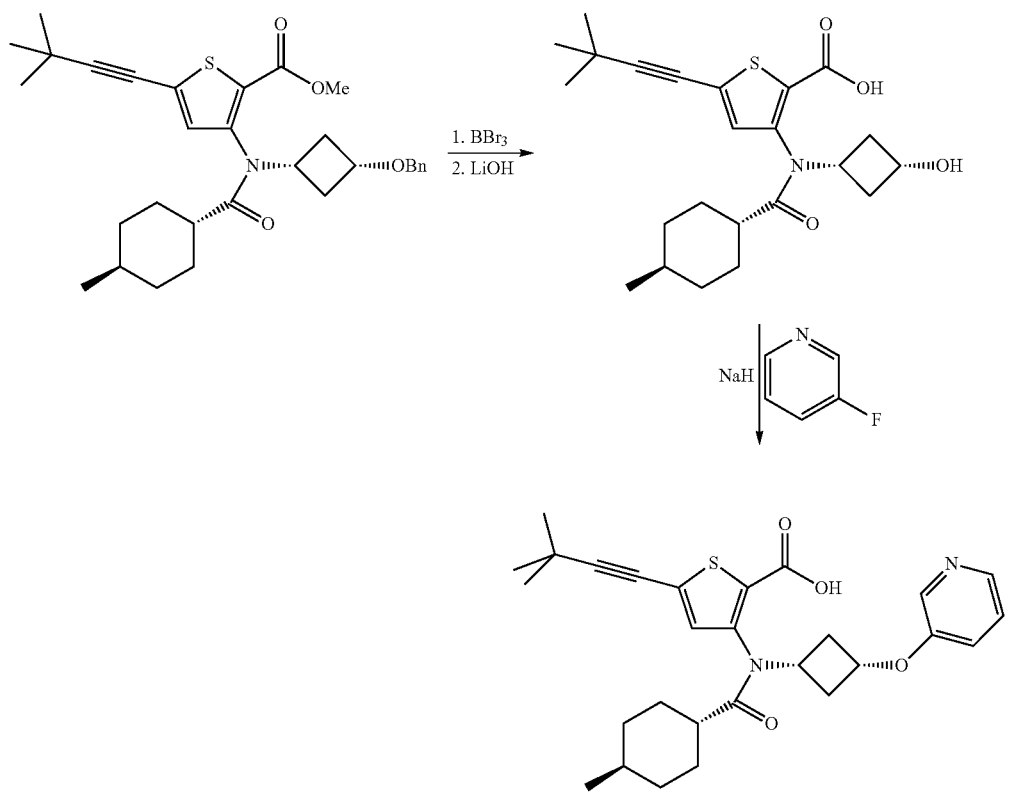

A mixture of 3-amino-5-(3,3-dimethyl-but-1-ynyl)-thiophene-2-carboxylic acid methyl ester, hydrochloride salt (750 mg, 2.74 mmol) and 3-benzyloxy-cyclobutanone (2.5 g, 14.3 mmol) in DCM (40 mL) was treated with sodium triacetoxyborohydride (3.34 g, 15.8 mmol) portionwise. The mixture was stirred at room temperature for 3 hours. The solution was diluted with ethyl acetate, washed sequentially with saturated aqueous sodium bicarbonate, water, and brine. The organic phase was dried over magnesium sulfate, filtered and concentrated. The residue was purified by silica gel chromatography (0-10% ethyl acetate:hexanes). This resulted in 1.26 g (quant. yield) of 3-(3-benzyloxy-cyclobutylamino)-5-(3,3-dimethyl-but-1-ynyl)-thiophene-2-carboxylic acid methyl ester as a mixture of cis- and trans-isomers.

A mixture of 3-(3-benzyloxy-cyclobutylamino)-5-(3,3-dimethyl-but-1-ynyl)-thiophene-2-carboxylic acid methyl ester (1.26 g, 3.17 mmol) and N,N-diisopropylethylamine (2.4 mL, 13.8 mmol) in DCE (8 mL) was treated with trans-4-methyl-cyclohexanecarbonyl chloride and heated to 100 deg C. for 5 hours. The reaction mixture was cooled to room temperature, adsorbed onto silica, and purified by silica gel chromatography (0-30% ethyl acetate:hexanes). This resulted in 590 mg (36% yield) of cis-cyclobutyl isomer (cis-3-[(3-benzyloxy-cyclobutyl)-(4-methyl-cyclohexanecarbonyl)-amino]-5-(3,3-dimethyl-but-1-ynyl)-thiophene-2-carboxylic acid methyl ester) and 230 mg (14% yield) of the trans-cyclobutyl isomer (trans-3-[(3-benzyloxy-cyclobutyl)-(4-methyl-cyclohexanecarbonyl)-amino]-5-(3,3-dimethyl-but-1-ynyl)-thiophene-2-carboxylic acid methyl ester).

3-[(cis-3-benzyloxy-cyclobutyl)-(trans-4-methyl-cyclohexanecarbonyl)-amino]-5-(3,3-dimethyl-but-1-ynyl)-thiophene-2-carboxylic acid methyl ester (290 mg, 0.55 mmol) in DCM (2 mL) at 0 deg C. was treated with boron tribromide (0.85 mL, 1.0 M solution in DCM). The mixture was stirred at 0 deg C. for 15 minutes and quenched with the addition of silica gel. Volatiles were evaporated under reduced pressure and the reaction mixture was purified by silica gel chromatography (0-100% ethyl acetate:hexanes). This resulted in 210 mg (88% yield) of 5-(3,3-Dimethyl-but-1-ynyl)-3-[(cis-3-hydroxy-cyclobutyl)-(trans-4-methyl-cyclohexanecarbonyl)-amino]-thiophene-2-carboxylic acid methyl ester.

5-(3,3-Dimethyl-but-1-ynyl)-3-[(cis-3-hydroxy-cyclobutyl)-(trans-4-methyl-cyclohexanecarbonyl)-amino]-thiophene-2-carboxylic acid methyl ester (400 mg, 0.93 mmol) in a 3:2:1 mixture of THF:MeOH:water (20 mL) was treated with lithium hydroxide (4.5 mL, 1.0 M aqueous solution) and heated to 60 deg C. for 2 hours. The organic volatiles were evaporated under reduced pressure and remaining solution was acidified with 10% $HCl_{(aq)}$. A white precipitate was collected by vacuum filtration, washed with water, and dried to afford 290 mg (74% yield) of 5-(3,3-dimethyl-but-1-ynyl)-3-[(cis-3-hydroxy-cyclobutyl)-(4-methyl-cyclohexanecarbonyl)-amino]-thiophene-2-carboxylic acid as a white powder. MS (m/z): 415.8 [M−H]⁻; HPLC retention time: 4.10 min (2-98% acetonitrile:water with 0.05% trifluoroacetic acid).

The title compound was synthesized in a manner analogous to Example 1, using 5-(3,3-dimethyl-but-1-ynyl)-3-[(cis-3-hydroxy-cyclobutyl)-(4-methyl-cyclohexanecarbonyl)-amino]-thiophene-2-carboxylic acid in place of 5-(3,3-Dimethyl-but-1-ynyl)-3-[(trans-4-hydroxy-cyclohexyl)-(trans-4-methyl-cyclohexanecarbonyl)-amino]-thiophene-2-carboxylic acid and 3-fluoro-pyridine in place of 2-fluoro-pyridine: MS (m/z): 492.8 [M−H]⁻; HPLC retention time:

3.44 min (2-98% acetonitrile:water with 0.05% trifluoroacetic acid).

Example 21

Compound 21: 5-(3,3-Dimethyl-but-1-ynyl)-3-[(trans-4-methyl-cyclohexanecarbonyl)-{trans-3-(pyridin-3-yloxy)-cyclobutyl]-amino}-thiophene-2-carboxylic acid Compound 21

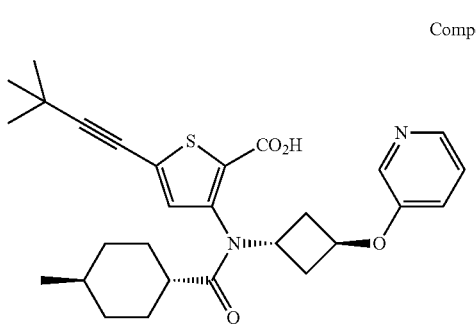

The title compound was synthesized in a manner analogous to Example 20, using 3-[(trans-3-benzyloxy-cyclobutyl)-(trans-4-methyl-cyclohexanecarbonyl)-amino]-5-(3,3-dimethyl-but-1-ynyl)-thiophene-2-carboxylic acid methyl ester in place of 3-[(cis-3-benzyloxy-cyclobutyl)-(trans-4-methyl-cyclohexanecarbonyl)-amino]-5-(3,3-dimethyl-but-1-ynyl)-thiophene-2-carboxylic acid methyl ester: MS (m/z): 492.8 [M−H]⁻; HPLC retention time: 3.45 min (2-98% acetonitrile:water with 0.05% trifluoroacetic acid).

Example 22

Compound 22: 5-(3,3-Dimethyl-but-1-ynyl)-3-{(trans-4-methyl-cyclohexanecarbonyl)-[cis-3-(pyrimidin-2-yloxy)-cyclobutyl]-amino}-thiophene-2-carboxylic acid Compound 22

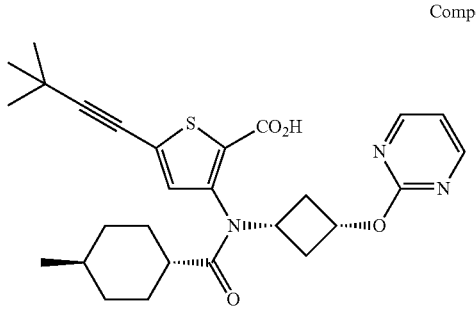

The title compound was synthesized in a manner analogous to Example 20, using 2-chloro-pyrimidine in place of 3-fluoro-pyridine: MS (m/z): 493.8 [M−H]⁻; HPLC retention time: 3.52 min (2-98% acetonitrile:water with 0.05% trifluoroacetic acid).

Example 23

Compound 23: 5-(3,3-Dimethyl-but-1-ynyl)-3-{(trans-4-methyl-cyclohexanecarbonyl)-[trans-3-(pyrimidin-2-yloxy)-cyclobutyl]-amino}-thiophene-2-carboxylic acid Compound 23

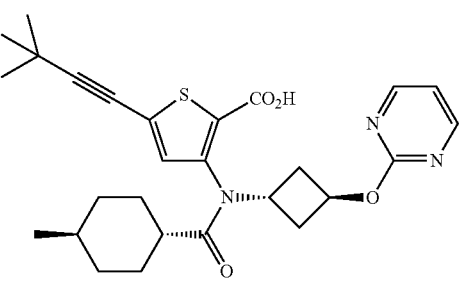

The title compound was synthesized in a manner analogous to Example 20, using 3-[(trans-3-benzyloxy-cyclobutyl)-(trans-4-methyl-cyclohexanecarbonyl)-amino]-5-(3,3-dimethyl-but-1-ynyl)-thiophene-2-carboxylic acid methyl ester in place of 3-[(cis-3-benzyloxy-cyclobutyl)-(trans-4-methyl-cyclohexanecarbonyl)-amino]-5-(3,3-dimethyl-but-1-ynyl)-thiophene-2-carboxylic acid methyl ester and 2-chloro-pyrimidine in place of 3-fluoro-pyridine: MS (m/z): 493.8 [M−H]⁻; HPLC retention time: 3.53 min (2-98% acetonitrile:water with 0.05% trifluoroacetic acid).

Example 24

Compound 24: 5-(3,3-Dimethyl-but-1-ynyl)-3-{(trans-4-methyl-cyclohexanecarbonyl)-[trans-4-(1-oxy-pyridin-3-yloxy)-cyclohexyl]-amino}-thiophene-2-carboxylic acid Compound 24

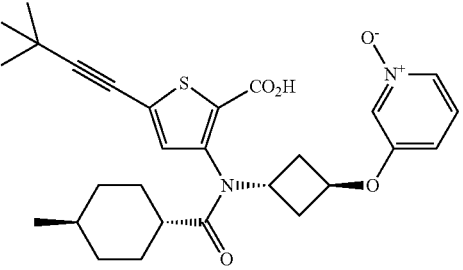

The title compound was synthesized in a manner analogous to Example 1, except 3-fluoro-pyridine 1-oxide was used in place of 2-fluoro-pyridine and the reaction was run at 60 deg C. for 1 h instead of 100 deg C. for 30 min: MS (m/z):

536.8 [M−H]⁻; HPLC retention time: 4.16 min (2-98% acetonitrile:water with 0.05% trifluoroacetic acid).

Example 25

Compound 25: 5-(3,3-Dimethyl-but-1-ynyl)-3-{(4-methyl-cyclohexanecarbonyl)-[4-(quinolin-4-yloxy)-cyclohexyl]-amino}-thiophene-2-carboxylic acid

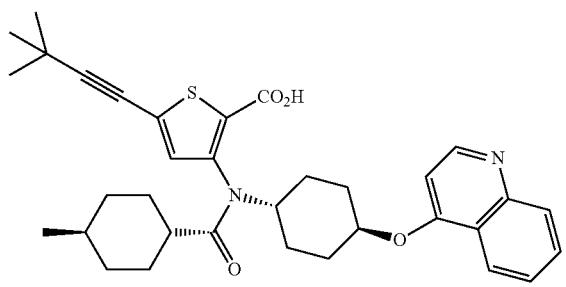

Compound 25

The title compound was synthesized in a manner analogous to Example 1, using 4-chloroquinoline in place of 2-fluoro-pyridine: MS (m/z): 572.8 [M+H]; HPLC retention time 3.66 min (2-98% acetonitrile: water with 0.05% trifluoroacetic acid).

Example 26

Compound 26: 3-[[4-(2,6-diethyl-pyridin-4-yloxy)-cyclohexyl]-(4-methyl-cyclohexanecarbonyl)-amino]-5-(3,3-Dimethyl-but-1-ynyl)-thiophene-2-carboxylic acid

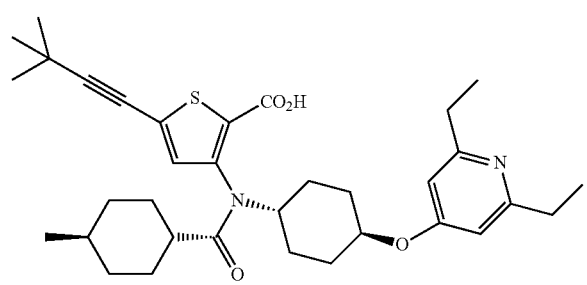

Compound 26

The title compound was synthesized in a manner analogous to Example 1, using 4-chloroquinoline in place of 2-fluoro-pyridine: MS (m/z): 578.0 [M+H]+; HPLC retention time 3.72 min (2-98% acetonitrile: water with 0.05% trifluoroacetic acid).

Example 27

Compound 27: 5-(3,3-Dimethyl-but-1-ynyl)-3-{(trans-4-methyl-cyclohexanecarbonyl)-[trans-4-(4-pyrrolidin-1-ylmethyl-pyridin-2-yloxy)-cyclohexyl]-amino}-thiophene-2-carboxylic acid

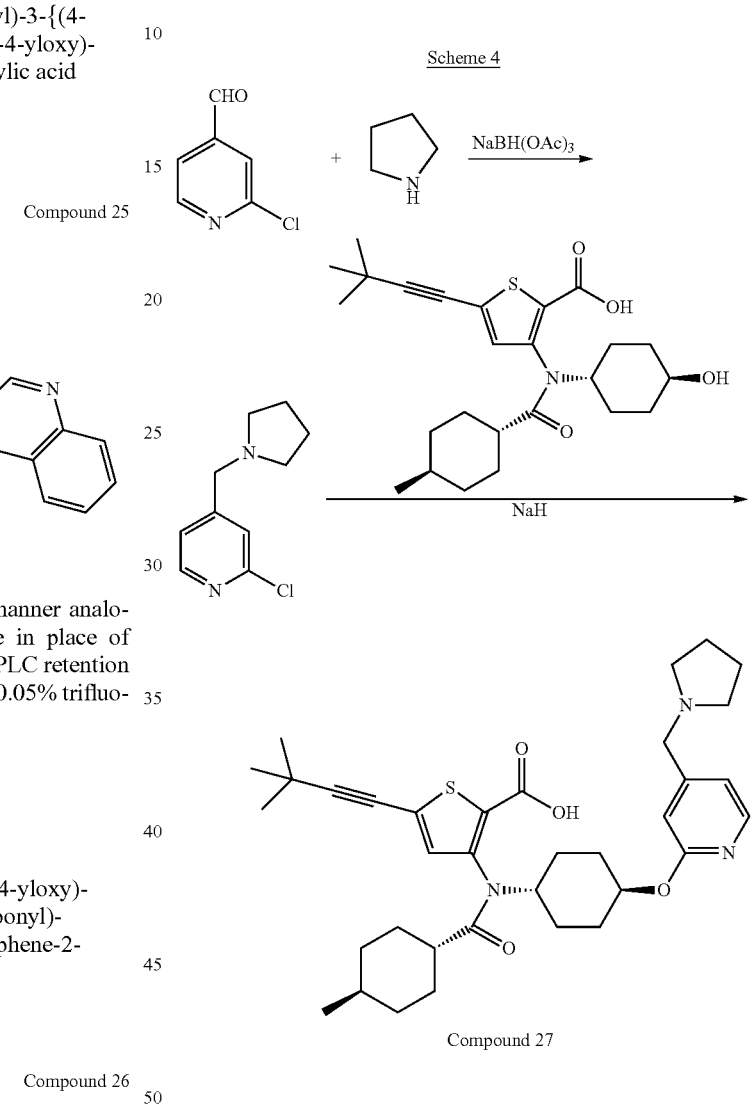

Compound 27

The mixture of 2-chloro-pyridine-4-carbaldehyde and (300 mg, 2.12 mmol) and pyrrolidine (0.19 mL, 2.12 mmol) in DCM (10 mL) was treated with acetic acid (0.25 mL, 4.24 mmol). The mixture was stirred at room temperature for 10 minutes and NaBH(OAc)₃ (899 mg, 4.24 mmol) was added. After overnight stirring, the reaction was washed with sat. NaHCO₃ and extracted twice with DCM. The organic layers were combined and washed with water, brine, dried over sodium sulfate, filtrated and concentrated. The crude material was purified by column chromatography with MeOH/DCM (0-10%) and concentrated to give 120 mg of 2-chloro-4-pyrrolidin-1-ylmethyl-pyridine as a clear oil.

The title compound was synthesized in a manner analogous to Example 1, using 2-chloro-4-pyrrolidin-1-ylmethyl-pyridine in place of 2-fluoro-pyridine: MS (m/z): 606.1

[M+H]+; HPLC retention time 3.64 min (2-98% acetonitrile:water with 0.05% trifluoroacetic acid).

Example 28

Compound 28: 5-(3,3-Dimethyl-but-1-ynyl)-3-{(4-methyl-cyclohexanecarbonyl)-[4-(4-morpholin-4-ylmethyl-pyridin-2-yloxy)-cyclohexyl]-amino}-thiophene-2-carboxylic acid

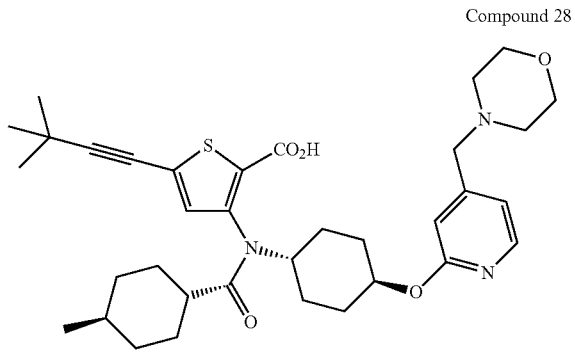

Compound 28

The title compound was synthesized in a manner analogous to Example 27, using 4-(2-chloro-pyridin-4-ylmethyl) morpholine (prepared from 2-chloro-pyridine-4-carbaldehyde and morpholine) in place of 2-chloro-4-pyrrolidin-1-ylmethyl-pyridine: MS (m/z): 622.0 [M+H]+; HPLC retention time 3.59 min (2-98% acetonitrile:water with 0.05% trifluoroacetic acid).

Example 29

Compound 29: 3-[[-4-(4-dimethylaminomethyl-pyridin-2-yloxy)-cyclohexyl]-(4-methyl-cyclohexanecarbonyl)-amino]-5-(3,3-Dimethyl-but-1-ynyl)-thiophene-2-carboxylic acid

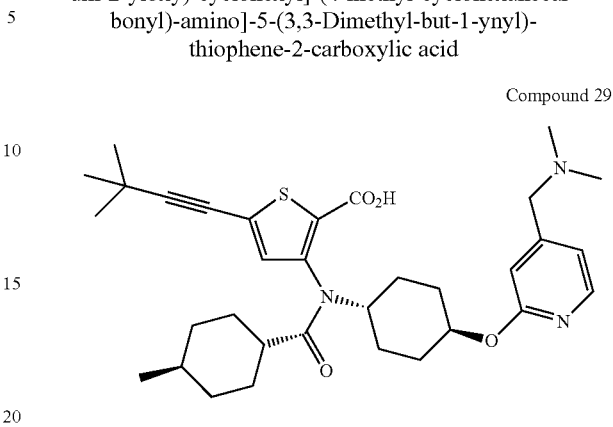

Compound 29

The title compound was synthesized in a manner analogous to Example 27, using (2-chloro-pyridin-4-ylmethyl) dimethyl-amine (prepared from 2-chloro-pyridine-4-carbaldehyde and dimethyl amine) in place of 2-chloro-4-pyrrolidin-1-ylmethyl-pyridine: MS (m/z): 580.1 [M+H]+; HPLC retention time 3.57 min (2-98% acetonitrile:water with 0.05% trifluoroacetic acid).

Example 30

Compound 30: 5-(3,3-Dimethyl-but-1-ynyl)-3-{(4-methyl-cyclohexanecarbonyl)-[4-(pyridin-2-yloxy)-phenyl]-amino}-thiophene-2-carboxylic acid Scheme 5

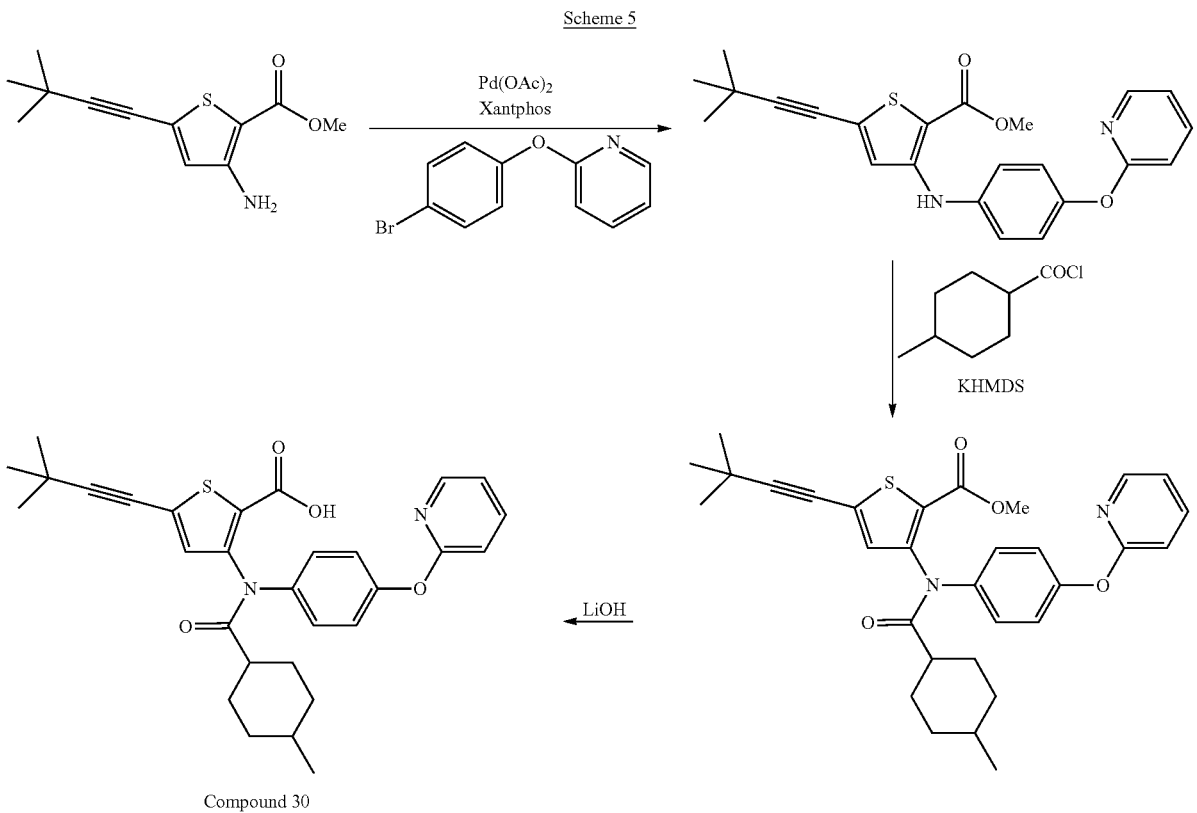

Compound 30

A mixture of 3-amino-5-(3,3-dimethyl-but-1-ynyl)-thiophene-2-carboxylic acid methyl ester (0.200 g, 0.843 mmol), palladium acetate (0.019 g, 0.084 mmol), xantphos (0.058 g, 0.101 mmol), cesium carbonate (0.767 g, 2.36 mmol) and 2-(4-Bromo-phenoxy)-pyridine (0.252 g, 1.01 mmol) in toluene (3 mL) was heated by microwave to 110° C. for 45 minutes. The reaction was diluted with ethyl acetate filtered through a Celite pad and purified by silica gel chromatography to give 5-(3,3-Dimethyl-but-1-ynyl)-3-[4-(pyridin-2-yloxy)-phenylamino]-thiophene-2-carboxylic acid methyl ester in 66% yield.

To a cooled (0° C.) THF (5 mL) solution of 5-(3,3-Dimethyl-but-1-ynyl)-3-[4-(pyridin-2-yloxy)-phenylamino]-thiophene-2-carboxylic acid methyl ester (0.225 g, 0.55 mmol) was first added KHMDS (0.66 mmol, 0.5 M in toluene), followed by neat trans-4-methyl-cyclohexanecarbonyl chloride (0.132 g, 0.825 mmol). The reaction was warmed slowly to room temperature and quenched with saturated ammonium chloride solution. The reaction mixture was diluted with EtOAc, washed with water, brine, dried over sodium sulfate, filtrated and concentrated. The crude material was purified by silica gel column chromatography to give 5-(3,3-dimethyl-but-1-ynyl)-3-{(4-methyl-cyclohexanecarbonyl)-[4-(pyridin-2-yloxy)-phenyl]-amino}-thiophene-2-carboxylic acid methyl ester in 60% yield.

5-(3,3-Dimethyl-but-1-ynyl)-3-{(4-methyl-cyclohexanecarbonyl)-[4-(pyridin-2-yloxy)-phenyl]-amino}-thiophene-2-carboxylic acid methyl ester (174 mg, 0.33 mmol) in a 3:2:1 mixture of THF:MeOH:water (5 mL) was treated with lithium hydroxide monohydrate (0.69 g, 1.65 mmol) and heated to 60° C. for 1 hour. The organic volatiles were evaporated under reduced pressure and the crude material was purified by reverse-phase HPLC to afford the title compound in 70% yield. MS (m/z): 517.0 [M+H]$^-$; HPLC retention time: 4.90 min (2-98% acetonitrile:water with 0.05% trifluoroacetic acid).

The hplc/mass spectrometer equipment used to analyze Example 31-77, unless otherwise indicated, were:
LC: Thermo Electron Surveyor HPLC
MS: Finnigan LCQ Advantage MAX Mass Spectrometer
Column: Phenomenex Polar RP 30 mm×4.6 mm
Solvents: Acetonitrile with 0.1% formic acid, Water with 0.1% formic acid.

Method A

Scheme 6

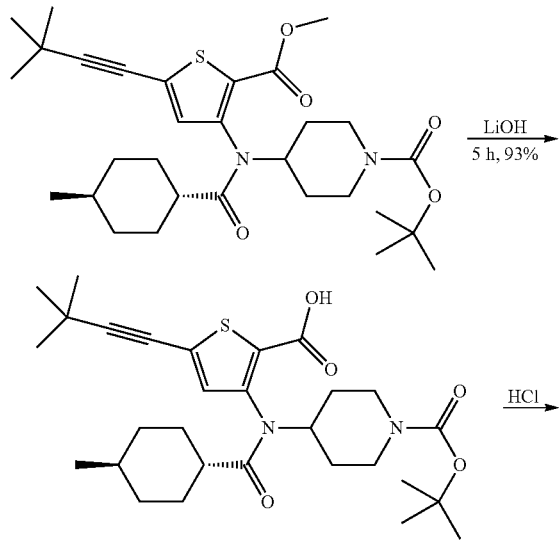

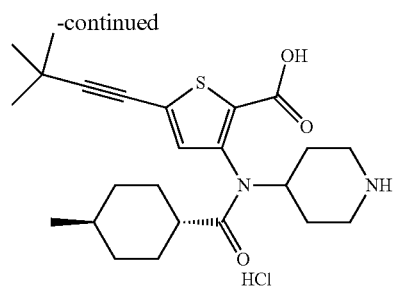

4-[[5-(3,3-dimethyl-but-1-ynyl)-2-methoxycarbonyl-thiophen-3-yl]-(4-trans-methyl-cyclohexanecarbonyl)-amino]-piperidine-1-carboxylic acid tert-butyl ester (1.5 g, 2.73 mmol) was dissolved in ACN (10 mL). To the solution was added a solution of lithium hydroxide (253 mg, 11.01 mmol) in water (10 mL). The reaction was stirred at room temperature for 6 hours. The reaction was complete as determined by LC/MS. The pH was adjusted to 5 with 1N HCl in water. The product was extracted with ethyl acetate (3×10 mL). The combined organics were dried with sodium sulfate, filtered and were concentrated under reduced pressure and 4-[[2-carboxy-5-(3,3-dimethyl-but-1-ynyl)-thiophen-3-yl]-(4-trans-methyl-cyclohexanecarbonyl)-amino]-piperidine-1-carboxylic acid tert-butyl ester (1.35 g, 93%) was recovered as a white solid.

4-[[2-carboxy-5-(3,3-dimethyl-but-1-ynyl)-thiophen-3-yl]-(4-trans-methyl-cyclohexanecarbonyl)-amino]-piperidine-1-carboxylic acid tert-butyl ester (1.35 g, 2.53 mmol) was dissolved in 4N HCl in dioxane (6 mL, 24 mmol). The reaction was stirred at room temperature for 0.5 hours and found to be complete as determined by LC/MS. The reaction was concentrated under reduced pressure to give the HCl salt of 5-(3,3-dimethyl-but-1-ynyl)-3-[(4-trans-methyl-cyclohexanecarbonyl)-piperidin-4-yl-amino]-thiophene-2-carboxylic acid.

Method B 5-(3,3-Dimethyl-but-1-ynyl)-3-[(4-trans-methyl-cyclohexanecarbonyl)-pyrrolidin-3-(S)-yl-amino]-thiophene-2-carboxylic acid was synthesized as follows:

a) Synthesis of 5-(3,3-dimethyl-but-1-ynyl)-3-iodo-thiophene-2-carboxylic acid methyl ester Scheme 8

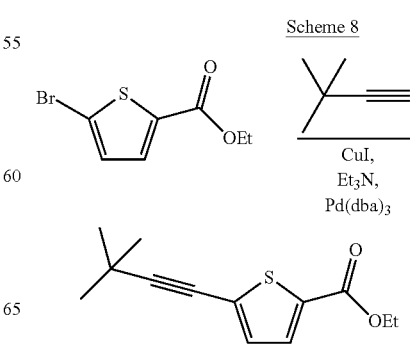

-continued

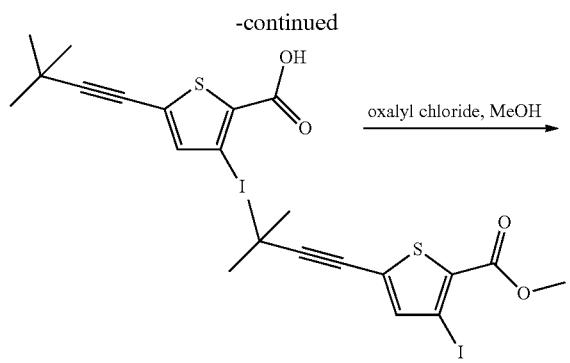

A mixture of 5-bromo-thiophene-2-carboxylic acid ethyl ester (7 g, 30 mmol), copper iodide (1.2 g, 6 mmol), triethylamine (20 mL) in DMF (100 mL) was degassed in a 350 mL pressure bottle. Then tris(dibenzylideneacetone)dipalladium (0) (2.1 g, 3 mmol) and 3,3-dimethyl-but-1-yne (18.3 mL, 150 mmol) were added and heated at 80 degree for 3 hours. The reaction mixture was filtered on celite and washed with ethyl acetate. The solution was diluted with water and extracted twice with ethyl acetate. The organic phases were combined and washed with water. After drying and concentration, the crude residue was purified by flash chromatography to yield 6.9 g (95%) of 5-(3,3-dimethyl-but-1-ynyl)-thiophene-2-carboxylic acid ethyl ester as a yellow oil.

A solution of 5-(3,3-dimethyl-but-1-ynyl)-thiophene-2-carboxylic acid ethyl ester (6.9 g) in THF (100 mL) was added LiOH (1.5N, 100 mL). The mixture was stirred at room temperature for 4 hours. Acidified reaction with HCl to pH=2, then remove volatiles under vacuo. The resulting beige color solid was collected by filtration, washed with water then dried overnight to give 6.2 g of product which was used without further purification.

To a solution of 5-(3,3-dimethyl-but-1-ynyl)-thiophene-2-carboxylic acid (6.2 g, 30 mmol; see patent application U.S. Pat. No. 5,861,421) in THF (100 mL) was added a solution of nBuLi (2.0 M in pentane, 33 mL, 66 mmol) via an addition funnel at −78° C. After addition, the reaction was stirred at −78° C. for 1 h. A solution of I$_2$ (7.7 g, 30 mmol) in THF (100 mL) was added slowly (ca. 15 min) to the flask. After a further 10 mins, the reaction was quenched with 1 N HCl (50 mL) and warmed to room temperature. The volatiles were removed in vacuo and the residue was dissolved in ether (500 mL). The organic solution was washed with 1 M Na$_2$S$_2$O$_3$ (100 mL×2), brine (100 mL) and dried over Na$_2$SO$_4$. After concentrated in vacuo, the residue was purified by silica gel chromatography (EtOAc/hexanes) to give 5-(3,3-Dimethyl-but-1-ynyl)-3-iodo-thiophene-2-carboxylic acid (5.9 g, 65%) as a white solid.

To a solution of 5-(3,3-dimethyl-but-1-ynyl)-3-iodo-thiophene-2-carboxylic acid (1.0 g, 3.0 mmol) and DMF (20 μL) in dry dichloromethane (10 mL) was added oxalyl chloride (508 μL, 6.0 mmol) at room temperature. After stirring at room temperature for 90 min, the reaction was concentrated in vacuo to remove volatiles. The residue was dissolved in pyridine (5 mL) and methanol (5 mL) and stirred for 2 h. The volatiles were removed in vacuo and the residue was participated between ether (150 mL) and saturated NH$_4$Cl solution (50 mL). The organic layer was washed with saturated NH$_4$Cl solution (50 mL) and dried over Na$_2$SO$_4$. After concentration in vacuo, the residue was purified by silica gel chromatography (EtOAc/hexanes) to give the desired product (835 mg, 80%).

b) Synthesis of 5-(3,3-dimethyl-but-1-ynyl)-3-[(4-methyl-cyclohexanecarbonyl)-pyrrolidin-3S-yl-amino]-thiophene-2-carboxylic acid methyl ester Scheme 9

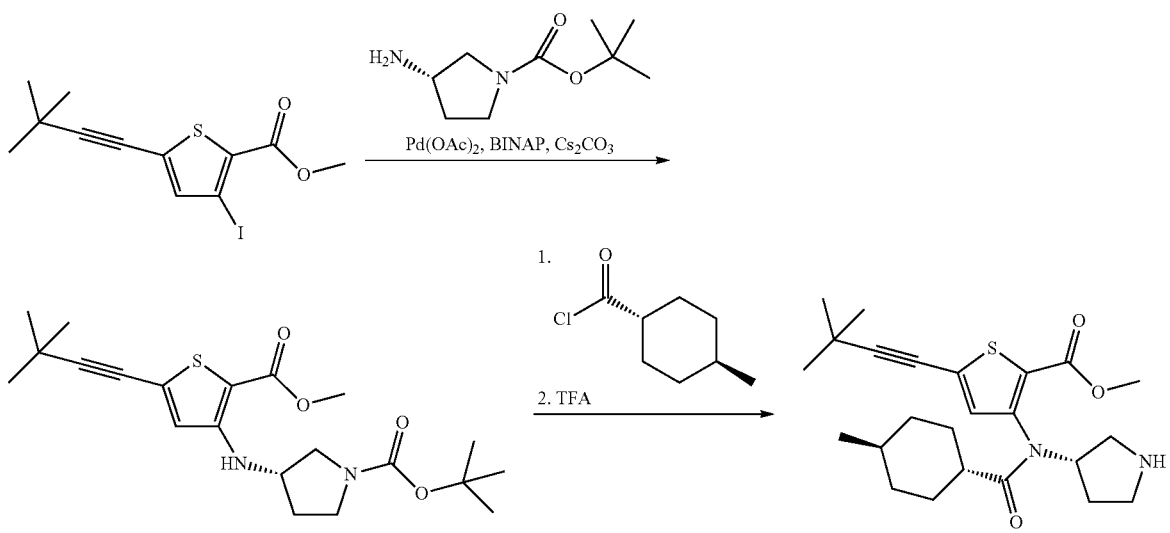

A mixture of 5-(3,3-dimethyl-but-1-ynyl)-3-iodo-thiophene-2-carboxylic acid methyl ester (0.5 g, 1.5 mmol), palladium acetate (0.015 g, 0.32 mmol), BINAP (0.009 g, 0.15 mmol), cesium carbonate (1.2 g, 4.5 mmol) and (3S)-Amino-pyrrolidine-1-carboxylic acid tert-butyl ester (0.252 g, 1.01 mmol) in toluene (8 mL) was heated to 110° C. for 8 h. The reaction was diluted with ethyl acetate filtered through a Celite pad and purified by silica gel chromatography to give 3-[5-(3,3-dimethyl-but-1-ynyl)-2-methoxycarbonyl-thiophen-3S-ylamino]-pyrrolidine-1-carboxylic acid tert-butyl ester in 70% yield.

To a cooled (0° C.) THF (3 mL) solution of 3-[5-(3,3-dimethyl-but-1-ynyl)-2-methoxycarbonyl-thiophen-3S-ylamino]-pyrrolidine-1-carboxylic acid tert-butyl ester was first added KHMDS (1.0 mmol, 0.5 M in toluene), followed by neat trans-4-methyl-cyclohexanecarbonyl chloride (0.2 mL, 1.24 mmol). The reaction was warmed slowly to room temperature and quenched with saturated ammonium chloride solution. The reaction mixture was diluted with EtOAc, washed with water, brine, dried over sodium sulfate, filtrated and concentrated. The crude was then diluted with EtOAc (10 mL), treated with 4M HCl in dioxane (0.5 mL) and heated to 50° C. for 30 min. The reaction mixture was cooled to room temperature concentrated and purified by silica gel column chromatography to give the title compound in 70% yield.

5-(3,3-dimethyl-but-1-ynyl)-3-[(4-methyl-cyclohexanecarbonyl)-pyrrolidin-3S-yl-amino]-thiophene-2-carboxylic acid methyl ester (0.3 g, 0.7 mmol) in a 3:2:1 mixture of THF:MeOH:water (5 mL) was treated with lithium hydroxide monohydrate (0.69 g, 1.65 mmol) and heated to 60° C. for 1 hour. The organic volatiles were evaporated under reduced pressure and the crude material was purified by reverse-phase HPLC to afford 5-(3,3-dimethyl-but-1-ynyl)-3-[(4-trans-methyl-cyclohexanecarbonyl)-pyrrolidin-3-(S)-yl-amino]-thiophene-2-carboxylic acid in 60% yield.

Method C

Example 58

Compound 58: 5-(3,3-Dimethyl-but-1-ynyl)-3-{(trans-4-methyl-cyclohexanecarbonyl)-[1-(S)-methyl-3-pyridin-3-yloxy)-propyl]-amino}-thiophene-2-carboxylic acid Compound 58

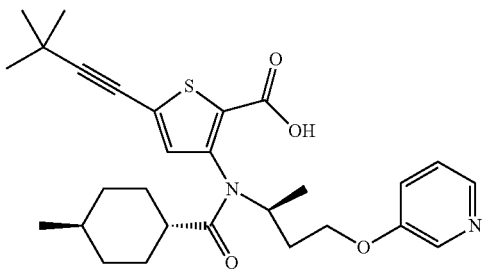

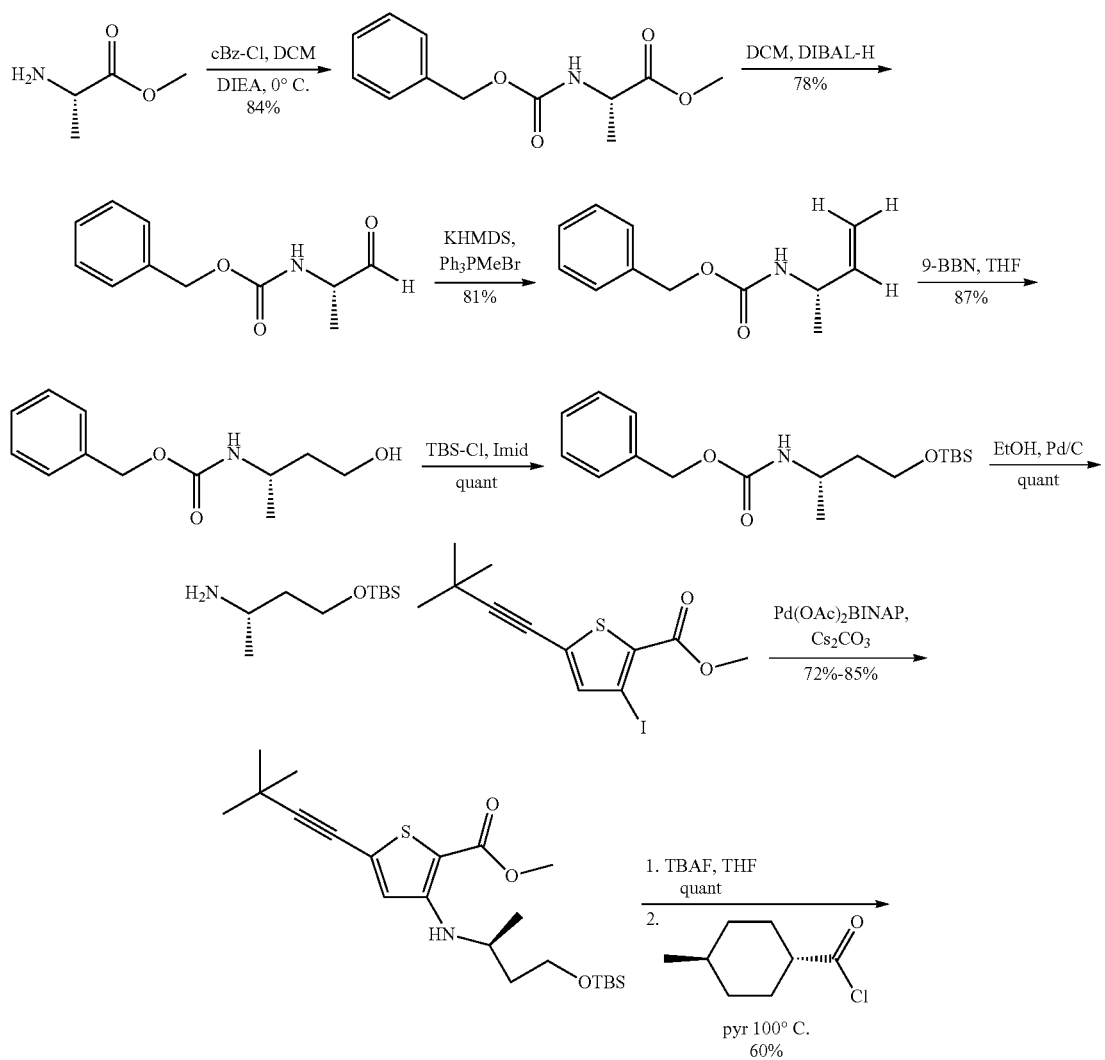

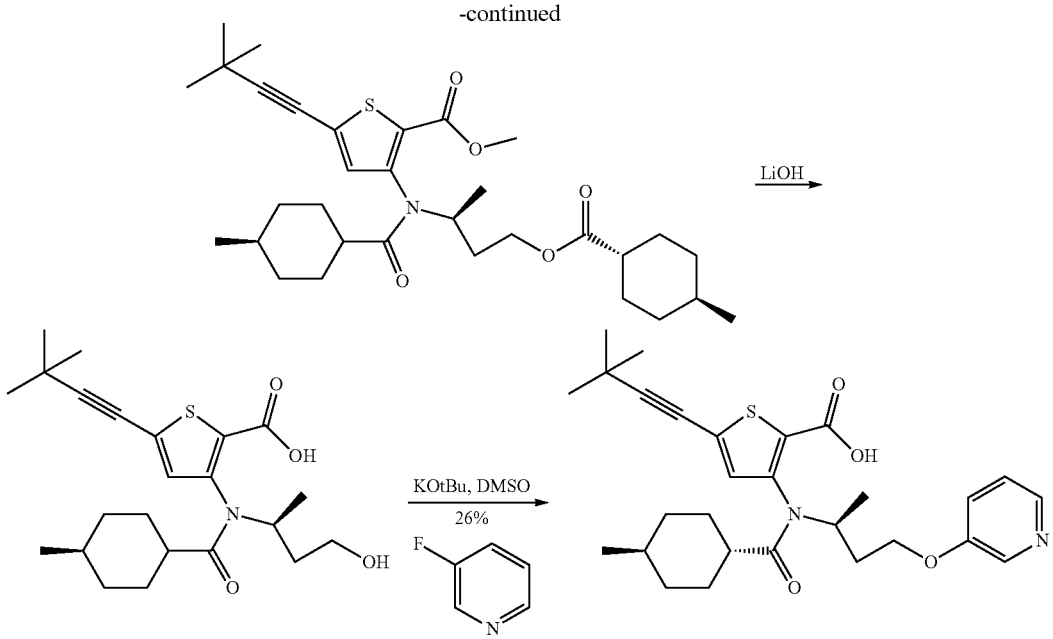

L-Alaninemethyl ester (10.0 g, 71.6 mmol) was taken up in CH$_2$Cl$_2$ (600 mL). The solution was cooled to 0° C. with an ice bath and benzylchloroformate (11.09 mL, 78.8 mmol) was added followed by a slow addition of diisopropylethyl amine (28.2 mL, 157.5 mmol). The reaction was allowed to warm to rt and stirred. The reaction was monitored and determined to be complete at 1 h by TLC. The reaction was quenched with ½ sat. NaHCO$_{3(aq)}$. The layers were separated and the aqueous was washed with CH$_2$Cl$_2$ (500 mL). The organics were combined and dried over Na$_2$SO$_4$. The solids were filtered and solvent removed under reduced pressure. S-2-benzyloxycarbonylamino-propionic acid methyl ester (14.22 g, 84%) was isolated by silica gel chromatography as a colorless oil.

To an Argon purged flask was added S-2-benzyloxycarbonylamino-propionicacid methyl ester (14.10 g, 59.4 mmol) and CH$_2$Cl$_2$ (500 mL). The solution was cooled to −78° C. internal using dry ice and methanol. DIBAL-H 1.0M in Toluene (119 mL, 119 mmol) was added over a period of 1 h ensuring the internal temperature does not exceed −68° C. The solution was allowed to stir at −78° C. for a period of 1.5 h. The reaction was quenched with a slow addition of CH$_3$OH (20 mL) followed by the addition of sat NH$_4$Cl$_{(aq)}$ (150 mL). The solution was then allowed to warm to rt. The solids were filtered through Celite. The layers were separated and the aqueous was washed with CH$_2$Cl$_2$ (500 mL). The organics were combined and washed with brine and dried over Na$_2$SO$_4$. Solids were removed by filtration and solvent removed under reduced pressure. (1-(S)-methyl-2-oxo-ethyl)-carbamic acid benzyl ester (9.78 g, 79%) was isolated by silica gel chromatography as a colorless oil.

Methyltriphenylphosphonium bromide (16.92 g, 47.30 mmol) was taken up in toluene (350 mL). The heterogeneous solution was cooled to 0° C. then KHMDS 0.5M in toluene (90 mL, 45 mmol) was added. The reaction was stirred at 0° C. for 30 min, then cooled to −78° C. and (1-(S)-methyl-2-oxo-ethyl)-carbamic acid benzyl ester (6.11 g, 29.56 mmol) that was dissolved in toluene (45 mL) was added. The solution was warm to rt, stirred at it for 30 min, then quenched with sat NH$_4$Cl$_{(aq)}$ (150 mL). The layers were separated and the aqueous was washed with EtOAc. The organics were combined and dried over Na$_2$SO$_4$. Solids were removed by filtration and solvent removed under reduced pressure. (1-(S)-methyl-allyl)-carbamic acid benzyl ester (4.90 g, 81%) was isolated by silica gel chromatography as a colorless oil.

(1-(S)-Methyl-allyl)-carbamic acid benzyl ester (1.96 g, 9.56 mmol) was taken up in THF (200 mL). 9-BBN 0.5M in THF (38 mL, 19.0 mmol) was added slowly to the reaction mixture. The solution was allowed to stir at rt for 16 h. Quenched with H$_2$O (65 mL), followed by 1.0M NaOH$_{(aq)}$ (20 mL). The solution was cooled to 0° C. in an ice bath and H$_2$O$_2$ 30% in H$_2$O (7.0 mL) was slowly added. The reaction was partitioned between Et$_2$O and H$_2$O. The layers were separated and the aqueous washed with Et$_2$O. The combine organics were dried over Na$_2$SO$_4$. Solids were filtered and the solvent removed under reduced pressure. (3-hydroxy-1-(S)-methyl-propyl)-carbamic acid benzyl ester (1.85 g, 87%) was isolated by silica gel chromatography as a white solid.

(3-Hydroxy-1-(S)-methyl-propyl)-carbamic acid benzyl ester (8.02 g, 35.9 mmol) was taken up in DMF (75 mL). tert-Butyl-dimethylsilyl chloride (8.12 g, 53.9 mmol) was added to the solution followed by imidazole (4.15 g, 61.0 mmol). The reaction was stirred at rt and monitored by TLC. The reaction was determined to be complete at 1 h by TLC. The reaction was taken up in EtOAc (200 mL) and partitioned between 5% LiCl$_{(aq)}$ (200 mL). The aqueous was back extracted with EtOAc. The organics were combined and washed with 3×200 mL 5% LiCl$_{(aq)}$, and dried over Na$_2$SO$_4$. Solids were filtered and solvent removed under reduced pressure. [3-(tert-Butyl-silanoxy)-1-(S)-methyl-propyl]-carbamic acid benzyl ester (12.73 g, 100%) was isolated by silica gel chromatography as a white solid.

3-(tert-Butyl-silanoxy)-1-(S)-methyl-propyl]-carbamic acid benzyl ester (12.37 g, 36.7 mmol) was taken up in EtOH (200 mL). The solution was purged with argon for 15 min, then 10% Pd/C (1.24 g) was added. The vessel was evacuated and backfilled with H$_{2(g)}$ three times. Stir under a H$_{2(g)}$ atmosphere monitoring by TLC. The reaction was determined to be complete after 2 h. The reaction was put through a PTFE filter and solids washed with CH$_2$Cl$_2$. Solvent was removed under reduced pressure and the colorless oil 3-(tert-butyl-dimethyl-silanoxy)-1-(S)-methylpropylamine (8.34 g, 100%) was used without any purification.

An argon purged flask was charged with 3-(tert-butyl-dimethyl-silanoxy)-1-(S)-methylpropylamine (3.50 g, 17.24 mmol), 5-(3,3-dimethyl-but-1ynyl)-3-iodo-thiophene-2-carboxylic acid methyl ester (3.0 g, 8.62 mmol), Pd(OAc)$_2$ (288 mg, 1.29 mmol), and ±-BINAP 801 mg, 1.29 mmol). Argon degassed toluene (90 mL) was add to the reaction mixture and the reaction was placed in a preheated 120° C. oil bath and stirred for 16 h. The solvent was removed under reduced pressure and taken up in hexanes. 3-[3-(tert-butly-dimethyl-silanoxy)-1-(S)-methyl-propylamino]-5-(3,3-dimethyl-but-1-ynyl)thiophene-2-carboxylic acid methyl ester was isolated by silica gel chromatography (2.87 g, 79%) as a yellow solid.

3-[3-(tert-Butyl-dimethyl-silanoxy)-1-(S)-methyl-propylamino]-5-(3,3-dimethyl-but-1-ynyl)thiophene-2-carboxylic acid methyl ester (8.2 g, 18.24 mmol) was taken up in THF (200 mL). TBAF 1.0M in THF (88.15 mL, 88.15 mmol) was added in 20 mL increments at rt. The reaction was monitored by LC/MS. The reaction was determined to be complete at 30 min. and was quenched with sat NH$_4$Cl$_{(aq)}$ (200 mL). After stirring at it for 1 h. the organics were removed under reduced pressure and the solution was dried over Na$_2$SO$_4$, solids were filtered and the solvent removed under reduced pressure. 5-(3,3-dimethyl-but-1-ynyl)3-(3-hydroxy-1-(S)-methyl-propylamino)-thiophene-2-carboxylic acid methyl ester (4.0 g, 73%) was isolated by silica gel chromatography as a yellow solid.

5-(3,3-Dimethyl-but-1-ynyl)3-(3-hydroxy-1-(S)-methyl-propylamino)-thiophene-2-carboxylic acid methyl ester (4.0 g, 12.94 mmol) was taken up in pyridine (100 mL). Trans-4-methyl-cyclohexanecarbonyl chloride (12.40 g, 77.66 mmol) was added and the reaction was placed in a 100° C. preheated oil bath and stirred for 16 h. After cooling to rt the solvent was removed under reduced pressure. The residue was partitioned between EtOAc and 2N HCl$_{(aq)}$, the organics dried over Na$_2$SO$_4$, and the solids filtered. Solvent was removed under reduced pressure and 5-(3,3-dimethyl-but-1-ynyl)-3-[(trans-4-methylcyclohexanecarbonyl)-[1-(S)-methyl-3-(trans-4-methyl-cyclohexanecarbonyloxy)-propyl]-amino]-thiophene-2-carboxylic acid methyl ester (4.15 g, 58%) was isolated by silica gel chromatography as a yellow solid.

A mixture of THF (20 mL) and CH$_3$OH (10 mL) and 5-(3,3-dimethyl-but-1-ynyl)-3-[(trans-4-methylcyclohexanecarbonyl)-[1-(S)-methyl-3-(trans-4-methyl-cyclohexanecarbonyloxy)-propyl]-amino]-thiophene-2-carboxylic acid methyl ester (4.15 g, 7.45 mmol) was treated with dissolved LiOH.H$_2$O (1.56 g, 37.20 mmol) in H$_2$O (10 mL). After stirring at it for 3 h., the reaction was determined to be complete by LC/MS. After adjusting pH=2 with 2N HCl$_{(aq)}$ the organics were removed under reduced pressure and the residue partitioned with EtOAc. The organics were separated, dried and the solvent removed under reduced pressure. 5-(3,3-Dimethyl-but-1-ynyl)-3-[(3-hydroxy-1-(S)-methyl-propyl)-(trans-4-methyl-cyclohexanecarbonyl)-amino]-thiophene-2-carboxylic acid TFA salt (3.96 g, 95%) was isolated by reverse phase HPLC as a white solid.

A mixture of 5-(3,3-dimethyl-but-1-ynyl)-3-[(3-hydroxy-1-(S)-methyl-propyl)-(trans-4-methyl-cyclohexanecarbonyl)-amino]-thiophene-2-carboxylic acid TFA salt (0.100 g, 0.238 mmol) and 3-fluoropyridine (0.046 g, 0.476 mmol) in DMSO (3.0 mL) was treated with KOtBu (0.106 g, 0.952 mmol) in one portion. The reaction was determined to be complete by LC/MS in 30 min. After quenching the reaction with 20% AcOH in H$_2$O (2 mL), 5-(3,3-dimethyl-but-1-ynyl)-3-[(trans-4-methyl-cyclohexanecarbonyl)-[1-(S)-methyl-3-pyridin-3-yloxy)-propyl]-amino]-thiophene-2-carboxylic acid TFA salt (0.029 g, 26%) was isolated by reverse phase HPLC as an off-white solid.
LC/MS=496.84 (M$^+$+1)
Retention time: 4.14 min
Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Example 59

Compound 59: 5-(3,3-dimethyl-but-1-ynyl)-3-[(trans-4-methyl-cyclohexanecarbonyl)-[1-(S)-methyl-3-pyrimidin-2-yloxy)-propyl]-amino]-thiophene-2-carboxylic acid Compound 59

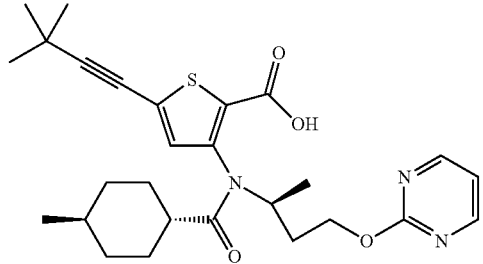

A mixture of 5-(3,3-dimethyl-but-1-ynyl)-3-[(3-hydroxy-1-(S)-methyl-propyl)-(trans-4-methyl-cyclohexanecarbonyl)-amino]-thiophene-2-carboxylic acid TFA salt (0.100 g, 0.238 mmol) and 2-chloropyrimidine (0.029 g, 0.250 mmol) in DMSO (3.0 mL) was treated with KOtBu (0.087 g, 0.776 mmol) in one portion. The reaction was determined to be complete by LC/MS in 30 min. After quenching the reaction with 20% AcOH in H$_2$O (2 mL), 5-(3,3-dimethyl-but-1-ynyl)-3-[(trans-4-methyl-cyclohexanecarbonyl)-[1-(S)-methyl-3-pyrimidin-2-yloxy)-propyl]-amino]-thiophene-2-carboxylic acid TFA salt (0.015 g, 13%) was isolated by reverse phase HPLC as an off-white solid.
LC/MS=520.18 (M$^+$+Na)
Retention time: 3.79 min
Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Example 60

Compound 60: 5-(3,3-dimethyl-but-1-ynyl)-3-[(trans-4-methyl-cyclohexanecarbonyl)-[1-(S)-methyl-3-pyridin-2-yloxy)-propyl]-amino]-thiophene-2-carboxylic acid Compound 60

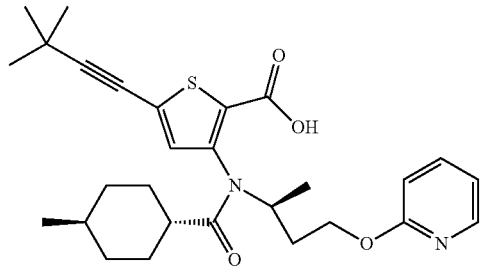

A mixture of 5-(3,3-dimethyl-but-1-ynyl)-3-[(3-hydroxy-1(S)-methyl-propyl)-(trans-4-methyl-cyclohexanecarbonyl)-amino]-thiophene-2-carboxylic acid TFA salt (0.182 g, 0.340 mmol) and 2-fluoropyridine (164 µL, 1.70 mmol) in DMSO (5.0 mL) was treated with KOtBu (0.152 g, 1.36 mmol) in one portion. The reaction was determined to be complete by LC/MS in 30 min. After quenching the reaction with 20% AcOH in H$_2$O (2 mL), 5-(3,3-dimethyl-but-1-ynyl)-3-[(trans-4-methyl-cyclohexanecarbonyl)-[1-(S)-methyl-3-pyridin-2-yloxy)-propyl]-amino]-thiophene-2-carboxylic acid TFA salt (0.195 g, 94%) was isolated by reverse phase HPLC as an off-white solid.

LC/MS=496.95 (M$^+$+1)

Retention time: 2.33 min

Gradient: 0 min-0.1 min 5% ACN, 0.1 min-1.95 min 5%-100% ACN, 1.95 min-3.50 min 100% ACN, 3.50 min-3.55 min 100%-5% ACN, 3.55 min-4.0 min 5% ACN.

Example 61

Compound 61: 3-[[3-(4-dimethylaminomethyl-pyridin-2-yloxy)-1-(S)-methyl-propyl]-(trans-4-methyl-cyclohexanecarbonyl)-amino]-5-(3,3-dimethyl-but-1-ynyl)-thiophene-2-carboxylic acid Compound 61

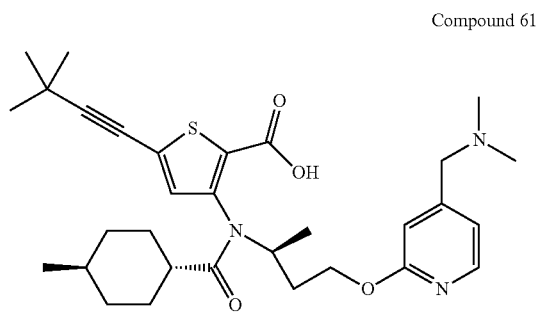 [SMILES: C[C@@H](CCOc1cc(CN(C)C)ccn1)N(c1cc(C#CC(C)(C)C)sc1C(=O)O)C(=O)[C@H]1CC[C@H](C)CC1]

A mixture of 5-(3,3-dimethyl-but-1-ynyl)-3-[(3-hydroxy-1-(S)-methyl-propyl)-(trans-4-methyl-cyclohexanecarbonyl)-amino]-thiophene-2-carboxylic acid TFA salt (0.218 g, 0.598 mmol) and (2-fluoropyridin-4-yl-methyl)-dimethylamine (0.400 g, 2.59 mmol) in DMSO (5.0 mL) was treated with KOtBu (0.267 g, 2.39 mmol) in one portion. The reaction was determined to be complete by LC/MS in 30 min. After quenching the reaction with 20% AcOH in H$_2$O (5 mL), 3-[[3-(4-dimethylaminomethyl-pyridin-2-yloxy)-1-(S)-methyl-propyl]-(trans-4-methyl-cyclohexanecarbonyl)-amino]-5-(3,3-dimethyl-but-1-ynyl)-thiophene-2-carboxylic acid TFA salt (0.272 g, 68%) was isolated by reverse phase HPLC as an off-white solid.

LC/MS=553.94 (M$^+$+1)

Retention time: 3.30 min

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Example 62

Compound 62: 5-(3,3-dimethyl-but-1-ynyl)-3-[(trans-4-methyl-cyclohexanecarbonyl)-[1-(S)-methyl-3-(4-pyrrolidin-1-yl-methyl-pyridin-2-yloxy)-propyl]-amino]-thiophene-2-carboxylic acid Compound 62

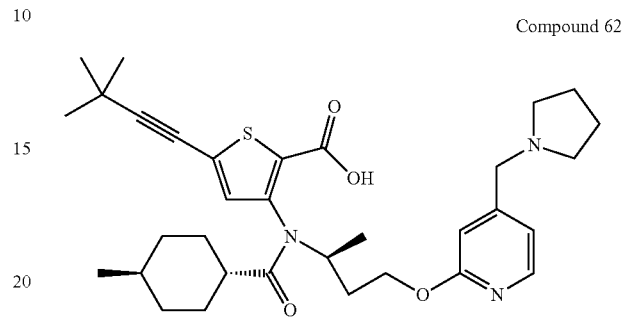

A mixture of 5-(3,3-dimethyl-but-1-ynyl)-3-[(3-hydroxy-1-(S)-methyl-propyl)-(trans-4-methyl-cyclohexanecarbonyl)-amino]-thiophene-2-carboxylic acid TFA salt (0.050 g, 0.119 mmol) and 2-fluoro-4-pyrrolidin-1-yl-methyl-pyridine (0.100 g, 0.555 mmol) in DMSO (1.5 mL) was treated with KOtBu (0.053 g, 0.476 mmol) in one portion. The reaction was determined to be complete by LC/MS in 30 min. After quenching the reaction with 20% AcOH in H$_2$O (1 mL), 5-(3,3-dimethyl-but-1-ynyl)-3-[(trans-4-methyl-cyclohexanecarbonyl)-[1-(S)-methyl-3-(4-pyrrolidin-1-yl-methyl-pyridin-2-yloxy)-propyl]-amino]-thiophene-2-carboxylic acid TFA salt (0.030 g, 37%) was isolated by reverse phase HPLC as an off-white solid.

LC/MS=580.00 (M$^+$+1)

Retention time: 3.25 min

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Example 63

Compound 63: 5-(3,3-dimethyl-but-1-ynyl)-3-[[3-(6-hydroxy-pyridazin-3-yloxy)-1-(S)-methyl-propyl]-(trans-4-methyl-cyclohexanecarbonyl)-amino]-thiophene-2-carboxylic acid Compound 63

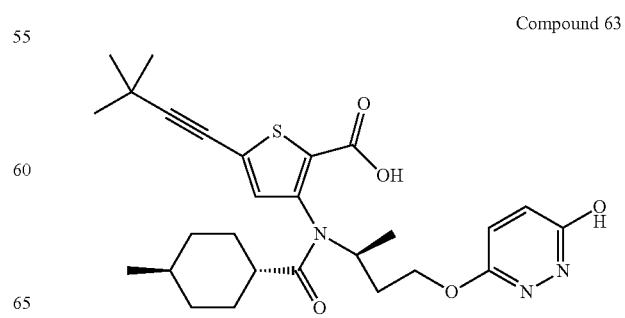

A mixture of 5-(3,3-dimethyl-but-1-ynyl)-3-[(3-hydroxy-1-(S)-methyl-propyl)-(trans-4-methyl-cyclohexanecarbonyl)-amino]-thiophene-2-carboxylic acid TFA salt (0.100 g, 0.238 mmol) and 2,6-dichloropyridazine (0.176 g, 1.19 mmol) in DMSO (3 mL) was treated with KOtBu (0.106 g, 0.952 mmol) in one portion. The reaction was determined to be complete by LC/MS in 30 min. After quenching the reaction with 20% AcOH in H$_2$O (5 mL), 3-[[3-(6-chloro-pyridazin-3-yloxy)-1-(S)-methyl-propyl]-(trans-4-methyl-cyclohexanecarbonyl)-amino]-5-(3,3-dimethyl-but-1-ynyl)-thiophene-2-carboxylic acid TFA salt (0.056 g, 36%) was isolated by reverse phase HPLC as an off-white solid.

A mixture of 3-[[3-(6-chloro-pyridazin-3-yloxy)-1(S)-methyl-propyl]-(trans-4-methyl-cyclohexanecarbonyl)-amino]-5-(3,3-dimethyl-but-1-ynyl)-thiophene-2-carboxylic acid TFA salt (0.56 g, 0.087 mmol) in AcOH (2.0 mL) and NaOAc (0.37 g, 0.434 mmol) was placed in a preheated 100° C. oil bath and stirred for 3 h. The reaction was determined to be complete by LC/MS. After cooling, the reaction was diluted with CH$_3$OH (5 mL). 5-(3,3-Dimethyl-but-1-ynyl)-3-[[3-(6-hydroxy-pyridazin-3-yloxy)-1-(S)-methyl-propyl]-(trans-4-methyl-cyclohexanecarbonyl)-amino]-thiophene-2-carboxylic acid TFA salt (0.07 g, 13%) was isolated by reverse phase HPLC as an off-white solid.

LC/MS=536.12 (M$^+$+Na)

Retention time: 3.50 min

Gradient: 0 min-0.2 min 5% ACN, 0.2 min-3.95 min 5%-100% ACN, 3.95 min-5.20 min 100% ACN, 5.20 min-5.5 min 100%-5% ACN, 5.5 min-6 min 5% ACN.

Example 84

Compound 84: 5-(3,3-dimethylbut-1-ynyl)-3-(4-methyl-N-(4-(4-methyl-4H-1,2,4-triazol-3-ylthio)cyclohexyl)cyclohexanecarboxamido)thiophene-2-carboxylic acid 3-[(4-Bromo-cyclohexyl)-(4-methyl-cyclohexanecarbonyl)-amino]-5-(3,3-dimethyl-but-1-ynyl)-thiophene-2-carboxylic acid methyl ester (75 mg, 0.143 mmol, 1.0 eq.) was weighed into a round-bottomed flask containing 1,4-dioxane (2 mL) and purged with N$_2$. 4-Methyl-4H-[1,2,4]triazole-3-thiol (83 mg, 0.718 mmol, 5.0 eq.) and DBU (107 µL, 0.718 mmol, 5 eq.) were then added to the solution. The reaction was stirred at 80° C. until the complete consumption of bromide. The solution was then cooled to room temperature and 50% KOH (1.0 mL) was added to the flask. The reaction was heated at 40° C. for 2 h. The reaction was cooled to 0° C. and acidified with 2 N HCl. After removing volatiles, the residue was purified by reverse phase preparative HPLC to afford Example 1 (5-(3,3-dimethyl-but-1-ynyl)-3-{(4-methyl-cyclohexanecarbonyl)-[4-(4-methyl-4H-[1,2,4]triazol-3-ylsulfanyl)-cyclohexyl]-amino}-thiophene-2-carboxylic acid, 32 mg, 41%).

MS (m/z) 543.2 [M+H]$^+$ HPLC retention time: 4.40 min (5-95% acetonitrile with 0.05% TFA:water with 0.05% TFA).

Example 85

Compound 85: 5-(3,3-dimethylbut-1-ynyl)-3-(4-methyl-N-(4-(4-methyl-4H-1,2,4-triazol-3-ylthio)cyclohexyl)cyclohexanecarboxamido)thiophene-2-carboxylic acid

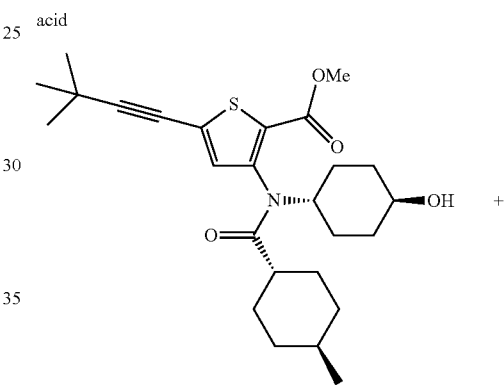

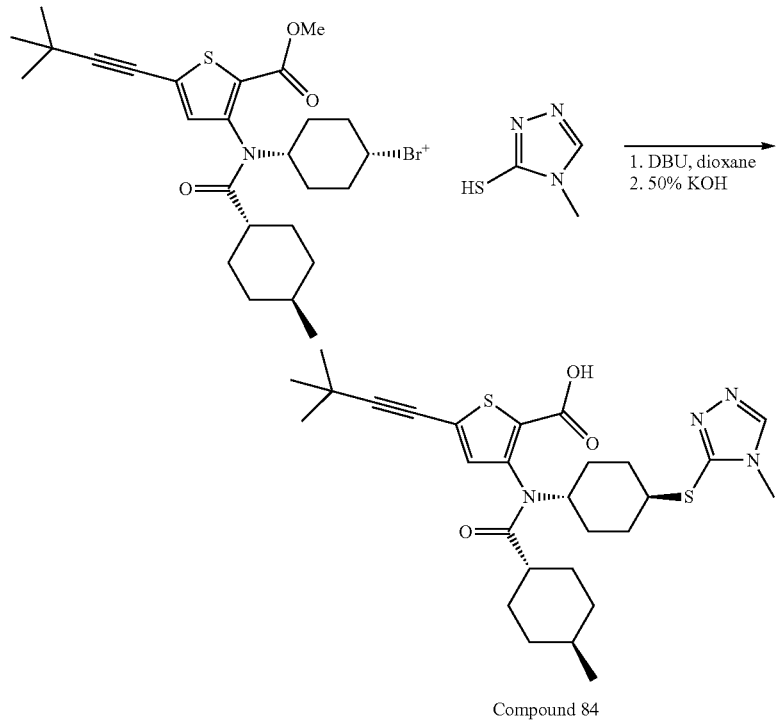

Compound 84

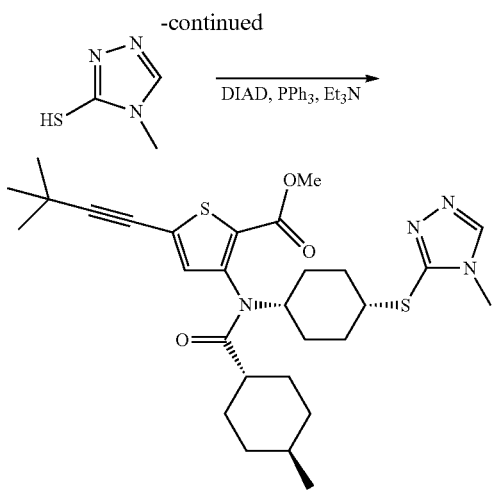

5-(3,3-Dimethyl-but-1-ynyl)-3-[(4-hydroxy-cyclohexyl)-(4-methyl-cyclohexanecarbonyl)-amino]-thiophene-2-carboxylic acid methyl ester (92 mg, 0.2 mmol, 1.0 eq.), 4-methyl-4H-[1,2,4]triazole-3-thiol (46 mg, 0.4 mmol, 2.0 eq.), triphenylphosphine (105 mg, 0.4 mmol, 2.0 eq.), DIAD (77 μL, 0.4 mmol, 2.0 eq.) and triethyl amine (42 μL, 0.3 mmol, 1.5 eq.) were weighed into a round-bottomed flask containing THF (2.0 mL). The solution was purged with $N_2$ and stirred at room temperature for 12 h. The solution was concentrated to an oil and then purified by silica gel chromatography (0-100% EtOAc in hexanes) to afford 5-(3,3-dimethyl-but-1-ynyl)-3-{(4-methyl-cyclohexanecarbonyl)-[4-(4-methyl-4H-[1,2,4]triazol-3-ylsulfanyl)-cyclohexyl]-amino}-thiophene-2-carboxylic acid methyl ester (63 mg, 57%).

5-(3,3-Dimethyl-but-1-ynyl)-3-{(4-methyl-cyclohexanecarbonyl)-[4-(4-methyl-4H-[1,2,4]triazol-3-ylsulfanyl)-cyclohexyl]-amino}-thiophene-2-carboxylic acid methyl ester (63 mg, 0.113 eq.) was dissolved in THF (2.0 mL) in a round-bottomed flask. A solution of LiOH (14 mg, 0.34 mmol, 3.0 eq.) in water (1.0 mL) was added. The reaction was stirred at room temperature overnight. The reaction was then neutralized with 0.2 mL 2 N HCl, concentrated, and purified by reverse phase preparative HPLC to afford Example 2 (5-(3,3-dimethyl-but-1-ynyl)-3-{(4-methyl-cyclohexanecarbonyl)-[4-(4-methyl-4H-[1,2,4]triazol-3-ylsulfanyl)-cyclohexyl]-amino}-thiophene-2-carboxylic acid, 27 mg, 44%).

MS (m/z) 543.2 [M+H]$^+$ HPLC retention time: 4.92 min (5-95% acetonitrile with 0.05% TFA:water with 0.05% TFA).

Examples 86-108 were synthesized by the same method as Examples 84 or 85 using the appropriate heterocyclic thiol as substrate.

Example 86

Compound 86: 3-(N-(4-(1,3,4-Thiadiazol-2-ylthio)cyclohexyl)-4-methylcyclohexanecarboxamido)-5-(3,3-dimethylbut-1-ynyl)thiophene-2-carboxylic acid

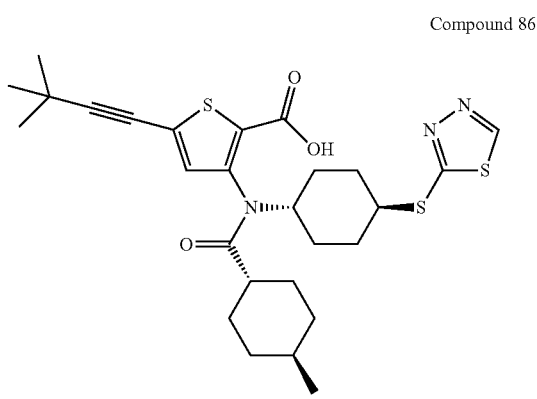 [SMILES: CC(C)(C)C#Cc1cc(N(C(=O)[C@H]2CC[C@H](C)CC2)[C@H]2CC[C@H](Sc3nncs3)CC2)c(C(=O)O)s1]

Compound 86

MS (m/z) 546 [M+H]$^+$ HPLC retention time: 3.3 min (50-98% acetonitrile:water with 0.05% trifluoroacetic acid; 6 min run).

Example 87

Compound 87: 5-(3,3-Dimethylbut-1-ynyl)-3-(4-methyl-N-(4-(pyridin-4-ylthio)cyclohexyl)cyclohexanecarboxamido)thiophene-2-carboxylic acid

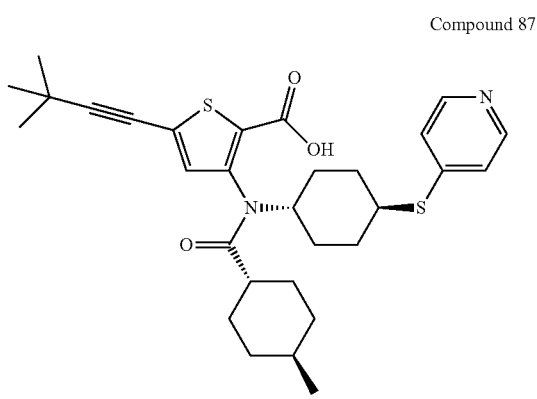

Compound 87

MS (m/z) 539 [M+H]$^+$ HPLC retention time: 4.08 min (6 min HPLC method 2-98% acetonitrile:water with 0.05% trifluoroacetic acid).

Example 88

Compound 88: 5-(3,3-Dimethylbut-1-ynyl)-3-(4-methyl-N-4-(pyridin-2-ylthio-N-oxide)cyclohexyl)cyclohexanecarboxamido)thiophene-2-carboxylic acid Compound 88

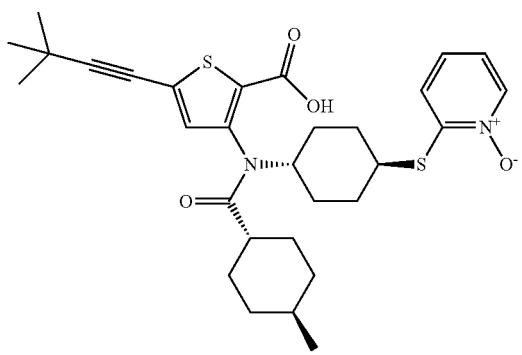

MS (m/z) 555 [M+H]⁺ HPLC retention time: 2.43 min (50-98% acetonitrile:water with 0.05% trifluoroacetic acid; 6 min run).

Example 89

Compound 89: 5-(3,3-Dimethylbut-1-ynyl)-3-(N-(4-(1-ethyl-1H-imidazol-2-ylthio)cyclohexyl)-4-methylcyclohexanecarboxamido)thiophene-2-carboxylic acid Compound 89

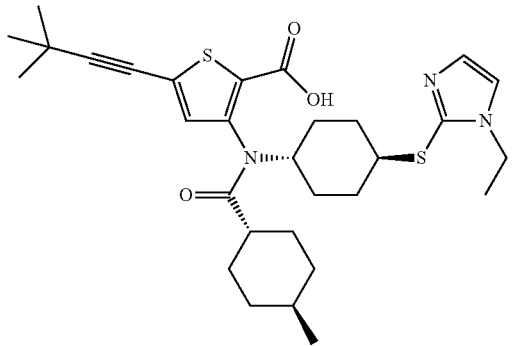

MS (m/z) 556 [M+H]⁺ HPLC retention time: 4.19 min (2-98% acetonitrile:water with 0.05% trifluoroacetic acid; 6 min run).

Example 90

Compound 90: 3-(N-(4-(4-Cyclopropyl-4H-1,2,4-triazol-3-ylthio)cyclohexyl)-4-methylcyclohexanecarboxamido)-5-(3,3-dimethylbut-1-ynyl)thiophene-2-carboxylic acid Compound 90

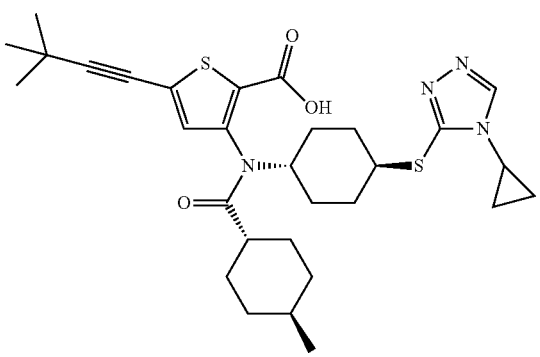

MS (m/z) 569 [M+H]⁺ HPLC retention time: 4.66 min (2-98% acetonitrile:water with 0.05% trifluoroacetic acid; 6 min run).

Example 91

Compound 91: 5-(3,3-Dimethylbut-1-ynyl)-3-(4-methyl-N-(4-(quinolin-2-ylthio)cyclohexyl)cyclohexanecarboxamido)thiophene-2-carboxylic acid Compound 91

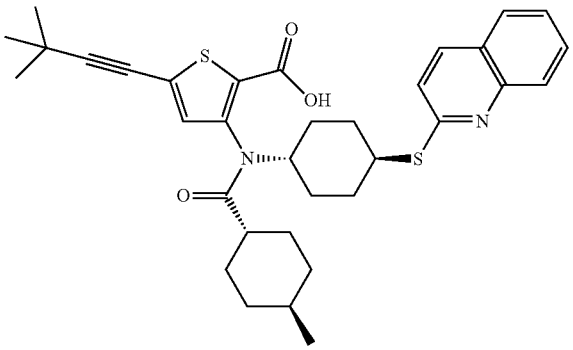

MS (m/z) 589 [M+H]+ HPLC retention time: 4.37 min (50-98% acetonitrile:water with 0.05% trifluoroacetic acid; 6 min run).

Example 92

Compound 92: 3-(N-(4-([1,2,4]-Triazolo[4,3-a]pyridin-3-ylthio)cyclohexyl)-4-methylcyclohexanecarboxamido)-5-(3,3-dimethylbut-1-ynyl)thiophene-2-carboxylic acid

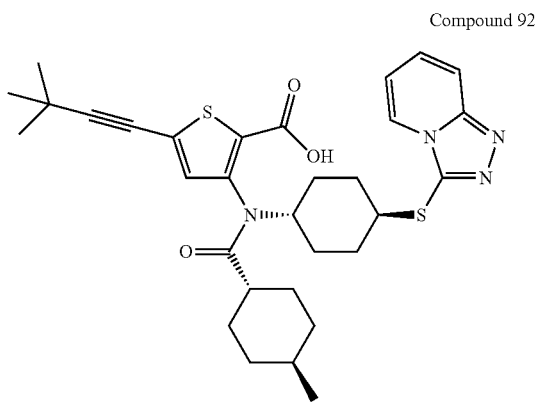 [SMILES: CC(C)(C)C#Cc1cc(N(C(=O)[C@H]2CC[C@H](C)CC2)[C@H]2CC[C@H](Sc3nnc4ccccn34)CC2)c(C(=O)O)s1]

Compound 92

MS (m/z) 579 [M+H]+ HPLC retention time: 2.44 min (50-98% acetonitrile:water with 0.05% trifluoroacetic acid; 6 min run).

Example 93

Compound 93: 5-(3,3-Dimethylbut-1-ynyl)-3-(4-methyl-N-(4-(thiophen-2-ylthio)cyclohexyl)cyclohexanecarboxamido)thiophene-2-carboxylic acid

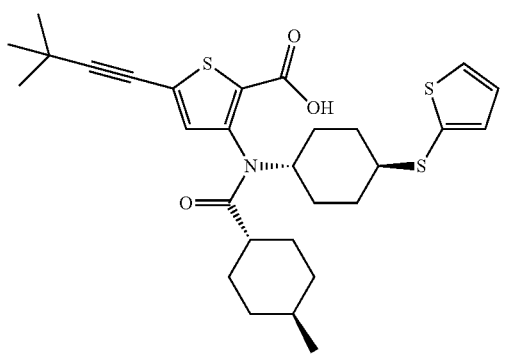

Compound 93

MS (m/z) 544 [M+H]+ HPLC retention time: 4.36 min (50-98% acetonitrile:water with 0.05% trifluoroacetic acid; 6 min run).

Example 94

Compound 94: 3-(N-(4-(1H-Imidazol-2-ylthio)cyclohexyl)-4-methylcyclohexanecarboxamido)-5-(3,3-dimethylbut-1-ynyl)thiophene-2-carboxylic acid

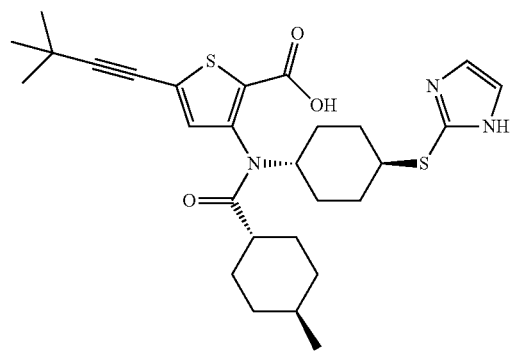

Compound 94

MS (m/z) 528 [M+H]+ HPLC retention time: 3.92 min (2-98% acetonitrile:water with 0.05% trifluoroacetic acid; 6 min run).

Example 95

Compound 95: 3-(N-(4-(5-Amino-2H-1,2,4-triazol-3-ylthio)cyclohexyl)-4-methylcyclohexanecarboxamido)-5-(3,3-dimethylbut-1-ynyl)thiophene-2-carboxylic acid

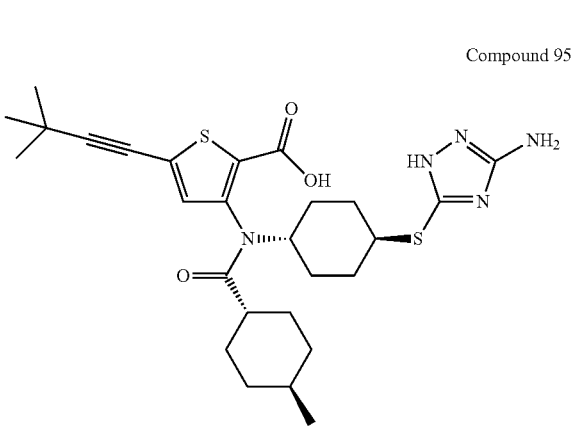 [SMILES: CC(C)(C)C#Cc1cc(N(C(=O)[C@H]2CC[C@H](C)CC2)[C@H]2CC[C@H](Sc3nc(N)n[nH]3)CC2)c(C(=O)O)s1]

Compound 95

MS (m/z) 544 [M+H]⁺ HPLC retention time: 3.99 min (2-98% acetonitrile:water with 0.05% trifluoroacetic acid; 6 min run).

Example 96

Compound 96: 3-(N-(4-(3H-1,2,3-Triazol-4-ylthio)cyclohexyl)-4-methylcyclohexanecarboxamido)-5-(3,3-dimethylbut-1-ynyl)thiophene-2-carboxylic acid

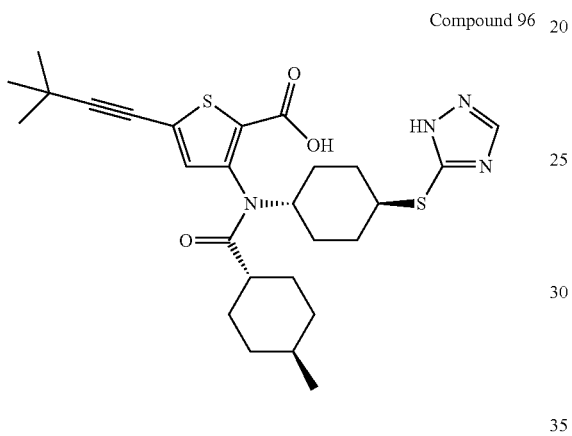

Compound 96

MS (m/z) 529 [M−H]⁺ HPLC retention time: 4.85 min (2-98% acetonitrile:water with 0.05% trifluoroacetic acid; 6 min run).

Example 97

Compound 97: 3-(N-(4-(1H-1,2,4-Triazol-3-ylthio)cyclohexyl)-4-methylcyclohexanecarboxamido)-5-(3,3-dimethylbut-1-ynyl)thiophene-2-carboxylic acid

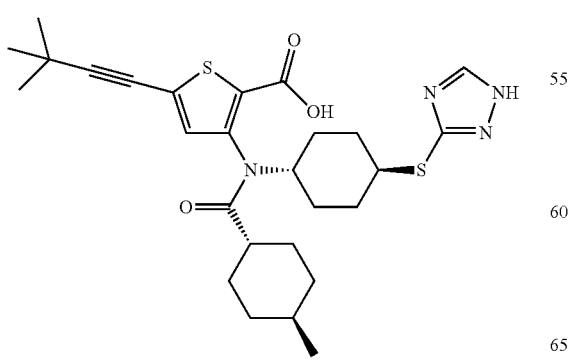

Compound 97

MS (m/z) 529 [M+H]⁺ HPLC retention time: 4.59 min (2-98% acetonitrile:water with 0.05% trifluoroacetic acid; 6 min run).

Example 98

Compound 98: 5-(3,3-Dimethylbut-1-ynyl)-3-(4-methyl-N-(4-(5-methyl-1,3,4-oxadiazol-2-ylthio)cyclohexyl)cyclohexanecarboxamido)thiophene-2-carboxylic acid

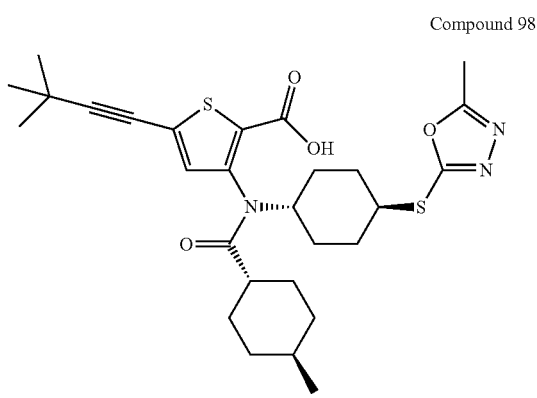 [SMILES: Cc1nnc(S[C@H]2CC[C@H](N(c3cc(C#CC(C)(C)C)sc3C(=O)O)C(=O)[C@H]3CC[C@H](C)CC3)CC2)o1]

Compound 98

MS (m/z) 540 [M+H]⁺ HPLC retention time: 5.21 min (2-98% acetonitrile:water with 0.05% trifluoroacetic acid; 6 min run).

Example 99

Compound 99: 5-(3,3-Dimethylbut-1-ynyl)-3-(4-methyl-N-(4-(pyridin-2-ylthio)cyclohexyl)cyclohexanecarboxamido)thiophene-2-carboxylic acid

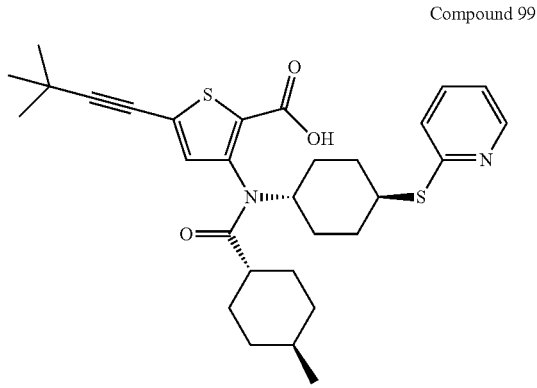 [SMILES: CC(C)(C)C#Cc1cc(N(C(=O)[C@H]2CC[C@H](C)CC2)[C@H]2CC[C@H](Sc3ccccn3)CC2)c(C(=O)O)s1]

Compound 99

MS (m/z) 539 [M+H]+ HPLC retention time: 5.23 min (2-98% acetonitrile:water with 0.05% trifluoroacetic acid; 6 min run).

Example 100

Compound 100: 5-(3,3-Dimethylbut-1-ynyl)-3-(4-methyl-N-(4-(pyrimidin-2-ylthio)cyclohexyl)cyclohexanecarboxamido)thiophene-2-carboxylic acid Compound 100

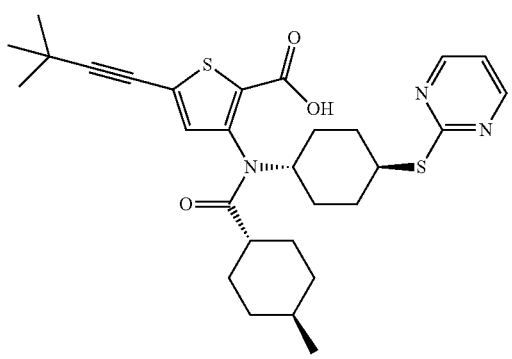

MS (m/z) 540 [M+H]+ HPLC retention time: 5.58 min (2-98% acetonitrile:water with 0.05% trifluoroacetic acid; 6 min run).

Example 101

Compound 101: 5-(3,3-Dimethylbut-1-ynyl)-3-(4-methyl-N-(4-(1-methyl-1H-tetrazol-5-ylthio)cyclohexyl)cyclohexanecarboxamido)thiophene-2-carboxylic acid Compound 101

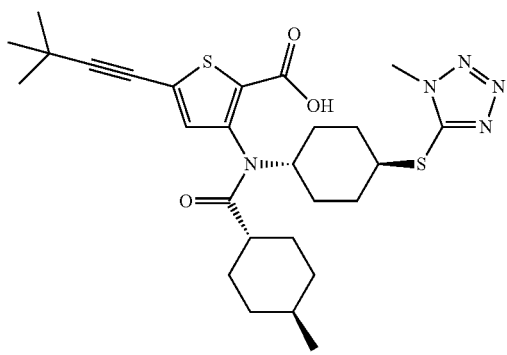

MS (m/z) 543 [M+H]+ HPLC retention time: 4.42 min (2-98% acetonitrile:water with 0.05% trifluoroacetic acid; 6 min run).

Example 102

Compound 102: 5-(3,3-Dimethylbut-1-ynyl)-3-(4-methyl-N-(4-(5-methyl-1,3,4-thiadiazol-2-ylthio)cyclohexyl)cyclohexanecarboxamido)thiophene-2-carboxylic acid Compound 102

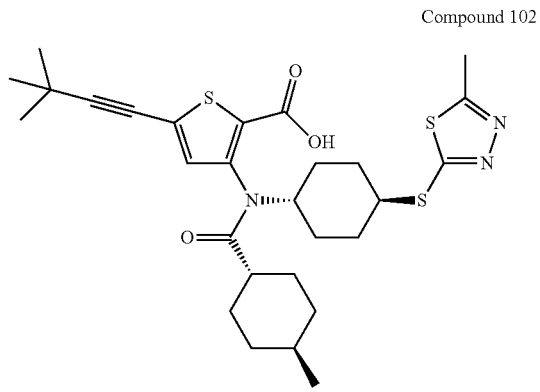 [SMILES: Cc1nnc(S[C@H]2CC[C@H](N(c3cc(C#CC(C)(C)C)sc3C(=O)O)C(=O)[C@H]3CC[C@H](C)CC3)CC2)s1]

MS (m/z) 560 [M+H]+ HPLC retention time: 5.42 min (2-98% acetonitrile:water with 0.05% trifluoroacetic acid; 6 min run).

Example 103

Compound 103: 5-(3,3-Dimethylbut-1-ynyl)-3-(4-methyl-N-(4-(5-methyl-1,3,4-thiadiazol-2-ylthio)cyclohexyl)cyclohexanecarboxamido)thiophene-2-carboxylic acid Compound 103

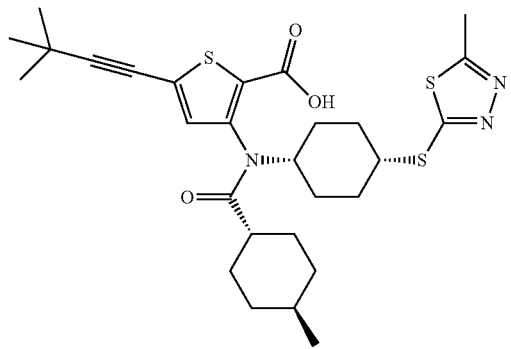

MS (m/z) 560 [M+H]+ HPLC retention time: 5.33 min (2-98% acetonitrile:water with 0.05% trifluoroacetic acid; 6 min run).

Example 104

Compound 104: 5-(3,3-Dimethylbut-1-ynyl)-3-(4-methyl-N-(4-(1-methyl-1H-tetrazol-5-ylthio)cyclohexyl)cyclohexanecarboxamido)thiophene-2-carboxylic acid

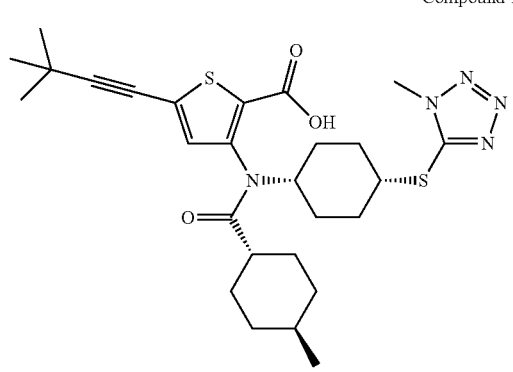

Compound 104

MS (m/z) 544 [M+H]+ HPLC retention time: 4.99 min (2-98% acetonitrile:water with 0.05% trifluoroacetic acid; 6 min run).

Example 105

Compound 105: 3-(N-(4-(1,3,4-Thiadiazol-2-ylthio)cyclohexyl)-4-methylcyclohexanecarboxamido)-5-(3,3-dimethylbut-1-ynyl)thiophene-2-carboxylic acid

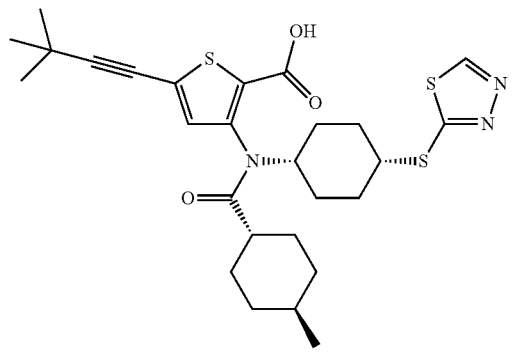

Compound 105

MS (m/z) 546.2 [M+H]+ HPLC retention time: 2.61 min (2-98% acetonitrile:water with 0.05% trifluoroacetic acid; 6 min run), Example 106

Compound 106: 5-(3,3-Dimethylbut-1-ynyl)-3-(4-methyl-N-(4-(thiazol-2-ylthio)cyclohexyl)cyclohexanecarboxamido)thiophene-2-carboxylic acid

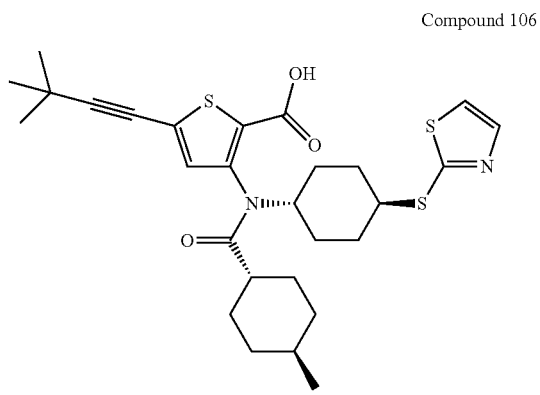 [SMILES: CC(C)(C)C#Cc1cc(N(C(=O)[C@H]2CC[C@H](C)CC2)[C@H]2CC[C@H](Sc3nccs3)CC2)c(C(=O)O)s1]

Compound 106

MS (m/z) 545.2 [M+H]+ HPLC retention time: 3.2 min (2-98% acetonitrile:water with 0.05% trifluoroacetic acid; 6 min run).

Example 107

Compound 107: 5-(3,3-Dimethylbut-1-ynyl)-3-(4-methyl-N-(4-(thiazol-2-ylthio)cyclohexyl)cyclohexanecarboxamido)thiophene-2-carboxylic acid

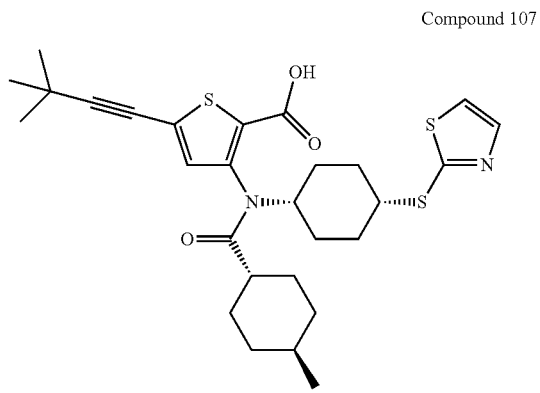 [SMILES: CC(C)(C)C#Cc1cc(N(C(=O)[C@H]2CC[C@H](C)CC2)[C@H]2CC[C@@H](Sc3nccs3)CC2)c(C(=O)O)s1]

Compound 107

Example 108

Compound 108: 5-(3,3-Dimethylbut-1-ynyl)-3-(4-methyl-N-(4-(pyrimidin-2-ylthio)cyclohexyl)cyclohexanecarboxamido)thiophene-2-carboxylic acid

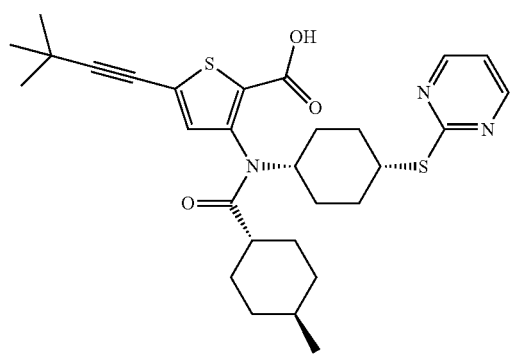

Compound 108

MS (m/z) 540.2 [M+H]+ HPLC retention time: 2.89 min (2-98% acetonitrile:water with 0.05% trifluoroacetic acid; 6 min run).

Examples 109-111 were synthesized from the corresponding thio compounds by oxidation with peracetic acid.

Example 109

Compound 109: 5-(3,3-Dimethylbut-1-ynyl)-3-(4-methyl-N-(4-(tetrahydro-2H-pyran-4-ylsulfonyl)cyclohexyl)cyclohexanecarboxamido)thiophene-2-carboxylic acid

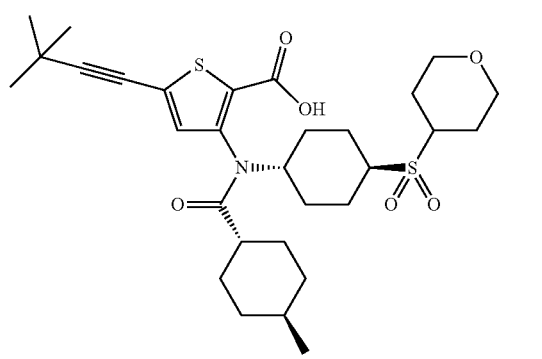

Compound 109

MS (m/z) 545.1 [M+H]+ HPLC retention time: 3.15 min (2-98% acetonitrile:water with 0.05% trifluoroacetic acid; 6 min run).

Example 110

Compound 110: 5-(3,3-Dimethylbut-1-ynyl)-3-(4-methyl-N-(4-(1-methyl-1H-tetrazol-5-ylsulfonyl)cyclohexyl)cyclohexanecarboxamido)thiophene-2-carboxylic acid

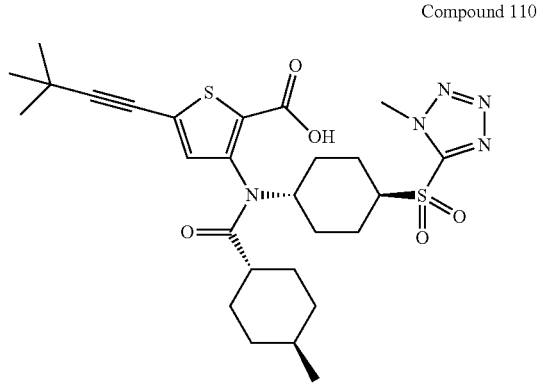 [SMILES: Cn1nnnc1S(=O)(=O)[C@H]1CC[C@H](N(c2cc(C#CC(C)(C)C)sc2C(=O)O)C(=O)[C@H]2CC[C@H](C)CC2)CC1]

Compound 110

MS (m/z) 558 [M+H]+ HPLC retention time: 4.09 min (50-98% acetonitrile:water with 0.05% trifluoroacetic acid; 6 min run).

MS (m/z) 576 [M+H]+ HPLC retention time: 4.95 min (2-98% acetonitrile:water with 0.05% trifluoroacetic acid; 6 min run).

Example 111

Compound 111: 5-(3,3-Dimethylbut-1-ynyl)-3-((1r,4S)-4-methyl-N-(4-((R)-1-methyl-1H-tetrazol-5-ylsulfinyl)cyclohexyl)cyclohexanecarboxamido)thiophene-2-carboxylic acid

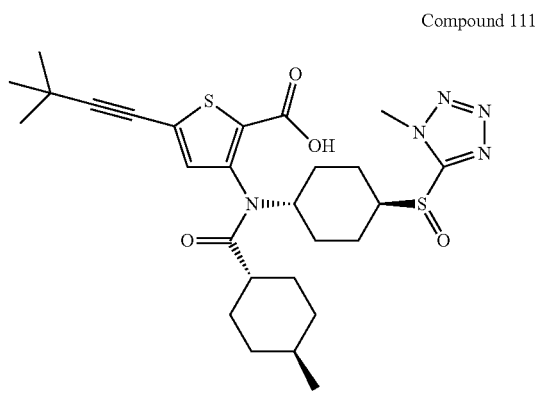 [SMILES: Cn1nnnc1S(=O)[C@H]1CC[C@H](N(c2cc(C#CC(C)(C)C)sc2C(=O)O)C(=O)[C@H]2CC[C@H](C)CC2)CC1]

Compound 111

MS (m/z) 560 [M+H]⁺ HPLC retention time: 4.73 min (2-98% acetonitrile:water with 0.05% trifluoroacetic acid; 6 min run).

Example 138

Compound 138: 5-(3,3-dimethyl-but-1-ynyl)-3-{(4-methyl-cyclohexanecarbonyl)-[3-(pyridin-3-yloxy)-ethyl]-amino}-thiophene-2-carboxylic acid

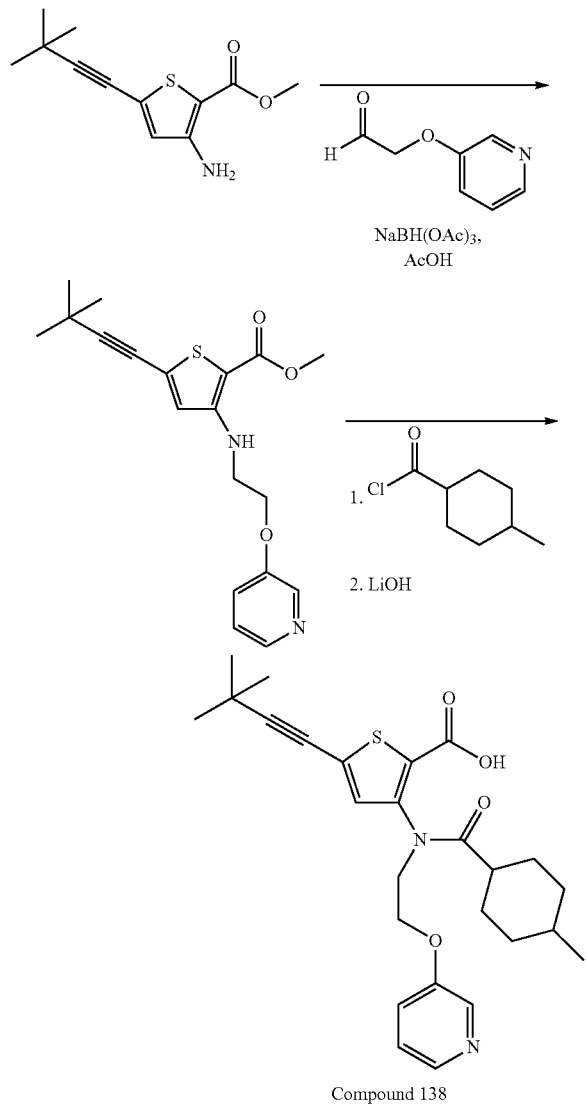

Compound 138

A mixture of 3-amino-5-(3,3-dimethyl-but-1-ynyl)-thiophene-2-carboxylic acid methyl ester (100 mg, 0.42 mmol), (pyridin-3-yloxy)-acetaldehyde (96 mg, 0.7 mmol), AcOH (300 mg, 5 mmol) in DCE (2 mL) was treated with NaBH(OAc)₃ (179 mg, 0.9 mmol) for 16 h. The reaction was quenched with water (10 mL) and extracted with EtOAc. The crude material was then dissolved in pyridine (5 mL) and treated with neat trans-4-methyl-cyclohexanecarbonyl chloride (0.132 g, 0.825 mmol). The reaction was heated for 16 h at 85° C. and quenched with saturated ammonium chloride solution. The reaction mixture was diluted with EtOAc, washed with water, brine, dried over sodium sulfate, filtered and concentrated. The crude material was then dissolved in a 3:2:1 mixture of THF:MeOH:water (5 mL), treated with lithium hydroxide monohydrate (0.69 g, 1.65 mmol) and heated to 60° C. for 1 hour. The organic volatiles were evaporated under reduced pressure and the crude material was purified by HPLC to afford the title compound. MS (m/z): 470.0 [M+H]⁻; HPLC retention time: 3.36 min (2-98% acetonitrile:water with 0.05% trifluoroacetic acid).

Example 139

Compound 139: 5-(3,3-dimethyl-but-1-ynyl)-3-{(4-methyl-cyclohexanecarbonyl)-[3-(pyridin-2-yloxy)-ethyl]-amino}-thiophene-2-carboxylic acid

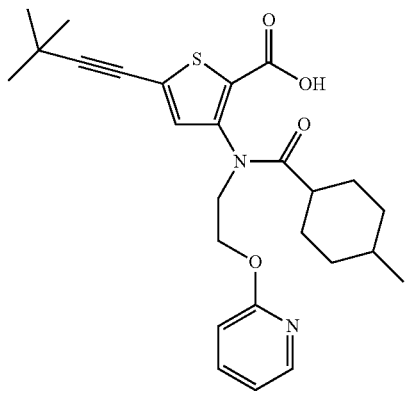

Compound 139

The title compound was synthesized in a manner analogous to Example 138, using (pyridin-2-yloxy)-acetaldehyde in place of (pyridin-3-yloxy)-acetaldehyde: MS (m/z): 468.9 [M−H]⁺; HPLC retention time: 4.47 min (2-98% acetonitrile: water with 0.05% trifluoroacetic acid) 30 min run.

Example 143

Compound 143: 5-(3,3-dimethyl-but-1-ynyl)-3-{(trans-4-methyl-cyclohexanecarbonyl)-[1-(S)-methyl-3-(pyrimidin-5-yloxy)-propyl]-amino}-thiophene-2-carboxylic acid

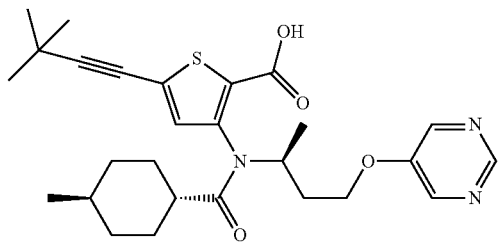

Compound 143

The 5-(3,3-dimethyl-but-1-ynyl)-3-[(3-hydroxy-1-(S)-methyl-propyl)-(trans-4-methyl-cyclohexanecarbonyl)-amino]-thiophene-2-carboxylic acid TFA salt (100 mg, 0.239 mmol) and 5-chloro-pyrimidine (137 mg, 1.194 mmol) were dissolved in DMSO (2 mL). To this solution tBuOK (107 mg, 0.956 mmol) was added in one portion at rt. The reaction was allowed to stir at rt for 1 h and then heated to 60° C. for 1.5 h. Additional tBuOK (50 mg) and 5-chloro-pyrimidine (69 mg) were added and the reaction was run at 60° C. for another 1 h. The reaction was then heated to 100° C. for another 1 h. Additional tBuOK (50 mg) and 5-chloro-pyrimidine (69 mg) were added and the reaction was run at 100° C. overnight. The reaction was cooled to rt and quenched with a 20% (v/v) solution of acetic acid in water. The reaction was diluted with MeOH and 5-(3,3-dimethyl-but-1-ynyl)-3-{(trans-4-methyl-cyclohexanecarbonyl)-[1-(S)-methyl-3-(pyrimidin-5-yloxy)-propyl]-amino}-thiophene-2-carboxylic acid (4 mg, 2.7%) was isolated by reverse phase HPLC as the TFA salt.

LC/MS (m/z): 497.88 [M+1]
Retention time: 2.56 min
LC: Thermo Electron Surveyor HPLC
MS: Finnigan LCQ Advantage MAX Mass Spectrometer
Column: Phenomenex Polar RP 30 mm×4.6 mm
Solvents: Acetonitrile with 0.1% formic acid, Water with 0.1% formic acid
Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN Example 144

Compound 144: 5-(3,3-dimethyl-but-1-ynyl)-3-[[3-(2-ethoxy-7-methoxy-8-methyl-quinolin-4-yloxy)-1-(S)-methyl-propyl]-(4-methyl-cyclohexanecarbonyl)-amino]-thiophene-2-carboxylic acid

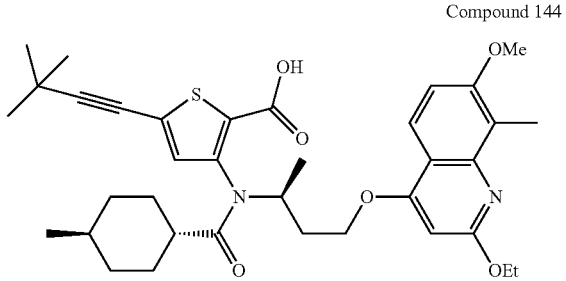 [SMILES: CCOc1cc(OCC[C@H](C)N(c2cc(C#CC(C)(C)C)sc2C(=O)O)C(=O)[C@H]2CC[C@H](C)CC2)c2ccc(OC)c(C)c2n1]

Compound 144

The 5-(3,3-dimethyl-but-1-ynyl)-3-[(3-hydroxy-1-(S)-methyl-propyl)-(trans-4-methyl-cyclohexanecarbonyl)-amino]-thiophene-2-carboxylic acid TFA salt (100 mg, 0.239 mmol) and 4-chloro-7-methoxy-2-ethoxy-8-methyl-quinoline (301 mg, 1.195 mmol) were dissolved in DMSO (3 mL). To this solution tBuOK (107 mg, 0.956 mmol) was added in one portion at rt. The reaction was run at it for 15 min and then cooled in an ice bath. The reaction was quenched with a 20% (v/v) solution of acetic acid in water. The reaction was partitioned between water and EtOAc. The phases were separated and the organic phase was extracted with brine. The organic phase was extracted with brine and then concentrated. The residue was suspended in MeOH and remaining solids were removed by filtration. The filtrate was concentrated, suspended in MeOH and filtered again. The filtrate was clarified with a small amount of EtOAc and 5-(3,3-dimethyl-but-1-ynyl)-3-[[3-(2-ethoxy-7-methoxy-8-methyl-quinolin-4-yloxy)-1-(S)-methyl-propyl]-(4-methyl-cyclohexanecarbonyl)-amino]-thiophene-2-carboxylic acid (29 mg, 16%) was isolated as the TFA salt by reverse phase HPLC.

LC/MS (m/z): 635.00 [M+1]
Retention time: 2.73 min
LC: Thermo Electron Surveyor HPLC
MS: Finnigan LCQ Advantage MAX Mass Spectrometer
Column: Phenomenex Polar RP 30 mm×4.6 mm
Solvents: Acetonitrile with 0.1% formic acid, Water with 0.1% formic acid
Gradient: 0 min-0.1 min 5% ACN, 0.1 min-1.95 min 5%-100% ACN, 1.95 min-3.5 min 100% ACN, 3.5 min-3.55 min 100%-5% ACN, 3.55 min-4 min 5% ACN Example 145

Compound 145: 5-(3,3-Dimethyl-but-1-ynyl)-3-{(trans-4-methyl-cyclohexanecarbonyl)-[cis-3-(pyridin-3-yloxy-N-oxide)-cyclobutyl]-amino}-thiophene-2-carboxylic acid

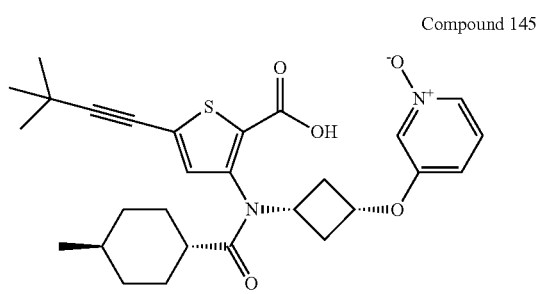

Compound 145

Prepared in the same manner as Example 20 by replacing 3-fluoropyridine with 3-chloropyridine-1-oxide. MS (m/z): 511.1 [M+H]$^+$; HPLC retention time: 4.00 min.

Example 146

Compound 146: 5-(3,3-Dimethylbut-1-ynyl)-3-(4-methyl-N-(3-(pyridin-2-yloxy)cyclobutyl)cyclohexanecarboxamido)thiophene-2-carboxylic acid

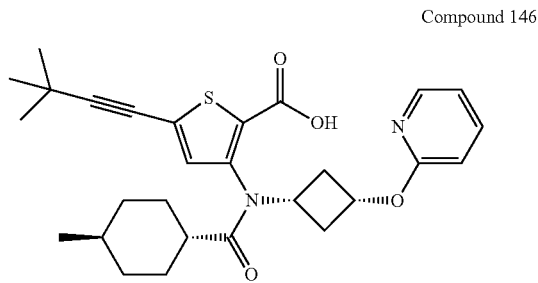 [SMILES: CC(C)(C)C#Cc1cc(N(C(=O)[C@H]2CC[C@H](C)CC2)[C@H]2C[C@@H](Oc3ccccn3)C2)c(C(=O)O)s1]

Compound 146

Prepared in the same manner as Example 20 by replacing 3-fluoropyridine with 2-fluoropyridine. MS (m/z): 495.1 [M+H]$^+$; HPLC retention time: 4.57 min.

Example 147

Compound 147: 5-(3,3-Dimethyl-but-1-ynyl)-3-{(trans-4-methyl-cyclohexanecarbonyl)-[trans-4-(2-oxo-1,2-dihydro-pyrimidin-4-yloxy)-cyclohexyl]-amino}-thiophene-2-carboxylic acid

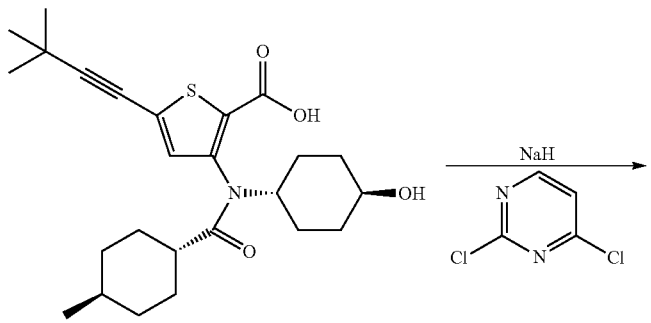
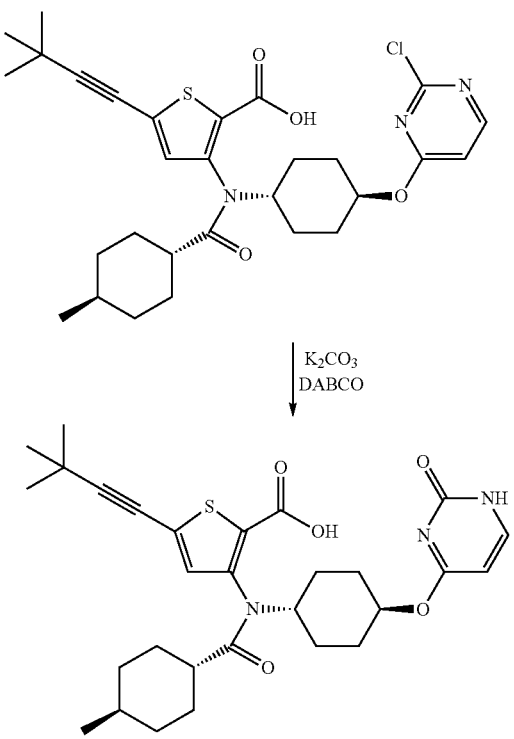

5-(3,3-Dimethyl-but-1-ynyl)-3-[(trans-4-hydroxy-cyclohexyl)-(trans-4-methyl-cyclohexanecarbonyl)-amino]-thiophene-2-carboxylic acid (211 mg, 0.46 mmol) in DMF (2 mL) at 0 deg C. was treated with sodium hydride (110 mg, 2.8 mmol, 60% oil dispersion) in portions. The mixture was stirred for 30 minutes at 0 deg C. and a solution of 2,4-dichloropyrimidine (210 mg, 1.4 mmol) in DMF (1 mL) was added dropwise. The reaction mixture was allowed to warm and stir at room temperature. After completion, ethyl acetate (2-3 mL) was added and the mixture was carefully quenched with citric acid (10% aqueous solution, 2-3 mL). Water was added and the mixture was extracted with ethyl acetate (2×30 mL). The combined organic layers were dried over magnesium sulfate, filtered and concentrated. The residue was passed through a plug of silica (0-5% MeOH:DCM eluent) and concentrated to yield 162 mg of 5-(3,3-dimethyl-but-1-ynyl)-3-{(trans-4-methyl-cyclohexanecarbonyl)-[trans-4-(2-chloro-pyrimidin-4-yloxy)-cyclohexyl]-amino}-thiophene-2-carboxylic acid as an impure black oil which was carried on without further purification.

A crude sample of (3,3-dimethyl-but-1-ynyl)-3-{(trans-4-methyl-cyclohexanecarbonyl)-[trans-4-(2-chloro-pyrimidin-4-yloxy)-cyclohexyl]-amino}-thiophene-2-carboxylic acid (162 mg, 0.29 mmol) was dissolved in a 1:1 mixture of dioxane:water (8 mL) and treated with potassium carbonate (120 mg, 0.87 mmol) and DABCO (27 mg, 0.24 mmol). The mixture was heated at 70 deg C. for 4 hours and then partitioned between water and ethyl acetate. The aqueous phase was neutralized by addition of aqueous citric acid and extracted with ethyl acetate (3×30 mL). The combined organic layers were dried over magnesium sulfate, filtered and concentrated. The residue was purified by HPLC (Gemini column; 25% acetonitrile:water, 2 min; 25-100% acetonitrile:water, 16 min; 100% acetonitrile, 3 min; both solvents containing 0.1% trifluoroacetic acid). This resulted in 22.6 mg (8% yield over 2 steps) of the title compound as a white powder (TFA salt): MS (m/z): 537.9 [M−H]⁻; HPLC retention time: 4.14 min (2-98% acetonitrile:water with 0.05% trifluoroacetic acid).

Example 148

Compound 148: 5-(3,3-Dimethylbut-1-ynyl)-3-(N-(4-(5-ethylpyrimidin-2-yloxy)cyclohexyl)-4-methyl-cyclohexanecarboxamido)thiophene-2-carboxylic acid

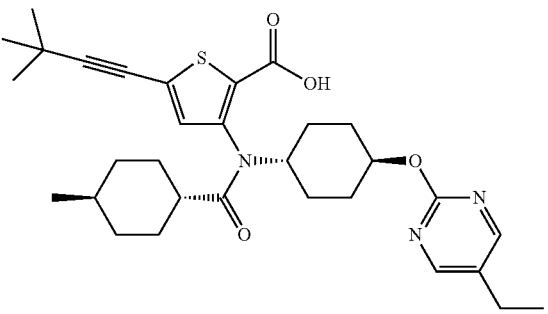

Compound 148

Prepared in the same manner as Example 1 by replacing 2-fluoropyridine with 2-chloro-5-ethylpyrimidine. MS (m/z): 552.1 [M+H]+; HPLC retention time: 5.07 min.

Example 149

Compound 149: 5-(3,3-Dimethylbut-1-ynyl)-3-(4-methyl-N-(4-(2-(pyrrolidin-1-yl)pyridin-3-yloxy)cyclohexyl)cyclohexanecarboxamido)thiophene-2-carboxylic acid Compound 149

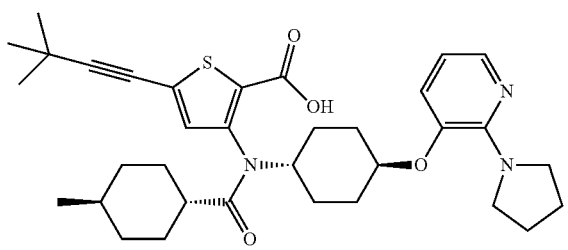

Prepared in the same manner as Example 1 by replacing 2-fluoropyridine with 3-fluoro-2-pyrrolidin-1-yl-pyridine. MS (m/z): 592.2 [M+H]+; HPLC retention time: 3.76 min.

Example 150

Compound 150: 5-(3,3-Dimethylbut-1-ynyl)-3-(4-methyl-N-(4-(6-(pyrrolidin-1-yl)pyrimidin-4-yloxy)cyclohexyl)cyclohexanecarboxamido)thiophene-2-carboxylic acid Compound 150

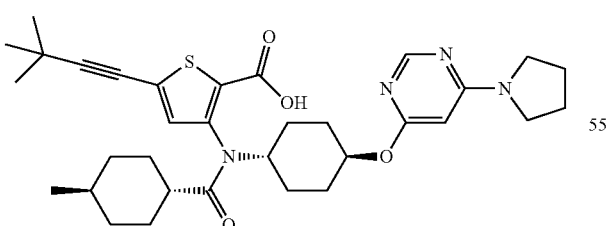

Prepared in the same manner as Example 1 by replacing 2-fluoropyridine with 4-chloro-6-pyrrolidin-1-yl-pyrimidine. MS (m/z): 593.0 [M+H]+; HPLC retention time: 3.73 min.

Example 151

Compound 151: 3-(N-(4-(4-(Dimethylamino)-5-fluoropyrimidin-2-yloxy)cyclohexyl)-4-methylcyclohexanecarboxamido)-5-(3,3-dimethylbut-1-ynyl)thiophene-2-carboxylic acid Compound 151

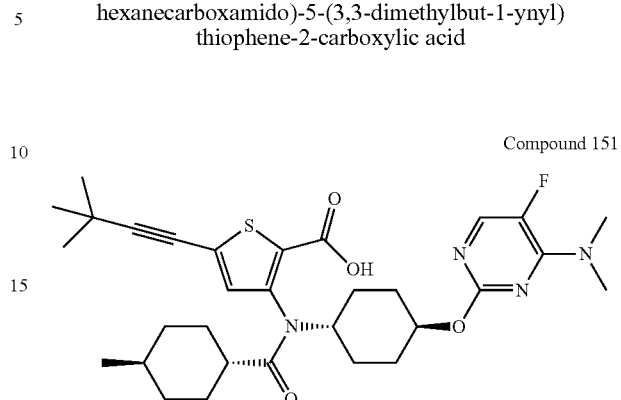

Prepared in the same manner as Example 1 by replacing 2-fluoropyridine with (2-chloro-5-fluoro-pyrimidin-4-yl)-dimethylamine. MS (m/z): 585.0 [M+H]+; HPLC retention time: 3.70 min.

Example 152

Compound 152: 5-(3,3-Dimethylbut-1-ynyl)-3-(4-methyl-N-(4-(6-(pyrrolidin-1-yl)pyridin-2-yloxy)cyclohexyl)cyclohexanecarboxamido)thiophene-2-carboxylic acid Compound 152

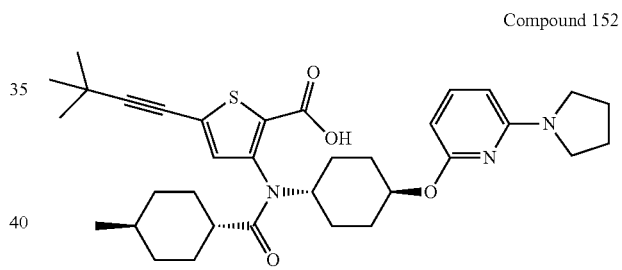

Prepared in the same manner as Example 1 by replacing 2-fluoropyridine with 2-bromo-6-pyrrolidin-1-yl-pyridine. MS (m/z): 592.1 [M+H]+; HPLC retention time: 4.04 min.

Example 153

Compound 153: 5-(3,3-Dimethylbut-1-ynyl)-3-(4-methyl-N-(4-(6-(pyrrolidin-1-yl)pyrazin-2-yloxy)cyclohexyl)cyclohexanecarboxamido)thiophene-2-carboxylic acid Compound 153

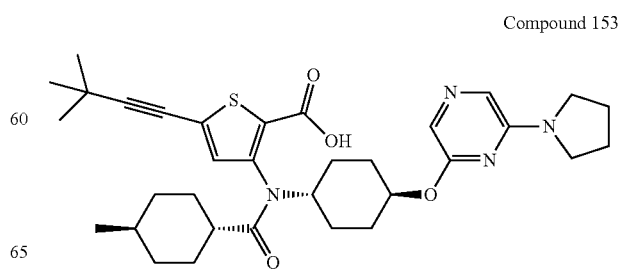

Prepared in the same manner as Example 1 by replacing 2-fluoropyridine with 2-chloro-6-pyrrolidin-1-yl-pyrazine. MS (m/z): 593.0 [M+H]$^+$; HPLC retention time: 4.40 min.

Example 154

Compound 154: 5-(3,3-Dimethylbut-1-ynyl)-3-(4-methyl-N-(4-(3-methyl-1,2,4-thiadiazol-5-yloxy)cyclohexyl)cyclohexanecarboxamido)thiophene-2-carboxylic acid Compound 154

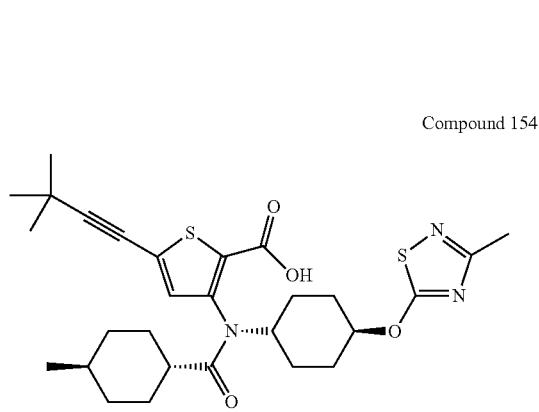

Prepared in the same manner as Example 1 by replacing 2-fluoropyridine with 5-chloro-3-methyl-[1,2,4]-thiadiazole. MS (m/z): 541.8 [M−H]$^-$; HPLC retention time: 5.10 min.

Synthesis of 2-Chloro-4-(pyrrolidin-1-ylmethyl)-thiazole

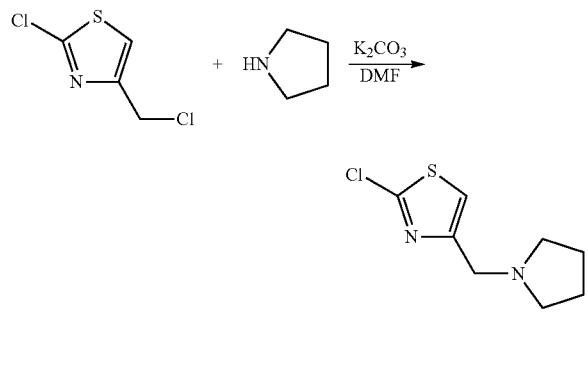

2-Chloro-4-chloromethyl-thiazole (610 mg, 3.6 mmol), pyrrolidine (0.4 mL, 4.8 mmol), and potassium carbonate (1.05 g, 7.6 mmol) were stirred in DMF (6 mL) for 5 hours. After completion, the reaction mixture was partitioned between ethyl acetate and water. The aqueous phase was thrice extracted with ethyl acetate and the combined organic phases were washed with brine, dried over magnesium sulfate, filtered and concentrated. The residue was purified by silica gel chromatography (0-5% [8:1 EtOH:NH$_4$OH$_{(aq)}$]/DCM). This resulted in 457 mg (63% yield) of the title compound as a white solid.

Example 155

Compound 155: 5-(3,3-Dimethylbut-1-ynyl)-3-(4-methyl-N-(4-(4-(pyrrolidin-1-ylmethyl)thiazol-2-yloxy)cyclohexyl)cyclohexanecarboxamido)thiophene-2-carboxylic acid Compound 155

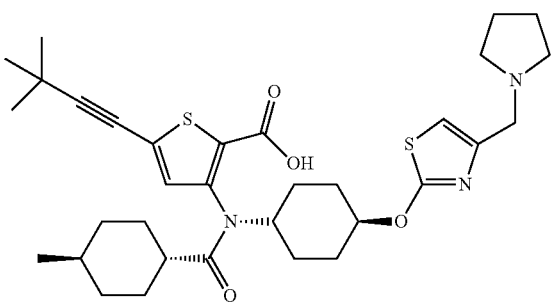

Prepared in the same manner as Example 1 by replacing 2-fluoropyridine with 2-chloro-4-(pyrrolidin-1-ylmethyl)-thiazole. MS (m/z): 612.1 [M+H]$^+$; HPLC retention time: 3.66 min.

Example 156

Compound 156: 3-(N-(4-(4-((Dimethylamino)methyl)thiazol-2-yloxy)cyclohexyl)-4-methylcyclohexanecarboxamido)-5-(3,3-dimethylbut-1-ynyl)thiophene-2-carboxylic acid Compound 156

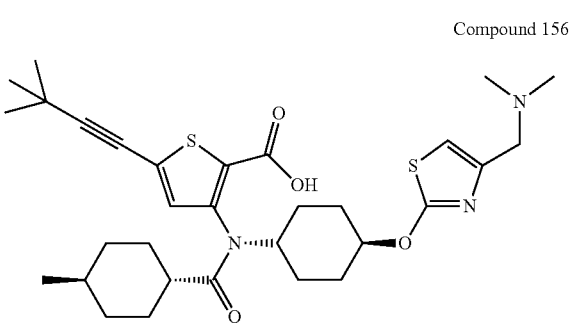

Prepared in the same manner as Example 1 by replacing 2-fluoropyridine with 2-chloro-4-(dimethylaminomethyl)-thiazole (prepared in the same manner as 2-chloro-4-(pyrrolidin-1-ylmethyl)-thiazole by substituting dimethylamine for pyrrolidine). MS (m/z): 586.1 [M+H]$^+$; HPLC retention time: 3.59 min.

Example 157

Compound 157: 5-(3,3-Dimethylbut-1-ynyl)-3-(4-methyl-N-(4-(pyridin-4-yloxy-N-oxide)cyclohexyl)cyclohexanecarboxamido)thiophene-2-carboxylic acid

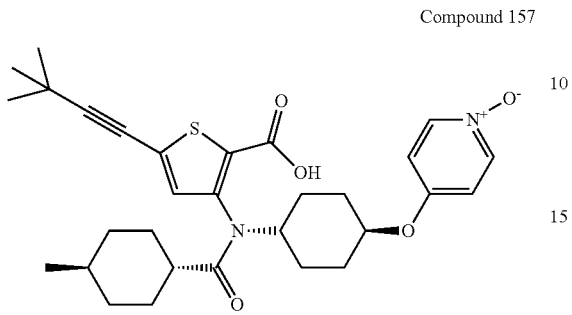

Compound 157

Prepared in the same manner as Example 1 by replacing 2-fluoropyridine with 4-nitro-pyridine-1-oxide. MS (m/z): 539.0 [M+H]$^+$; HPLC retention time: 3.73 min.

Example 158

Compound 158: 3-(N-(4-(6-(Dimethylamino)pyrimidin-4-yloxy)cyclohexyl)-4-methylcyclohexanecarboxamido)-5-(3,3-dimethylbut-1-ynyl)thiophene-2-carboxylic acid

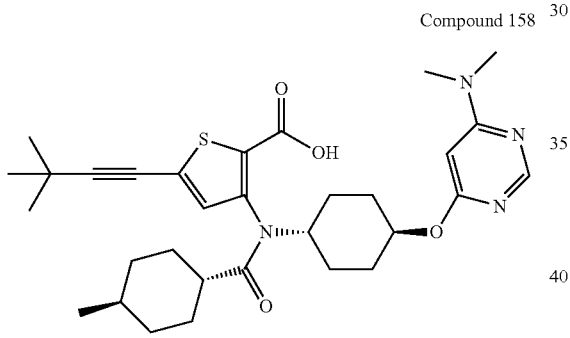

Compound 158

Prepared in the same manner as Example 1 by replacing 2-fluoropyridine with (6-chloro-pyrimidin-4-yl)-dimethylamine. MS (m/z): 566.9 [M+H]$^+$; HPLC retention time: 3.67 min.

Example 159

Compound 159: 5-(3,3-Dimethylbut-1-ynyl)-3-(4-methyl-N-(4-(6-(pyrrolidin-1-yl)pyridazin-3-yloxy)cyclohexyl)cyclohexanecarboxamido)thiophene-2-carboxylic acid

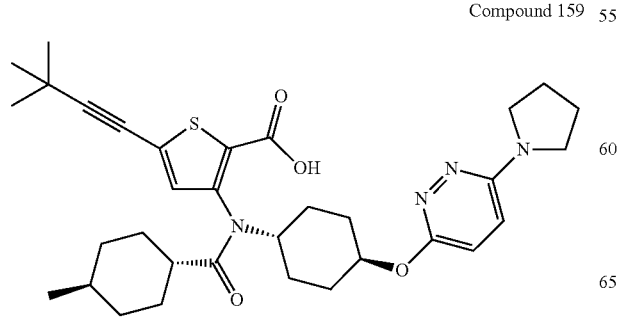

Compound 159

Prepared in the same manner as Example 1 by replacing 2-fluoropyridine with 3-chloro-6-pyrrolidin-1-yl-pyridazine. MS (m/z): 592.9 [M+H]$^+$; HPLC retention time: 3.59 min.

Example 160

Compound 160: 3-(N-(4-(6-(Dimethylamino)pyridazin-3-yloxy)cyclohexyl)-4-methylcyclohexanecarboxamido)-5-(3,3-dimethylbut-1-ynyl)thiophene-2-carboxylic acid

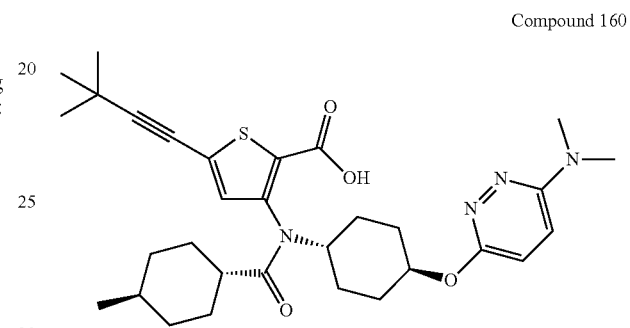

Compound 160

Prepared in the same manner as Example 1 by replacing 2-fluoropyridine with (6-chloro-pyridazin-3-yl)-dimethylamine. MS (m/z): 564.9 [M−H]$^-$; HPLC retention time: 3.51 min.

Example 161

Compound 161: 5-(3,3-Dimethylbut-1-ynyl)-3-(4-methyl-N-(4-(3-(pyrrolidin-1-ylmethyl)-1,2,4-thiadiazol-5-yloxy)cyclohexyl)cyclohexanecarboxamido)thiophene-2-carboxylic acid

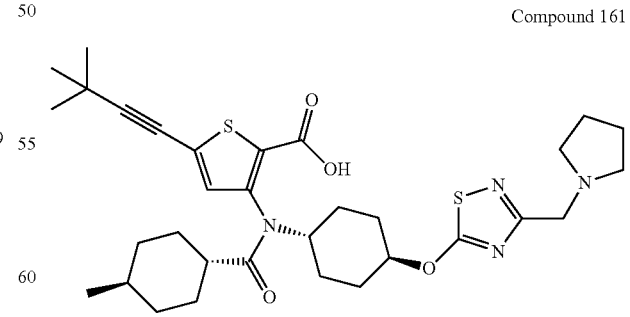

Compound 161

Prepared in the same manner as Example 1 by replacing 2-fluoropyridine with 5-chloro-3-(pyrrolidin-1-ylmethyl)[1,2,4]-thiadiazole MS (m/z): 613.1 [M+H]$^+$; HPLC retention time: 4.88 min.

Example 162

Compound 162: 5-(3,3-Dimethylbut-1-ynyl)-3-(4-methyl-N-(4-(pyrimidin-5-yloxy)cyclohexyl)cyclohexanecarboxamido)thiophene-2-carboxylic acid Compound 162

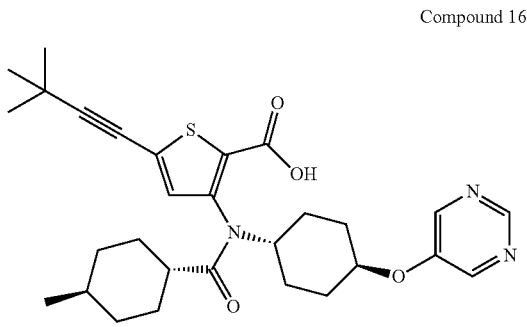

Prepared in the same manner as Example 1 by replacing 2-fluoropyridine with 5-chloro-pyrimidine. MS (m/z): 524.0 [M+H]⁺; HPLC retention time: 4.58 min.

Example 163

Compound 163: 5-(3,3-Dimethylbut-1-ynyl)-3-(4-methyl-N-(4-(pyrimidin-4-yloxy)cyclohexyl)cyclohexanecarboxamido)thiophene-2-carboxylic acid Compound 163

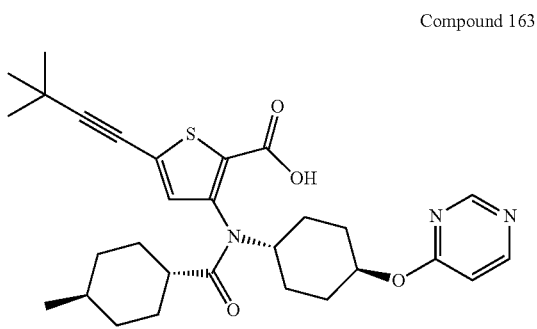 [SMILES: CC(C)(C)C#Cc1cc(N(C(=O)[C@H]2CC[C@H](C)CC2)[C@H]2CC[C@H](Oc3ccncn3)CC2)c(C(=O)O)s1]

Prepared in the same manner as Example 1 by replacing 2-fluoropyridine with 4-chloro-pyrimidine. MS (m/z): 529.1 [M−H]⁻; HPLC retention time: 4.14 min.

Example 166

Compound 166: Sodium 5-(3,3-dimethylbut-1-ynyl)-3-(4-methyl-N-(4-(4-(pyrrolidine-1-carbonyl)pyridin-2-yloxy)cyclohexyl)cyclohexanecarboxamido)thiophene-2-carboxylate

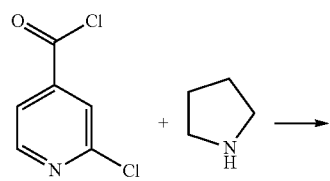

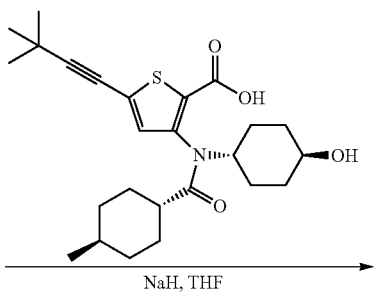

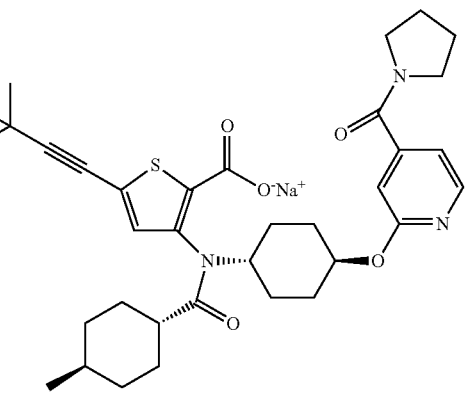

Compound 166

Neat 2-chloro-isonicotinoyl chloride (500 mg, 2.84 mmol) was added dropwise to a solution of pyrrolidine (1.18 mL, 14.2 mmol) in dichloromethane (20 mL) at 0° C. After 30 min the ice bath was removed and the reaction was allowed to warm to room temperature. The reaction mixture was evaporated to dryness and the residue was partitioned between ethyl ether and sat. NaHCO₃. The aqueous layer was separated, extracted with ethyl ether and the combined organic layers were washed with brine, dried over Na₂SO₄ and concentrated to provide the product as a viscous oil (614 mg, quantitative). Use in the next step without further purification.

NaH (50 mg of a 60% oil dispersion, 1.14 mmol) was added in portions to a solution of 5-(3,3-dimethyl-but-1-ynyl)-3-[(4-hydroxy-cyclohexyl)-(4-methyl-cyclohexanecarbonyl)-amino]-thiophene-2-carboxylic acid (128 mg, 0.287 mmol) and (2-chloro-pyridin-4-yl)-pyrrolidin-1-yl-methanone from the previous step (300 mg, 1.42 mmol) in THF (5.0 mL) at 0° C. After 5 min the reaction was warmed to room temperature and then heated at 85° C. overnight. The reaction was cooled, aqueous NaOH (0.5 mL of a 1.0 N solution) was added and the reaction evaporated to dryness to give a solid residue. The solid was suspended in ethyl ether and sonicated for several minutes. The ether layer was removed to give an orange solid that was dried under vacuum and purified by column chromatography on reverse phase C₁₈ silica gel (100% water to 20% acetonitrile/water). Fractions containing product were pooled and lyophilized to give the desired product as a colorless solid (30 mg, 16%). MS (m/z): 618.0 [M−H]⁻; HPLC retention time: 6.43 min (2-98% acetonitrile:water with 0.05% trifluoroacetic acid).

Example 167

Compound 167: Sodium 3-(N-(4-(4-((1-methylpiperidin-4-yl)carbamoyl)pyridin-2-yloxy)cyclohexyl)-4-methylcyclohexanecarboxamido)-5-(3,3-dimethylbut-1-ynyl)thiophene-2-carboxylate

Example 168

Compound 168: Sodium 3-(N-(4-(4-(azetidine-1-carbonyl)pyridin-2-yloxy)cyclohexyl)-4-methylcyclohexanecarboxamido)-5-(3,3-dimethylbut-1-ynyl)thiophene-2-carboxylate

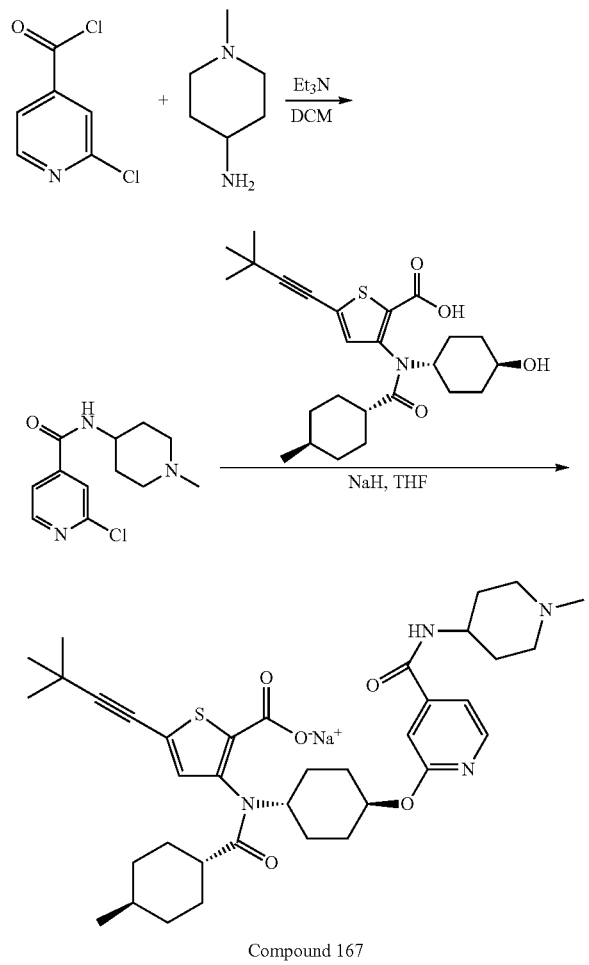

Compound 167

Compound 168

Neat 2-chloro-isonicotinoyl chloride (1.0 g, 5.69 mmol) was added dropwise to a solution of 1-methyl-piperidin-4-ylamine (1.0 g, 8.75 mmol) and triethylamine (2.4 mL, 17.22 mmol) in dichloromethane (25 mL) at 0° C. After 1 h the reaction was evaporated to dryness and partitioned between ethyl ether and sat. NaHCO₃. The aqueous layer was separated, extracted with ethyl ether and the combined organic layers were washed with brine, dried over Na₂SO₄ and concentrated to give the product as a pale yellow solid (190 mg, 13%). Used in the next step without further purification.

The title compound (23 mg, 20%) was synthesized in a manner analogous to Example 166 using 2-chloro-N-(1-methyl-piperidin-4-yl)-isonicotinamide from the previous step in place of (2-chloro-pyridin-4-yl)-pyrrolidin-1-yl-methasone: MS (m/z): 663.1 [M+H]+; HPLC retention time 5.59 min (2-98% acetonitrile:water with 0.05% trifluoroacetic acid).

Azetidine (800 mg, 14.01 mmol) was added dropwise to a solution of 2-chloro-isonicotinoyl chloride (500 mg, 2.84 mmol) in dichloromethane (20 mL) at 0° C. The reaction was allowed to slowly warm to room temperature over a 90 min period and then evaporated to dryness. The residue was partitioned between ethyl ether and sat. NaHCO₃. The aqueous layer was separated, extracted with ethyl ether and the combined organic layers were washed with brine, dried over Na₂SO₄ and concentrated to give the product as a colorless solid (291 mg, 55%). Use in the next step without further purification.

NaH (60 mg of a 60% oil dispersion, 1.50 mmol) was added in portions to a solution of 5-(3,3-dimethyl-but-1-ynyl)-3-[(4-hydroxy-cyclohexyl)-(4-methyl-cyclohexanecarbonyl)-amino]-thiophene-2-carboxylic acid (130 mg, 0.291 mmol) and azetidin-1-yl-(2-chloro-pyridin-4-yl)-methanone from the previous step (290 mg, 1.47 mmol) in DMF (3.0 mL) at 0° C. After 30 min the reaction was warmed to room temperature and then heated at 85° C. for 3.5 h. The reaction was cooled, aqueous NaOH (0.5 mL of a 1.0 N solution) was added and the reaction evaporated to dryness to give a solid residue. The solid was purified by column chromatography on reverse phase C₁₈ silica gel (100% water to 20% acetonitrile/water). Fractions containing product were pooled and lyophilized to give the desired product as a colorless solid (140 mg, 77%). HPLC retention time: 6.41 min (2-98% acetonitrile:water with 0.05% trifluoroacetic acid).

Example 169

Compound 169: Sodium 3-(N-(4-(4-(3-(dimethylamino)pyrrolidine-1-carbonyl)pyridin-2-yloxy)cyclohexyl)-4-methylcyclohexanecarboxamido)-5-(3,3-dimethylbut-1-ynyl)thiophene-2-carboxylate

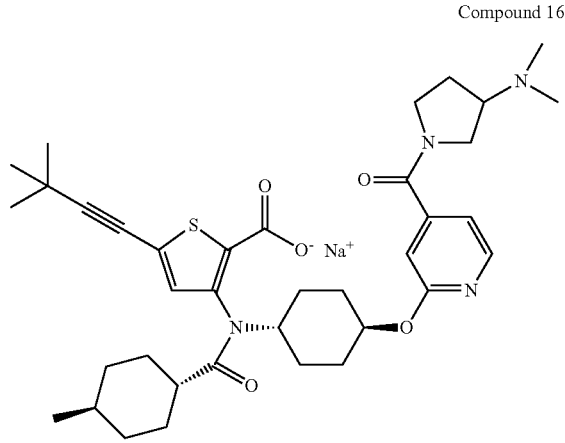

Compound 169

The title compound (87 mg, 38%) was synthesized in a manner analogous to Example 168, using dimethyl-pyrrolidin-3-yl-amine in place of azetidine and in the second step the reaction was heated at 65° C. MS (m/z): 663.1 [M+H]+; HPLC retention time 5.18 min (2-98% acetonitrile:water with 0.05% trifluoroacetic acid).

Example 170

Compound 170: Sodium 5-(3,3-dimethylbut-1-ynyl)-3-(4-methyl-N-(4-(5-((2-oxopyrrolidin-1-yl)methyl)pyridin-2-yloxy)cyclohexyl)cyclohexanecarboxamido)thiophene-2-carboxylate

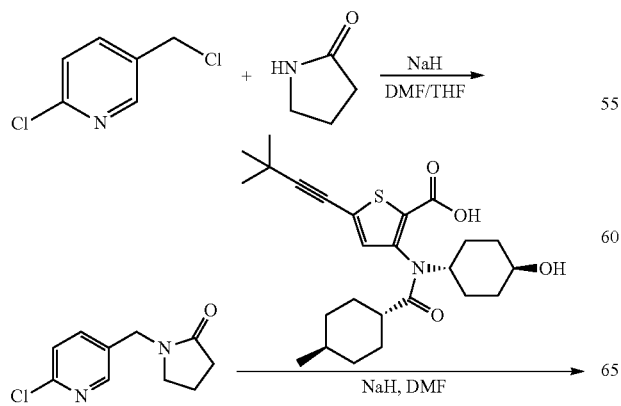

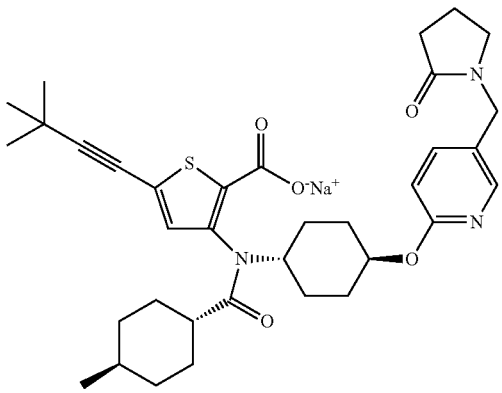

Compound 170

NaH (520 mg of a 60% oil dispersion, 13.00 mmol) was added in portions to a solution of 2-pyrrolidinone (1.1 g, 13.00 mmol) in DMF/THF (60 mL, 1:10) at 0° C. After stirring at this temperature for 1.5 h, solid 2-chloro-5-chloromethyl-pyridine (2.0 g, 12.34 mmol) was added along with a catalytic amount of TBAI. The reaction was allowed to warm to room temperature and stirred overnight. The reaction was hydrolyzed with the addition of satd. NH₄Cl, concentrated to near dryness and partitioned between ethyl acetate and water. The organic layer was separated, washed with 5% aqueous LiCl, brine, dried over Na₂SO₄ and concentrated to give a dark orange residue. Purification by flash column chromatography on silica gel with ethyl acetate provided the desired product as a pale yellow solid (942 mg, 36%).

The title compound (22 mg, 10%) was synthesized in a manner analogous to Example 168, using 1-(6-chloro-pyridin-3-ylmethyl)-pyrrolidin-2-one from the previous step in place of azetidine. MS (m/z): 618.0 [M−H]⁻; HPLC retention time: 6.00 min (2-98% acetonitrile:water with 0.05% trifluoroacetic acid).

Example 171

Compound 171: Sodium 5-(3,3-dimethylbut-1-ynyl)-3-(4-methyl-N-((1R)-4-(pyridin-2-yloxy)-3-(pyrrolidin-1-ylmethyl)cyclohexyl)cyclohexanecarboxamido)thiophene-2-carboxylate

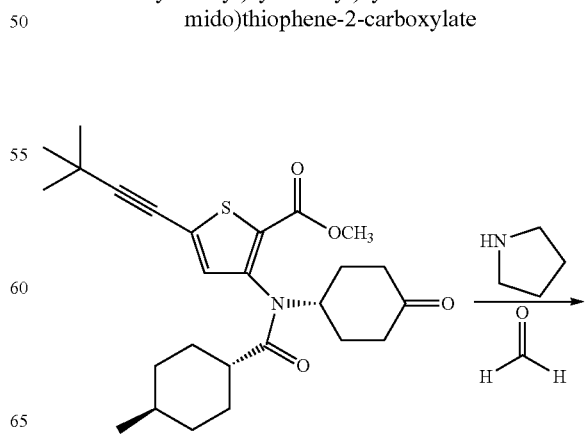

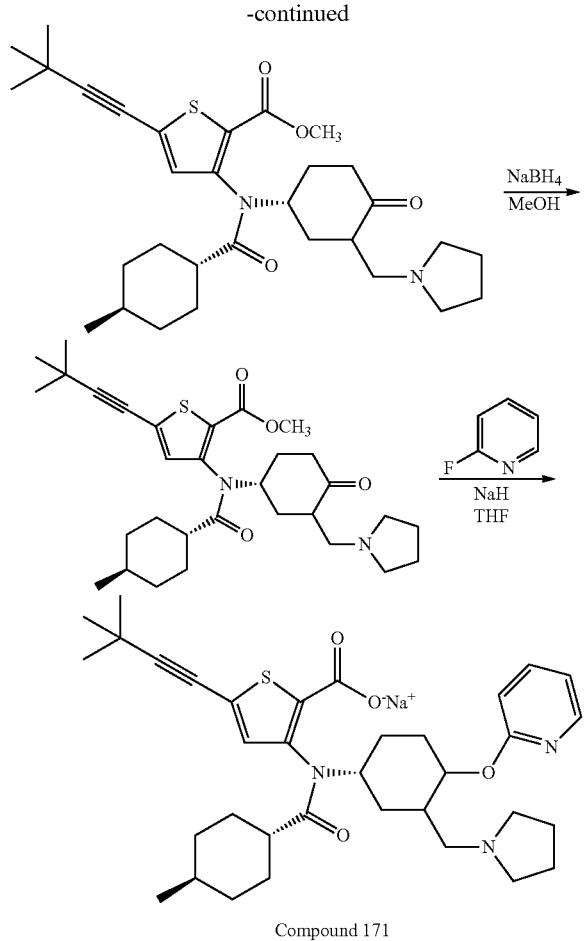

Compound 171

5-(3,3-Dimethyl-but-1-ynyl)-3-[(4-methyl-cyclohexanecarbonyl)-(4-oxo-cyclohexyl)-amino]-thiophene-2-carboxylic acid methyl ester (350 mg, 0.76 mmol), pyrrolidine HCl (160 mg, 1.48) and paraformaldehyde (100 mg) were combined in ethanol (2.5 mL). A catalytic drop of concentrated HCl was added and the reaction was heated at 85° C. for 24 h. The reaction was cooled, partitioned between ethyl acetate and sat. NaHCO$_3$/water. The aqueous layer was extracted and the combined organic layers were washed with brine, dried over Na$_2$SO$_4$ and concentrated to give a foam that was purified by flash column chromatography on silica gel with 10% methanol in dichloromethane to provide the desired product (262 mg, 63%) as a colorless foam.

To a solution of the ketone from the previous step (262 mg, 0.484 mmol) in MeOH (5.0 mL) cooled to 0° C. was added NaBH$_4$ (40 mg, 1.05 mmol) in several portions. After stirring for 2 h, dilute HCl was added and the reaction was concentrated to dryness to give a residue that was partitioned between ethyl acetate and sat. NaHCO$_3$/brine. The organic layer was separated, washed with brine, dried over Na$_2$SO$_4$ and concentrated to give the product as a pale foam (275 mg, quantitative).

NaH (10 mg of a 60% oil dispersion, 0.25 mmol) was added in one portion to a solution of the alcohol from the previous step (43 mg, 0.08 mmol) in THF (1.0 mL) at 0° C. After stirring for 5 min, 2-fluoropyridine (0.07 mL, 0.81 mmol) was added and the reaction was warmed to room temperature and then heated at 80° C. overnight. After cooling to room temperature, 1.0 N NaOH (0.10 mL) was added and the reaction was concentrated to dryness to give an orange solid. The solid was purified by column chromatography on reverse phase C$_{18}$ silica gel (100% water to 50% acetonitrile/water) to provide the desired product as a colorless solid (15 mg, 30%) after lyophilization. MS (m/z): 606.2 [M+H]; HPLC retention time: 5.90 min (2-98% acetonitrile:water with 0.05% trifluoroacetic acid).

Example 173

Compound 173: Sodium 5-(3,3-dimethylbut-1-ynyl)-3-(4-methyl-N-(4-(1-methyl-6-oxo-1,6-dihydropyridazin-3-yloxy)cyclohexyl)cyclohexanecarboxamido)thiophene-2-carboxylate

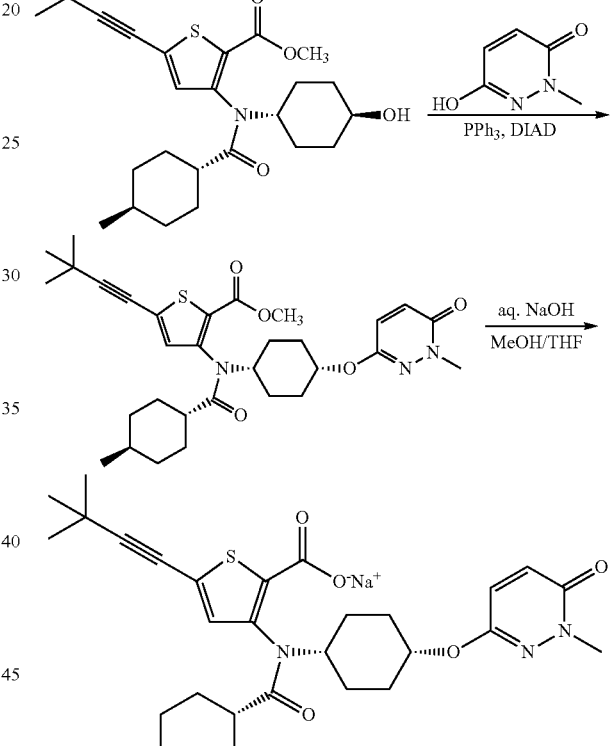

Compound 173

To a solution of 5-(3,3-dimethyl-but-1-ynyl)-3-[(4-hydroxy-cyclohexyl)-(4-methyl-cyclohexanecarbonyl)-amino]-thiophene-2-carboxylic acid methyl ester (250 mg, 0.54 mmol) and 6-hydroxy-2-methyl-2H-pyridazin-3-one (86 mg, 0.68 mmol) in THF (4.0 mL) was added PPh$_3$ (157 mg, 0.60 mmol) at 0° C. DIAD (0.12 mL, 0.60 mmol) was added dropwise and the reaction was allowed to slowly warm to room temperature and stirred overnight. Sat. NH$_4$Cl was added and the reaction mixture was extracted with ethyl ether. The combined organic layers were washed with water, brine, dried over Na$_2$SO$_4$ and concentrated to give a pale yellow foam. Purification by flash column chromatography on silica gel with 3% methanol in dichloromethane provided 335 mg of the desired product as a colorless foam that was contaminated with triphenylphosphine oxide.

To a solution of the methyl ester from the previous step (335 mg, assume 0.50 mmol) in methanol (0.75 mL) and THF (0.75 mL) was added aqueous NaOH (0.75 mL of a 1.0 N solution) at room temperature. After stirring for 90 min the reaction was concentrated to dryness to give a pale yellow solid. Purification by column chromatography on reverse phase $C_{18}$ silica gel (100% water to 5% acetonitrile/water) provided the desired product as a colorless solid (28 mg, 9% for two steps) after lyophilization. HPLC retention time: 6.00 min (2-98% acetonitrile:water with 0.05% trifluoroacetic acid).

Example 174

Compound 174: 5-(3,3-Dimethylbut-1-ynyl)-3-(4-methyl-N-(4-(1-methyl-6-oxo-1,6-dihydropyridazin-3-yloxy)cyclohexyl)cyclohexanecarboxamido)thiophene-2-carboxylic acid

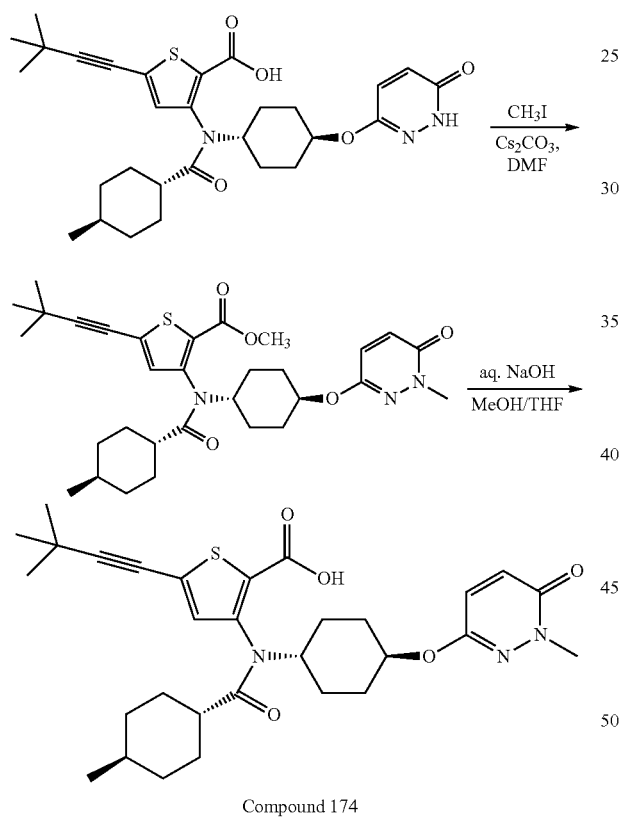

Compound 174

$Cs_2CO_3$ (90 mg, 0.28 mmol) was added to a solution of (5-(3,3-dimethyl-but-1-ynyl)-3-{(4-methyl-cyclohexanecarbonyl)-[4-(6-oxo-1,6-dihydro-pyridazin-3-yloxy)-cyclohexyl]-amino}-thiophene-2-carboxylic acid methyl ester (50 mg, 0.09 mmol) in DMF (2.0 mL) at room temperature. After stirring for 5 min, neat methyl iodide (40 mg, 0.28 mmol) was added and the reaction was stirred for 2 h. The reaction was filtered, concentrated and partitioned between ethyl acetate and 5% aqueous LiCl. The organic layer was separated, washed with brine, dried over $Na_2SO_4$ and concentrated to give an orange foam that was used in the next step without further purification.

To a solution of the crude methyl ester from the previous step (assume 0.09 mmol) in methanol (0.50 mL) and THF (0.50 mL) was added aqueous NaOH (0.10 mL of a 1.0 N solution) at 0° C. The reaction was warmed to room temperature and after 90 min the reaction is evaporated to dryness to give a colorless solid. Purification by column chromatography on reverse phase $C_{18}$ silica gel (100% water to 20% acetonitrile/water) provided a colorless solid that was taken up in a minimum amount of water and acidified with 1.0 N HCl to give a colorless precipitate that was collected by filtration and dried under vacuum to provide the desired product (19 mg, 37% for two steps). MS (m/z): 553.9 [M+]; HPLC retention time: 4.50 min (2-98% acetonitrile:water with 0.05% trifluoroacetic acid).

Example 175

Compound 175: Sodium 3-(N-(4-(4-((dimethylamino)methyl)pyridin-2-yloxy)cyclohexyl)-4-methylcyclohexanecarboxamido)-5-(3,3-dimethylbut-1-ynyl)thiophene-2-carboxylate

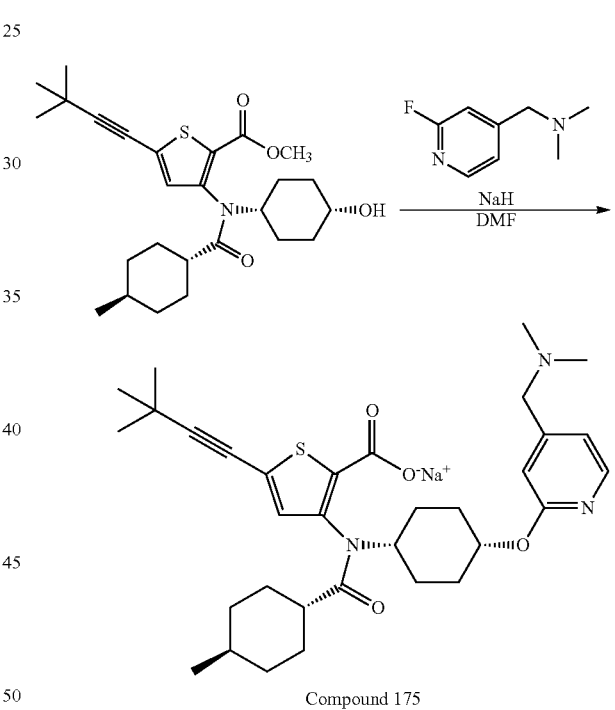

Compound 175

NaH (65 mg of a 60% oil dispersion, 1.62 mmol) was added to solution 5-(3,3-dimethyl-but-1-ynyl)-3-[(4-hydroxy-cyclohexyl)-(4-methyl-cyclohexanecarbonyl)-amino]-thiophene-2-carboxylic acid methyl ester (155 mg, 0.34 mmol) and (2-fluoro-pyridin-4-ylmethyl)-dimethylamine (130 mg, 0.84 mmol) in DMF (4.0 mL) at 0° C. After 5 min the reaction was warmed to room temperature and then heated at 65° C. for 2 h. The reaction was cooled, aqueous NaOH (0.5 mL of a 1.0 N solution) was added and the reaction mixture evaporated to dryness. Purification by column chromatography on reverse phase $C_{18}$ silica gel (100% water to 20% acetonitrile/water) provided the desired product as a colorless solid (62 mg, 31%) after lyophilization. MS (m/z): 580.2 [M+H]; HPLC retention time: 5.05 min (2-98% acetonitrile:water with 0.05% trifluoroacetic acid).

Example 176

Compound 176: Sodium 5-(3,3-dimethylbut-1-ynyl)-3-(N-(4-(imidazo[1,2-b]pyridazin-6-yloxy)cyclohexyl)-4-methylcyclohexanecarboxamido)thiophene-2-carboxylate

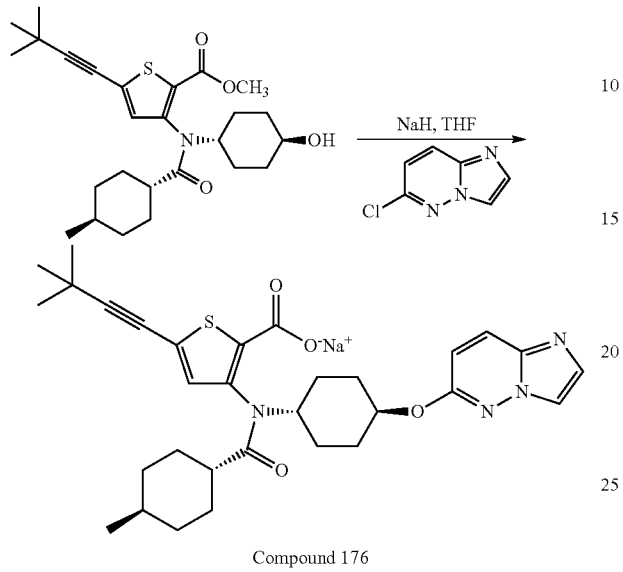

Compound 176

NaH (30 mg of a 60% oil dispersion, 0.75 mmol) was added to a solution of 5-(3,3-dimethyl-but-1-ynyl)-3-[(4-hydroxy-cyclohexyl)-(4-methyl-cyclohexanecarbonyl)-amino]-thiophene-2-carboxylic acid methyl ester (100 mg, 0.22 mmol) and 6-chloro-imidazo[1,2-b]pyridazine (167 mg, 1.08 mmol) in THF (4.0 mL) at room temperature. The reaction was heated at 80° C. overnight, cooled, aqueous NaOH (1.0 mL of a 1.0 N solution) was added and the reaction evaporated to dryness to give a brown solid. Purification by column chromatography on reverse phase $C_{18}$ silica gel (100% water to 30% acetonitrile/water) provided the desired product as a solid (17 mg, 14%) after lyophilization. MS (m/z): 563.0 [M+H]; HPLC retention time: 5.55 min (2-98% acetonitrile:water with 0.05% trifluoroacetic acid).

Examples 177-183 were prepared by the same methods described for either Example 173 or 175 by substituting the appropriate heterocycle.

Example 177

Compound 177: 3-(N-(4-(6-Chloropyridazin-3-yloxy)cyclohexyl)-4-methylcyclohexanecarboxamido)-5-(3,3-dimethylbut-1-ynyl)thiophene-2-carboxylic acid Compound 177

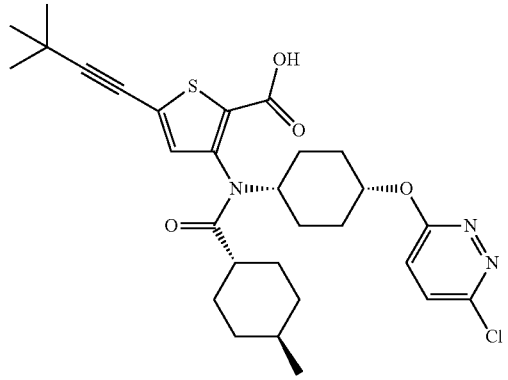

MS (m/z): 558.1 [M+H]; HPLC retention time: 3.16 min (2-98% acetonitrile:water with 0.05% trifluoroacetic acid).

Example 178

Compound 178: 5-(3,3-Dimethylbut-1-ynyl)-3-(N-(4-(6-hydroxypyridazin-3-yloxy)cyclohexyl)-4-methylcyclohexanecarboxamido)thiophene-2-carboxylic acid Compound 178

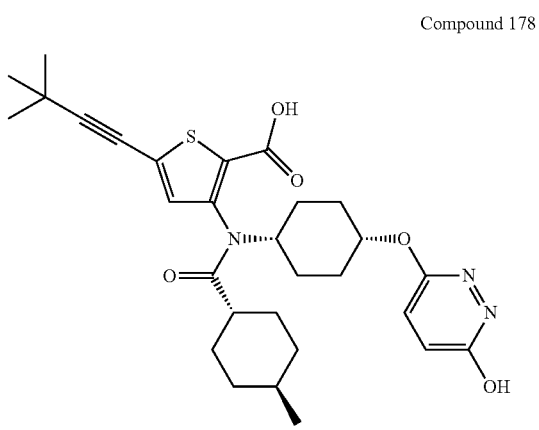 [SMILES: CC(C)(C)C#Cc1cc(N(C(=O)[C@H]2CC[C@H](C)CC2)[C@H]2CC[C@@H](Oc3ccc(O)nn3)CC2)c(C(=O)O)s1]

MS (m/z): 540.2 [M+H]; HPLC retention time: 2.96 min (2-98% acetonitrile:water with 0.05% trifluoroacetic acid).

Example 179

Compound 179: 5-(3,3-Dimethylbut-1-ynyl)-3-(4-methyl-N-(4-(pyrimidin-5-yloxy)cyclohexyl)cyclohexanecarboxamido)thiophene-2-carboxylic acid Compound 179

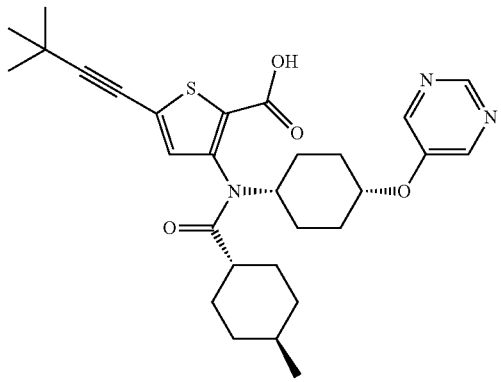

MS (m/z): 524.2 [M+H]; HPLC retention time: 2.46 min (2-98% acetonitrile:water with 0.05% trifluoroacetic acid).

Example 180

Compound 180: 5-(3,3-Dimethylbut-1-ynyl)-3-(4-methyl-N-(4-(pyridin-3-yloxy)cyclohexyl)cyclohexanecarboxamido)thiophene-2-carboxylic acid

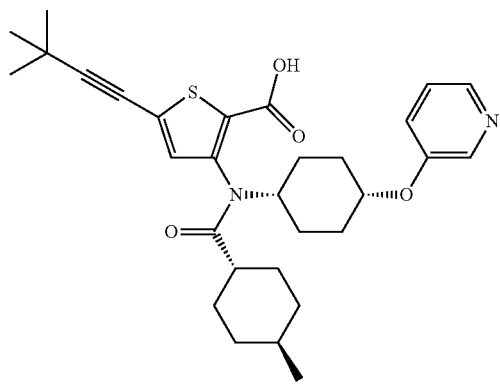

Compound 180

MS (m/z): 523.2 [M+H]; HPLC retention time: 2.14 min (2-98% acetonitrile:water with 0.05% trifluoroacetic acid).

Example 181

Compound 181: 5-(3,3-Dimethylbut-1-ynyl)-3-(4-methyl-N-(4-(pyrimidin-2-yloxy)cyclohexyl)cyclohexanecarboxamido)thiophene-2-carboxylic acid

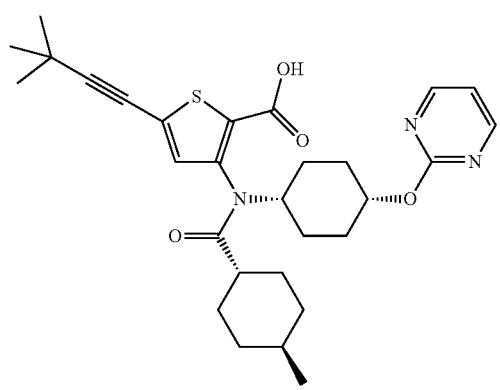

Compound 181

MS (m/z): 524.2 [M+H]; HPLC retention time: 2.49 min (2-98% acetonitrile:water with 0.05% trifluoroacetic acid).

Example 182

Compound 182: 3-(N-(4-(5-Chloropyrazin-2-yloxy)cyclohexyl)-4-methylcyclohexanecarboxamido)-5-(3,3-dimethylbut-1-ynyl)thiophene-2-carboxylic acid

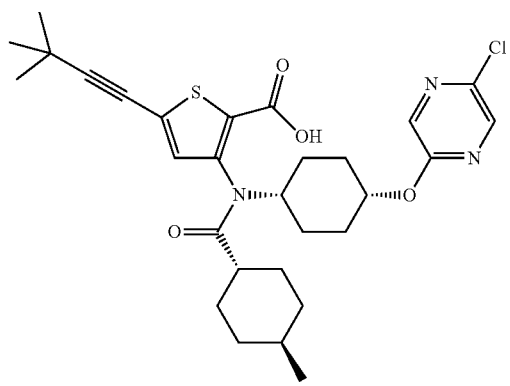

Compound 182

MS (m/z): 558.1 [M+H]; HPLC retention time: 4.09 min (2-98% acetonitrile:water with 0.05% trifluoroacetic acid).

Example 183

Compound 183: 5-(3,3-Dimethylbut-1-ynyl)-3-(4-methyl-N-(4-(pyridazin-4-yloxy)cyclohexyl)cyclohexanecarboxamido)thiophene-2-carboxylic acid

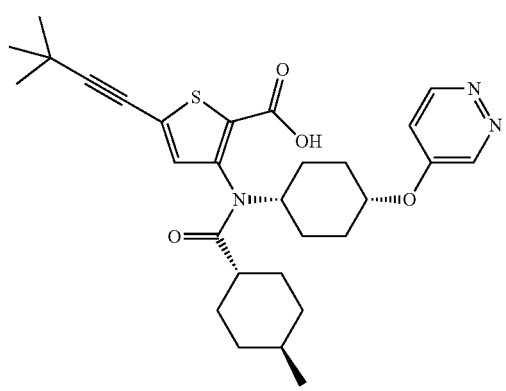

Compound 183

MS (m/z): 524.2 [M+H]; HPLC retention time: 4.02 min (2-98% acetonitrile:water with 0.05% trifluoroacetic acid).

Examples 184 and 185 were prepared by the same method described for Example 1 by substituting the appropriate heterocycle.

Example 184

Compound 184: 3-(N-(4-(5-Chloropyrazin-2-yloxy)cyclohexyl)-4-methylcyclohexanecarboxamido)-5-(3,3-dimethylbut-1-ynyl)thiophene-2-carboxylic acid

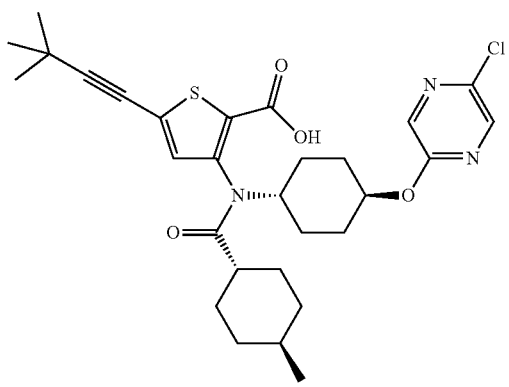

Compound 184

MS (m/z): 558.1 [M+H]; HPLC retention time: 4.32 min (2-98% acetonitrile:water with 0.05% trifluoroacetic acid).

Example 185

Compound 185: 5-(3,3-Dimethylbut-1-ynyl)-3-(4-methyl-N-(4-(pyridazin-4-yloxy)cyclohexyl)cyclohexanecarboxamido)thiophene-2-carboxylic acid

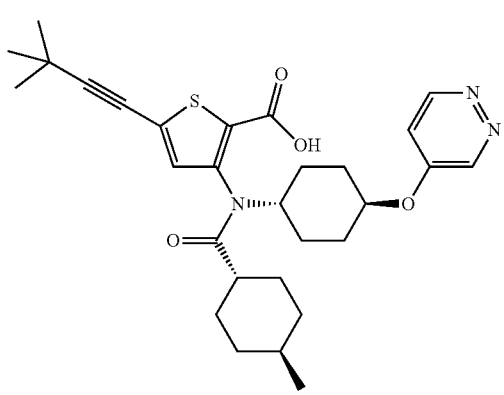

Compound 185

MS (m/z): 524.1 [M+H]; HPLC retention time: 3.71 min (2-98% acetonitrile:water with 0.05% trifluoroacetic acid).

Example 187

Compound 187: 3-[[-4-(6-pyrrolidin-1-ylmethyl-pyridin-2-yloxy)-cyclohexyl]-(4-methyl-cyclohexanecarbonyl)-amino]-5-(3,3-Dimethyl-but-1-ynyl)-thiophene-2-carboxylic acid

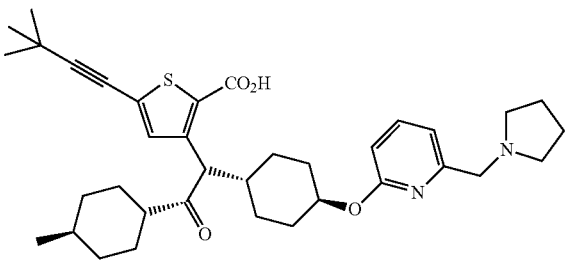

Compound 187

The title compound was synthesized in a manner analogous to Example 27, using (2-fluoro-pyridin-6-ylmethyl)pyrrolidine (prepared from 2-fluoro-pyridine-6-carbaldehyde and pyrrolidine in a manner analogous to Example 27) in place of 2-chloro-4-pyrrolidin-1-ylmethyl-pyridine: MS (m/z): 606.2 [M+H]+; HPLC retention time 3.65 min (2-98% acetonitrile:water with 0.05% trifluoroacetic acid).

Example 188

Compound 188: 3-[[-4-(6-morpholin-1-ylmethyl-pyridin-2-yloxy)-cyclohexyl]-(4-methyl-cyclohexanecarbonyl)-amino]-5-(3,3-Dimethyl-but-1-ynyl)-thiophene-2-carboxylic acid

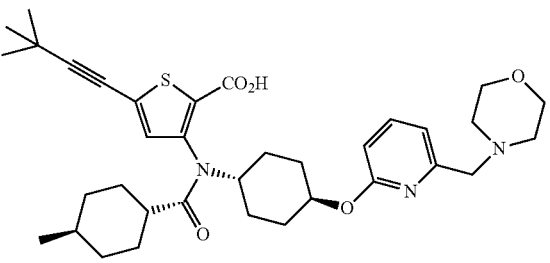

Compound 188

The title compound was synthesized in a manner analogous to Example 27, using 4-(2-chloro-pyridin-6-ylmethyl)morpholine (prepared from 2-chloro-pyridine-6-carbaldehyde and morpholine) in place of 2-chloro-4-pyrrolidin-1-

Example 189

Compound 189: 3-[[-4-(4-pyrrolidin-2-one-1-ylmethyl-pyridin-2-yloxy)-cyclohexyl]-(4-methyl-cyclohexanecarbonyl)-amino]-5-(3,3-Dimethyl-but-1-ynyl)-thiophene-2-carboxylic acid

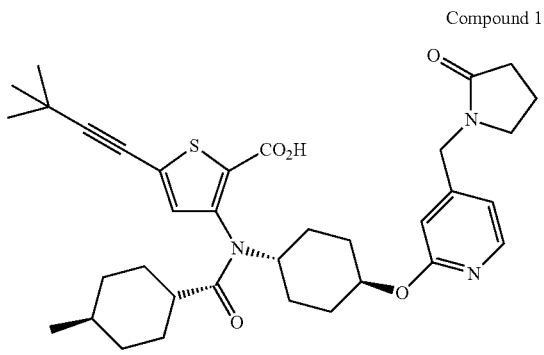

Compound 189

The title compound was synthesized in a manner analogous to Example 27, using 4-(2-chloro-pyridin-4-ylmethyl)pyrrolidin-2-one (prepared from 4-bromomethyl-2-chloropyridine and pyrrolidin-2-one) in place of 2-chloro-4-pyrrolidin-1-ylmethyl-pyridine: MS (m/z): 618.3 [M+H]+; HPLC retention time 4.20 min (2-98% acetonitrile:water with 0.05% trifluoroacetic acid).

Example 190

Compound 190: 3-[[-4-[4-(3-hydroxy-pyrrolidin-1-ylmethyl)-pyridin-2-yloxy]-cyclohexyl]-(4-methyl-cyclohexanecarbonyl)-amino]-5-(3,3-Dimethyl-but-1-ynyl)-thiophene-2-carboxylic acid

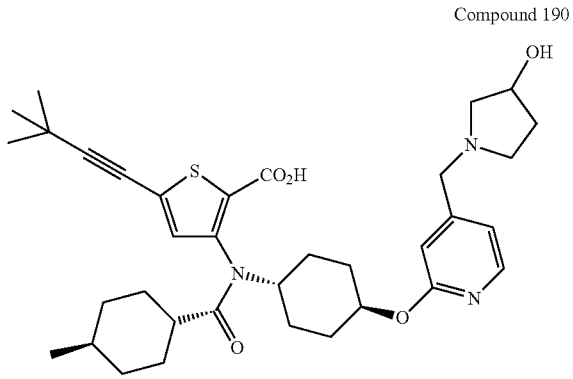

Compound 190

The title compound was synthesized in a manner analogous to Example 27, using 4-(2-fluoro-pyridin-4-ylmethyl)pyrrolidin-3-ol (prepared from 2-fluoro-pyridine-4-carbaldehyde and pyrrolidin-3-ol) in place of 2-chloro-4-pyrrolidin-

Example 191

Compound 191: 3-[[-4-[4-{[(2-hydroxy-ethyl)-methyl-amino]-1-ylmethyl}-pyridin-2-yloxy]-cyclohexyl]-(4-methyl-cyclohexanecarbonyl)-amino]-5-(3,3-Dimethyl-but-1-ynyl)-thiophene-2-carboxylic acid

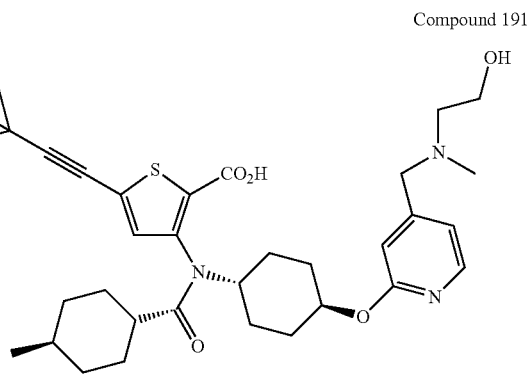

Compound 191

The title compound was synthesized in a manner analogous to Example 27, using 2-[(2-fluoro-pyridin-4-ylmethyl)-methyl-amino]-ethanol (prepared from 2-fluoro-pyridine-4-carbaldehyde and 2-methylamino-ethanol) in place of 2-chloro-4-pyrrolidin-1-ylmethyl-pyridine: MS (m/z): 610.1 [M+H]+; HPLC retention time 3.54 min (2-98% acetonitrile:water with 0.05% trifluoroacetic acid).

Example 192

Compound 192: 3-[[-4-(5-dimethylaminomethyl-pyridin-3-yloxy)-cyclohexyl]-(4-methyl-cyclohexanecarbonyl)-amino]-5-(3,3-dimethyl-but-1-ynyl)-thiophene-2-carboxylic acid

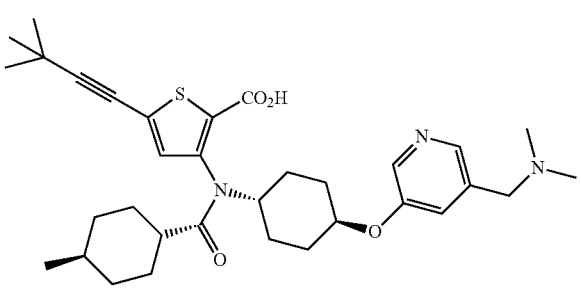

Compound 192

The title compound was synthesized in a manner analogous to Example 27, using (5-fluoro-pyridin-3-ylmethyl)-dimethyl-amine (prepared from 5-fluoro-pyridine-3-carbaldehyde and dimethylamine) in place of 2-chloro-4-pyrrolidin-1-ylmethyl-pyridine: MS (m/z): 580.2 [M+H]+;

HPLC retention time 4.30 min (2-98% acetonitrile: water with 0.05% trifluoroacetic acid).

Example 193

Compound 193: 3-[[-4-(5-pyrrolidin-1-ylmethyl-pyridin-3-yloxy)-cyclohexyl]-(4-methyl-cyclohexanecarbonyl)-amino]-5-(3,3-dimethyl-but-1-ynyl)-thiophene-2-carboxylic acid Compound 193

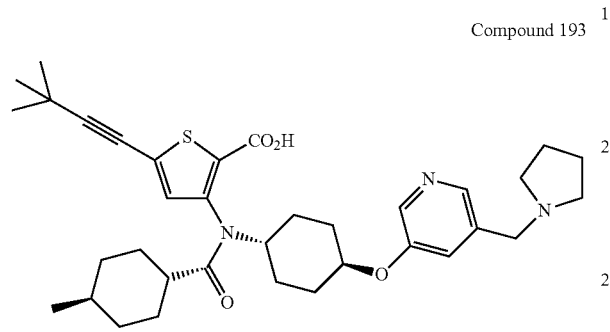

The title compound was synthesized in a manner analogous to Example 27, using (3-fluoro-5-pyrrolidin-1-ylmethyl)-pyridine (prepared from 5-fluoro-pyridine-3-carbaldehyde and pyrrolidine) in place of 2-chloro-4-pyrrolidin-1-ylmethyl-pyridine: MS (m/z): 606.2 [M+H]+; HPLC retention time 3.38 min (2-98% acetonitrile:water with 0.05% trifluoroacetic acid).

Example 194

Compound 194: 3-[[4-(5-morpholin-4-ylmethyl-pyridin-3-yloxy)-cyclohexyl]-(4-methyl-cyclohexanecarbonyl)-amino]-5-(3,3-dimethyl-but-1-ynyl)-thiophene-2-carboxylic acid Compound 194

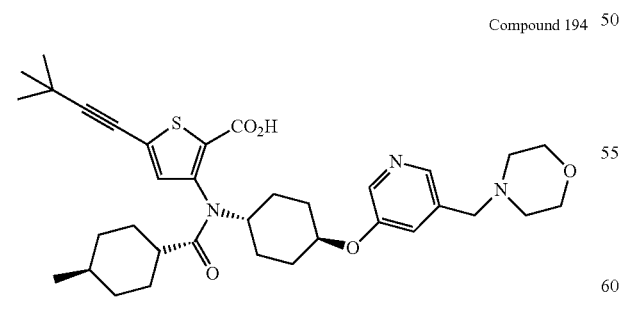

The title compound was synthesized in a manner analogous to Example 27, using (5-fluoro-pyridin-3-ylmethyl)-morpholine (prepared from 5-fluoro-pyridine-3-carbaldehyde and morpholine) in place of 2-chloro-4-pyrrolidin-1-ylmethyl-pyridine: MS (m/z): 622.2 [M+H]+; HPLC retention time 3.39 min (2-98% acetonitrile:water with 0.05% trifluoroacetic acid).

Example 195

Compound 195: 3-[[-4-(3-dimethylamino-pyrrolidin-1-ylmethyl-pyridin-3-yloxy)-cyclohexyl]-(4-methyl-cyclohexanecarbonyl)-amino]-5-(3,3-dimethyl-but-1-ynyl)-thiophene-2-carboxylic acid Compound 195

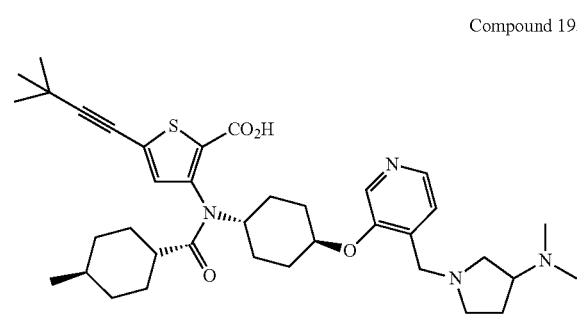

The title compound was synthesized in a manner analogous to Example 27, using [1-(3-fluoro-pyridin-4-ylmethyl)-pyrrolidin-3-yl]-dimethyl-amine (prepared from 3-fluoro-pyridine-4-carbaldehyde and dimethyl-pyrrolidine-3-yl-amine) in place of 2-chloro-4-pyrrolidin-1-ylmethyl-pyridine: MS (m/z): 649.3 [M+H]+; HPLC retention time 2.98 min (2-98% acetonitrile:water with 0.05% trifluoroacetic acid).

Example 196

Compound 196: 3-[[-4-(4-pyrrolidin-1-ylmethyl-pyridin-3-yloxy)-cyclohexyl]-(4-methyl-cyclohexanecarbonyl)-amino]-5-(3,3-dimethyl-but-1-ynyl)-thiophene-2-carboxylic acid Compound 196

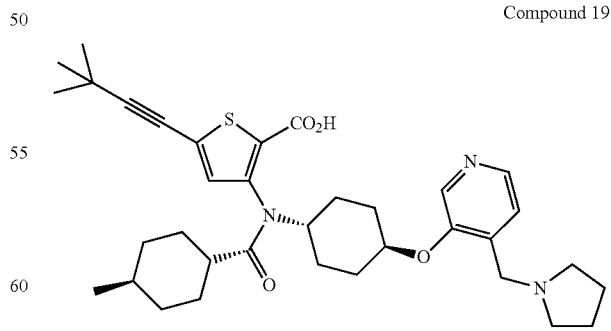

The title compound was synthesized in a manner analogous to Example 27, using 3-fluoro-4-pyrrolidine-1-ylmethyl-pyridine (prepared from 3-fluoro-pyridine-4-carbaldehyde and pyrrolidine) in place of 2-chloro-4-pyrrolidin-1- ylmethyl-pyridine: MS (m/z): 606.2 [M+H]+; HPLC retention time 3.23 min (2-98% acetonitrile:water with 0.05% trifluoroacetic acid).

Example 197

Compound 197: 3-[[-4-(4-azetidin-1-ylmethyl-pyridin-3-yloxy)-cyclohexyl]-(4-methyl-cyclohexanecarbonyl)-amino]-5-(3,3-dimethyl-but-1-ynyl)-thiophene-2-carboxylic acid Compound 197

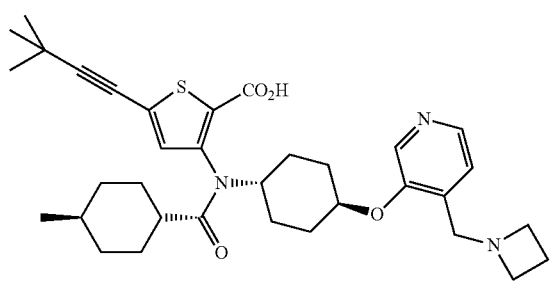

The title compound was synthesized in a manner analogous to Example 27, using 4-azetidine-1-ylmethyl-3-fluoro-pyridine (prepared from 3-fluoro-pyridine-4-carbaldehyde and azetidine) in place of 2-chloro-4-pyrrolidin-1-ylmethyl-pyridine: MS (m/z): 592.3 [M+H]+; HPLC retention time 3.18 min (2-98% acetonitrile:water with 0.05% trifluoroacetic acid).

Example 198

Compound 198: 3-[[-4-(4-dimethylaminomethyl-pyridin-3-yloxy)-cyclohexyl]-(4-methyl-cyclohexanecarbonyl)-amino]-5-(3,3-dimethyl-but-1-ynyl)-thiophene-2-carboxylic acid Compound 198

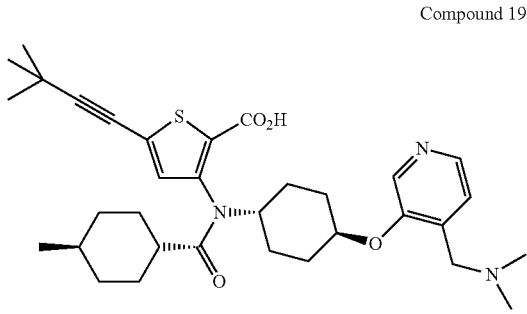

The title compound was synthesized in a manner analogous to Example 27, using (3-fluoro-pyridin-4-ylmethyl)-dimethyl-amine (prepared from 3-fluoro-pyridine-4-carbaldehyde and dimethylamine) in place of 2-chloro-4-pyrrolidin-1-ylmethyl-pyridine: MS (m/z): 580.2 [M+H]+; HPLC retention time 3.18 min (2-98% acetonitrile: water with 0.05% trifluoroacetic acid).

Example 199

Compound 199: 3-[[-4-(2-pyrrolidin-1-ylmethyl-pyridin-4-yloxy)-cyclohexyl]-(4-methyl-cyclohexanecarbonyl)-amino]-5-(3,3-dimethyl-but-1-ynyl)-thiophene-2-carboxylic acid Compound 199

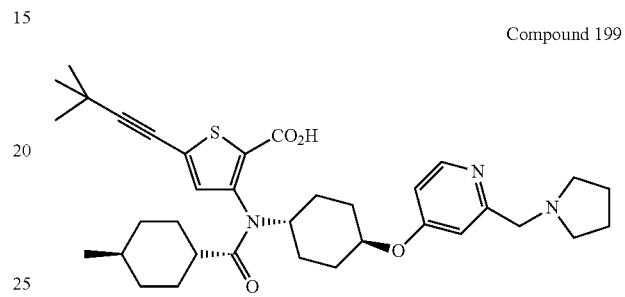

The title compound was synthesized in a manner analogous to Example 27, using 4-chloro-2-pyrrolidin-1-ylmethyl-pyridine (prepared from 4-chloro-pyridine-2-carbaldehyde and pyrrolidine) in place of 2-chloro-4-pyrrolidin-1-ylmethyl-pyridine: MS (m/z): 606.1 [M+H]+; HPLC retention time 3.46 min (2-98% acetonitrile:water with 0.05% trifluoroacetic acid).

Example 200

Compound 200: 3-[[-4-(2-dimethylaminomethyl-pyridin-4-yloxy)-cyclohexyl]-(4-methyl-cyclohexanecarbonyl)-amino]-5-(3,3-dimethyl-but-1-ynyl)-thiophene-2-carboxylic acid Compound 200

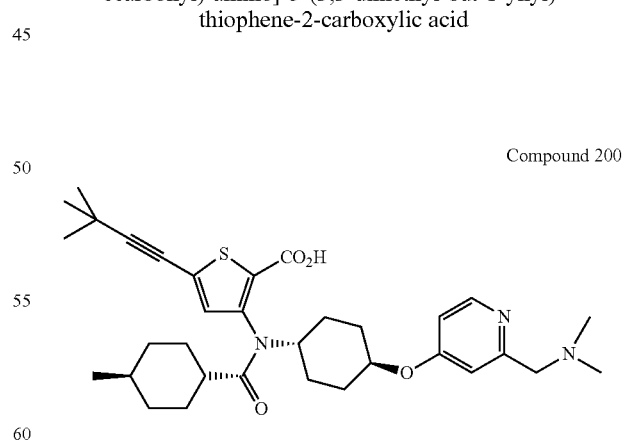

The title compound was synthesized in a manner analogous to Example 27, using (4-chloro-pyridin-2-ylmethyl)-dimethyl-amine (prepared from 4-chloro-pyridine-2-carbaldehyde and dimethylamine) in place of 2-chloro-4-pyrrolidin-1-ylmethyl-pyridine: MS (m/z): 580.1 [M+H]+;

HPLC retention time 3.43 min (2-98% acetonitrile: water with 0.05% trifluoroacetic acid).

Example 201

Compound 201: 5-(3,3-Dimethyl-but-1-ynyl)-3-{(4-methyl-cyclohexanecarbonyl)-[1-(1-methyl-1'-1-imidazole-4-sulfonyl)-piperidin-4-yl]-amino}-thiophene-2-carboxylic acid

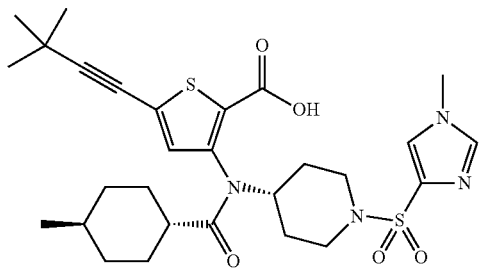

Compound 201

The title compound was synthesized in a manner analogous to Example 140, using 1-methyl-1H-imidazole-4-sulfonyl chloride in place of pyridine-2-carbonyl chloride: MS (m/z): 575.1 [M+H]; HPLC retention time: 4.34 min (2-98% acetonitrile:water with 0.05% trifluoroacetic acid; 6 min run).

Example 202

Compound 202: 5-(3,3-Dimethyl-but-1-ynyl)-3-{(4-methyl-cyclohexanecarbonyl)-[1-(4H-[1,2,4]triazole-3-sulfonyl)-piperidin-4-yl]-amino}-thiophene-2-carboxylic acid

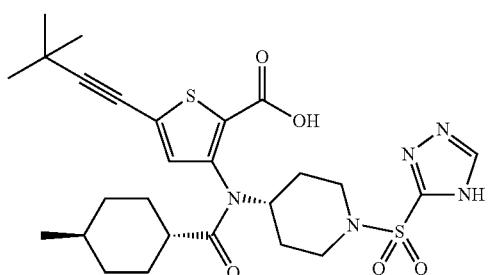

Compound 202

The title compound was synthesized in a manner analogous to Example 140, using 4H-[1,2,4]-triazole-3-sulfonyl chloride in place of pyridine-2-carbonyl chloride: MS (m/z): 561.7 [M+H]; HPLC retention time: 4.34 min (2-98% acetonitrile:water with 0.05% trifluoroacetic acid) 6 min run.

Example 203

Compound 203: 5-(3,3-Dimethyl-but-1-ynyl)-3-{(4-methyl-cyclohexanecarbonyl)-[1-(2-methyl-2H-pyrazole-3-sulfonyl)-piperidin-4-yl]-amino}-thiophene-2-carboxylic acid

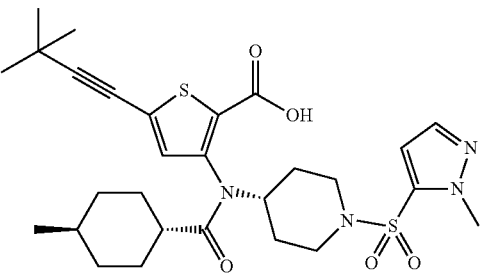

Compound 203

The title compound was synthesized in a manner analogous to Example 140, using 2-methyl-2H-pyrazole-3-sulfonyl chloride in place of pyridine-2-carbonyl chloride: MS (m/z): 575.1 [M+H]; HPLC retention time: 4.85 min (2-98% acetonitrile:water with 0.05% trifluoroacetic acid) 6 min run.

Example 204

Compound 204: 3-[[1-(2-Dimethylamino-pyrimidine-5-sulfonyl)-piperidin-4-yl]-(4-methyl-cyclohexanecarbonyl)-amino]-5-(3,3-dimethyl-but-1-ynyl)-thiophene-2-carboxylic acid

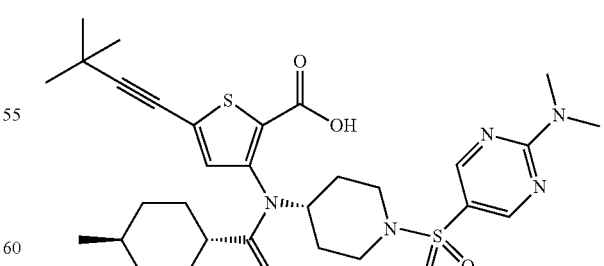

Compound 204

The title compound was synthesized in a manner analogous to Example 140, using 2-dimethylamino-pyrimidine-5-sulfonyl chloride in place of pyridine-2-carbonyl chloride:

MS (m/z): 616.1 [M+H]; HPLC retention time: 5.00 min (2-98% acetonitrile:water with 0.05% trifluoroacetic acid) 6 min run.

Example 205

Compound 205: 5-(3,3-Dimethyl-but-1-ynyl)-3-{(4-methyl-cyclohexanecarbonyl)-[1-(thiophene-3-sulfonyl)-piperidin-4-yl]-amino}-thiophene-2-carboxylic acid

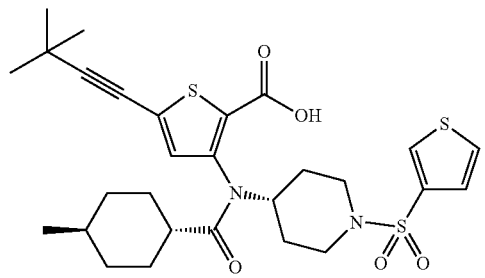

Compound 205

The title compound was synthesized in a manner analogous to Example 140, using thiophene-3-sulfonyl chloride in place of pyridine-2-carbonyl chloride: MS (m/z): 576.9 [M+H]; HPLC retention time: 4.94 min (2-98% acetonitrile:water with 0.05% trifluoroacetic acid) 6 min run.

Example 206

Compound 206: 5-(3,3-Dimethyl-but-1-ynyl)-3-[[1-(1,2-dimethyl-1H-imidazole-4-sulfonyl)-piperidin-4-yl]-(4-methyl-cyclohexanecarbonyl)-amino]-thiophene-2-carboxylic acid

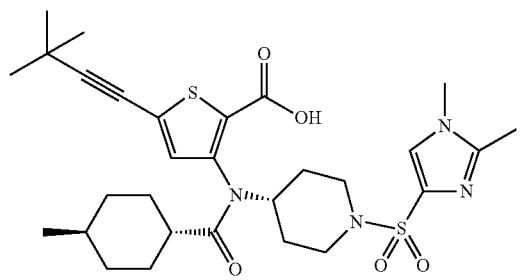

Compound 206

The title compound was synthesized in a manner analogous to Example 140, using 1,2-dimethyl-1H-imidazole-4-sulfonyl chloride in place of pyridine-2-carbonyl chloride:

MS (m/z): 589.1 [M+H]; HPLC retention time: 4.14 min (2-98% acetonitrile:water with 0.05% trifluoroacetic acid) 6 min run.

Example 207

Compound 207: 5-(3,3-Dimethyl-but-1-ynyl)-3-{(4-methyl-cyclohexanecarbonyl)-[1-(thiophene-2-sulfonyl)-piperidin-4-yl]-amino}-thiophene-2-carboxylic acid

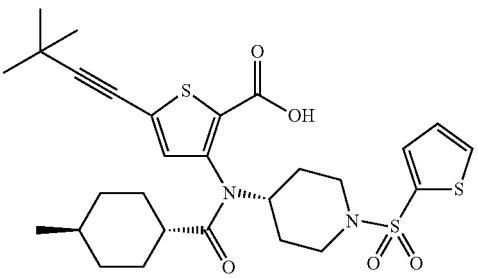

Compound 207

The title compound was synthesized in a manner analogous to Example 140, using Thiophene-2-sulfonyl chloride in place of pyridine-2-carbonyl chloride: MS (m/z): 576.9 [M+H]; HPLC retention time: 5.02 min (2-98% acetonitrile:water with 0.05% trifluoroacetic acid) 6 min run.

Example 208

Compound 208: 5-(3,3-Dimethyl-but-1-ynyl)-3-{(4-methyl-cyclohexanecarbonyl)-[1-(2-oxo-1,2-dihydro-pyrimidine-5-sulfonyl)-piperidin-4-yl]-amino}-thiophene-2-carboxylic acid

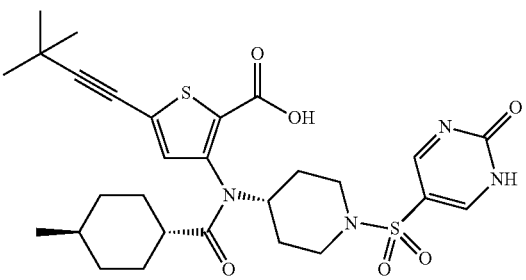

Compound 208

The title compound was synthesized in a manner analogous to Example 140, using 2-oxo-1,2-dihydro-pyrimidine-5-sulfonyl chloride in place of pyridine-2-carbonyl chloride:

MS (m/z): 589.1 [M+H]; HPLC retention time: 4.22 min (2-98% acetonitrile:water with 0.05% trifluoroacetic acid) 6 min run.

Example 209

Compound 209: 5-(3,3-Dimethyl-but-1-ynyl)-3-{(4-methyl-cyclohexanecarbonyl)-[1-(pyridine-2-sulfonyl)-piperidin-4-yl]-amino}-thiophene-2-carboxylic acid Compound 209

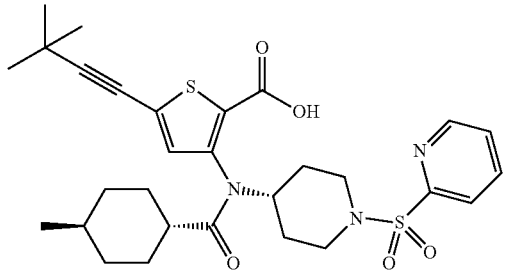

The title compound was synthesized in a manner analogous to Example 140, using pyridine-2-sulfonyl chloride in place of pyridine-2-carbonyl chloride: MS (m/z): 572.2 [M+H]; HPLC retention time: 4.71 min (2-98% acetonitrile:water with 0.05% trifluoroacetic acid) 6 min run.

Example 210

Compound 210: 5-(3,3-Dimethyl-but-1-ynyl)-3-{(4-methyl-cyclohexanecarbonyl)-[1-(pyridine-3-sulfonyl)-piperidin-4-yl]-amino}-thiophene-2-carboxylic acid Compound 210

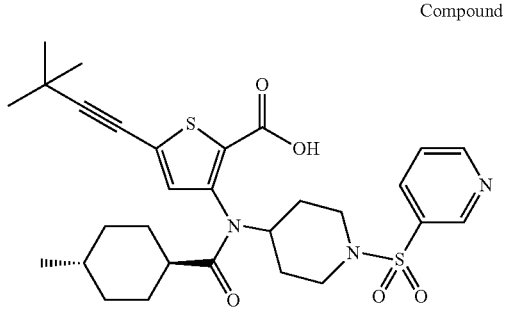

The title compound was synthesized in a manner analogous to Example 140, using pyridine-3-sulfonyl chloride in place of pyridine-2-carbonyl chloride: MS (m/z): 572.2

[M+H]; HPLC retention time: 4.67 min (2-98% acetonitrile:water with 0.05% trifluoroacetic acid) 6 min run.

Example 211

Compound 211: 5-(3,3-Dimethyl-but-1-ynyl)-3-{(4-methyl-cyclohexanecarbonyl)-[1-(thiophene-3-sulfonyl)-pyrrolidin-3-yl]-amino}-thiophene-2-carboxylic acid Compound 211

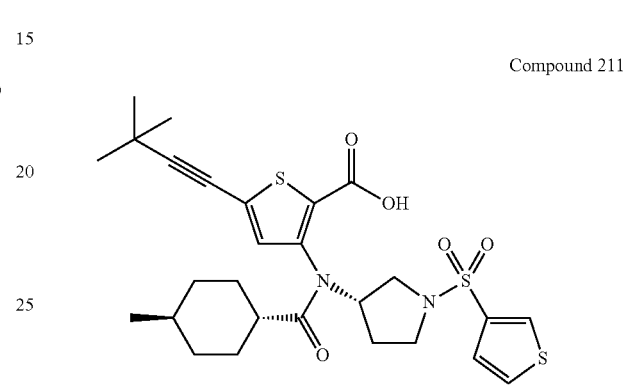

The title compound was synthesized in a manner analogous to Example 142, using thiophene-3-sulfonyl chloride in place of pyridine-2-carbonyl chloride: MS (m/z): 563.0 [M+H]; HPLC retention time: 4.82 min (2-98% acetonitrile:water with 0.05% trifluoroacetic acid) 6 min run.

Example 212

Compound 212: 5-(3,3-Dimethyl-but-1-ynyl)-3-[[1-(1,2-dimethyl-1H-imidazole-4-sulfonyl)-pyrrolidin-3-yl]-(4-methyl-cyclohexanecarbonyl)-amino]-thiophene-2-carboxylic acid Compound 212

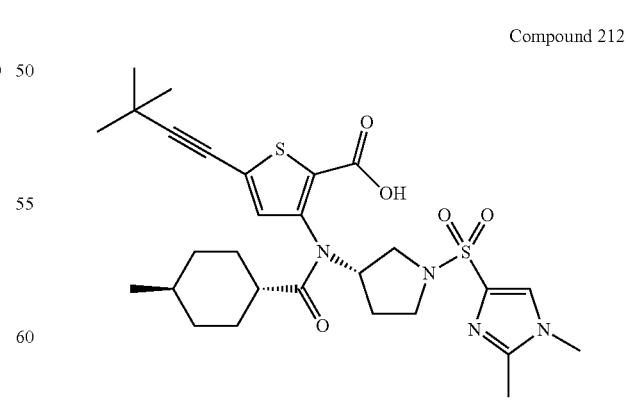

The title compound was synthesized in a manner analogous to Example 142, using 1,2-Dimethyl-1H-imidazole-4-sulfonyl chloride in place of pyridine-2-carbonyl chloride:

MS (m/z): 575.1 [M+H]; HPLC retention time: 4.13 min (2-98% acetonitrile:water with 0.05% trifluoroacetic acid) 6 min run.

Example 213

Compound 213: 5-(3,3-Dimethyl-but-1-ynyl)-3-{(4-methyl-cyclohexanecarbonyl)-[1-(thiophene-2-sulfonyl)-pyrrolidin-3-yl]-amino}-thiophene-2-carboxylic acid

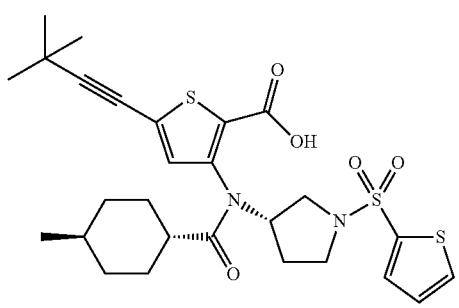

Compound 213

The title compound was synthesized in a manner analogous to Example 142, using thiophene-2-sulfonyl chloride in place of pyridine-2-carbonyl chloride: MS (m/z): 563.1 [M+H]; HPLC retention time: 4.88 min (2-98% acetonitrile:water with 0.05% trifluoroacetic acid) 6 min run.

Example 214

Compound 214: 5-(3,3-Dimethyl-but-1-ynyl)-3-{(4-methyl-cyclohexanecarbonyl)-[1-(2-oxo-1,2-dihydro-pyrimidine-5-sulfonyl)-pyrrolidin-3-yl]-amino}-thiophene-2-carboxylic acid

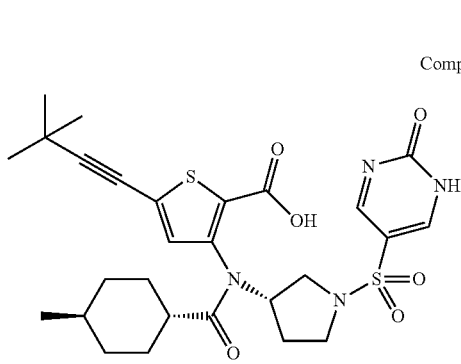

Compound 214

The title compound was synthesized in a manner analogous to Example 142, using 2-oxo-1,2-dihydro-pyrimidine-5-sulfonyl chloride in place of pyridine-2-carbonyl chloride:

MS (m/z): 575.1 [M+H]; HPLC retention time: 4.10 min (2-98% acetonitrile:water with 0.05% trifluoroacetic acid) 6 min run.

Example 215

Compound 215: 5-(3,3-Dimethyl-but-1-ynyl)-3-{(4-methyl-cyclohexanecarbonyl)-[1-(pyridine-2-sulfonyl)-pyrrolidin-3-yl]-amino}-thiophene-2-carboxylic acid

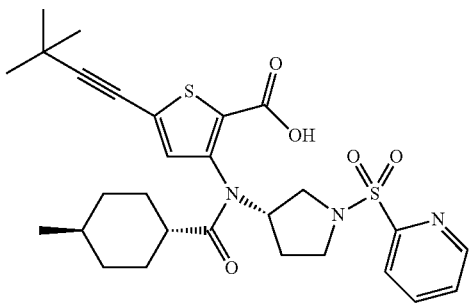

Compound 215

The title compound was synthesized in a manner analogous to Example 142, using pyridine-2-sulfonyl chloride in place of pyridine-2-carbonyl chloride: MS (m/z): 558.2 [M+H]; HPLC retention time: 4.47 min (2-98% acetonitrile:water with 0.05% trifluoroacetic acid) 6 min run.

Example 216

Compound 216: 5-(3,3-Dimethyl-but-1-ynyl)-3-{(4-methyl-cyclohexanecarbonyl)-[1-(pyridine-3-sulfonyl)-pyrrolidin-3-yl]-amino}-thiophene-2-carboxylic acid

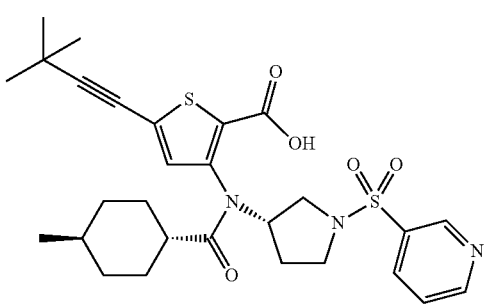

Compound 216

The title compound was synthesized in a manner analogous to Example 142, using pyridine-3-sulfonyl chloride in place of pyridine-2-carbonyl chloride: MS (m/z): 558.2 [M+H]; HPLC retention time: 4.56 min (2-98% acetonitrile:water with 0.05% trifluoroacetic acid) 6 min run.

Example 219 and 220
Compound 219: 5-(3,3-dimethylbut-1-ynyl)-3-((1r,4R)-4-methyl-N-((1r,4R)-4-(tetrahydro-2H-pyran-4-yloxy)cyclohexyl)cyclohexanecarboxamido)thiophene-2-carboxylic acid and Compound 220: 5-(3,3-dimethylbut-1-ynyl)-3-(1r,4R)-4-methyl-N-((1s,4S)-4-(tetrahydro-2H-pyran-4-yloxy)cyclohexyl)cyclohexanecarboxamido)thiophene-2-carboxylic acid
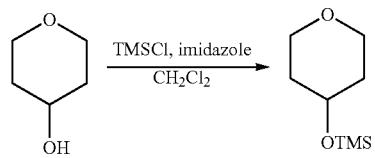
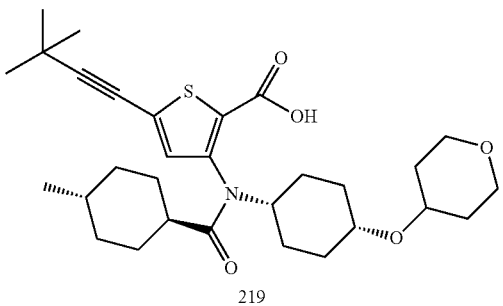
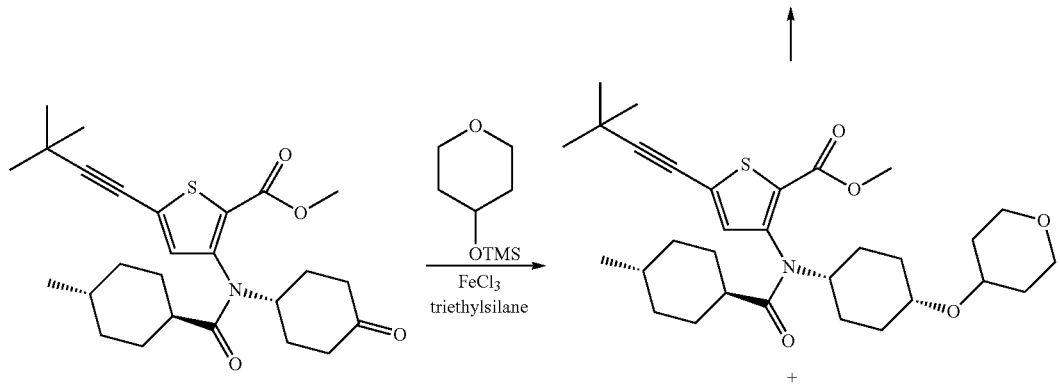
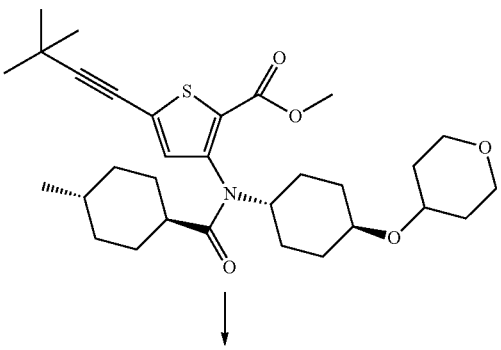

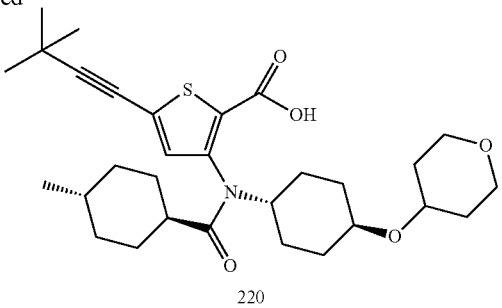

220

Tetrahydro-4-pyranol (1 g, 9.8 mmol) was dissolved in 30 mL of methylene chloride. To it was added imidazole (1.7 g, 24.5 mmol) followed by TMSCl (1.5 mL, 11.76 mmol). The reaction was allowed to stir at room temperature overnight. Insoluble material was removed by filtration, and the filtrate was washed with half saturated aqueous sodium bicarbonate and brine, and dried over MgSO₄. The solids were filtered and solvent removed under reduced pressure to afford 1.6 g of trimethyl(tetrahydro-2H-pyran-4-yloxy)silane as a clear liquid.

To a mixture of Iron (III) chloride (3.6 mg, 0.022 mmol) and methyl 5-(3,3-dimethylbut-1-ynyl)-3-((1r,4R)-4-methyl-N-(4-oxocyclohexyl)cyclohexanecarboxamido)thiophene-2-carboxylate (100 mg, 0.22 mmol) in 0.7 mL of nitromethane) were added trimethyl(tetrahydro-2H-pyran-4-yloxy)silane (77 mg, 0.44 mmol) and triethylsilane (31 µL, 0.264 mmol) successively, with stirring at 0° C. under argon. The reaction was allowed to warm to room temperature and stirred at room temperature for 2 hours. The reaction was quenched with a phosphate buffer. The organic materials were extracted with methylene chloride, washed with brine and dried over MgSO₄. The solids were filtered and solvent removed under reduced pressure. The residue was purified by reverse phase HPLC eluting with acetonitrile/H₂O with 0.1% TFA to afford 36 mg of methyl 5-(3,3-dimethylbut-1-ynyl)-3-((1r,4R)-4-methyl-N-((1r,4R)-4-(tetrahydro-2H-pyran-4-yloxy)cyclohexyl)cyclohexanecarboxamido)thiophene-2-carboxylate (front peak) and 20 mg of methyl 5-(3,3-dimethylbut-1-ynyl)-3-(1r,4R)-4-methyl-N-((1s,4S)-4-(tetrahydro-2H-pyran-4-yloxy)cyclohexyl) cyclohexanecarboxamido)thiophene-2-carboxylate (back peak).

30 mg of methyl 5-(3,3-dimethylbut-1-ynyl)-3-(1r,4R)-4-methyl-N-((1r,4R)-4-(tetrahydro-2H-pyran-4-yloxy)cyclohexyl)cyclohexanecarboxamido)thiophene-2-carboxylate was dissolved in 2 mL of THF:H₂O:MeOH (3:1:2) and to it was added 0.3 mL of 1N LiOH. The reaction was stirred at room temperature for 5 hours. The solvent was removed and purified by reverse phase HPLC, eluting with acetonitrile/H₂O with 0.1% TFA, to afford 24 mg of 5-(3,3-dimethylbut-1-ynyl)-3-((1r,4R)-4-methyl-N-((1r,4R)-4-(tetrahydro-2H-pyran-4-yloxy)cyclohexyl)cyclohexanecarboxamido) thiophene-2-carboxylic acid as a white solid. MS (m/z): 529.7 [M+H]; HPLC retention time: 4.76 min (2-98% acetonitrile:water with 0.05% trifluoroacetic acid) 6 min run.

15 mg of methyl 5-(3,3-dimethylbut-1-ynyl)-3-(1r,4R)-4-methyl-N-((1s,4S)-4-(tetrahydro-2H-pyran-4-yloxy)cyclohexyl)cyclohexanecarboxamido)thiophene-2-carboxylate was dissolved in 1 mL of THF:H₂O:MeOH (3:1:2) and to the solution was added 0.15 mL of 1N LiON. The reaction was stirred at room temperature for 5 hours. The solvent was removed and purified by reverse phase HPLC eluting with acetonitrile/H₂O with 0.1% TFA to afford 7 mg of 5-(3,3-dimethylbut-1-ynyl)-3-((1r,4R)-4-methyl-N-((1s,4S)-4-(tetrahydro-2H-pyran-4-yloxy)cyclohexyl)cyclohexanecarboxamido)thiophene-2-carboxylic acid as a white solid. MS (m/z): 530.0 [M+H]; HPLC retention time: 4.94 min (2-98% acetonitrile:water with 0.05% trifluoroacetic acid) 6 min run.

Example 221

Compound 221: 5-(3,3-dimethylbut-1-ynyl)-3-((1r,4R)-4-methyl-N-(4-((3S,3aS,6aR)-tetrahydro-2H-furo[2,3-b]furan-3-yloxy)cyclohexyl)cyclohexanecarboxamido)thiophene-2-carboxylic acid Compound 221

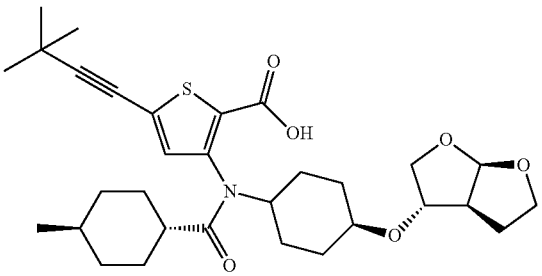

The title compound was synthesized in a manner analogous to Example 219, using (3S,3aS,6aR)-tetrahydro-2H-furo[2,3-b]furan-3-ol instead of tetrahydro-4-pyranol: MS (m/z): 558.2 [M+H]; HPLC retention time: 4.67 min (2-98% acetonitrile:water with 0.05% trifluoroacetic acid) 6 min run.

Example 222

Compound 222: 3-(N-(4-(1-(tert-butoxycarbonyl) piperidin-4-yloxy)cyclohexyl)-4-methylcyclohexanecarboxamido)-5-(3,3-dimethylbut-1-ynyl) thiophene-2-carboxylic acid Compound 222

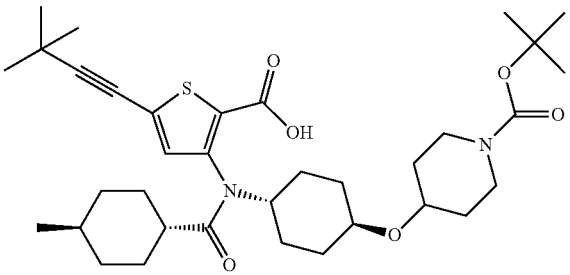

The title compound was synthesized in a manner analogous to Example 219, using tert-butyl 4-hydroxypiperidine-1-carboxylate instead of tetrahydro-4-pyranol: MS (m/z): 629.3 [M+H]; HPLC retention time: 5.47 min (2-98% acetonitrile:water with 0.05% trifluoroacetic acid) 6 min run.

Example 223

Compound 223: 5-(3,3-dimethylbut-1-ynyl)-3-(4-methyl-N-(4-(piperidin-4-yloxy)cyclohexyl)cyclohexanecarboxamido)thiophene-2-carboxylic acid

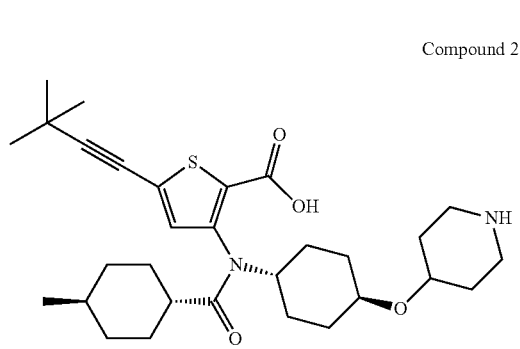

Compound 223

The title compound was synthesized from Example 222 by treatment with 20% TFA in methylene chloride at room temperature for 4 hours. MS (m/z): 529.1 [M+H]; HPLC retention time: 3.20 min (2-98% acetonitrile:water with 0.05% trifluoroacetic acid) 6 min run.

Example 224

Compound 224: 5-(3,3-dimethylbut-1-ynyl)-3-(4-methyl-N-(4-(tetrahydrofuran-3-yloxy)cyclohexyl)cyclohexanecarboxamido)thiophene-2-carboxylic acid

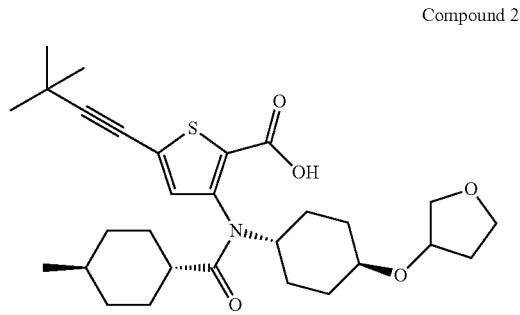

Compound 224

The title compound was synthesized in a manner analogous to Example 219, using tetrahydrofuran-3-ol instead of tetrahydro-4-pyranol: MS (m/z): 516.2 [M+H]; HPLC retention time: 4.824 min (2-98% acetonitrile:water with 0.05% trifluoroacetic acid) 6 min run.

Example 225

Compound 225: 3-(N-((1S,4R)-4-(S)-1-(tert-butoxycarbonyl)pyrrolidin-3-yloxy)cyclohexyl)-4-methylcyclohexanecarboxamido)-5-(3,3-dimethylbut-1-ynyl)thiophene-2-carboxylic acid

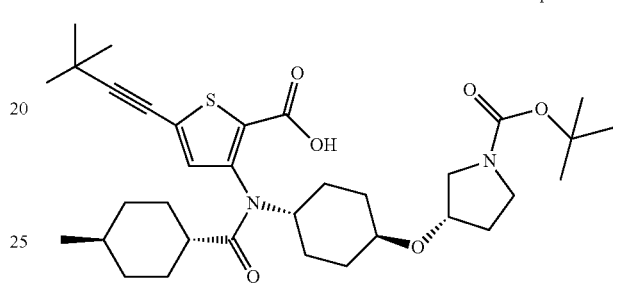

Compound 225

The title compound was synthesized in a manner analogous to Example 219, using (S)-tert-butyl 3-hydroxypyrrolidine-1-carboxylate instead of tetrahydro-4-pyranol: MS (m/z): 615.3 [M+H]; HPLC retention time: 5.36 min (2-98% acetonitrile:water with 0.05% trifluoroacetic acid) 6 min run.

Example 226

Compound 226: 5-(3,3-dimethylbut-1-ynyl)-3-(4-methyl-N-(4-((S)-pyrrolidin-3-yloxy)cyclohexyl)cyclohexanecarboxamido)thiophene-2-carboxylic acid

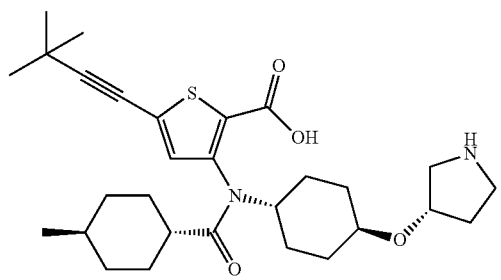

Compound 226

The title compound was synthesized from Example 225 by treatment with 20% TFA in methylene chloride at room temperature for 4 hours. MS (m/z): 515.2 [M+H]; HPLC retention time: 3.12 min (2-98% acetonitrile:water with 0.05% trifluoroacetic acid) 6 min run.

Example 227

Compound 227: 5-(3,3-dimethylbut-1-ynyl)-3-(1R,2S,4R)-2-hydroxy-4-methyl-N-(4-(tetrahydrofuran-3-yloxy)cyclohexyl)cyclohexanecarboxamido)thiophene-2-carboxylic acid

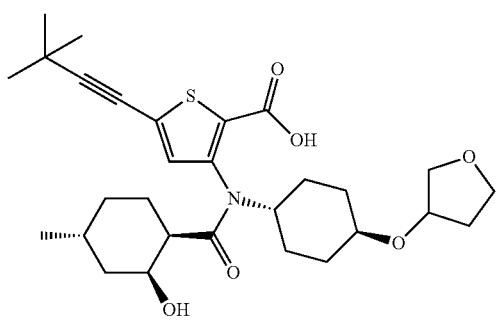

Compound 227

The title compound was synthesized in a manner analogous to Example 219, using initially methyl 5-(3,3-dimethylbut-1-ynyl)-3-(4-oxocyclohexylamino)thiophene-2-carboxylate and tetrahydrofuran-3-ol instead of methyl 5-(3,3-dimethylbut-1-ynyl)-3-(4-methyl-N-(4-oxocyclohexyl)cyclohexanecarboxamido)thiophene-2-carboxylate and tetrahydro-4-pyranol; then purified by reverse phase HPLC to afford two products. Upon isolation of the front peak, the initial product was acylated with (1S,2R,5R)-2-(chlorocarbonyl)-5-methylcyclohexyl acetate and then subjected to ester hydrolysis with LiOH: MS (m/z): 532.2 [M+H]; HPLC retention time: 4.530 min (2-98% acetonitrile:water with 0.05% trifluoroacetic acid)

Example 228

Compound 228: 5-(3,3-dimethylbut-1-ynyl)-3-((1R,2S,4R)-2-hydroxy-4-methyl-N-(4-((R)-tetrahydrofuran-3-yloxy)cyclohexyl)cyclohexanecarboxamido)thiophene-2-carboxylic acid

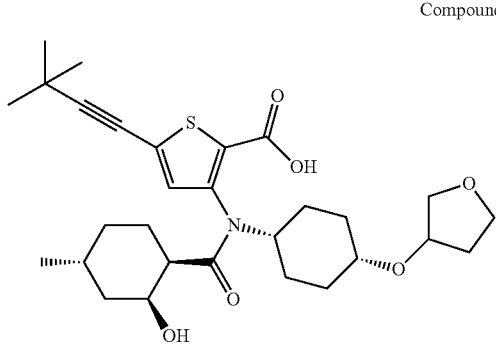

Compound 228

The title compound was synthesized in a manner analogous to Example 227 but from the second peak isolated in the first reaction therein: MS (m/z): 532.2 [M+H]; HPLC retention time: 4.582 min (2-98% acetonitrile:water with 0.05% trifluoroacetic acid) 6 min run.

Example 229

Compound 229: 5-(2-cyclopropylethynyl)-3-(4-methyl-N-(4-(pyridin-2-yloxy)cyclohexyl)cyclohexanecarboxamido)thiophene-2-carboxylic acid

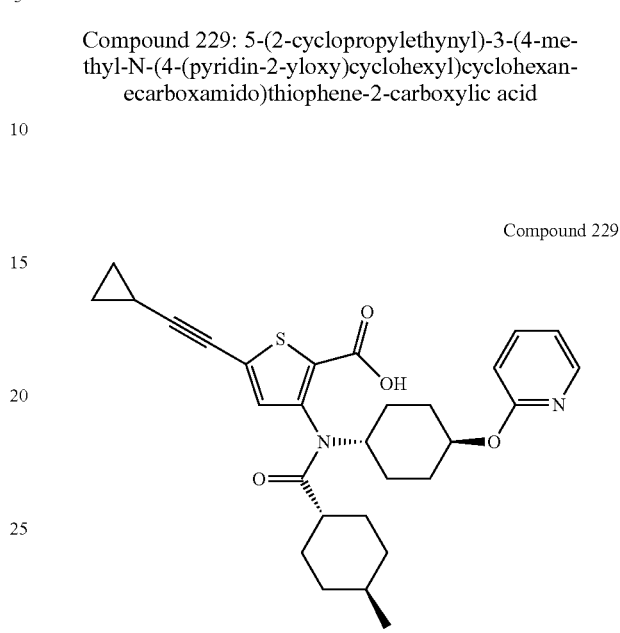

Compound 229

Compound 229 was synthesized in the same manner as Example 1 using 5-(2-cyclopropylethynyl)-3-(N-(4-hydroxycyclohexyl)-4-methylcyclohexanecarboxamido)thiophene-2-carboxylic acid as a starting material. [M+H$^+$]=507.1. HPLC retention time=4.65 min (6 minute method 2-98% acetonitrile:water with 0.05% trifluoroacetic acid.

Example 230

Compound 230: 3-(N-(4-((R)-1-(tert-butoxycarbonyl)pyrrolidin-3-yloxy)cyclohexyl)-4-methylcyclohexanecarboxamido)-5-(3,3-dimethylbut-1-ynyl)thiophene-2-carboxylic acid

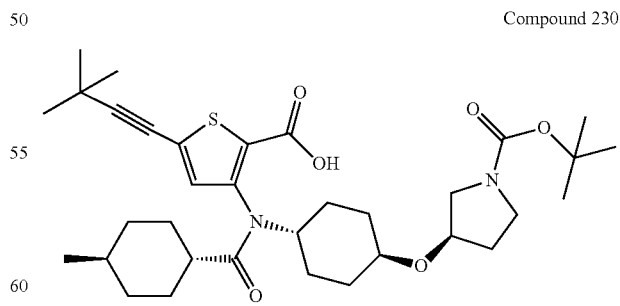

Compound 230

The title compound was synthesized in a manner analogous to Example 219, using (R)-tert-butyl 3-hydroxypyrrolidine-1-carboxylate instead of tetrahydro-4-pyranol: MS (m/z): 615.3 [M+H]; HPLC retention time: 5.429 min (2-98% acetonitrile:water with 0.05% trifluoroacetic acid) 6 min run.

Example 231

Compound 231: 5-(3,3-dimethylbut-1-ynyl)-3-(4-methyl-N-(4-((R)-pyrrolidin-3-yloxy)cyclohexyl)cyclohexanecarboxamido)thiophene-2-carboxylic acid Compound 231

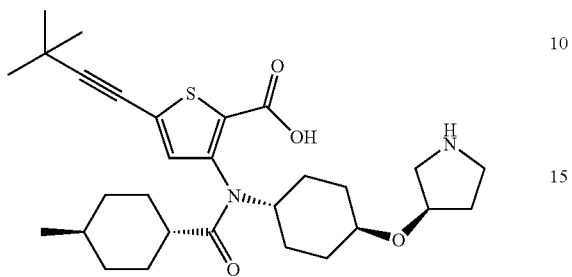

The title compound was synthesized from Example 230 by treatment with 20% TFA in methylene chloride at room temperature for 4 hours. MS (m/z): 515.2 [M+H]; HPLC retention time: 3.418 min (2-98% acetonitrile:water with 0.05% trifluoroacetic acid) 6 min run.

Example 301

Compound 301: Synthesis of 5-(3,3-dimethyl-but-1-ynyl)-3-{(4,6S-dimethyl-cyclohex-3-enecarbonyl)-[4-(tetrahydro-furan-3S-yloxy)-trans-cyclohexyl]-amino}-thiophene-2-carboxylic acid (Isomer 1)

Scheme 1

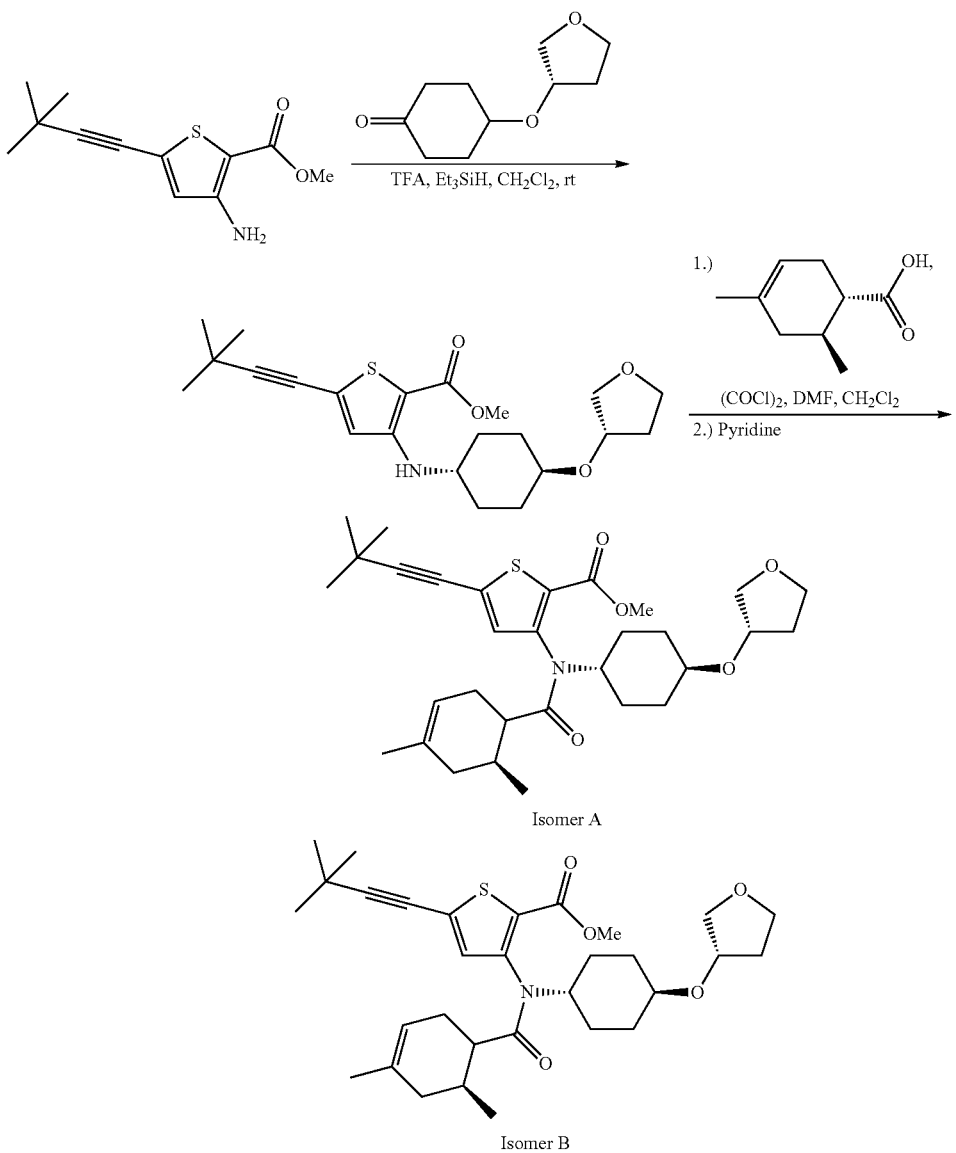

Isomer A

Isomer B

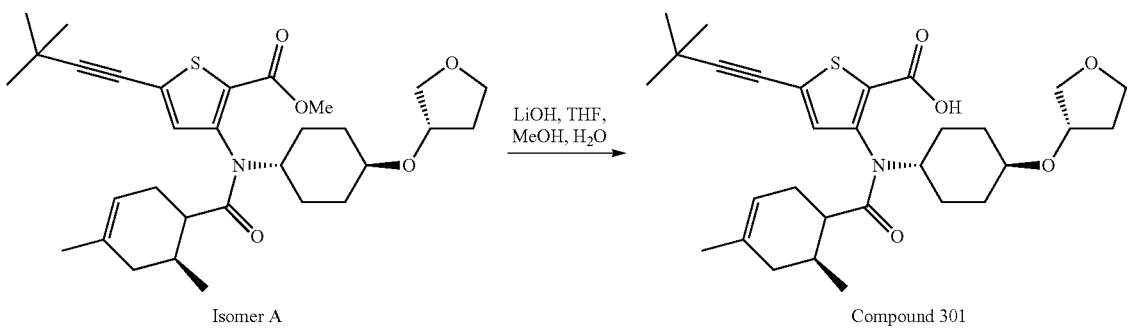

Isomer A → Compound 301 (LiOH, THF, MeOH, H₂O)

A mixture of 3-amino-5-(3,3-dimethyl-but-1-ynyl)-thiophene-2-carboxylic acid methyl ester (2.62 g, 11.06 mmol), 4-(tetrahydro-furan-3S-yloxy)-cyclohexanone (1.7 g, 9.22 mmol), TFA (2.84 mL, 36.9 mmol) and triethylsilane (2.94 mL, 18.44 mmol) in CH₂Cl₂ (15 mL) was stirred for 24 h at room temperature. The reaction was concentrated in vacuo to remove volatiles and the crude oil was dissolved in toluene (50 mL) and concentrated (repeat) to give a yellow solid. The crude solid was purified by column chromatography (hexane/ethylacetate) to give 5-(3,3-dimethyl-but-1-ynyl)-3-[4-(tetrahydro-furan-3-yloxy)-cyclohexylamino]-thiophene-2-carboxylic acid methyl ester (1.35 g, 3.33 mmol) as a single isomer.

4,6-S-dimethyl-cyclohex-3-ene-1S-carboxylic acid (944 mg, 6.17 mmol) was dissolved in CH₂Cl₂ (10 mL) and DMF (20 µL) was added. The solution was cooled to 0° C. and then (COCl)₂ (700 µL, 7.38 mmol) was slowly added to the solution. The reaction was stirred in the ice bath for 1 hour and then concentrated. The residue was taken up in hexanes and concentrated; this hexanes coevaporation was repeated once more. To the residue was added 5-(3,3-dimethyl-but-1-ynyl)-3-[4-(tetrahydro-furan-3S-yloxy)-trans-cyclohexylamino]-thiophene-2-carboxylic acid methyl ester (500 mg, 1.23 mmol) and pyridine (3 mL). The solution was heated to 90° C. overnight. The reaction was cooled to rt, concentrated and taken up in minimal CH₂Cl₂. The two resulting isomers were purified and separated from each other by silica gel column chromatography, eluting with a mixture of EtOAc and hexanes. Isomer A yield=115 mg, Isomer B yield=162 mg Isomer A (105 mg, 0.19 mmol) was dissolved in THF (1 mL) and MeOH (0.5 mL). To this solution was added a solution of LiOH·H₂O (39.8 mg, 0.95 mmol) in H₂O (0.5 mL). The reaction was stirred at it for 3 h and then quenched with TFA. The entire reaction mixture was injected onto a reverse phase HPLC and Compound 301 was isolated (77 mg).

LC/MS=528 (M⁺+1)

Retention time: 5.71 min

LC: Thermo Electron Surveyor HPLC

MS: Finnigan LCQ Advantage MAX Mass Spectrometer

Column: Phenomenex Polar RP 30 mm×4.6 mm

Solvents: (B): Acetonitrile with 0.1% formic acid, (A): Water with 0.1% formic acid Gradient: 2 mL/min, 0 min-0.5 min 5% ACN, 0.5 min-6.5 min 5%-100% ACN, 6.5 min-9.0 min 100% ACN, 9.0 min-9.1 min 100%-5% ACN, 9.1 min-9.5 min 5% ACN Synthesis of (1S,6S)-4,6-dimethyl-cyclohex-3-enecarboxylic acid Scheme 2

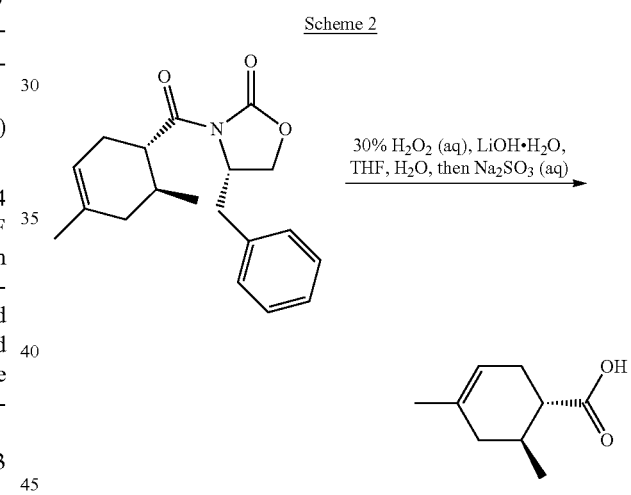

4S-benzyl-3-(4,6S-dimethyl-cyclohex-3-ene-1S-carbonyl)-oxazolidin-2-one, prepared in a method similar to that described in *J. Am. Chem. Soc.* 110(4), 1988, 1238-1256, was dissolved in THF (1000 mL) and H₂O (350 mL). The solution was cooled in an ice bath and 30% H₂O₂ (36 mL, 354 mmol) was slowly added followed by LiOH·H₂O₍s₎ (9.90 g, 263 mmol) in one portion. The reaction was allowed to slowly warm to rt and was stirred for 16 h. The reaction was then cooled in an ice bath. Na₂SO₃ (60 g, 472 mmol) was dissolved H₂O (400 mL) and very slowly added to the cooled reaction mixture. The solution was stirred for 1 h, then the layers were separated. The organics were removed under reduced pressure. The aqueous was added back to the organics concentrate and was washed with CH₂Cl₂ (2×500 mL). Adjust the aqueous pH to 2 with a slow addition of con HCl. Extract the aqueous with EtOAc (4×300 mL) and dry over Na₂SO₄. Remove organics under reduced pressure and co-evaporate with hexanes to afford (1S,6S)-4,6-dimethyl-cyclohex-3-enecarboxylic acid (14.14 g, 78%) as a white solid.

Synthesis of 4-(tetrahydro-furan-3S-yloxy)-cyclohexanone

Scheme 3

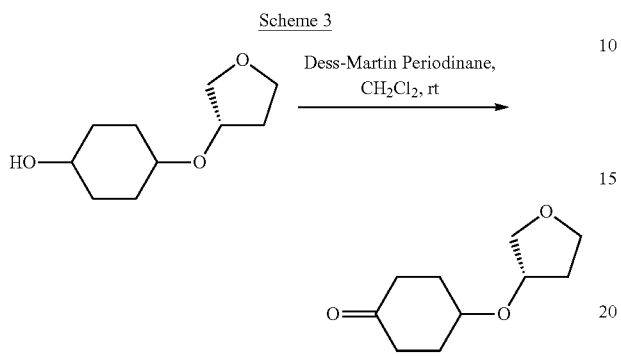

4-(tetrahydro-furan-3S-yloxy)-cyclohexanol (40.86 mmol) was dissolved in DCM (200 mL) under an atmosphere of nitrogen. Dess-Martin Periodinane (20.78 g, 49.03 mmol) was added in 4 portions. The reaction was stirred for 3 hours at room temperature until complete by TLC. The reaction was cooled to 0° C. and 100 mL of a 1:1 solution of saturated aqueous $NaS_2O_3$:saturated aqueous $NaHCO_3$ was added. The reaction was allowed to warm to room temperature and was stirred for 1 hour. The layers were separated. The aqueous layer was extracted with DCM (50 mL×2). The combined organics were dried with sodium sulfate, filtered and were concentrated. 4-(Tetrahydro-furan-3S-yloxy)-cyclohexanone was purified by silica gel chromatography to afford 5.2 g of a yellow oil (69%).

Example 302

Compound 302: 5-(3,3-dimethyl-but-1-ynyl)-3-{(4,6S-dimethyl-cyclohex-3-enecarbonyl)-[4-(tetrahydro-furan-3S-yloxy)-trans-cyclohexyl]-amino}-thiophene-2-carboxylic acid (Isomer 2)

Compound 302

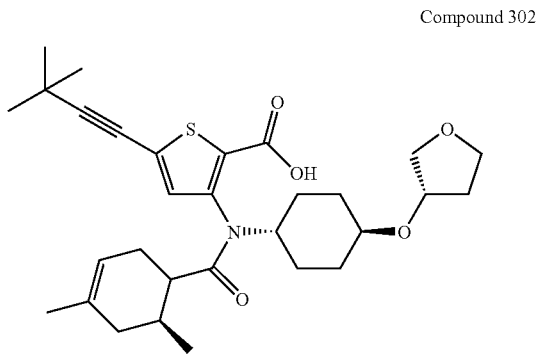 [SMILES: CC1=CCC(C(=O)N(c2cc(C#CC(C)(C)C)sc2C(=O)O)[C@H]2CC[C@H](O[C@H]3CCOC3)CC2)[C@@H](C)C1]

5-(3,3-dimethyl-but-1-ynyl)-3-{(4,6S-dimethyl-cyclohex-3-enecarbonyl)-[4-(tetrahydro-furan-3S-yloxy)-trans-cyclohexyl]-amino}-thiophene-2-carboxylic acid (Compound 302) was prepared in a similar fashion as 5-(3,3-dimethyl-but-1-ynyl)-3-{(4,6S-dimethyl-cyclohex-3-enecarbonyl)-[4-(tetrahydro-furan-3S-yloxy)-trans-cyclohexyl]-amino}-thiophene-2-carboxylic acid (Isomer 1).

LC/MS=528 (M$^+$+1)

Retention time: 5.65 min

LC: Thermo Electron Surveyor HPLC

MS: Finnigan LCQ Advantage MAX Mass Spectrometer

Column: Phenomenex Polar RP 30 mm×4.6 mm

Solvents: (B): Acetonitrile with 0.1% formic acid, (A): Water with 0.1% formic acid Gradient: 2 mL/min, 0 min-0.5 min 5% ACN, 0.5 min-6.5 min 5%-100% ACN, 6.5 min-9.0 min 100% ACN, 9.0 min-9.1 min 100%-5% ACN, 9.1 min-9.5 min 5% ACN.

Example 303

Compound 303: 5-(3,3-dimethyl-but-1-ynyl)-3-{4,6R-dimethyl-cyclohex-3-enecarbonyl)-[4-(tetrahydro-furan-3S-yloxy)-trans-cyclohexyl]-amino}-thiophene-2-carboxylic acid (Isomer 1)

Compound 303

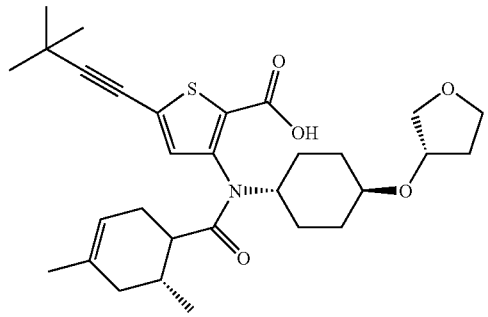

5-(3,3-dimethyl-but-1-ynyl)-3-{(4,6R-dimethyl-cyclohex-3-enecarbonyl)-[4-(tetrahydro-furan-3S-yloxy)-trans-cyclohexyl]-amino}-thiophene-2-carboxylic acid (Compound 303) was prepared in a similar fashion as 5-(3,3-dimethyl-but-1-ynyl)-3-{(4,6S-dimethyl-cyclohex-3-enecarbonyl)-[4-(tetrahydro-furan-3S-yloxy)-trans-cyclohexyl]-amino}-thiophene-2-carboxylic acid (Isomer 1) using Method A, except that 4,6R-dimethyl-cyclohex-3-ene-1R-carboxylic acid (prepared in a similar manner to 4,6S-dimethyl-cyclohex-3-ene-1S-carboxylic acid, using the chiral auxiliary 4R-benzyl-oxazolidin-2-one) was used instead of 4,6S-dimethyl-cyclohex-3-ene-1S-carboxylic acid.

LC/MS=528 (M$^+$+1)

Retention time: 5.64 min

LC: Thermo Electron Surveyor HPLC

MS: Finnigan LCQ Advantage MAX Mass Spectrometer

Column: Phenomenex Polar RP 30 mm×4.6 mm

Solvents: (B): Acetonitrile with 0.1% formic acid, (A): Water with 0.1% formic acid Gradient: 2 mL/min, 0 min-0.5 min 5% ACN, 0.5 min-6.5 min 5%-100% ACN, 6.5 min-9.0 min 100% ACN, 9.0 min-9.1 min 100%-5% ACN, 9.1 min-9.5 min 5% ACN.

Example 304

Compound 304: 5-(3,3-dimethyl-but-1-ynyl)-3-{(4,6R-dimethyl-cyclohex-3-enecarbonyl)-[4-(tetrahydro-furan-3S-yloxy)-trans-cyclohexyl]-amino}-thiophene-2-carboxylic acid

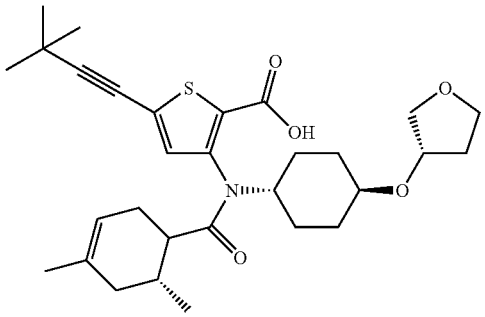

Compound 304

5-(3,3-Dimethyl-but-1-ynyl)-3-{(4,6R-dimethyl-cyclohex-3-enecarbonyl)-[4-(tetrahydro-furan-3S-yloxy)-trans-cyclohexyl]-amino}-thiophene-2-carboxylic acid (Compound 304) was prepared in a similar fashion as 5-(3,3-dimethyl-but-1-ynyl)-3-{(4,6S-dimethyl-cyclohex-3-enecarbonyl)-[4-(tetrahydro-furan-3S-yloxy)-trans-cyclohexyl]-amino}-thiophene-2-carboxylic acid (Isomer 1), except that 4,6R-dimethyl-cyclohex-3-ene-1R-carboxylic acid was used instead of 4,6S-dimethyl-cyclohex-3-ene-1S-carboxylic acid.

LC/MS=528 ($M^+$+1)
Retention time: 5.31 min
LC: Thermo Electron Surveyor HPLC
MS: Finnigan LCQ Advantage MAX Mass Spectrometer
Column: Phenomenex Polar RP 30 mm×4.6 mm
Solvents: (B): Acetonitrile with 0.1% formic acid, (A): Water with 0.1% formic acid
Gradient: 2 mL/min, 0 min-0.5 min 5% ACN, 0.5 min-6.5 min 5%-100% ACN, 6.5 min-9.0 min 100% ACN, 9.0 min-9.1 min 100%-5% ACN, 9.1 min-9.5 min 5% ACN.

Example 305

Compound 305: 5-(3,3-dimethyl-but-1-ynyl)-3-{(4,6R-dimethyl-cyclohex-3-enecarbonyl)-[4-(tetrahydro-furan-3R-yloxy)-trans-cyclohexyl]-amino}-thiophene-2-carboxylic acid (Isomer 1)

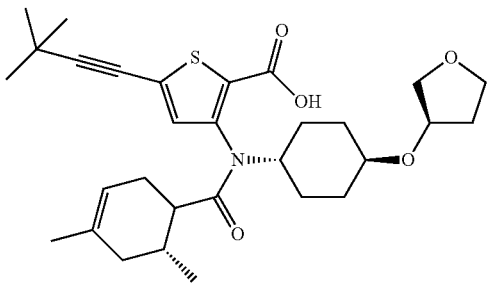

Compound 305

5-(3,3-Dimethyl-but-1-ynyl)-3-{(4,6R-dimethyl-cyclohex-3-enecarbonyl)-[4-(tetrahydro-furan-3R-yloxy)-trans-cyclohexyl]amino}-thiophene-2-carboxylic acid (Compound 305) was prepared in a similar fashion as 5-(3,3-dimethyl-but-1-ynyl)-3-{(4,6S-dimethyl-cyclohex-3-enecarbonyl)-[4-(tetrahydro-furan-3S-yloxy)-trans-cyclohexyl]-amino}-thiophene-2-carboxylic acid (Isomer 1) except that 4-(tetrahydro-furan-3R-yloxy)-cyclohexanone was used instead of 4-(tetrahydro-furan-3S-yloxy)-cyclohexanone and 4,6R-dimethyl-cyclohex-3-ene-1S-carboxylic acid was used instead of 4,6S-dimethyl-cyclohex-3-ene-1S-carboxylic acid.

LC/MS=528 ($M^+$+1)
Retention time: 5.59 min
LC: Thermo Electron Surveyor HPLC
MS: Finnigan LCQ Advantage MAX Mass Spectrometer
Column: Phenomenex Polar RP 30 mm×4.6 mm
Solvents: (B): Acetonitrile with 0.1% formic acid, (A): Water with 0.1% formic acid
Gradient: 2 mL/min, 0 min-0.5 min 5% ACN, 0.5 min-6.5 min 5%-100% ACN, 6.5 min-9.0 min 100% ACN, 9.0 min-9.1 min 100%-5% ACN, 9.1 min-9.5 min 5% ACN.

Example 306

Compound 306: 5-(3,3-Dimethyl-but-1-ynyl)-3-{(4,6R-dimethyl-cyclohex-3-enecarbonyl)-[4-(tetrahydro-furan-3R-yloxy)-trans-cyclohexyl]-amino}-thiophene-2-carboxylic acid (Isomer 2)

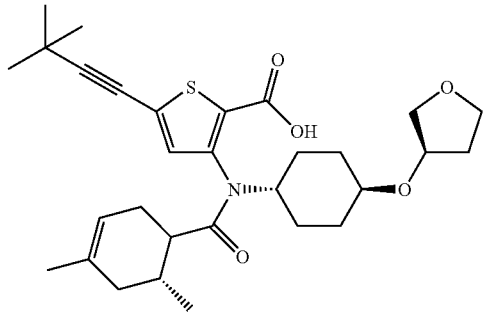

Compound 306

5-(3,3-Dimethyl-but-1-ynyl)-3-{(4,6R-dimethyl-cyclohex-3-enecarbonyl)-[4-(tetrahydro-furan-3R-yloxy)-trans-cyclohexyl]-amino}-thiophene-2-carboxylic acid (Compound 306) was prepared in a similar fashion as 5-(3,3-dimethyl-but-1-ynyl)-3-{(4,6S-dimethyl-cyclohex-3-enecarbonyl)-[4-(tetrahydro-furan-3S-yloxy)-trans-cyclohexyl]-amino}-thiophene-2-carboxylic acid (Isomer 1) except that 4-(tetrahydro-furan-3R-yloxy)-cyclohexanone was used instead of 4-(tetrahydro-furan-3S-yloxy)-cyclohexanone and 4,6R-dimethyl-cyclohex-3-ene-1S-carboxylic acid was used instead of 4,6S-dimethyl-cyclohex-3-ene-1S-carboxylic acid.

LC/MS=528 ($M^+$+1)
Retention time: 5.66 min
LC: Thermo Electron Surveyor HPLC
MS: Finnigan LCQ Advantage MAX Mass Spectrometer
Column: Phenomenex Polar RP 30 mm×4.6 mm
Solvents: (B): Acetonitrile with 0.1% formic acid, (A): Water with 0.1% formic acid
Gradient: 2 mL/min, 0 min-0.5 min 5% ACN, 0.5 min-6.5 min 5%-100% ACN, 6.5 min-9.0 min 100% ACN, 9.0 min-9.1 min 100%-5% ACN, 9.1 min-9.5 min 5% ACN.

Example 7

Compound 307: 5-(3,3-Dimethyl-but-1-ynyl)-3-{(4,6S-dimethyl-cyclohex-3-enecarbonyl)-[4-(tetrahydro-furan-3R-yloxy)-trans-cyclohexyl]-amino}-thiophene-2-carboxylic acid (Isomer 1)

Compound 307

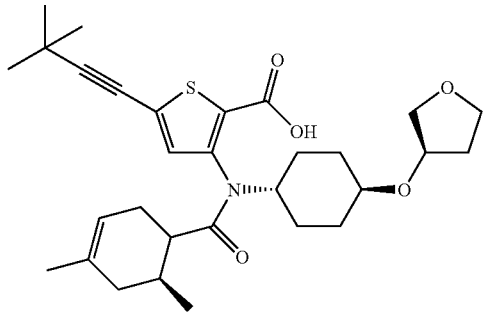

5-(3,3-Dimethyl-but-1-ynyl)-3-{(4,6S-dimethyl-cyclohex-3-enecarbonyl)-[4-(tetrahydro-furan-3R-yloxy)-trans-cyclohexyl]-amino}-thiophene-2-carboxylic acid (Compound 307) was prepared in a similar fashion as 5-(3,3-dimethyl-but-1-ynyl)-3-{(4,6S-dimethyl-cyclohex-3-enecarbonyl)-[4-(tetrahydro-furan-3S-yloxy)-trans-cyclohexyl]-amino}thiophene-2-carboxylic acid (Isomer 1) except that 4-(tetrahydro-furan-3R-yloxy)-cyclohexanone was used instead of 4-(tetrahydro-furan-3S-yloxy)-cyclohexanone, LC/MS=528 (M$^+$+1)
Retention time: 5.30 min
LC: Thermo Electron Surveyor HPLC
MS: Finnigan LCQ Advantage MAX Mass Spectrometer
Column: Phenomenex Polar RP 30 mm×4.6 mm
Solvents: (B): Acetonitrile with 0.1% formic acid, (A): Water with 0.1% formic acid
Gradient: 2 mL/min, 0 min-0.5 min 5% ACN, 0.5 min-6.5 min 5%-100% ACN, 6.5 min-9.0 min 100% ACN, 9.0 min-9.1 min 100%-5% ACN, 9.1 min-9.5 min 5% ACN.

Example 308

Compound 308: 5-(3,3-Dimethyl-but-1-ynyl)-3-{(4,6S-dimethyl-cyclohex-3-enecarbonyl)-[4-(tetrahydro-furan-3R-yloxy)-trans-cyclohexyl]-amino}-thiophene-2-carboxylic acid (Isomer 2)

Compound 308

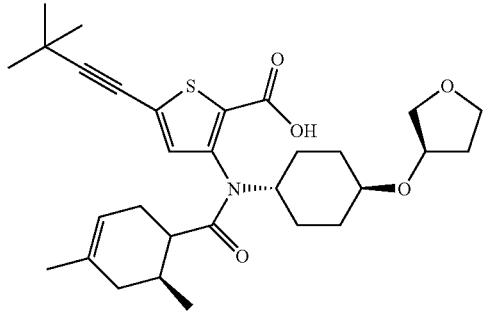

5-(3,3-Dimethyl-but-1-ynyl)-3-{(4,6S-dimethyl-cyclohex-3-enecarbonyl)-[4-(tetrahydro-furan-3R-yloxy)-trans-cyclohexyl]-amino}-thiophene-2-carboxylic acid (Compound 308) was prepared in a similar fashion as 5-(3,3-dimethyl-but-1-ynyl)-3-{(4,6S-dimethyl-cyclohex-3-enecarbonyl)-[4-(tetrahydro-furan-3S-yloxy)-trans-cyclohexyl]-amino}-thiophene-2-carboxylic acid (Isomer 1) except that 4-(tetrahydro-furan-3R-yloxy)-cyclohexanone was used instead of 4-(tetrahydro-furan-3S-yloxy)-cyclohexanone.

LC/MS=528 (M$^+$+1)
Retention time: 5.21 min
LC: Thermo Electron Surveyor HPLC
MS: Finnigan LCQ Advantage MAX Mass Spectrometer
Column: Phenomenex Polar RP 30 mm×4.6 mm
Solvents: (B): Acetonitrile with 0.1% formic acid, (A): Water with 0.1% formic acid
Gradient: 2 mL/min, 0 min-0.5 min 5% ACN, 0.5 min-6.5 min 5%-100% ACN, 6.5 min-9.0 min 100% ACN, 9.0 min-9.1 min 100%-5% ACN, 9.1 min-9.5 min 5% ACN.

Example 309

Compound 309: 5-(3,3-dimethylbut-1-ynyl)-3-((1R,2S,4R)-2-hydroxy-4-methyl-N-(4-(tetrahydrofuran-3S-yloxy)cyclohexyl)cyclohexanecarboxamido)thiophene-2-carboxylic acid Compound 309

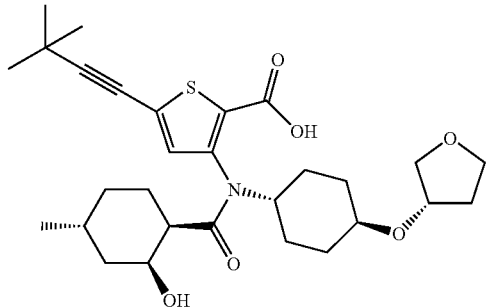

Compound 309 was synthesized in a manner analogous to Example 301, acylating with (1S,2R,5R)-2-(chlorocarbonyl)-5-methylcyclohexyl acetate. MS (m/z): 532.2 [M+H]; HPLC retention time: 4.530 min (2-98% acetonitrile:water with 0.05% trifluoroacetic acid).

Example 310

Compound 310: 5-(3,3-dimethylbut-1-ynyl)-3-((1R,2S,4R)-2-hydroxy-4-methyl-N-(4-(tetrahydrofuran-3R-yloxy)cyclohexyl)cyclohexanecarboxamido)thiophene-2-carboxylic acid Compound 310

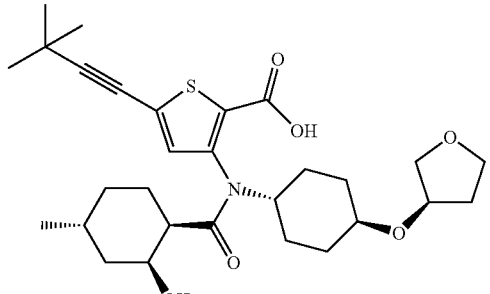

Compound 310 was synthesized in a manner analogous to Example 303, acylating with (1S,2R,5R)-2-(chlorocarbonyl)-5-methylcyclohexyl acetate. MS (m/z): 532.2 [M+H]; HPLC retention time: 4.530 min (2-98% acetonitrile:water with 0.05% trifluoroacetic acid).

Example 311

Compound 311: 5-[3,3-Dimethyl-4-(tetrahydro-pyran-2-yloxy)-but-1-ynyl]-3-{(4-methyl-cyclohexanecarbonyl)-[4-(pyridin-2-yloxy)-cyclohexyl]-amino}-thiophene-2-carboxylic acid Scheme 4

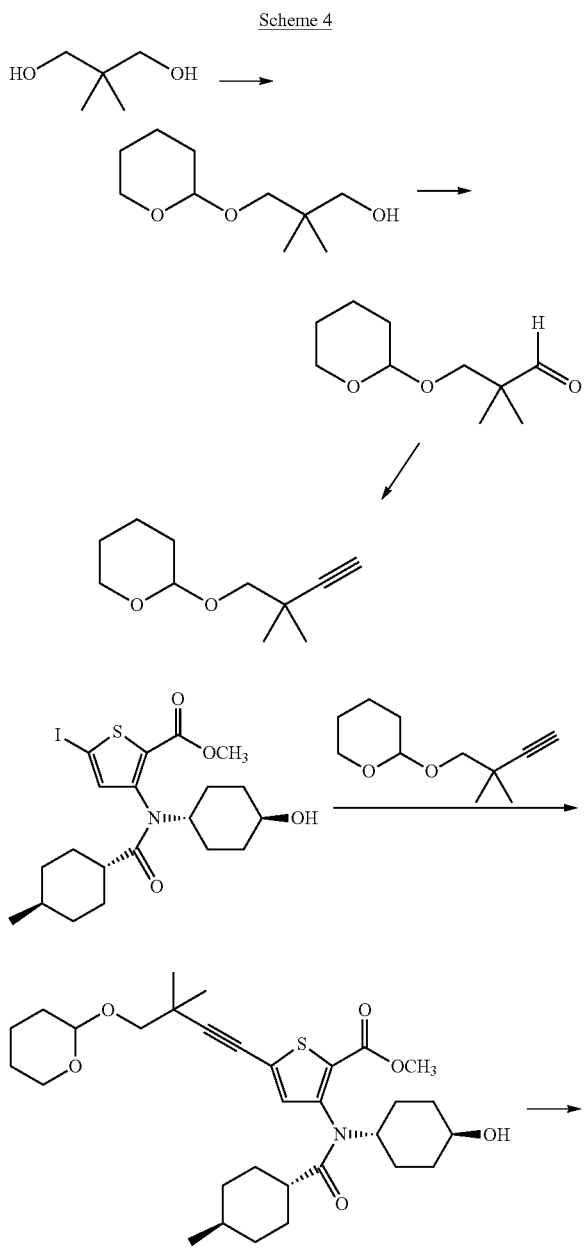

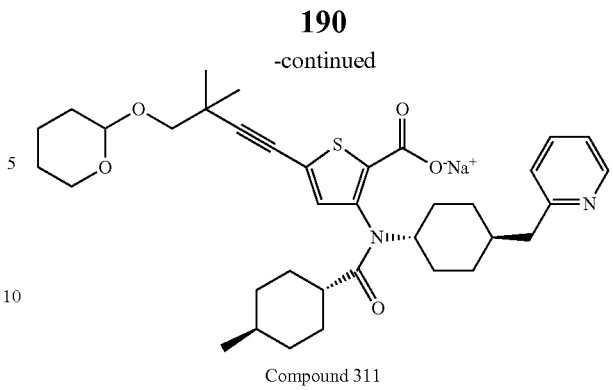

Compound 311

To a solution of neopentyl glycol (6.0 g, 57.6 mmol) and 3,4-dihydro-2H-pyran (2.64 mL, 28.94 mmol) in 2:1 THF/dichloromethane (135 mL) was added p-TsOH.H$_2$O (100 mg, 0.53 mmol) and the reaction stirred overnight. Solid NaHCO$_3$ was then added and after rapid stirring for 15 min the reaction was filtered and concentrated to give a pale liquid. Purification by flash column chromatography on silica gel using 50% ethyl acetate in hexanes provided 2,2-dimethyl-3-(tetrahydro-pyran-2-yloxy)-propan-1-ol (3.21 g, 59%) as a pale liquid.

DMSO (2.69 mL, 50.97 mmol) was added dropwise to a solution of oxalyl chloride (2.87 mL, 33.98 mmol) in dichloromethane (85.0 mL) at −78° C. After several minutes, neat 2,2-dimethyl-3-(tetrahydro-pyran-2-yloxy)-propan-1-ol (3.2 g, 16.99 mmol) was added dropwise and after stirring for 1 h at −78° C., triethylamine (9.5 mL, 68.0 mmol) was added. The reaction was allowed to warm to room temperature and stirred for 30 min. Sat. NH$_4$Cl was added and the organic layer was separated. The aqueous layer was extracted with ethyl acetate and washed with brine. The organic layers were combined, dried over Na$_2$SO$_4$ and concentrated to give a pale liquid. The crude liquid was passed through a short silica gel column and eluted with 50% ethyl acetate in hexanes to provide 2,2-dimethyl-3-(tetrahydro-pyran-2-yloxy)-propionaldehyde (3.09 g, 97%) as a pale liquid after removal of solvents under reduced pressure.

(1-Diazo-2-oxo-propyl)-phosphonic acid dimethyl ester (486 mg, 2.54 mmol) was added to a stirred suspension of 2,2-dimethyl-3-(tetrahydro-pyran-2-yloxy)-propionaldehyde (315 mg, 1.69 mmol) and K$_2$CO$_3$ (700 mg, 5.07 mmol) in methanol (20.0 mL) at room temperature. After overnight stirring, the reaction was diluted with diethyl ether, washed with sat. NaHCO$_3$, brine, dried over Na$_2$SO$_4$ and concentrated to provide a crude oil. Purification by flash column chromatography on silica gel using 20% ethyl ether in hexanes provided 2-(2,2-dimethyl-but-3-ynyloxy)-tetrahydropyran (147 mg, 48%) as a pale liquid.

A solution of 2-(2,2-dimethyl-but-3-ynyloxy)-tetrahydropyran (147 mg, 0.806 mmol), 3-[(4-hydroxy-cyclohexyl)-(4-methyl-cyclohexanecarbonyl)-amino]-5-iodo-thiophene-2-carboxylic acid methyl ester (326 mg, 0.645 mmol) and triethylamine (1.0 mL, 7.17 mmol) in DMF (1.0 mL) was degassed for 10 minutes with nitrogen. PdCl$_2$(PPh$_3$)$_2$ (20 mg, 0.028 mmol) and CuI (5.0 mg, 0.026 mmol) was added and the resulting mixture was degassed with nitrogen for an additional 5 minutes after which the reaction was in a 60° C. oil bath and heated for 4 h. The reaction was cooled and partitioned between ethyl acetate and sat. NaHCO$_3$. The organic layer was separated, washed with 5% LiCl, brine, dried over Na$_2$SO$_4$ and concentrated to give a dark orange-brown foam. Purification by flash column chromatography on silica gel using 20% hexanes in ethyl acetate provided the desired product (251 mg, 69%) as a pale yellow foam.

NaH (45 mg of a 60% oil dispersion, 1.12 mmol) was added in one portion to a solution of 5-[3,3-dimethyl-4-(tetrahydro-pyran-2-yloxy)-but-1-ynyl]-3-[(4-hydroxy-cyclohexyl)-(4-methyl-cyclohexanecarbonyl)-amino]-thiophene-2-carboxylic acid methyl ester (124 mg, 0.221 mmol) and 2-fluoropyridine (0.095 mL, 1.1 mmol) in dry DMF (2.0 mL). After several minutes, the reaction was placed in a 85° C. oil bath and heated for 4 h. The reaction was cooled, water (0.50 mL) was added and the reaction mixture evaporated to dryness to provide a solid residue. The solid was washed with ethyl ether/hexanes then water, collected by centrifugation and washed with ethyl ether followed by water. The solid was collected and dried under vacuum to provide 5-[3,3-dimethyl-4-(tetrahydro-pyran-2-yloxy)-but-1-ynyl]-3-{(4-methyl-cyclohexanecarbonyl)-[4-(pyridin-2-yloxy)-cyclohexyl]-amino}-thiophene-2-carboxylic acid (Compound 311) (60 mg, 42%) as an off-white solid. MS (m/z): 528.3 [M+H-(2-hydroxypyridine)]+; HPLC retention time: 4.61 min (2-98% acetonitrile:water with 0.05% trifluoroacetic acid).

Example 312

Compound 312: 5-[3,3-Dimethyl-4-(tetrahydro-furan-3-yloxy)-but-1-ynyl]-3-[(4-(pyridin-2-yloxy)-cyclohexyl)-(4-methyl-cyclohexanecarbonyl)-amino]-thiophene-2-carboxylic acid Scheme 5

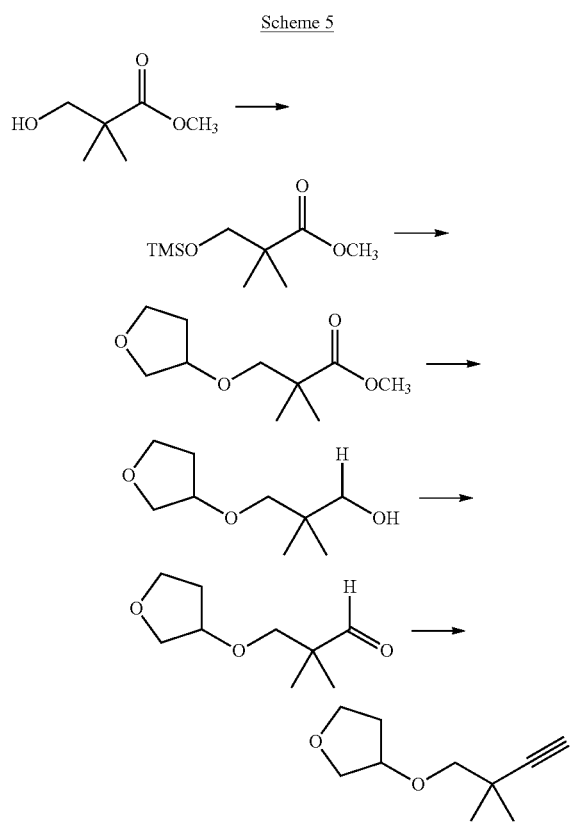

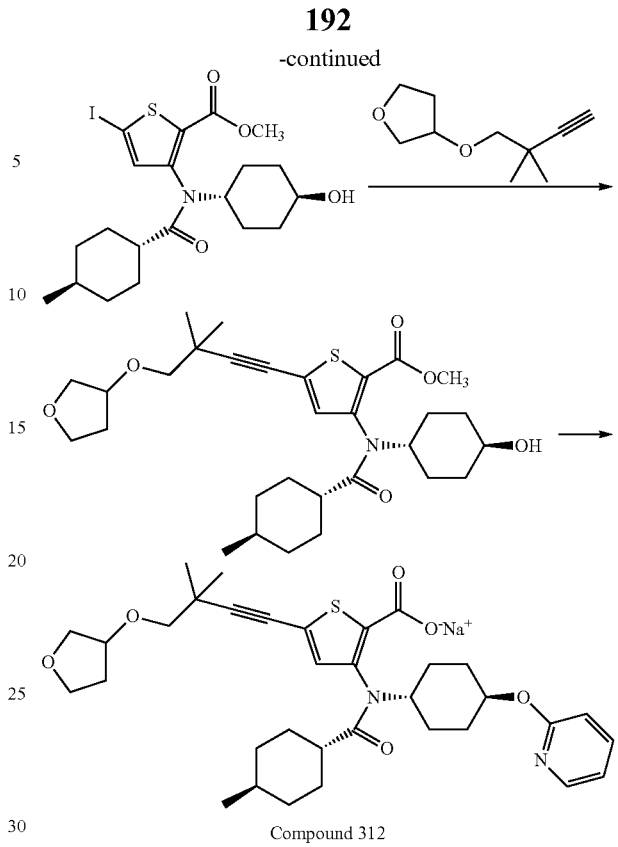

Compound 312

TMSCl (2.30 mL, 0.018 mol) was added dropwise to a solution of 3-hydroxy-2,2-dimethyl-propionic acid methyl ester (2.0 g, 0.015 mot) and triethylamine (3.16 mL, 0.023 mol) in dichloromethane at 0° C. After stirring for 1 h, the reaction was warmed to room temperature and stirred for an additional 1.5 h. Volatiles were removed under reduced pressure to provide a solid that was slurried in a mixture of ethyl ether and hexanes. The solid was removed by filtration and the filtrate was concentrated to provide a yellow liquid that was purified by bulb to bulb distillation under reduced pressure to provide 2,2-dimethyl-3-trimethylsilanyloxy-propionic acid methyl ester (2.8 g, 91%) as a colorless liquid.

2,2-Dimethyl-3-trimethylsilanyloxy-propionic acid methyl ester (478 mg, 2.34 mmol) was added to a solution of dihydro-furan-3-one (168 mg, 1.95 mmol) and FeCl$_3$ (16 mg, 0.097 mmol) in nitromethane (6.0 mL) at 0° C. Triethylsilane (0.374 mL, 2.33 mmol) was added and the reaction was warmed to room temperature and stirred for 2 h. Sat. NaHCO$_3$ was added and the reaction was extracted with dichloromethane. The organic layer was separated, washed with brine, dried over Na$_2$SO$_4$ and concentrated to give a pale liquid. Purification by flash column chromatography on silica gel using 30% ethyl acetate in hexanes provided dimethyl-3-(tetrahydro-furan-3-yloxy)-propionic acid methyl ester (353 mg, 75%) as a colorless liquid.

DIBAL (1.74 mL of a 1.0 M solution in hexanes) was added dropwise to a solution of 2,2-dimethyl-3-(tetrahydro-furan-3-yloxy)-propionic acid methyl ester (353 mg, 1.74 mmol) in dichloromethane (9.0 mL) at −78° C. After 2 h at this temperature, an additional equivalent of DIBAL was added and after 1 h the reaction was warmed to 0° C. After an additional 1 h at 0° C., 1.0 N HCl was added dropwise to quench the reaction. The reaction was warmed to room temperature and partitioned between dichloromethane and brine. The layers were separated and the aqueous layer extracted with dichloromethane. The combined organic layers were dried over Na₂SO₄ and concentrated to give an oil. Purification by flash column chromatography on silica gel using 50% ethyl acetate in hexanes provided 2,2-dimethyl-3-(tetrahydro-furan-3-yloxy)-propan-1-ol (250 mg, 82%) as a colorless oil.

DMSO (0.226 mL, 4.29 mmol) was added dropwise to a solution of oxalyl chloride (0.242 mL, 2.86 mmol) in dichloromethane (6.0 mL) at −78° C. After several minutes a solution of 2,2-dimethyl-3-(tetrahydro-furan-3-yloxy)-propan-1-ol (250 mg, 1.43 mmol) in dichloromethane (1.0 mL, with an additional 1.0 mL rinse) was added dropwise and after stirring for 1 h at −78° C., triethylamine (0.800 mL, 5.72 mmol) was added. The reaction was allowed to warm to room temperature and stirred for 30 min. Sat. NH₄Cl was added and the reaction mixture was extracted with dichloromethane. The organic layer was washed with brine, dried over Na₂SO₄ and concentrated to give a yellow residue. The residue was passed through a short silica gel plug eluting with 50% ethyl acetate in hexanes to provide 2,2-dimethyl-3-(tetrahydro-furan-3-yloxy)-propionaldehyde (245 mg, 99%) as a greenish-brown oil.

(1-Diazo-2-oxo-propyl)-phosphonic acid dimethyl ester (418 mg, 2.17 mmol) was added to a stirred suspension of 2,2-dimethyl-3-(tetrahydro-furan-3-yloxy)-propionaldehyde (250 mg, 1.45 mmol) and K₂CO₃ (601 mg, 4.35 mmol) in methanol (17.0 mL) at room temperature. After overnight stirring the bulk of the methanol was removed by rotary evaporation and the reaction mixture partitioned between ethyl ether and NaHCO₃. The organic layer was separated, washed with brine, dried over Na₂SO₄ and concentrated to provide a crude liquid. Purification by flash column chromatography on silica gel using 30% ethyl acetate in hexanes followed by bulb to bulb distillation under reduced pressure provided 3-(2,2-dimethyl-but-3-ynyloxy)-tetrahydro-furan (169 mg, 69%) as a colorless liquid.

A solution of 3-(2,2-dimethyl-but-3-ynyloxy)-tetrahydro-furan (169 mg, 1.00 mmol), 3-[(4-hydroxy-cyclohexyl)-(4-methyl-cyclohexanecarbonyl)-amino]-5-iodo-thiophene-2-carboxylic acid methyl ester (404 mg, 0.80 mmol) and triethylamine (1.2 mL, 8.61 mmol) in DMF (1.2 mL) was degassed for 10 minutes with nitrogen. PdCl₂(PPh₃)₂ (25 mg, 0.036 mmol) and CuI (6.0 mg, 0.031 mmol) was added and the resulting mixture was degassed with nitrogen for an additional 5 minutes after which the reaction was placed in a 65° C. oil bath and heated for 2.5 h. The reaction was cooled and partitioned between ethyl acetate and sat. NaHCO₃. The organic layer was separated, washed with 5% LiCl, brine, dried over Na₂SO₄ and concentrated to give a dark brown foam. Purification by flash column chromatography on silica gel using 50% ethyl acetate in hexanes then 5% methanol in ethyl acetate provided 5-[3,3-dimethyl-4-(tetrahydro-furan-3-yloxy)-but-1-ynyl]-3-[(4-hydroxy-cyclohexyl)-(4-methyl-cyclohexanecarbonyl)-amino]-thiophene-2-carboxylic acid methyl ester (331 mg, 75%) as a pale yellow foam.

Compound 312 may be prepared in the same manner as Compound 311 using 5-[3,3-dimethyl-4-(tetrahydro-furan-3-yloxy)-but-1-ynyl]-3-[(4-hydroxy-cyclohexyl)-(4-methyl-cyclohexanecarbonyl)-amino]-thiophene-2-carboxylic acid methyl ester.

Example 313

Compound 313: 5-[3,3-dimethyl-4-(tetrahydro-pyran-4-yloxy)-but-1-ynyl]-3-[(4-((pyridin-2-yloxy)-cyclohexyl)-(4-methyl-cyclohexanecarbonyl)-amino]-thiophene-2-carboxylic acid Synthesis of 5-[3,3-dimethyl-4-(tetrahydro-pyran-4-yloxy)-but-1-ynyl]-3-[(4-((hydroxy)-cyclohexyl)-(4-methyl-cyclohexanecarbonyl)-amino]-thiophene-2-carboxylic acid methyl ester

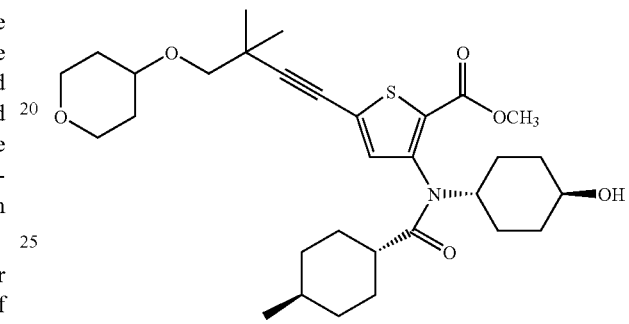

This thiophene ester (126 mg, 51%) was synthesized in a manner analogous to 5-[3,3-dimethyl-4-(tetrahydro-furan-3-yloxy)-but-1-ynyl]-3-[(4-hydroxy-cyclohexyl)-(4-methyl-cyclohexanecarbonyl)-amino]-thiophene-2-carboxylic acid methyl ester in Example 312, using tetrahydro-pyran-4-one in place of dihydro-furan-3-one.

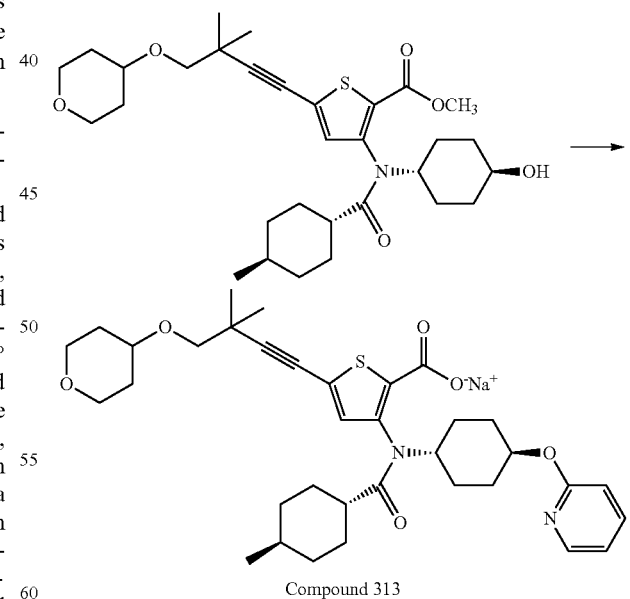

Compound 313

Compound 313 may be prepared in the same manner as Compound 311 using 5-[3,3-dimethyl-4-(tetrahydro-pyran-4-yloxy)-but-1-ynyl]-3-[(4-((hydroxy)-cyclohexyl)-(4-methyl-cyclohexanecarbonyl)-amino]-thiophene-2-carboxylic acid methyl ester.

Example 314

Compound 314: 5-(5-Hydroxy-3,3-dimethyl-pent-1-ynyl)-3-{(4-methyl-cyclohexanecarbonyl)-[4-(tetrahydro-furan-3-yloxy)-cyclohexyl]-amino}-thiophene-2-carboxylic acid

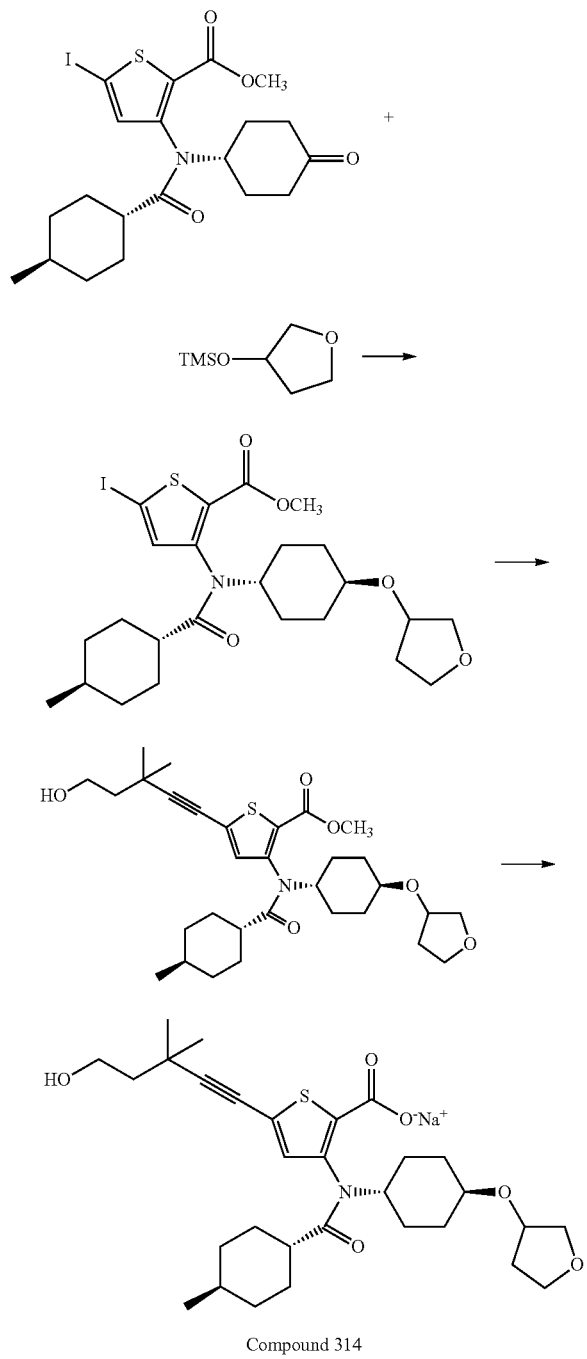

Compound 314

To a solution of 3-hydroxytetrahydrofuran (5.0 mL, 61.85 mmol) and triethylamine (13.0 mL, 93.27 mmol) in dichloromethane cooled to 0° C. was added TMSCl (9.38 mL, 74.17 mmol) dropwise. The reaction was allowed to warm to room temperature and then stirred overnight. Volatiles were removed under reduced pressure to provide a dark red solid that was filtered through a short column of silica gel eluting with ethyl ether. The filtrate was concentrated to afford an orange oil that was purified by bulb to bulb distillation under reduced pressure to provide 5-iodo-3-{(4-methyl-cyclohexanecarbonyl)-[4-(tetrahydro-furan-3-yloxy)-cyclohexyl]-amino}-thiophene-2-carboxylic acid methyl ester (9.2 g, 93%) as a colorless liquid.

To a suspension of 5-iodo-3-[(4-methyl-cyclohexanecarbonyl)-(4-oxo-cyclohexyl)-amino]-thiophene-2-carboxylic acid methyl ester (2.5 g, 4.96 mmol) and $FeCl_3$ (41 mg, 0.252 mmol) in nitromethane (15.0 mL) cooled to 0° C. was added neat trimethyl-(tetrahydro-furan-3-yloxy)-silane (955 mg, 5.95 mmol) followed by the dropwise addition of triethylsilane (0.947 mL, 5.92 mmol). The reaction was allowed to slowly warm to room temperature and stirred overnight. Sat. $NaHCO_3$ was added and the reaction mixture was extracted with dichloromethane. The organic layer was washed with brine, dried over $Na_2SO_4$ and concentrated to give a solid. The crude solid was heated in methanol, cooled and collected by filtration to provide 3-[(4-hydroxy-cyclohexyl)-(4-methyl-cyclohexanecarbonyl)-amino]-5-iodo-thiophene-2-carboxylic acid methyl ester (1.27 g, 44%) as a colorless solid.

A solution of 3-[(4-hydroxy-cyclohexyl)-(4-methyl-cyclohexanecarbonyl)-amino]-5-iodo-thiophene-2-carboxylic acid methyl ester (303 mg, 0.53 mmol), 3,3-dimethyl-pent-4-yn-1-ol (70 mg, 0.63 mmol) and triethylamine (1.2 mL, 8.61 mmol) in DMF (1.2 mL) was degassed for 10 minutes with nitrogen. $PdCl_2(PPh_3)_2$ (17 mg, 0.024 mmol) and CuI (5.0 mg, 0.026 mmol) was added and the resulting mixture was degassed with nitrogen for an additional 5 minutes after which the reaction was placed in a 65° C. oil bath and heated for 1.5 h. The reaction was cooled and partitioned between ethyl acetate and sat. $NaHCO_3$. The organic layer was separated, washed with 5% LiCl, brine, dried over $Na_2SO_4$ and concentrated to give a dark foam. Purification by flash column chromatography on silica gel using 100% ethyl acetate provided 5-(5-hydroxy-3,3-dimethyl-pent-1-ynyl)-3-{(4-methyl-cyclohexanecarbonyl)-[4-(tetrahydro-furan-3-yloxy)-cyclohexyl]-amino}-thiophene-2-carboxylic acid methyl ester (157 mg, 53%) as a pale yellow foam.

NaOH (0.500 mL of a 1.0 N aqueous solution) was added dropwise to a solution of 5-(5-hydroxy-3,3-dimethyl-pent-1-ynyl)-3-{(4-methyl-cyclohexanecarbonyl)-[4-(tetrahydro-furan-3-yloxy)-cyclohexyl]-amino}-thiophene-2-carboxylic acid methyl ester (157 mg, 0.28 mmol) in methanol (1.5 mL) and THF (1.5 mL) at room temperature. The reaction was stirred until TLC indicated that all of the starting material was consumed. The reaction was evaporated to dryness to give a solid residue that was purified by column chromatography on reverse phase $C_{18}$ silica gel (100% water to 5% acetonitrile/water). Fractions containing product were pooled and evaporated to provide 5-(5-hydroxy-3,3-dimethyl-pent-1-ynyl)-3-{(4-methyl-cyclohexanecarbonyl)-[4-(tetrahydro-furan-3-yloxy)-cyclohexyl]-amino}-thiophene-2-carboxylic acid (Compound 314)(52 mg, 33%) as a solid. MS (m/z): 546.0

[M+H]+; HPLC retention time 3.75 min (2-98% acetonitrile:water with 0.05% trifluoroacetic acid).

Example 317

Compound 317: 5-(3,3-Dimethyl-but-1-ynyl)-3-[[4-(4-cis-hydroxy-tetrahydro-furan-3-yloxy)-cyclohexyl]-(4-methyl-cyclohexanecarbonyl)-amino]-thiophene-2-carboxylic acid

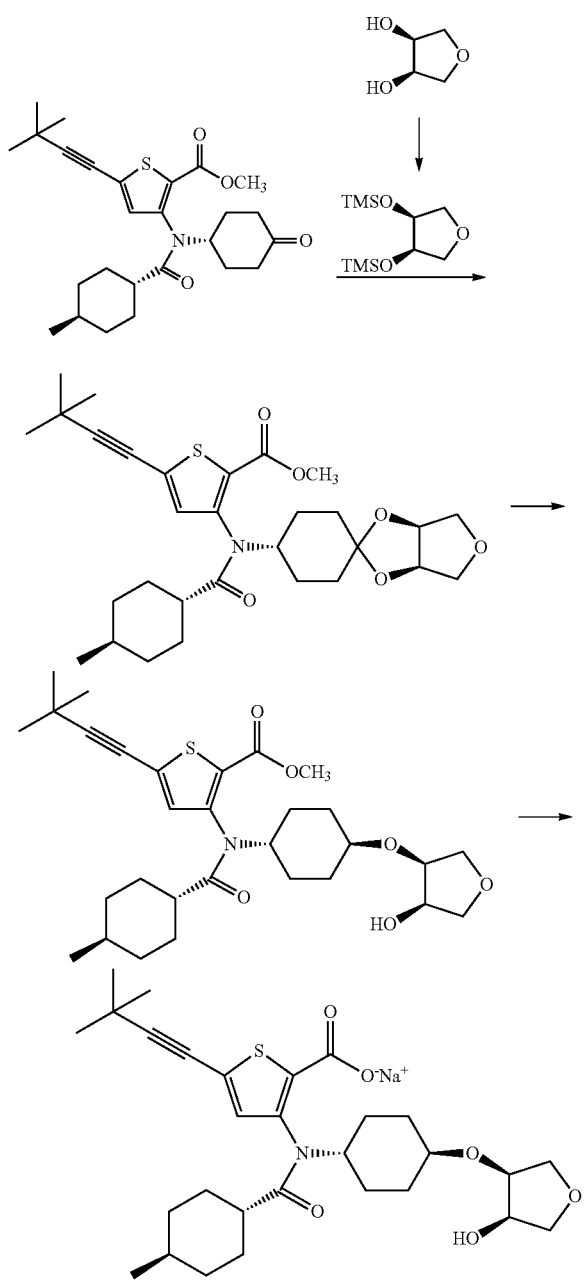

Compound 317

TMSCl (8.0 mL, 63.32 mmol) was added dropwise to a solution of 1,4-anhydroerythritol (3.0 g, 28.81 mmol), triethylamine (9.2 mL, 66.0 mmol) and DMAP (few crystals) in dichloromethane (200 mL) at 0° C. The reaction was allowed to slowly warm to room temperature over 1 h and then stirred for an additional 3 h. The solid was filtered and the filtrate concentrated to give a solid. The solid was then filtered through a short silica gel column eluting with 33% hexanes in ethyl ether. Removal of solvents under reduced pressure provided 3,4-bis-trimethylsilanyloxy-tetrahydro-furan (7.7 g, ~100%) as a colorless liquid.

TMSOTf (0.020 mL, 0.109 mmol) was added to a solution of 3,4-bis-trimethylsilanyloxy-tetrahydro-furan (595 mg, 2.39 mmol) in dichloromethane (5.0 mL) cooled to −78° C. A solution of 5-(3,3-dimethyl-but-1-ynyl)-3-[(4-methyl-cyclohexanecarbonyl)-(4-oxo-cyclohexyl)-amino]-thiophene-2-carboxylic acid methyl ester (1.0 g, 2.18 mmol) in dichloromethane (7.0 mL) was then added dropwise and the reaction allowed to slowly warm to room temperature and then stirred overnight. Sat. $NaHCO_3$ was added and the reaction mixture was extracted with dichloromethane. The organic layer was dried over $Na_2SO_4$ and concentrated to give a blue-green solid. The crude solid was triturated with ethyl ether and hexanes to give the desired ketal (525 mg, 44%) as an off-white solid.

Triethylsilane (0.255 mL, 1.59 mmol) was added to a solution of the ketal from the previous reaction (332 mg, 0.61 mmol) in dichloromethane (3.0 mL) cooled to −78° C. $TiCl_4$ (1.34 mL of a 1.0 M solution in dichloromethane) was then added dropwise over 5 min. The reaction was stirred at −78° C. 2 h and then warmed to room temperature. After stirring for 2 h, an additional equivalent of triethylsilane and $TiCl_4$ was added and stirring was continued until the reaction was deemed complete by TLC. Brine was added followed by the cautious dropwise addition of sat. $NaHCO_3$. The reaction was diluted with water and extracted with dichloromethane. The organic layer was washed with brine, dried over $Na_2SO_4$ and concentrated to give an orange oil. Purification by flash column chromatography on silica gel using 3% methanol in dichloromethane provided 5-(3,3-dimethyl-but-1-ynyl)-3-[[4-(4-hydroxy-tetrahydro-furan-3-yloxy)-cyclohexyl]-(4-methyl-cyclohexanecarbonyl)-amino]-thiophene-2-carboxylic acid methyl ester 267 mg, 80%) as a colorless foam.

NaOH (0.25 mL of a 1.0 N aqueous solution) was added dropwise to a solution of 5-(3,3-dimethyl-but-1-ynyl)-3-[[4-(4-cis-hydroxy-tetrahydro-furan-3-yloxy)-cyclohexyl]-(4-methyl-cyclohexanecarbonyl)-amino]-thiophene-2-carboxylic acid methyl ester (80 mg, 0.147 mmol) in methanol (1.0 mL) and THF (1.0 mL) at room temperature. After 2 h, an additional equivalent of NaOH was added and the reaction stirred until all of the starting material was consumed. The reaction was evaporated to dryness to give a residue that was purified by column chromatography on reverse phase $C_{18}$ silica gel (100% water to 20% acetonitrile/water). Fractions containing product were pooled and evaporated to provide 5-(3,3-dimethyl-but-1-ynyl)-3-[[4-(4-cis-hydroxy-tetrahydro-furan-3-yloxy)-cyclohexyl]-(4-methyl-cyclohexanecarbonyl)-amino]-thiophene-2-carboxylic acid (Compound 317) (53 mg, 65%) as a glassy foam. MS (m/z): 532.2 [M+H]+; HPLC retention time 4.24 min (2-98% acetonitrile:water with 0.05% trifluoroacetic acid).

Example 318

Compound 318: 5-(3,3-Dimethyl-but-1-ynyl)-3-[[4-(4-trans-hydroxy-tetrahydro-furan-3-yloxy)-cyclohexyl]-(4-methyl-cyclohexanecarbonyl)-amino]-thiophene-2-carboxylic acid Scheme 9

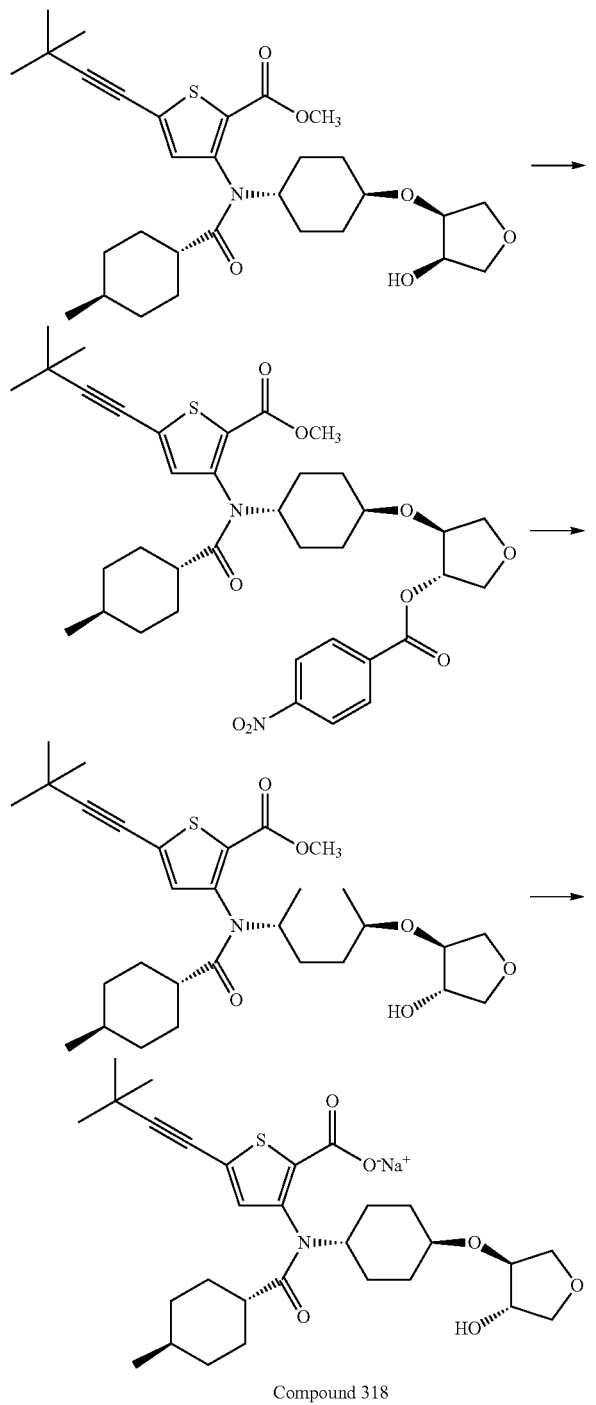

Compound 318

To a solution of 5-(3,3-dimethyl-but-1-ynyl)-3-[[4-(4-cis-hydroxy-tetrahydro-furan-3-yloxy)-cyclohexyl]-(4-methyl-cyclohexanecarbonyl)-amino]-thiophene-2-carboxylic acid methyl ester (267 mg, 0.49 mmol) in dry THF (9.0 mL) cooled to 0° C. was added, sequentially, triphenylphosphine (462 mg, 1.76 mmol) and DIAD (0.29 mL, 1.47 mmol). After 5 min, solid 4-nitrobenzoic acid (295 mg, 1.76 mmol) was added and after stirring for 1 h the reaction was allowed to warm to room temperature. After 3 h the reaction was concentrated to dryness and partitioned between ethyl acetate, sat. NaHCO$_3$ and water. The layers were separated and the aqueous layer was extracted with ethyl acetate. The combined organic layers were washed with water, 1.0 N HCl, sat. NaHCO$_3$, brine, dried over Na$_2$SO$_4$ and concentrated to give a viscous oil. Purification by flash column chromatography on silica gel using 3% methanol in dichloromethane provided 5-(3,3-dimethyl-but-1-ynyl)-3-((4-methyl-cyclohexanecarbonyl)-{4-trans-[4-(4-nitro-benzoyloxy)-tetrahydro-furan-3-yloxy]-cyclohexyl}-amino)-thiophene-2-carboxylic acid methyl ester (328 mg, 96%) as a pale yellow foam. Analysis by $^1$H NMR indicated a minor impurity due to DIAD.

Solid K$_2$CO$_3$ (100 mg, 0.72 mmol) was added to a solution of 5-(3,3-dimethyl-but-1-ynyl)-3-((4-methyl-cyclohexanecarbonyl)-{4-trans-[4-(4-nitro-benzoyloxy)-tetrahydro-furan-3-yloxy]-cyclohexyl}-amino)-thiophene-2-carboxylic acid methyl ester (320 mg, 0.46 mmol) in methanol (3.0 mL) at room temperature. After 1 h, the reaction was evaporated to dryness and then partitioned between ethyl ether and water. The organic layer was washed with sat. NaHCO$_3$, brine, dried over Na$_2$SO$_4$ and concentrated to give a waxy solid. Purification by flash column chromatography on silica gel using 3% methanol in dichloromethane provided 5-(3,3-dimethyl-but-1-ynyl)-3-[[4-(4-trans-hydroxy-tetrahydro-furan-3-yloxy)-cyclohexyl]-(4-methyl-cyclohexanecarbonyl)-amino]-thiophene-2-carboxylic acid methyl ester (191 mg, 76%) as a pale foam.

NaOH (0.22 mL of a 1.0 N aqueous solution) was added to a solution of 5-(3,3-dimethyl-but-1-ynyl)-3-[[4-(4-hydroxy-tetrahydro-furan-3-yloxy)-cyclohexyl]-(4-methyl-cyclohexanecarbonyl)-amino]-thiophene-2-carboxylic acid methyl ester (80 mg, 0.147 mmol) in THF (1.0 mL) and methanol (1.0 mL) at room temperature. After stirring for 48 h, the reaction was evaporated to dryness to give a residue that was purified by column chromatography on reverse phase C$_{18}$ silica gel (100% water to 10% acetonitrile/water). Fractions containing product were pooled and evaporated to provide 5-(3,3-dimethyl-but-1-ynyl)-3-[[4-(4-trans-hydroxy-tetrahydro-furan-3-yloxy)-cyclohexyl]-(4-methyl-cyclohexanecarbonyl)-amino]-thiophene-2-carboxylic acid (Compound 318) (53 mg, 43%) as a colorless solid. MS (m/z): 532.2 [M+H]+; HPLC retention time 4.17 min (2-98% acetonitrile:water with 0.05% trifluoroacetic acid).

Example 319

Compound 319: 5-[3,3-Dimethyl-5-(tetrahydro-pyran-4-yloxy)-pent-1-ynyl-]-3-[(4-(pyridin-2-yloxy)-cyclohexyl)-(4-methyl-cyclohexanecarbonyl)-amino]-thiophene-2-carboxylic acid Scheme 10

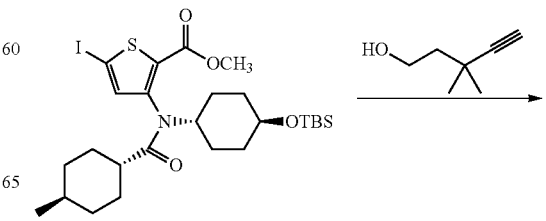

-continued

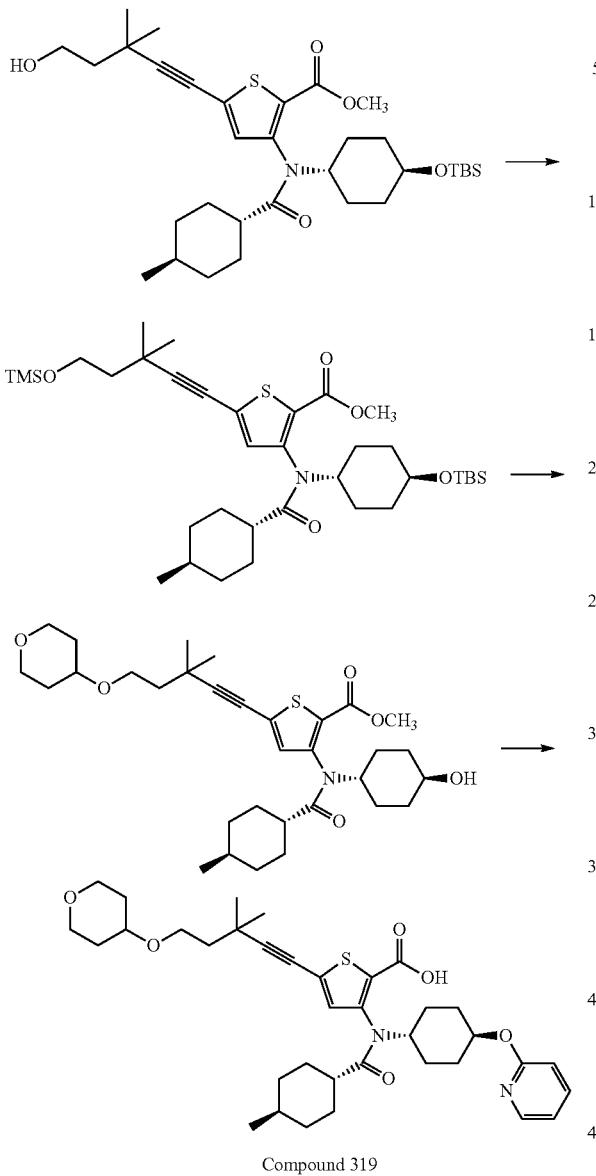

Compound 319

A solution of the 3,3-dimethyl-pent-4-yn-1-ol (600 mg, 5.36 mmol), 3-[[4-(tert-Butyl-dimethyl-silanyloxy)-cyclohexyl]-(4-methyl-cyclohexanecarbonyl)-amino]-5-iodo-thiophene-2-carboxylic acid methyl ester (2767 mg, 4.46 mmol) and triethylamine (10.8 mL, 77.48 mmol) in DMF (25 mL) was degassed for 10 minutes with nitrogen. PdCl$_2$(PPh$_3$)$_2$ (314 mg, 0.45 mmol) and CuI (170 mg, 0.90 mmol) was added and the resulting mixture was degassed with nitrogen for an additional 5 minutes after which the reaction was placed in a 80° C. oil bath and heated for 3.5 h. The reaction was cooled and partitioned between ethyl acetate and sat. NaHCO$_3$. The organic layer was separated, washed with 5% LiCl, brine, dried over Na$_2$SO$_4$ and concentrated to give a dark brown foam. Purification by flash column chromatography on silica gel using 30% ethyl acetate in hexanes then 5% methanol in ethyl acetate provided 3-[[4-(tert-butyl-dimethyl-silanyloxy)-cyclohexyl]-(4-methyl-cyclohexanecarbonyl)-amino]-5-(5-hydroxy-3,3-dimethyl-pent-1-ynyl)-thiophene-2-carboxylic acid methyl ester (2.43 g, 90%) as a pale yellow foam.

TMSCl (0.08 mL, 0.596 mmol) was added dropwise to a solution of 3-[[4-(tert-butyl-dimethyl-silanyloxy)-cyclohexyl]-(4-methyl-cyclohexanecarbonyl)-amino]-5-(5-hydroxy-3,3-dimethyl-pent-1-ynyl)-thiophene-2-carboxylic acid methyl ester (300 mg, 0.497 mmol) and triethylamine (0.11 mL, 0.745 mmol) in dichloromethane at 0° C. After stirring for 1 h, the reaction was warmed to room temperature and stirred for an additional 1.5 h. The solution was washed with water, brine, dried and concentrated to give crude 3-[[4-(tert-butyl-dimethyl-silanyloxy)-cyclohexyl]-(4-methyl-cyclohexanecarbonyl)-amino]-5-(3,3-dimethyl-5-trimethylsilanyloxy-pent-1-ynyl)-thiophene-2-carboxylic acid methyl ester (330 mg) which was carried to next step without further purification.

3-[[4-(tert-Butyl-dimethyl-silanyloxy)-cyclohexyl]-(4-methyl-cyclohexanecarbonyl)-amino]-5-(3,3-dimethyl-5-trimethylsilanyloxy-pent-1-ynyl)-thiophene-2-carboxylic acid methyl ester (230 mg, 0.34 mmol) was added to a solution of tetrahydro-pyran-4-one (29 mg, 0.29 mmol) and FeCl$_3$ (2.8 mg, 0.017 mmol) in nitromethane (5.0 mL) at 0° C. Triethylsilane (0.054 mL, 0.34 mmol) was added and the reaction warmed to room temperature and stirred for 2 h. Sat. NaHCO$_3$ was added and the reaction extracted with dichloromethane. The organic layer was separated, washed with brine, dried over Na$_2$SO$_4$ and concentrated to give the crude product. Purification by HPLC with CH$_3$CN (0.1% TFA)/H$_2$O (0.1% TFA) provided 5-[3,3-dimethyl-5-(tetrahydro-pyran-4-yloxy)-pent-1-ynyl]-3-[(4-hydroxy-cyclohexyl)-(4-methyl-cyclohexanecarbonyl)-amino]-thiophene-2-carboxylic acid methyl ester (8 mg, 4%) as solid.

Compound 319 may be prepared in the same manner as Compound 311 using 5-[3,3-dimethyl-5-(tetrahydro-pyran-4-yloxy)-pent-1-ynyl]-3-[(4-hydroxy-cyclohexyl)-(4-methyl-cyclohexanecarbonyl)-amino]thiophene-2-carboxylic acid methyl ester.

Example 321

Compound 321: 5-(3,3-Dimethyl-but-1-ynyl)-3-(4-methyl-cyclohexanecarbonyl)-{1-[2-(pyridin-2-yloxy)-ethyl]-pyrrolidin-3-yl}-amino)-thiophene-2-carboxylic acid

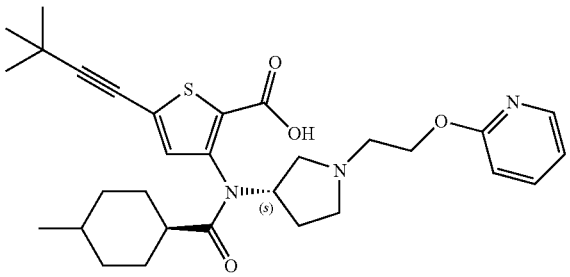

Compound 321

To a solution of 5-(3,3-dimethyl-but-1-ynyl)-3-[(4-methyl-cyclohexanecarbonyl)-pyrrolidin-3S-yl-amino]-thiophene-2-carboxylic acid methyl ester (0.1 g, 0.214 mmol) and acetic acid (37 μL) in dry dichloromethane (1 mL) was added NaBH(OAc)$_3$ (0.092 g, 0.428 mmol) at room temperature. After stirring at room temperature for 90 min, the reaction was concentrated in vacuo to remove volatiles. The crude oil was dissolved in methanol (2 mL), treated with HCl (1.7 mL, 1M in methanol) and heated to 60° C. for 1 h. Upon cooling the reaction was concentrated, diluted with ethyl acetate, and neutralized with NaHCO₃. The organic layer was washed with saturated NaCl solution (30 mL), dried over Na₂SO₄, filtered, concentrated and purified by silica gel column chromatography. A solution of 5-(3,3-dimethyl-but-1-ynyl)-3-[[1-(2-hydroxy-ethyl)-pyrrolidin-3-yl]-(4-methyl-cyclohexanecarbonyl)-amino]-thiophene-2-carboxylic acid methyl ester (Compound 321) (0.083 g, 0.175 mmol) in THF (1 mL) was treated with KHMDS (0.42 mL, 0.2 mmol, 0.5 M in toluene) at −78° C. After 30 min 2-fluoro-pyridine (30 □L, 0.35 mmol) was added. The reaction was quenched after 1 h with saturated NH₄Cl and the organic phase was collected and concentrated. The crude material was purified by reverse-phase HPLC to afford the title compound. MS (m/z): 538.2 [M+H]⁻; HPLC retention time: 3.55 min (2-98% acetonitrile:water with 0.05% trifluoroacetic acid) 6 min run.

Example 322

Compound 322: 5-(3,3-Dimethyl-but-1-ynyl)-3-{(4-methyl-cyclohexanecarbonyl)-[4-(4-methyl-cyclohexanecarbonyloxy)-4-(tetrahydro-furan-3-yloxymethy)-cyclohexyl]-amino}-thiophene-2-carboxylic acid Compound 322

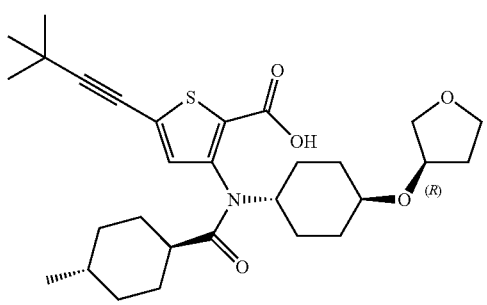

4-Methyl-cyclohexanecarboxylic acid (57 mg, 0.4 mmol) was dissolved in CH₂Cl₂ (5 mL) and DMF (2 µL) was added. The solution was cooled to 0° C. and then (COCl)₂ (175 µL, 2 mmol) was slowly added to the solution. The reaction was stirred in the ice bath for 1 hour and then concentrated. The residue was taken up in hexanes and concentrated; this hexanes co-evaporation was repeated once more. To the residue was added 5-(3,3-dimethyl-but-1-ynyl)-3-[4-(tetrahydro-furan-3R-yloxy)-trans-cyclohexylamino]-thiophene-2-carboxylic acid methyl ester (84 mg, 0.2 mmol) and pyridine (3 mL). The solution was heated to 85° C. overnight. The reaction was cooled to rt, concentrated and taken up in THF/MeOH (5:1). The solution was then treated with LiOH (1 mmol, 41 mg) and heated to 65° C. for 1 h. Volatiles were removed under vacuum and the resulting residue purified by HPLC with CH₃CN (0.1% TFA)/H₂O (0.1% TFA) to provide Compound 322 as colorless solid. MS (m/z): 516.3 [M+H]+; HPLC retention time 8.53 min (2-98% acetonitrile:water with 0.05% trifluoroacetic acid) 30 min run.

Example 325

Compound 325: 3-[[4-(4-dimethylaminomethyl-pyridin-2-yloxy)-cyclohexyl]-(4-methylene-cyclohexanecarbonyl)-amino]-5-(3,3-dimethyl-but-1-ynyl)-thiophene-2-carboxylic acid Scheme 13

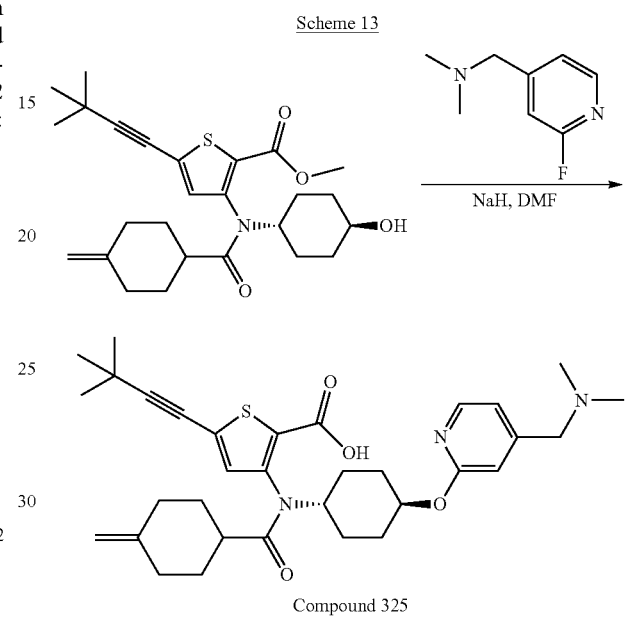

Compound 325

Compound 325 was synthesized in a manner analogous to Example 311:MS (m/z): 579.0 [M+H]+; HPLC retention time 3.48 min (2-98% acetonitrile:water with 0.05% trifluoroacetic acid).

Example 326

Compound 326: 5-(3,3-Dimethyl-but-1-ynyl)-3-{(4-methyl-cyclohexanecarbonyl)-[4-(6-oxo-1,6-dihydro-pyrimidin-2-yloxy)-cyclohexyl]-amino}-thiophene-2-carboxylic acid Compound 326

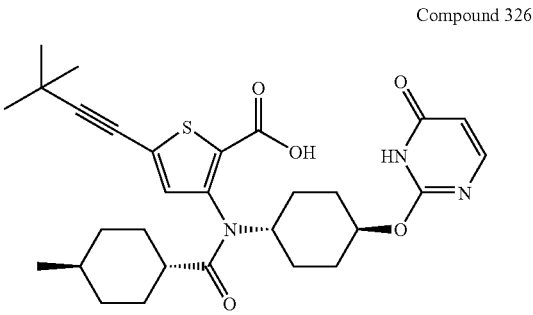 [SMILES: CC(C)(C)C#Cc1cc(N(C(=O)[C@H]2CC[C@H](C)CC2)[C@H]2CC[C@H](Oc3nccc(=O)[nH]3)CC2)c(C(=O)O)s1]

Scheme 14

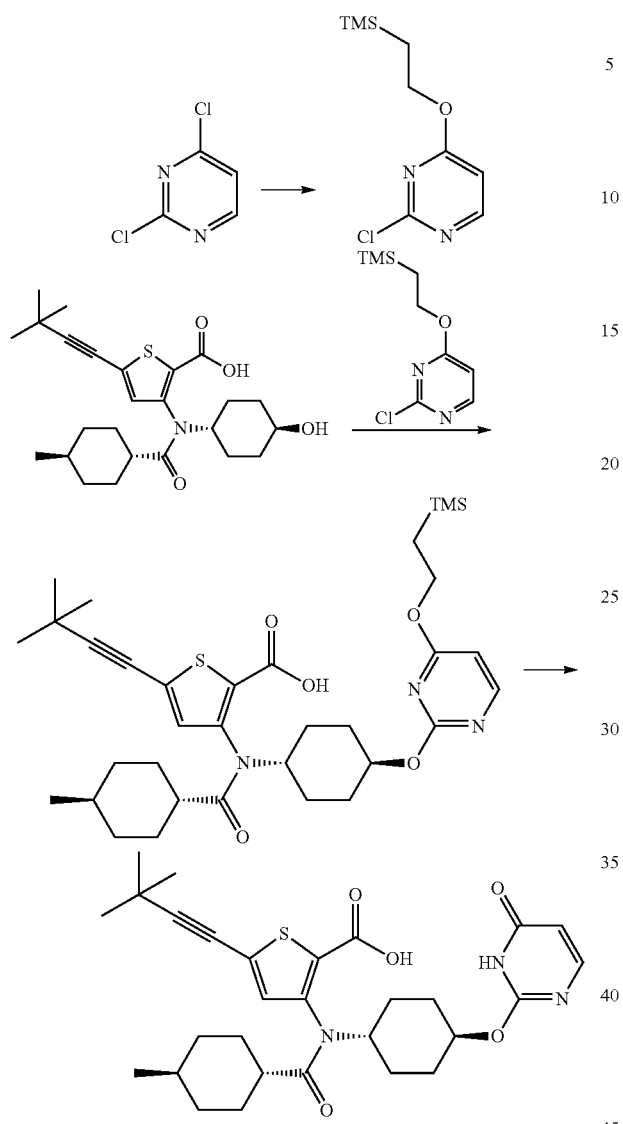

2,4-Dichloro-pyrimidine (2.00 g, 13.4 mmol) in THF (30 mL) was treated with sodium hydride (670 mg, 60% oil dispersion, 16.8 mmol) followed by 2-trimethylsilanyl-ethanol (2.01 mL, 14.1 mmol) in portions over 15 minutes. The reaction mixture was stirred for 16 hours and treated with 1 M HCl (20 mL). Water (20 mL) was added and the mixture was extracted with 1:1 ethyl acetate:hexanes (100 mL) followed by ethyl acetate (100 mL). The combined organic layers were dried over sodium sulfate, filtered and concentrated. Purification by flash chromatography (10-30% EtOAc:hexanes, 80 g column), afforded 2.45 g (79% yield) of 2-chloro-4-(2-trimethylsilanyl-ethoxy)-pyrimidine as a mixture of regioisomers.

2-Chloro-4-(2-trimethylsilanyl-ethoxy)-pyrimidine (388 mg, 1.68 mmol) and 6-(3,3-dimethyl-but-1-ynyl)-3-[(4-hydroxy-cyclohexyl)-(4-methyl-cyclohexanecarbonyl)-amino]-thiophene-2-carboxylic acid (150 mg, 0.337 mmol) were dissolved in DMF (2 mL) and treated with sodium hydride (67 mg, 60% oil dispersion, 1.68 mmol). The mixture was stirred under nitrogen until the bubbling slowed, then was sealed and heated by microwave (90° C., 65 min). An additional portion of 2-chloro-4-(2-trimethylsilanyl-ethoxy)-pyrimidine (388 mg, 1.68 mmol) and sodium hydride (67 mg, 60% oil dispersion, 1.68 mmol) were added and the mixture was stirred under nitrogen until the bubbling slowed. The reaction mixture was sealed and heated by microwave (100° C., 45 min). After cooling, the mixture was diluted with ethyl acetate (about 5 mL) and quenched with 10% citric acid (about 2 mL). Water was added and the mixture was extracted twice with ethyl acetate. After concentration the resulting residue was purified by HPLC with $CH_3CN$ (0.1% TFA)/$H_2O$ (0.1% TFA) to afford 39 mg of 5-(3,3-dimethyl-but-1-ynyl)-3-((4-methyl-cyclohexanecarbonyl)-{4-[4-(2-trimethylsilanyl-ethoxy)-pyrimidin-2-yloxy]-cyclohexyl}-amino)-thiophene-2-carboxylic acid.

5-(3,3-Dimethyl-but-1-ynyl)-3-((4-methyl-cyclohexanecarbonyl)-{4-[4-(2-trimethylsilanyl-ethoxy)-pyrimidin-2-yloxy]-cyclohexyl}-amino)-thiophene-2-carboxylic acid (37 mg, 0.058 mmol) in THF (1 mL) was treated with tetrabutylammonium fluoride (0.087 mL, 1M in THF, 0.087 mmol) and stirred at ambient temperature for 1.5 h. An additional portion of tetrabutylammonium fluoride (0.290 mL) was added and the reaction mixture was stirred at ambient temperature for 3 h. After concentration the residue was purified by HPLC with $CH_3CN$ (0.1% TFA)/$H_2O$ (0.1% TFA) to afford 18 mg (58% yield) of Compound 326: MS (m/z): 537.9 [M+H]−; HPLC retention time 4.28 min (2-98% acetonitrile: water with 0.05% trifluoroacetic acid).

Scheme 15

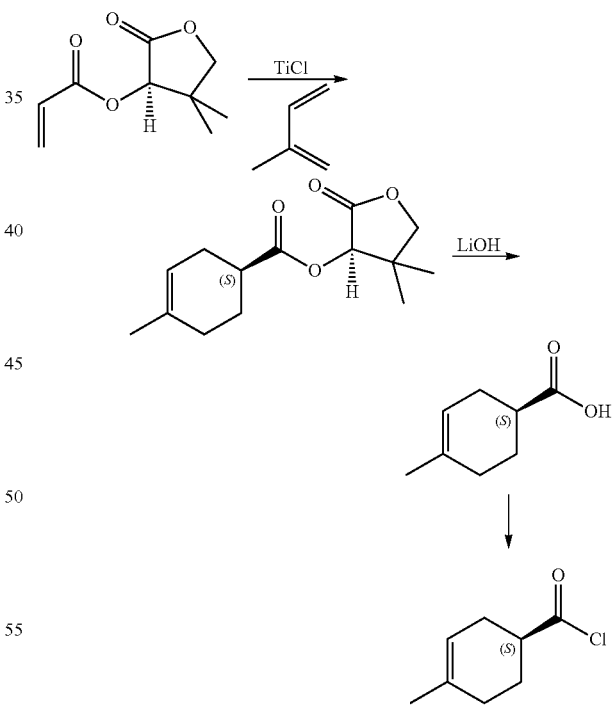

Acrylic acid 4,4-dimethyl-2-oxo-tetrahydro-furan-3-yl ester (R) (2.92 g, 15.9 mmol) in dichloromethane (20 mL) and hexanes (3 mL) was cooled to −10° C. and treated with titanium tetrachloride (2.4 mL, 2.4 M in dichloromethane, 2.4 mmol). The red solution was stirred for 15 min and treated with isoprene (2.4 mL, 23.8 mmol) dropwise over 5 min. After stirring for 1.5 h, an additional portion of isoprene (2.4 mL, 23.8 mmol) was added and the reaction mixture was stirred at −10 to 0° C. for 2.5 h. After cooling to −10° C., the reaction mixture was quenched with ammonium chloride (sat. aq.). Water and ethyl acetate:hexanes (1:1) were added. The organic layer was separated and the aqueous layer was extracted again with ethyl acetate:hexanes (1:1). The combined organic layers were dried over sodium sulfate, filtered and concentrated. The residue was purified by flash chromatography (10-40% EtOAc:Hex, 80 g column) to afford 3.35 g (84% yield) of 4-methyl-cyclohex-3-(S)-enecarboxylic acid 4,4-dimethyl-2-oxo-tetrahydro-furan-3-yl ester as a clear oil.

4-Methyl-cyclohex-3-(S)-enecarboxylic acid 4,4-dimethyl-2-oxo-tetrahydro-furan-3-yl ester (3.34 g, 13.2 mmol) in THF (25 mL), water (2.5 mL) and methanol (2.5 mL) was treated with lithium hydroxide monohydrate (2.8 g, 66.2 mmol) and warmed to 50° C. with stirring. After 1 h, the reaction mixture treated with 1M HCl (about 25 mL). The mixture was extracted with hexanes:ethyl acetate (200 mL:15 mL), dried over sodium sulfate, filtered and concentrated to 2.4 g of a white semi-solid. The residue was redissolved in hexanes:dichloromethane (100 mL, 95:5), washed with water, dried over sodium sulfate, filtered and concentrated to 1.68 g (91% yield) of (1S)-4-methyl-cyclohex-3-enecarboxylic acid as a white powder.

(1S)-4-Methyl-cyclohex-3-enecarboxylic acid (209 mg, 1.5 mmol), azeotropically dried by evaporation from toluene, was treated with potassium phosphate tribasic (383 mg, 1.8 mmol), suspended in dichloromethane (4 mL) and treated with dimethylformamide (2 drops). The reaction mixture was cooled to 0° C. and treated dropwise with oxalyl chloride (0.3 mL, 3.2 mmol). The reaction mixture was allowed to warm to ambient temperature while stirring for 2 h. After filtering the solids, the solution was concentrated, treated with hexanes and concentrated again to afford 4-methyl-cyclohex-3-enecarbonyl chloride (S) as a light yellow oil which was used immediately in the next step.

Example 327

Compound 331: 5-(3,3-Dimethyl-but-1-ynyl)-3-{(trans-4-methyl-cyclohexanecarbonyl)-[4-(tetrahydro-furan-3(S)-yloxy)-trans-cyclohexyl]-amino}-thiophene-2-carboxylic acid Compound 332: 5-(3,3-Dimethyl-but-1-ynyl)-3-{(trans-4-methyl-cyclohexanecarbonyl)-[4-(tetrahydro-furan-3(S)-yloxy)-cis-cyclohexyl]-amino}-thiophene-2-carboxylic acid

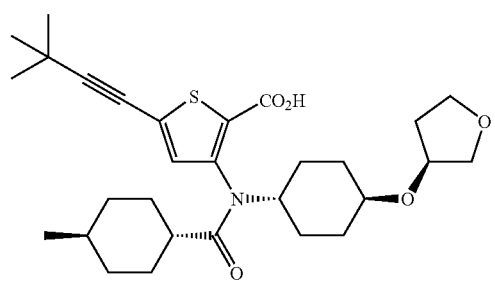

Compound 331

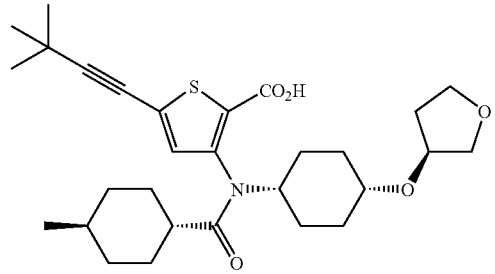

Compound 332

Scheme 17

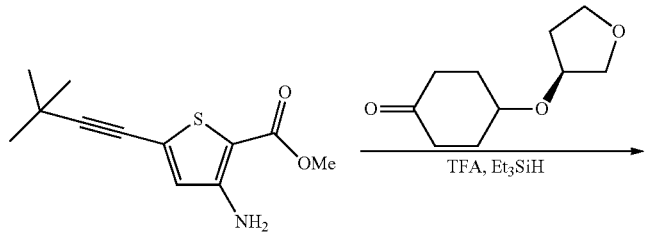

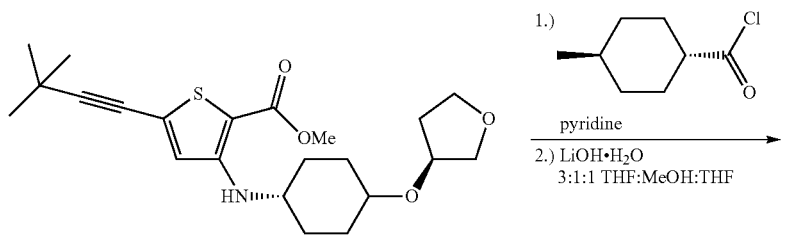

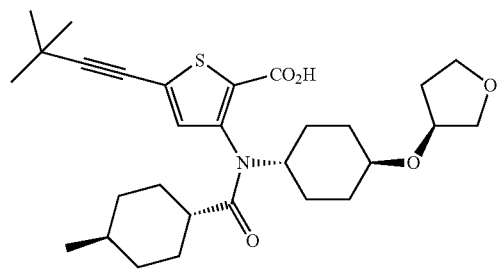

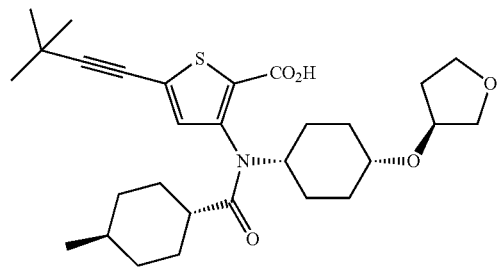

A mixture of 3-amino-5-(3,3-dimethyl-but-1-ynyl)-thiophene-2-carboxylic acid methyl ester (2.41 g, 10.2 mmol), 4-(tetrahydro-furan-3S-yloxy)-cyclohexanone (1.6 g, 8.5 mmol), TFA (2.6 mL, 34 mmol) and triethylsilane (2.7 mL, 17 mmol) in $CH_2Cl_2$ (12 mL) was stirred for 22 h at room temperature. The reaction was concentrated in vacuo and the crude oil was dissolved in toluene (50 mL) and concentrated (repeat) to give a yellow solid. The crude solid was purified by column chromatography (10-25% ethyl acetate/hexanes) to give 5-(3,3-dimethyl-but-1-ynyl)-3-[4-(tetrahydro-furan-3S-yloxy)-cyclohexylamino]-thiophene-2-carboxylic acid methyl ester (2.28 g, 5.63 mmol) as a mixture of isomers.

5-(3,3-Dimethyl-but-1-ynyl)-3-[4-(tetrahydro-furan-3S-yloxy)-cyclohexylamino]-thiophene-2-carboxylic acid methyl ester (105 mg, 0.26 mmol, 6:4 mixture of trans:cis isomers) was dissolved in pyridine (1 mL) and trans-4-methylcyclohexanecarbonyl chloride (160 mg, 1.0 mmol) was added. The solution was stirred for 18 h at 90° C. The reaction was cooled to ambient temperature, partitioned between ethyl acetate and water, and the aqueous phase thrice extracted with ethyl acetate. The combined organic layers were sequentially washed with saturated aqueous ammonium chloride, brine, dried over magnesium sulfate, filtered, concentrated, and purified by column chromatography (0-70% ethyl acetate/hexanes) to give 5-(3,3-Dimethyl-but-1-ynyl)-3-{(trans-4-methyl-cyclohexanecarbonyl)-[4-(tetrahydro-furan-3S-yloxy)-cyclohexyl]-amino}-thiophene-2-carboxylic acid methyl ester (90 mg, 0.17 mmol) as a mixture of isomers.

5-(3,3-Dimethyl-but-1-ynyl)-3-{(trans-4-methyl-cyclohexanecarbonyl)-[4-(tetrahydro-furan-3S-yloxy)-cyclohexyl]-amino}-thiophene-2-carboxylic acid methyl ester (90 mg, 0.17 mmol) was dissolved in THF (1.5 mL), MeOH (0.5 mL), and $H_2O$ (0.5 mL). To this solution was added $LiOH \cdot H_2O$ (74 mg, 1.8 mmol). The reaction was stirred at 45° C. for 1 h and then acidified with 10% $HCl_{(aq)}$. The reaction solution was thrice extracted to ethyl acetate, dried over magnesium sulfate, filtered, concentrated, and purified by reverse phase HPLC to give 5-(3,3-Dimethyl-but-1-ynyl)-3-{(trans-4-methyl-cyclohexanecarbonyl)-[4-(tetrahydro-furan-3(S)-yloxy)-trans-cyclohexyl]-amino}-thiophene-2-carboxylic acid (Compound 331) (39 mg, 0.08 mmol): MS (m/z): 516.0 [M+H]+; HPLC retention time 4.64 min (2-98% acetonitrile: water with 0.05% trifluoroacetic acid), and 5-(3,3-Dimethyl-but-1-ynyl)-3-{(trans-4-methyl-cyclohexanecarbonyl)-[4-(tetrahydro-furan-3(S)-yloxy)-cis-cyclohexyl]-amino}-thiophene-2-carboxylic acid (Compound 332) (9 mg, 0.02 mmol): MS (m/z): 515.9 [M+H]+; HPLC retention time 4.70 min (2-98% acetonitrile:water with 0.05% trifluoroacetic acid).

Example 333

Compound 333: 5-(3,3-Dimethyl-but-1-ynyl)-3-{(1S)-4-methyl-cyclohex-3-enecarbonyl)-[4-(tetrahydro-furan-3(S)-yloxy)-trans-cyclohexyl]-amino}-thiophene-2-carboxylic acid Compound 333

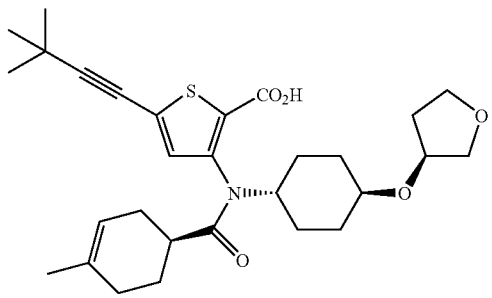

Scheme 18

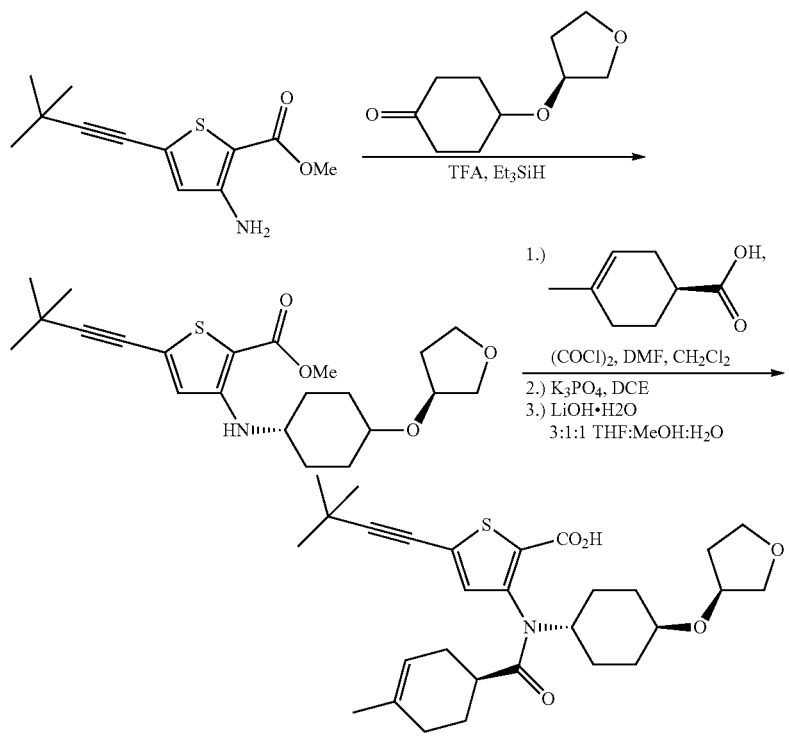

A mixture of 3-amino-5-(3,3-dimethyl-but-1-ynyl)-thiophene-2-carboxylic acid methyl ester (2.41 g, 10.2 mmol), 4-(tetrahydro-furan-3(S)-yloxy)-cyclohexanone (1.6 g, 8.5 mmol), TFA (2.6 mL, 34 mmol) and triethylsilane (2.7 mL, 17 mmol) in $CH_2Cl_2$ (12 mL) was stirred for 22 h at room temperature. The reaction was concentrated in vacuo and the crude oil was dissolved in toluene (50 mL) and concentrated (repeat) to give a yellow solid. The crude solid was purified by column chromatography (10-25% ethyl acetate/hexanes) to give 5-(3,3-dimethyl-but-1-ynyl)-3-[4-(tetrahydro-furan-3-yloxy)-trans-cyclohexylamino]-thiophene-2-carboxylic acid methyl ester (1.09 g, 2.69 mmol) as a single isomer.

(1S)-4-Methyl-cyclohex-3-ene-1-carboxylic acid (130 mg, 0.93 mmol) was dissolved in $CH_2Cl_2$ (2 mL). $K_3PO_4$ (400 mg, 1.9 mmol) and DMF (20 µL) were added. The solution was cooled to 0° C. and then $(COCl)_2$ (200 µL, 2.1 mmol) was slowly added to the solution. The reaction was warmed to rt and stirred for 2 hours. The reaction solution was decanted from insoluble $K_3PO_4$ and concentrated. The residue was taken up in hexanes and concentrated; this hexanes coevaporation was repeated once more. To the residue was added 5-(3,3-dimethyl-but-1-ynyl)-3-[4-(tetrahydro-furan-3S-yloxy)-trans-cyclohexylamino]-thiophene-2-carboxylic acid methyl ester (100 mg, 0.25 mmol), $K_3PO_4$ (200 mg, 0.98 mmol), DCE (1.2 mL). The solution was heated to 90° C. overnight. The reaction was cooled to rt, partitioned between ethyl acetate and water, and the aqueous phase thrice extracted with ethyl acetate. The combined organic layers were sequentially washed with saturated aqueous ammonium chloride, brine, dried over magnesium sulfate, filtered, concentrated, and purified by column chromatography (0-70% ethyl acetate/hexanes) to give 5-(3,3-dimethyl-but-1-ynyl)-3-{(1S)-4-methyl-cyclohex-3-enecarbonyl)-[4-(tetrahydro-furan-3S-yloxy)-trans-cyclohexyl]-amino}-thiophene-2-carboxylic acid methyl ester (24 mg, 0.05 mmol).

5-(3,3-Dimethyl-but-1-ynyl)-3-{(1S)-4-methyl-cyclohex-3-enecarbonyl)-[4-(tetrahydro-furan-3S-yloxy)-trans-cyclohexyl]-amino}-thiophene-2-carboxylic acid methyl ester (19 mg, 0.04 mmol) was dissolved in THF (0.6 mL), MeOH (0.2 mL), and $H_2O$ (0.2 mL). To this solution was added $LiOH \cdot H_2O$ (20 mg, 0.5 mmol). The reaction was stirred at rt for 1 h, diluted with water, and acidified with 10% $HCl_{(aq)}$. The reaction solution was thrice extracted to ethyl acetate, dried over magnesium sulfate, filtered, concentrated, and purified by reverse phase HPLC to give 5-(3,3-dimethyl-but-1-ynyl)-3-{(1S)-4-methyl-cyclohex-3-enecarbonyl)-[4-(tetrahydro-furan-3S-yloxy)-trans-cyclohexyl]-amino}-thiophene-2-carboxylic acid (Compound 333) (11 mg, 0.02 mmol): MS (m/z): 514.0 [M+H]+; HPLC retention time 4.53 min (2-98% acetonitrile: water with 0.05% trifluoroacetic acid).

Example 334

Compound 334: 5-(3,3-Dimethyl-but-1-ynyl)-3-{(1S)-4-methyl-cyclohex-3-enecarbonyl)-[4-(tetrahydro-furan-3(R)-yloxy)-trans-cyclohexyl]-amino}-thiophene-2-carboxylic acid Compound 334

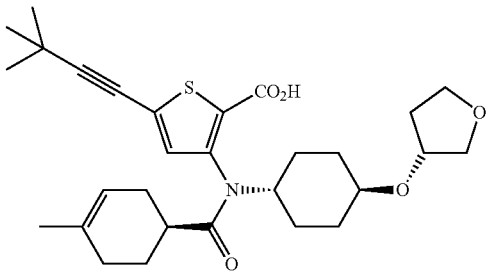

Compound 334 was prepared in a manner similar to Example 333 using 4-(tetrahydro-furan-3(R)-yloxy)-cyclohexanone in place of 4-(tetrahydro-furan-3(S)-yloxy)-cyclohexanone: MS (m/z): 516.0 [M+H]+; HPLC retention time 4.64 min (2-98% acetonitrile:water with 0.05% trifluoroacetic acid): MS (m/z): 514.1 [M+H]+; HPLC retention time 4.53 min (2-98% acetonitrile:water with 0.05% trifluoroacetic acid).

Example 335

Compound 335: 5-(3,3-Dimethyl-but-1-ynyl)-3-{(1R)-4-methyl-cyclohex-3-enecarbonyl)-[4-(tetrahydro-furan-3(R)-yloxy)-trans-cyclohexyl]-amino}-thiophene-2-carboxylic acid

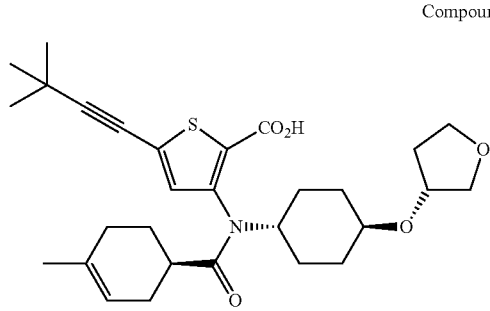

Compound 335

Compound 335 was prepared in a manner similar to Example 333 using 4-(tetrahydro-furan-3(R)-yloxy)-cyclohexanone in place of 4-(tetrahydro-furan-3(S)-yloxy)-cyclohexanone and (1R)-4-methyl-cyclohex-3-ene-1-carboxylic acid in place of (1S)-4-methyl-cyclohex-3-ene-1-carboxylic acid: MS (m/z): 514.1 [M+H]+; HPLC retention time 4.52 min (2-98% acetonitrile:water with 0.05% trifluoroacetic acid).

Example 336

Compound 336: 5-(3,3-Dimethyl-but-1-ynyl)-3-{(1R)-4-methyl-cyclohex-3-enecarbonyl)-[4-(tetrahydro-furan-3(S)-yloxy)-trans-cyclohexyl]-amino}-thiophene-2-carboxylic acid

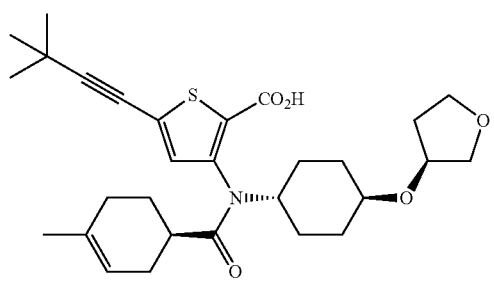

Compound 336

Compound 336 was prepared in a manner similar to Example 333 using (1R)-4-methyl-cyclohex-3-ene-1-carboxylic acid in place of (1S)-4-methyl-cyclohex-3-ene-1-carboxylic acid: MS (m/z): 514.0 [M+H]+; HPLC retention time 4.53 min (2-98% acetonitrile:water with 0.05% trifluoroacetic acid).

Example 337

Compound 337: 3-[[4-(4-Dimethylaminomethyl-pyridin-2-yloxy)-trans-cyclohexyl]-(4-methyl-cyclohex-3-enecarbonyl)-amino]-5-(3,3-dimethyl-but-1-ynyl)-thiophene-2-carboxylic acid

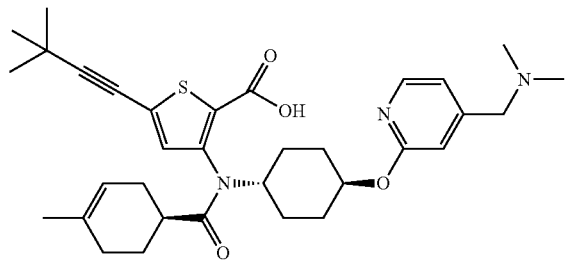

Compound 337

Scheme 19

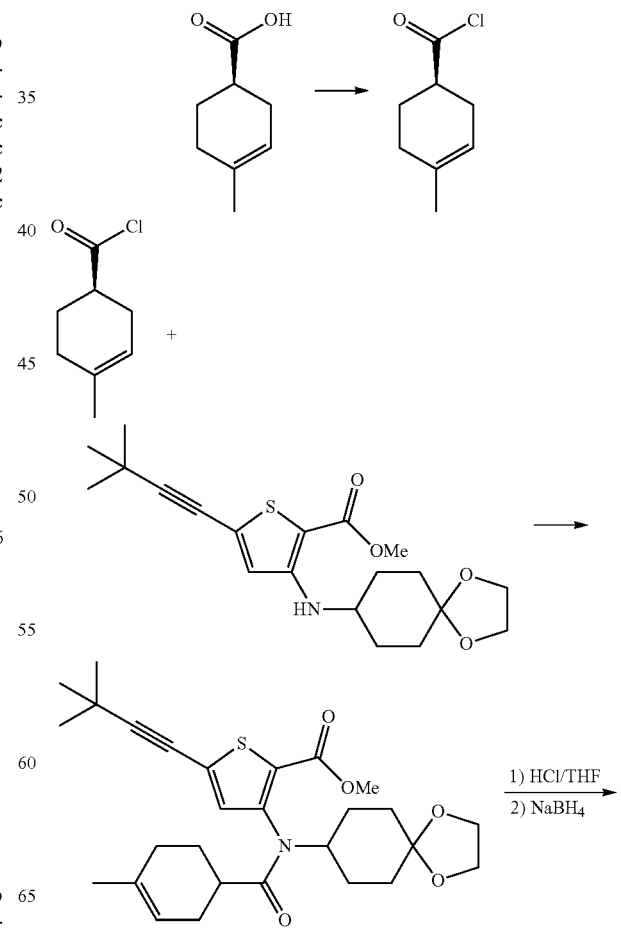

1) HCl/THF
2) NaBH4

-continued

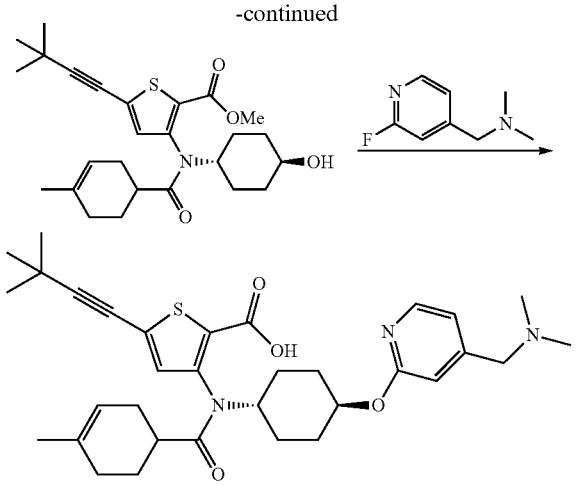

(1S)-4-Methyl-cyclohex-3-ene-1-carboxylic acid (250 mg, 1.78 mmol), azeotropically dried by evaporation from toluene was dissolved in dichloromethane (4 mL) and treated with dimethylformamide (1 drop). The reaction mixture was cooled to 0° C. and treated dropwise with oxalyl chloride (0.42 mL, 4.5 mmol). The reaction mixture was allowed to warm to ambient temperature while stirring for 4 h. The solution was concentrated, treated with hexanes and concentrated again to afford (1S)-4-methyl-cyclohex-3-ene-1-carboxylic acid chloride as a light yellow oil which was used immediately in the next step.

(1S)-4-Methyl-cyclohex-3-ene-1-carboxylic acid chloride (1.8 mmol), dimethyl-but-1-ynyl)-3-(1,4-dioxa-spiro[4.5]dec-8-ylamino)-thiophene-2-carboxylic acid methyl ester (336 mg, 0.89 mmol) and DMAP (217 mg, 1.8 mmol) were dissolved in dichloroethane (2.2 mL), sealed with a cap and heated to 80° C. After 2 h, the temperature was increased to 90° C., and the solution was stirred 16 h. The reaction mixture was further heated to 100° C., stirred 24 h and partitioned between water and ethyl acetate:hexanes (1:1). The layers were separated and the aqueous layer was extracted again with ethyl acetate:hexanes (1:1). The combined organic layers were dried over sodium sulfate, filtered and concentrated. Flash chromatography (5% EtOAc:hexanes 5 min then 5-40% EtOAc:hexanes, 20 min, 24 g column) afforded 250 mg (56% yield) of the desired 5-(3,3-dimethyl-but-1-ynyl)-3-[(1,4-dioxa-spiro[4.5]dec-8-yl)-(4-methyl-cyclohex-3-enecarbonyl)-amino]-thiophene-2-carboxylic acid methyl ester as a white foam.

5-(3,3-Dimethyl-but-1-ynyl)-3-[(1,4-dioxa-spiro[4.5]dec-8-yl)-(4-methyl-cyclohex-3-enecarbonyl)-amino]-thiophene-2-carboxylic acid methyl ester (240 mg, 0.48 mmol) was dissolved in THF (3.2 mL) and treated with 4M HCl (1.6 mL, 0.8 mmol). The reaction mixture was heated to 45° C. and stirred at ambient temperature. After 2 h, methanol was added (15-20 drops) and the solution was stirred for 3 h. An additional portion of 4M HCl (1.6 mL, 0.8 mmol) and methanol (1 mL) were added and the solution was stirred 16 h at ambient temperature followed by 40° C. for 4 h. The solution was partitioned between water and ethyl acetate. The organic layer was washed with sodium bicarbonate (sat. aq.) and brine, dried over sodium sulfate and concentrated to 233 mg (quantitative yield) of the desired 5-(3,3-dimethyl-but-1-ynyl)-3-[(4-methyl-cyclohex-3-enecarbonyl)-(4-oxo-cyclohexyl)-amino]-thiophene-2-carboxylic acid methyl ester as a white foam.

5-(3,3-Dimethyl-but-1-ynyl)-3-[(4-methyl-cyclohex-3-enecarbonyl)-(4-oxo-cyclohexyl)-amino]-thiophene-2-carboxylic acid methyl ester (233 mg, 0.51 mmol) in THF (3 mL) and water (0.3 mL) was treated with sodium borohydride (19 mg, 0.48 mmol). After stirring for 20 min, water was added and the reaction mixture was extract twice with ethyl acetate. The combined organic layers were dried over sodium sulfate, filtered and concentrated. Flash chromatography (10% EtOAc:hexanes, 4 min, 10-70% EtOAc:hexanes, 12 min, 12 g column) afforded 130 mg (59% yield) of the desired 5-(3,3-dimethyl-but-1-ynyl)-3-[(4-hydroxy-trans-cyclohexyl)-(4-methyl-cyclohex-3-enecarbonyl)-amino]-thiophene-2-carboxylic acid methyl ester.

5-(3,3-Dimethyl-but-1-ynyl)-3-[(4-hydroxy-trans-cyclohexyl)-(4-methyl-cyclohex-3-enecarbonyl)-amino]-thiophene-2-carboxylic acid methyl ester (40 mg, 0.088 mmol) and (N,N-dimethyl)-(2-fluoro-pyridin-4-ylmethyl)amine (84 mg, 0.55 mmol) in DMF (1 mL) were treated with sodium hydride (22 mg, 60% oil dispersion, 0.55 mmol). After the bubbling slowed, the reaction mixture was sealed and heated by microwave (90° C.) for 70 min. The reaction mixture was treated with 10% citric acid (2-3 mL) followed by water (2-3 mL). The organics were extracted twice with ethyl acetate, dried over sodium sulfate, filtered and concentrated. The residue was purified by reverse phase HPLC to give the Compound 337, 18 mg (35% yield): MS (m/z): 578.0 [M+H]+; HPLC retention time 3.53 min (2-98% acetonitrile:water with 0.05% trifluoroacetic acid).

Example 338

Compound 338: 3-((1r,4R)—N-((1r,4R)-4-(4-((dimethylamino)methyl)pyridin-2-yloxy)cyclohexyl)-4-methylcyclohexanecarboxamido)-5-((1-(trifluoromethyl)cyclobutyl)ethynyl)thiophene-2-carboxylic acid Scheme 20

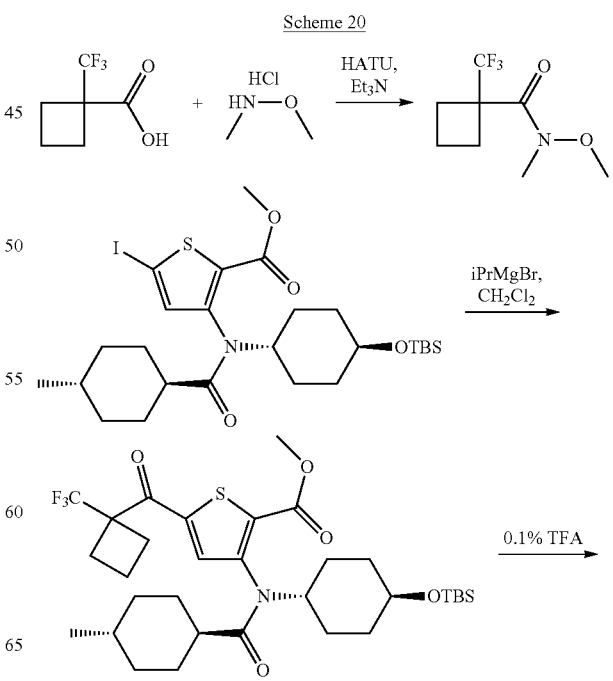

-continued

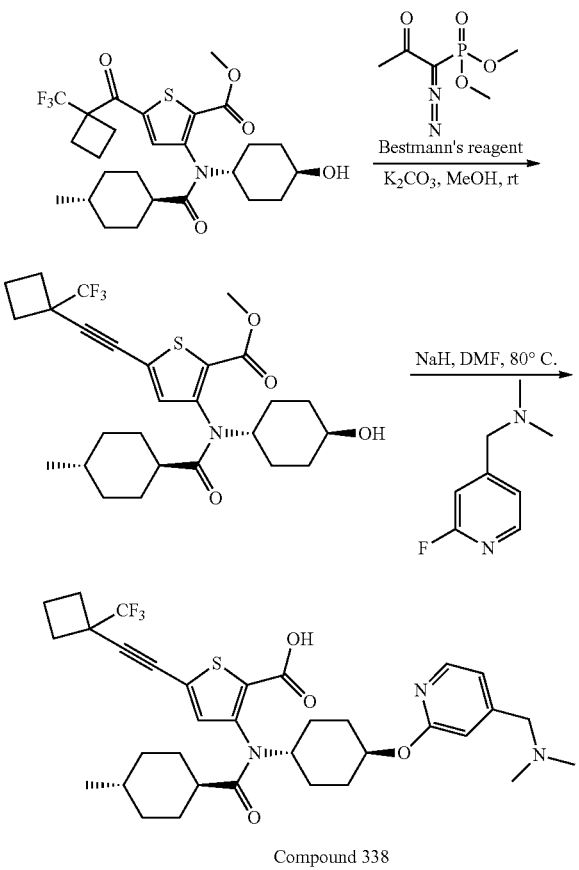

Compound 338

HATU (14.9 g, 39.3 mmol, 1.1 equiv) and N,O-dimethylhydroxylamine hydrochloride (3.9 g, 39.3 mmol, 1.1 equiv) were charged into a round-bottomed flask containing 200 mL dichloromethane. Triethylamine (14.9 mL, 107 mmol, 3.0 equiv) was added, and then a solution of (1-trifluoromethyl)cyclobutanecarboxylic acid (6.0 g, 35.7 mmol, 1.0 equiv) in DCM (25 mL) was added. The reaction was stirred at room temperature until complete consumption of the carboxylic acid. The solution was concentrated in vacuo to remove volatiles and the residue was partitioned between DCM (200 mL) and saturated NH$_4$Cl (100 mL). The aqueous was extract with DCM (200 mL) and the combined organics were dried over Na$_2$SO$_4$ and then concentrated. The crude was purified by silica gel chromatography to afford the product (5.64 g, 27 mmol, 75% yield) as colorless oil.

A solution of methyl 3-((1r,4R)—N-((1r,4R)-4-(tert-butyldimethylsilyloxy)cyclohexyl)-4-methylcyclohexanecarboxamido)-5-iodothiophene-2-carboxylate (620 mg, 1 mmol, 1.0 equiv) in DCM (5.0 mL) in a round-bottomed flask was cooled to −78° C. Isopropylmagnesium chloride (2.0 M in THF, 1.1 mmol, 1.1 equiv) was added dropwise and then stirred for 30 min. A solution of amide (232 mg, 1.1 mmol, 1.1 equiv) in DCM (1.0 mL) was added slowly and the resulting solution was gradually warmed to room temperature and stirred overnight. The reaction was poured into saturated NH$_4$Cl (100 mL) and extracted with DCM (2×100 mL). The combined organics were dried over Na$_2$SO$_4$ and then concentrated. The crude was purified by silica gel chromatography to afford the product (186 mg, 0.3 mmol, 29% yield) as a white solid.

Methyl 3-((1r,4R)—N-((1r,4R)-4-(tert-butyldimethylsilyloxy)cyclohexyl)-4-methylcyclohexanecarboxamido)-5-(1-(trifluoromethyl)cyclobutanecarbonyl)thiophene-2-carboxylate (550 mg, 0.85 mmol) was dissolved in acetonitrile (5 mL), H$_2$O (1 mL) and trifluoroacetic acid (0.1 mL). The reaction was stirred at room temperature until complete consumption of the starting material. After concentrated to remove volatiles, the resulting residue was purified by silica gel chromatography to afford the product (430 mg, 0.81 mmol, 95% yield) as a white solid.

To a solution of methyl 3-((1r,4R)—N-((1r,4R)-4-hydroxycyclohexyl)-4-methylcyclohexanecarboxamido)-5-(1-(trifluoromethyl)cyclobutanecarbonyl)thiophene-2-carboxylate (400 mg, 0.75 mmol, 1.0 equiv) and dimethyl 1-diazo-2-oxopropylphosphonate (232 mg, 1.2 mmole, 1.6 equiv) in MeOH (3.0 mL) was added K$_2$CO$_3$ (259 mg, 1.9 mmol, 2.5 equiv). The resulting solution was stirred over night at room temperature. The reaction was then partitioned between EtOAc (100 mL) and 1 N HCl (100 mL). The organic was dried over Na$_2$SO$_4$ and then concentrated. The crude was purified by reverse phase preparative HPLC to afford the product (200 mg, 0.38 mmol, 51% yield) as a white solid.

To a solution of methyl 3-((1r,4R)—N-((1r,4R)-4-hydroxycyclohexyl)-4-methylcyclohexanecarboxamido)-5-((1-(trifluoromethyl)cyclobutyl)ethynyl)thiophene-2-carboxylate (50 mg, 0.1 mmol) in DMF (1 mL) was added NaH (20 mg, 0.5 mmol). After stirred at room temperature for 10 min, (N,N-dimethyl)-(2-fluoro-pyridin-4-ylmethyl)amine (46 mg, 0.3 mmol) was added and reaction was stirred over night at 80° C. After cooling to room temperature, the mixture was purified by reverse phase preparative HPLC to afford Compound 338 (27 mg, 0.042 mmol, 42%) as a white solid: MS (m/z) 646.3 [M+H]$^+$ HPLC retention time: 1.76 min (50-95% acetonitrile with 0.05% TFA:water with 0.05% TFA).

Example 339

Compound 339: 3-((1r,4R)—N-((1r,4R)-4-(6-hydroxypyridazin-3-yloxy)cyclohexyl)-4-methylcyclohexanecarboxamido)-5-((1-(trifluoromethyl)cyclobutyl)ethynyl)thiophene-2-carboxylic acid Scheme 21

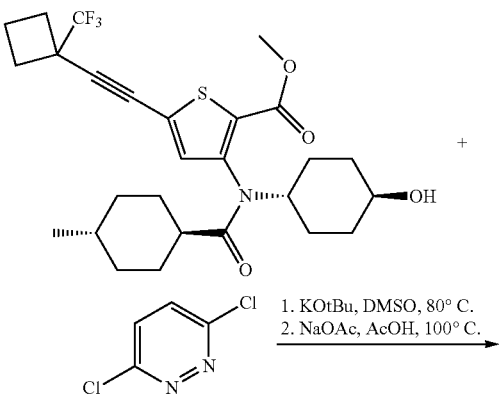

1. KOtBu, DMSO, 80° C.
2. NaOAc, AcOH, 100° C.

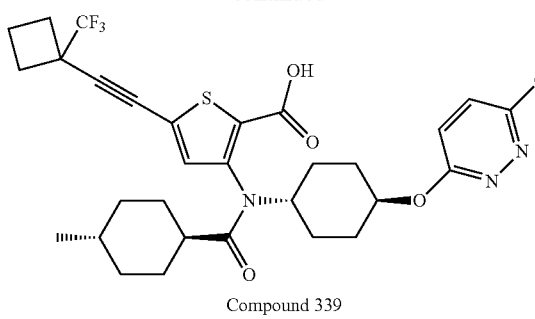

Compound 339

To a solution of methyl 3-((1r,4R)—N-((1r,4R)-4-hydroxycyclohexyl)-4-methylcyclohexanecarboxamido)-5-(1-(trifluoromethyl)cyclobutyl)ethynyl)thiophene-2-carboxylate (50 mg, 0.1 mmol) in DMSO (2 mL) was added KOtBu (168 mg, 1.5 mmol). After stirred at room temperature for 10 min, 1-(2-fluoropyridin-4-yl)-N,N-dimethylmethanamine (149 mg, 1.0 mmol) was added and reaction was heated at 80° C. in a microwave reactor for 1 h. After cooling to room temperature, the mixture was purified by reverse phase preparative HPLC.

The product from previous step was dissolved in AcOH (2.0 mL) and NaOAc (82 mg, 1 mmol) was added. The mixture was stirred overnight at 110° C. After removing the volatiles, the resulting residue was purified by reverse phase preparative HPLC to afford Compound 338 (18 mg, 0.03 mmol, 30%) as a white solid: MS (m/z) 606.1 [M+H]$^+$ HPLC retention time: 3.1 min (5-95% acetonitrile with 0.05% TFA:water with 0.05% TFA).

Example 340

Compound 340: 3-((1r,4R)—N-((1r,4R)-4-(4-((dimethylamino)methyl)pyridin-2-yloxy)cyclohexyl)-4-methylcyclohexanecarboxamido)-5-((1-(trifluoromethyl)cyclopropyl)ethynyl)thiophene-2-carboxylic acid Scheme 22

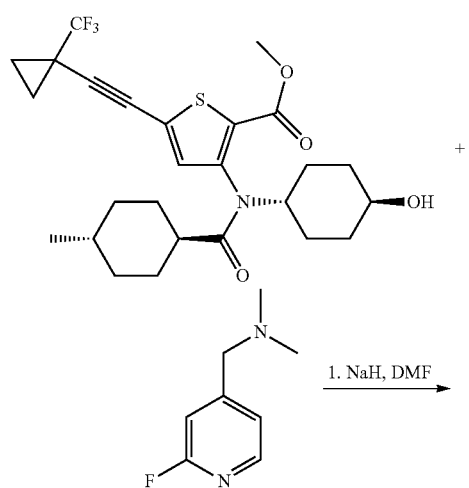

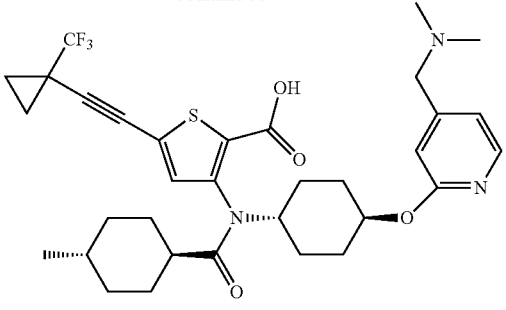

Compound 340

Compound 340 was prepared by the same route as example 338, excepting the substitution of 1-(trifluoromethyl)cyclopropanecarboxylic acid in the formation of the Weinreb amide: MS (m/z) 632.2 [M+H]$^+$ HPLC retention time: 3.96 min (50-95% acetonitrile with 0.05% TFA:water with 0.05% TFA).

Example 341

Compound 341: 3-((1r,4R)—N-((1r,4R)-4-(4-((dimethylamino)methyl)pyridin-2-yloxy)cyclohexyl)-4-methylcyclohexanecarboxamido)-5-(4,4,4-trifluoro-3,3-dimethylbut-1-ynyl)thiophene-2-carboxylic acid Scheme 23

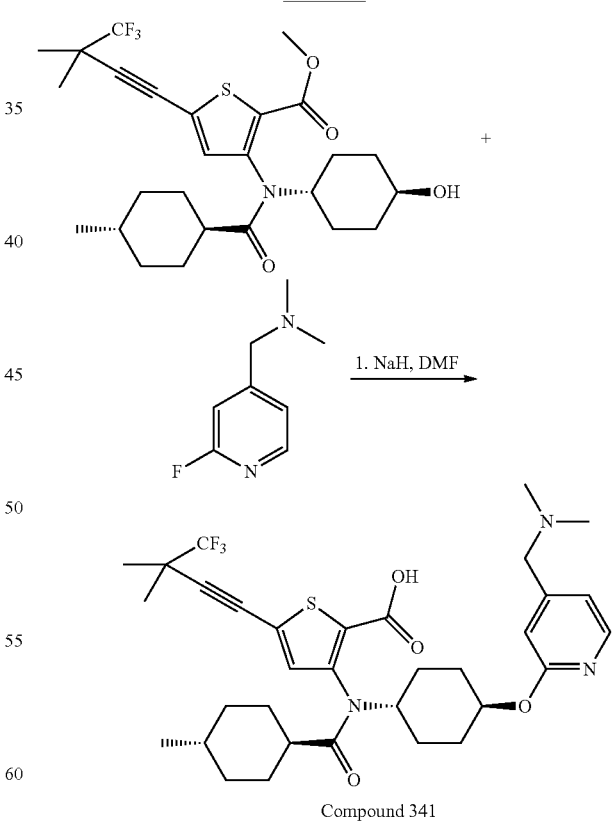

Compound 341

Compound 341 was prepared by the same route as example 338, excepting the substitution of 3,3,3-trifluoro-2,2-dimethylpropanoic acid in the formation of the Weinreb amide: MS (m/z) 634.3 [M+H]$^+$ HPLC retention time: 4.10 min (5-95% acetonitrile with 0.05% TFA:water with 0.05% TFA).

Example 342

Compound 342: 3-((1r,4R)—N-((1r,4R)-4-(6-hydroxypyridazin-3-yloxy)cyclohexyl)-4-methylcyclohexanecarboxamido)-5-((1-(trifluoromethyl)cyclopropyl)ethynyl)thiophene-2-carboxylic acid Scheme 24

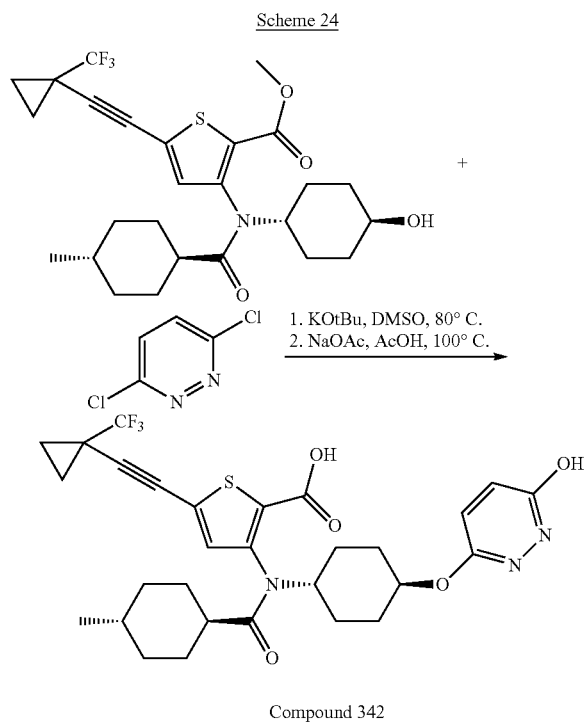

Compound 342

Compound 342 was prepared by the same route as example 339, excepting the substitution of the different secondary alcohol intermediate shown above in the ether formation: MS (m/z) 614.1 [M+Na]$^+$ HPLC retention time: 4.34 min (5-95% acetonitrile with 0.05% TFA:water with 0.05% TFA).

Example 343

Compound 343: 3-((1r,4R)—N-((1r,4R)-4-(6-hydroxypyridazin-3-yloxy)cyclohexyl)-4-methylcyclohexanecarboxamido)-5-(4,4,4-trifluoro-3,3-dimethyl-but-1-ynyl)thiophene-2-carboxylic acid Scheme 25

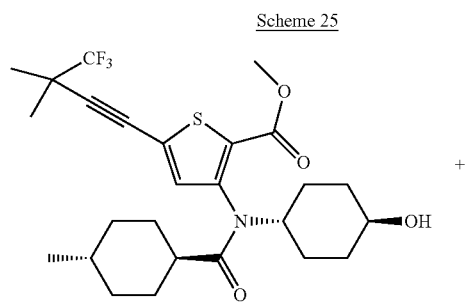

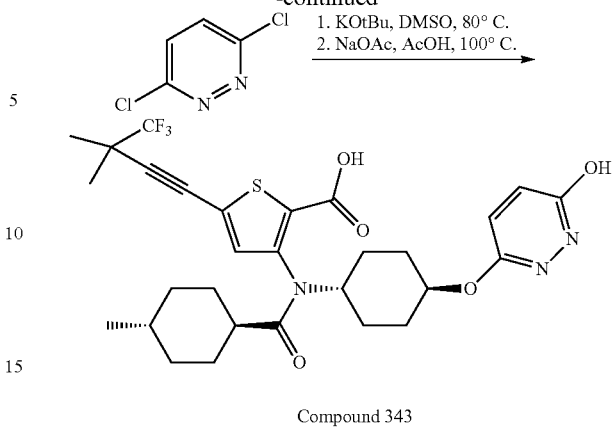

Compound 343

Compound 343 was prepared by the same route as example 339, excepting the substitution of the different secondary alcohol intermediate shown above in the ether formation: MS (m/z) 616.2 [M+Na]$^+$ HPLC retention time: 448 min (5-95% acetonitrile with 0.05% TFA:water with 0.05% TFA).

Example 344

Compound 344: 3-((1r,4R)-4-methyl-N-((1r,4R)-4-(pyrimidin-4-yloxy)cyclohexyl)cyclohexanecarboxamido)-5-(2-(1-(trifluoromethyl)cyclopropyl)ethynyl)thiophene-2-carboxylic acid Scheme 26

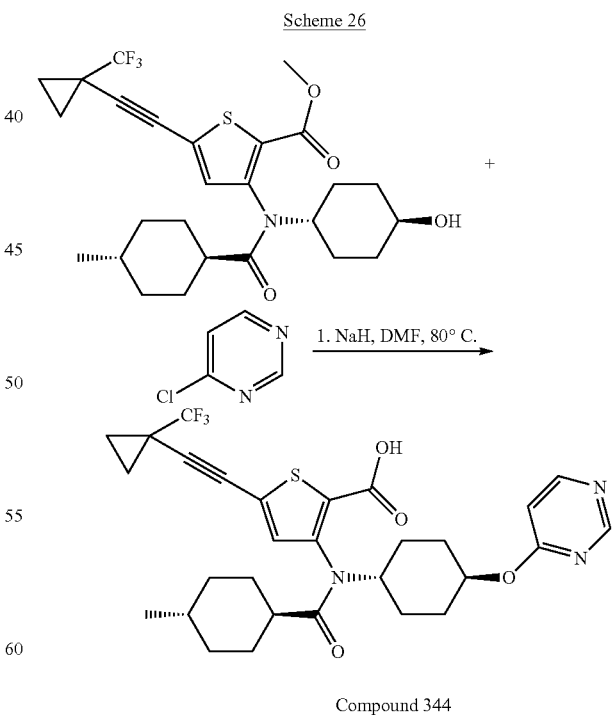

Compound 344

Compound 344 was prepared by the same route as example 340, excepting the substitution of 4-chloropyrimidine hydrochloride as the electrophile in the final ether formation step:

MS (m/z) 574.3 [M−H]⁻ HPLC retention time: 4.38 min (5-95% acetonitrile with 0.05% TFA:water with 0.05% TFA).

Example 345

Compound 345: 3-((1r,4R)-4-methyl-N-((1r,4R)-4-(tetrahydrofuran-3-yloxy)cyclohexyl)cyclohexanecarboxamido)-5-(2-(1-(trifluoromethyl)cyclopropyl)ethynyl)thiophene-2-carboxylic acid

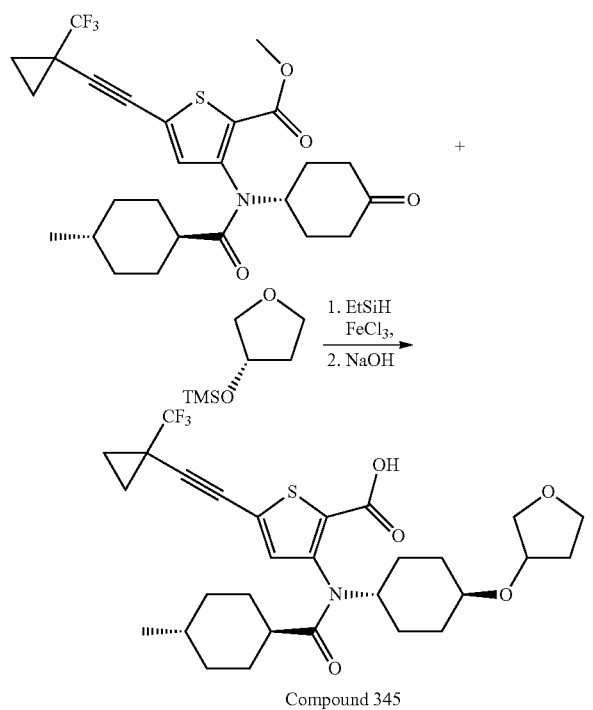

Compound 345

To a suspension of methyl 3-((1r,4R)-4-methyl-N-((1r,4R)-4-(oxocyclohexyl)cyclohexanecarboxamido)-5-(2-(1-(trifluoromethyl)cyclopropyl)ethynyl)thiophene-2-carboxylate (82 mg, 0.161 mmol) and FeCl₃ (3 mg, 0.016 mmol) in nitromethane (1 mL), cooled to 0° C., was added neat trimethyl-(tetrahydro-furan-3-yloxy)-silane (200 mg, 1.25 mmol) followed by the addition of triethylsilane (0.051 mL, 0.322 mmol). The reaction was allowed to slowly warm to room temperature and stirred overnight. Phosphate buffer of pH 4.5 was added and the reaction mixture was extracted with dichloromethane. The organic layer was dried over Na₂SO₄ and concentrated. Purification by HPLC with CH₃CN (0.1% TFA)/H₂O (0.1% TFA) provided both methyl 3-((1r,4R)-4-methyl-N-((1r,4R)-4-(tetrahydrofuran-3-yloxy)cyclohexyl)cyclohexanecarboxamido)-5-(2-(1-(trifluoromethyl)cyclopropyl)ethynyl)thiophene-2-carboxylate and methyl 3-((1r,4R)-4-methyl-N-((1s,4S)-4-(tetrahydrofuran-3-yloxy)cyclohexyl)cyclohexanecarboxamido)-5-(2-(1-(trifluoromethyl)cyclopropyl)ethynyl)thiophene-2-carboxylate. Each of the diastereomers was then subjected to ester hydrolysis separately.

Methyl 3-((1r,4R)-4-methyl-N-((1r,4R)-4-(tetrahydrofuran-3-yloxy)cyclohexyl)cyclohexanecarboxamido)-5-(2-(1-(trifluoromethyl)cyclopropyl)ethynyl)thiophene-2-carboxylate (75 mg, 0.129 mmol) was dissolved in tetrahydrofuran (1 mL). To this was added 2N NaOH (0.65 mL, 1.3 mmol) and 2 drops of methanol, and the solution was stirred 1 hour at room temperature. The reaction solution was then partitioned between ethyl acetate (30 mL) and 2N HCl (30 mL). The aqueous layer was washed once with 30 mL ethyl acetate, and the combined organic layer was concentrated. Purification by HPLC with CH₃CN (0.1% TFA)/H₂O (0.1% TFA) provided 3-((1r,4R)-4-methyl-N-((1r,4R)-4-(tetrahydrofuran-3-yloxy)cyclohexyl)cyclohexanecarboxamido)-5-(2-(1-(trifluoromethyl)cyclopropyl)ethynyl)thiophene-2-carboxylic acid (31 mg, 0.55 mmol, 42%) as a white solid: MS (m/z) 568.2 [M+H]⁺ HPLC retention time: 2.61 min (50-95% acetonitrile with 0.05% TFA:water with 0.05% TFA).

Example 346

Compound 346: 3-((1r,4R)-4-methyl-N-((1s,4S)-4-(tetrahydrofuran-3-yloxy)cyclohexyl)cyclohexanecarboxamido)-5-(2-(1-(trifluoromethyl)cyclopropyl)ethynyl)thiophene-2-carboxylic acid

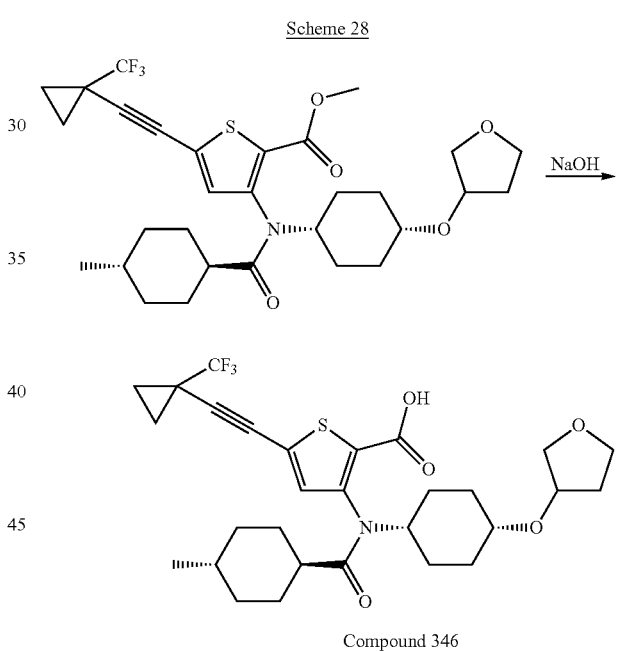

Compound 346

Methyl 3-((1r,4R)-4-methyl-N-((1s,4S)-4-(tetrahydrofuran-3-yloxy)cyclohexyl)cyclohexanecarboxamido)-5-(2-(1-(trifluoromethyl)cyclopropyl)ethynyl)thiophene-2-carboxylate (12 mg, 0.021 mmol) was dissolved in tetrahydrofuran (1 mL). To this was added 2N NaOH (0.2 mL, 0.4 mmol) and 2 drops of methanol, and the solution was stirred 1 hour at room temperature. The reaction solution was then partitioned between ethyl acetate (15 mL) and 2N HCl (15 mL). The aqueous layer was washed once with 15 mL ethyl acetate, and the combined organic layer was concentrated. Purification by HPLC with CH₃CN (0.1% TFA)/H₂O (0.1% TFA) provided 3-((1r,4R)-4-methyl-N-((1s,4S)-4-(tetrahydrofuran-3-yloxy)cyclohexyl)cyclohexanecarboxamido)-5-(2-(1-(trifluoromethyl)cyclopropyl)ethynyl)thiophene-2-carboxylic acid (4 mg, 0.007 mmol, 34%) as a white solid: MS (m/z)

568.2 [M+H]⁺ HPLC retention time: 2.73 min (50-95% acetonitrile with 0.05% TFA:water with 0.05% TFA).

Example 347

Compound 347: 5-(3,3-dimethylbut-1-ynyl)-3-((1r,4R)-4-methyl-N-((1s,4S)-4-(oxetan-3-yloxy)cyclohexyl)cyclohexanecarboxamido)-5-(2-(1-(trifluoromethyl)cyclopropyl)ethynyl)thiophene-2-carboxylic acid

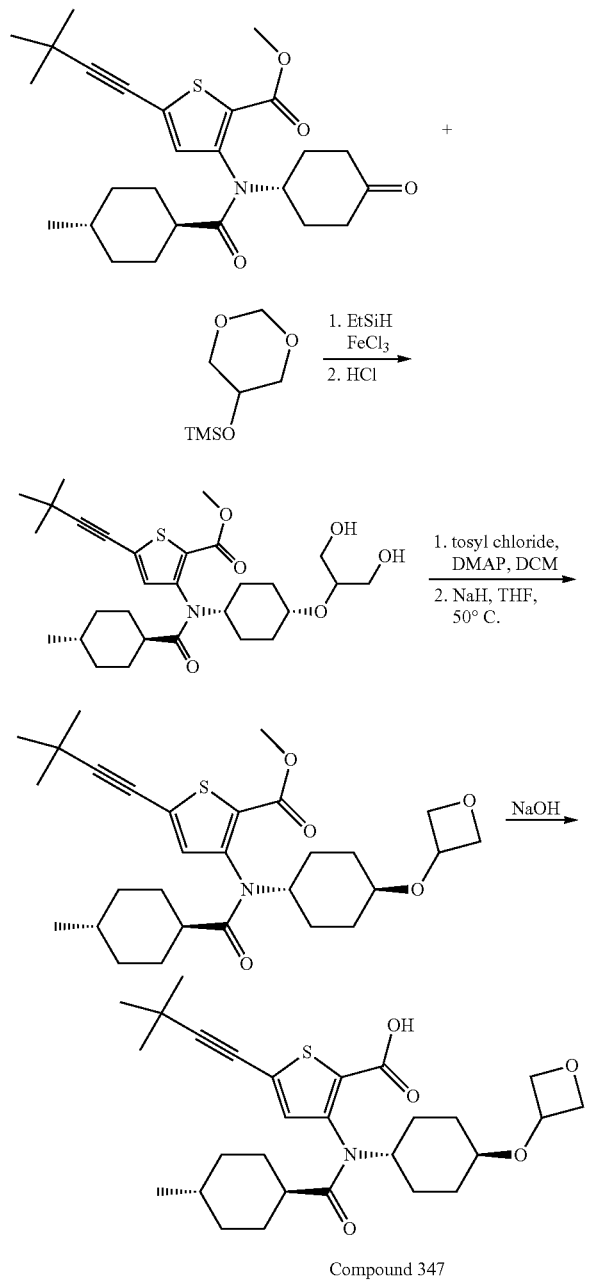

Compound 347

To a suspension of methyl 5-(3,3-dimethylbut-1-ynyl)-3-((1r,4r)-4-methyl-N-4-(oxocyclohexyl)cyclohexanecarboxamido)thiophene-2-carboxylate (1.0 g, 2.185 mmol) and FeCl₃ (35 mg, 0.22 mmol) in nitromethane (15 mL) cooled to 0° C. was added neat (1,3-dioxan-3-yloxy)trimethylsilane (1.05, 6 mmol) followed by the addition of triethylsilane (0.59 mL, 4.37 mmol). The reaction was allowed to slowly warm to room temperature and stirred overnight. Phosphate buffer of pH 4.5 was added and the reaction mixture was extracted with dichloromethane. The organic layer was dried over Na₂SO₄ and concentrated. The crude was purified by silica gel chromatography (45% ethyl acetate in hexanes) to afford the ether product (704 mg, 1.29 mmol, 59% yield) as a yellow oil: MS (m/z) 546.5 [M+H]⁺ HPLC retention time: 4.13 min (50-95% acetonitrile with 0.05% TFA: water with 0.05% TFA). This oil was dissolved in 1,4-dioxane (3 mL) and 2N HCl (7 mL) and was then heated and stirred at reflux overnight. The reaction was then cooled and diluted with water (50 mL). The mixture was then extracted twice with ethyl acetate (100 mL). The combined ethyl acetate extracts were washed with brine, dried over Na₂SO₄ and concentrated. The crude product was taken on directly to the next step.

Dimethylaminopyridine (175 mg, 1.434 mmol) and the crude diol starting material (255 mg, 0.478 mmol) were dissolved in dichloromethane (4 mL). 4-Toluenesulfonyl chloride (109 mg, 0.574 mmol) was then added and the solution was stirred 30 minutes at room temperature. The excess tosyl chloride was then quenched by aqueous NH₄Cl (30 mL), and the mixture was extracted twice with dichloromethane (30 mL). The organic layer was dried over Na₂SO₄ and concentrated. The residue was dissolved in tetrahydrofuran (4 mL) and sodium hydride (50 mg, 1.195 mmol) was added. The reaction was stirred at 50° C. overnight. 2N HCl (30 mL) was then added, and the solution was extracted twice with ethyl acetate (50 mL). The organic layer was dried over Na₂SO₄ and concentrated. Purification by HPLC with CH₃CN (0.1% TFA)/H₂O (0.1% TFA) provided methyl 5-(3,3-dimethylbut-1-ynyl)-3-((1r,4R)-4-methyl-N-((1s,4S)-4-(oxetan-3-yloxy)cyclohexyl)cyclohexanecarboxamido)-5-(2-(1-(trifluoromethyl)cyclopropyl)ethynyl)thiophene-2-carboxylate (32 mg, 0.62 mmol, 13%) as an off-white solid: MS (m/z) 516.2 [M+H]⁺ HPLC retention time: 3.02 min (50-95% acetonitrile with 0.05% TFA:water with 0.05% TFA).

Methyl 5-(3,3-dimethylbut-1-ynyl)-3-(1r,4R)-4-methyl-N-((1s,4S)-4-(oxetan-3-yloxy)cyclohexyl)cyclohexanecarboxamido)-5-(2-(1-(trifluoromethyl)cyclopropyl)ethynyl)thiophene-2-carboxylate (92 mg, 0.184 mmol) was dissolved in tetrahydrofuran (5 mL). To this was added 2N NaOH (0.92 mL, 1.84 mmol) and 2 drops of methanol, and the solution was stirred 30 minutes at room temperature. The reaction solution was then acidified with 2N HCl (1.5 mL). The mixture was extracted twice with ethyl acetate (30 mL) and concentrated. Purification by HPLC with CH₃CN (0.1% TFA)/H₂O (0.1% TFA) provided 5-(3,3-dimethylbut-1-ynyl)-3-((1r,4R)-4-methyl-N-((1s,4S)-4-(oxetan-3-yloxy)cyclohexyl)cyclohexanecarboxamido)-5-(2-(1-(trifluoromethyl)cyclopropyl)ethynyl)thiophene-2-carboxylic acid (10 mg, 0.02 mmol, 11%) as a white solid: MS (m/z) 502.2 HPLC retention time: 5.03 min (5-95% acetonitrile with 0.05% TFA:water with 0.05% TFA).

Example 348

Synthesis 5-(3,3-Dimethyl-but-1-ynyl)-3-[(1S,6S)-(4,6-dimethyl-cyclohex-3-enecarbonyl)-(4-hydroxy-cyclohexyl)-amino]-thiophene-2-carboxylic acid

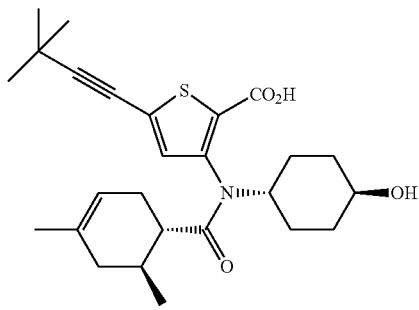 [SMILES: CC1=CC[C@H](C(=O)N(c2cc(C#CC(C)(C)C)sc2C(=O)O)[C@H]2CC[C@H](O)CC2)[C@@H](C)C1]

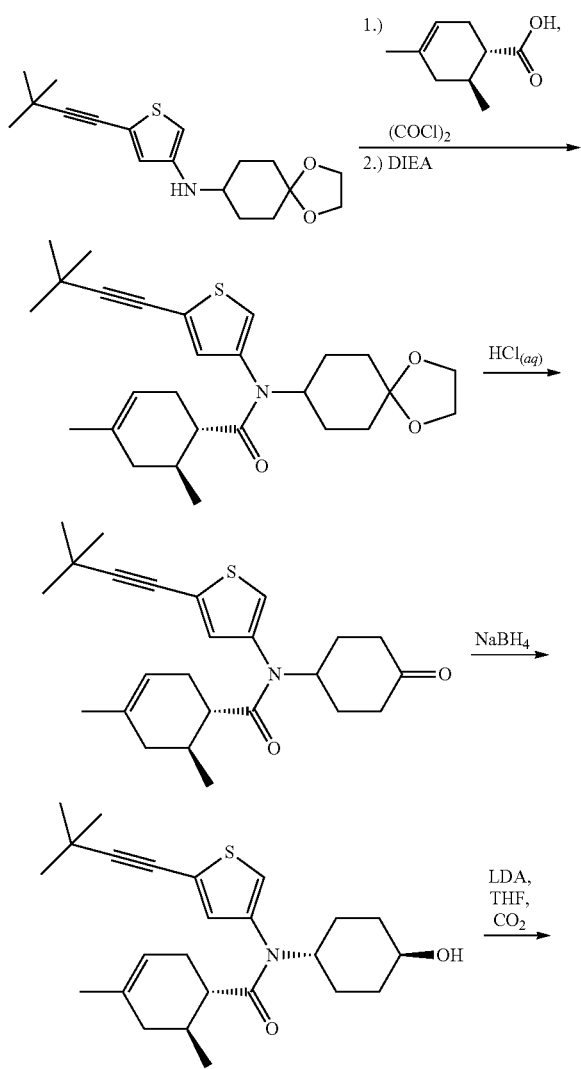

Scheme 1

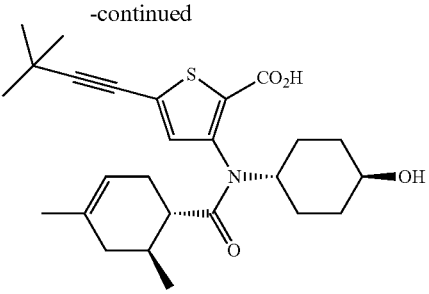

(1S,6S)-4,6-dimethyl-cyclohex-3-ene-carboxylic acid (3.04 g, 19.7 mmol) was dissolved in CH₂Cl₂ (30 mL) and DMF (20 µL) was added. The solution was cooled to 0° C. and then (COCl)₂ (3.7 mL, 39 mmol) was added slowly. The reaction was stirred in an ice bath for 2 hours and then concentrated. The residue was taken up in hexanes and concentrated; this hexanes coevaporation was repeated once more. To the residue was added [5-(3,3-dimethyl-but-1-ynyl)-thiophen-3-yl]-(1,4-dioxa-spiro[4.5]dec-8-yl)-amine (4.16 g, 13 mmol), diisopropylethylamine (4.5 mL, 26 mmol), and 1,2-dichloroethane (40 mL) at 0° C. The solution was warmed to room temperature and stirred overnight. The reaction was diluted with CH₂Cl₂, twice washed with saturated NH₄Cl$_{(aq)}$, dried over MgSO₄, filtered, concentrated, and purified by silica gel column chromatography, eluting with a mixture of 0-75% EtOAc/hexanes, to give (1S,6S)-4,6-dimethyl-cyclohex-3-ene-carboxylic acid [5-(3,3-dimethyl-but-1-ynyl)-thiophen-3-yl]-(1,4-dioxa-spiro[4.5]dec-8-yl)-amide (5.6 g, 12 mmol) as a single isomer.

(1S,6S)-4,6-Dimethyl-cyclohex-3-ene-carboxylic acid [5-(3,3-dimethyl-but-1-ynyl)-thiophen-3-yl]-(1,4-dioxa-spiro[4.5]dec-8-yl)-amide (5.6 g, 12 mmol) was dissolved in THF (70 mL) and treated with 4M HCl (35 mL). The reaction mixture was heated to 45° C. and stirred for 2.5 h. THF was removed in vacuo, and the aqueous layer was thrice extracted into ethyl acetate. The combined organic layers were washed with saturated NaHCO₃$_{(aq)}$, water, and brine, dried over MgSO₄, filtered, and concentrated to give (1S,6S)-4,6-dimethyl-cyclohex-3-ene-carboxylic acid [5-(3,3-dimethyl-but-1-ynyl)-thiophen-3-yl]-(4-oxo-cyclohexyl)-amide (5.05 g, 12 mmol).

(1S,6S)-4,6-Dimethyl-cyclohex-3-ene-carboxylic acid [5-(3,3-dimethyl-but-1-ynyl)-thiophen-3-yl]-(4-oxo-cyclohexyl)-amide (2.0 g, 4.9 mmol) in MeOH (100 mL) was treated with sodium borohydride (230 mg, 6.0 mmol) at 0° C. After stirring for 30 min, 4M HCl (6 mL) was added and the reaction mixture was twice extracted with ethyl acetate. The combined organic layers washed with saturated NaHCO₃$_{(aq)}$, brine, dried over MgSO₄, filtered, and concentrated. Silica gel chromatography (20-60% ethyl acetate/hexanes) gave the desired (1S,6S)-4,6-dimethyl-cyclohex-3-ene-carboxylic acid [5-(3,3-dimethyl-but-1-ynyl)-thiophen-3-yl]-(trans-4-hydroxy-cyclohexyl)-amide (1.74 g, 4.2 mmol).

(1S,6S)-4,6-Dimethyl-cyclohex-3-ene-carboxylic acid [5-(3,3-dimethyl-but-1-ynyl)-thiophen-3-yl]-(trans-4-hydroxy-cyclohexyl)-amide (1.74 g, 4.2 mmol) in THF (50 mL) was cooled to −78° C. and treated with lithium diisopropylamine (8.4 mL, 2.0M in heptane/THF/PhEt, 16.8 mmol) and allowed to warm to 0° C. over the course of 2 hours. CO₂ was vigorously bubbled through the reaction solution for 10 minutes. The reaction was then quenched with the addition of iPrOH, diluted with ethyl acetate, washed with saturated NH₄Cl$_{(aq)}$, dried over MgSO₄, filtered, and concentrated. Silica gel chromatography (0-100% ethyl acetate/dichloromethane) afforded 530 mg (1.2 mmol) of the title compound: MS (m/z): 458.1 [M+H]+; HPLC retention time 4.35 min (2-98% acetonitrile:water with 0.05% trifluoroacetic acid).

Example 349

Compound 349: 5-(3,3-Dimethyl-but-1-ynyl)-3-{(1S,6S)-(4,6-dimethyl-cyclohex-3-enecarbonyl)-[trans-4-(pyrimidin-2-yloxy)-cyclohexyl]-amino}-thiophene-2-carboxylic acid Scheme 2

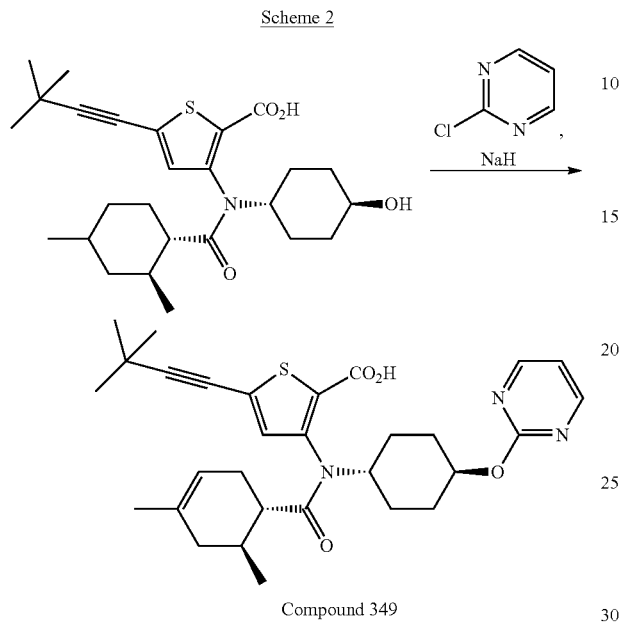

Compound 349

5-(3,3-Dimethyl-but-1-ynyl)-3S-[(4,6S-dimethyl-cyclohex-3-enecarbonyl)-(4-hydroxy-cyclohexyl)-amino]-thiophene-2-carboxylic acid (51 mg, 0.11 mmol) and 2-chloropyrimidine (100 mg, 0.87 mmol) were dissolved in DMF (0.5 mL) and treated with sodium hydride (49 mg, 60% oil dispersion, 1.2 mmol). The mixture was stirred under nitrogen until the bubbling slowed, then was sealed and heated by microwave (90° C., 30 min). After cooling, the mixture was diluted with ethyl acetate (about 5 mL) and quenched with 10% citric acid (about 2 mL). Water was added and the mixture was extracted twice with ethyl acetate. After concentration the resulting residue was purified by HPLC with $CH_3CN$ (0.1% TFA)/$H_2O$ (0.1% TFA) to afford 39 mg of Compound 349: MS (m/z): 533.9 [M−H]−; HPLC retention time 4.93 min (2-98% acetonitrile:water with 0.05% trifluoroacetic acid).

Example 350

Compound 350: 5-(3,3-Dimethyl-but-1-ynyl)-3-{(1S,6S)-(4,6-dimethyl-cyclohex-3-enecarbonyl)-[trans-4-(pyrimidin-4-yloxy)-cyclohexyl]-amino}-thiophene-2-carboxylic acid Compound 350

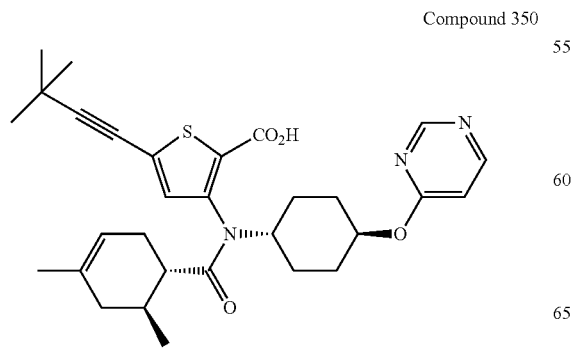

Compound 350 was synthesized in a manner similar to Example 349 using 4-chloropyrimidine hydrochloride in place of 2-chloropyrimidine: MS (m/z): 534.0 [M−H]−; HPLC retention time 4.27 min (2-98% acetonitrile:water with 0.05% trifluoroacetic acid).

Example 351

Compound 351: 5-(3,3-Dimethyl-but-1-ynyl)-3S-{(4,6S-dimethyl-cyclohex-3-enecarbonyl)-[trans-4-(pyridin-2-yloxy)-cyclohexyl]-amino}-thiophene-2-carboxylic acid Compound 351

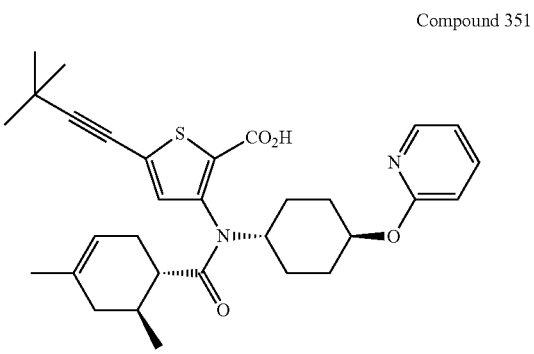 [SMILES: CC1=CC[C@H](C(=O)N(c2cc(C#CC(C)(C)C)sc2C(=O)O)[C@H]2CC[C@H](Oc3ccccn3)CC2)[C@@H](C)C1]

Compound 351 was synthesized in a manner similar to Example 349 using 2-chloropyridine in place of 2-chloropyrimidine: MS (m/z): 532.9 [M−H]−; HPLC retention time 4.75 min (2-98% acetonitrile:water with 0.05% trifluoroacetic acid).

Example 352

Compound 352: 5-(3,3-Dimethyl-but-1-ynyl)-3-{(1S,6S)-(4,6-dimethyl-cyclohex-3-enecarbonyl)-[trans-4-(1-oxy-pyridin-3-yloxy)-cyclohexyl]-amino}-thiophene-2-carboxylic acid Compound 352

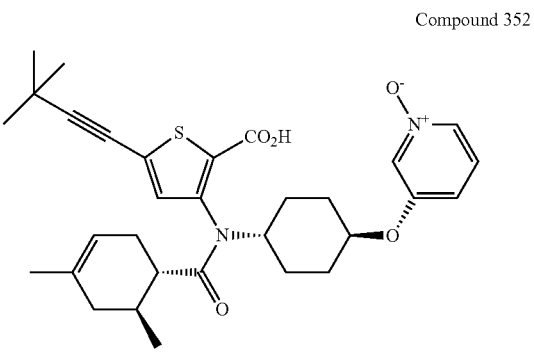

Compound 352 was synthesized in a manner similar to Example 349 using 3-fluoropyridine-N-oxide in place of 2-chloropyrimidine: MS (m/z): 551.1 [M+H]+; HPLC retention time 4.21 min (2-98% acetonitrile:water with 0.05% trifluoroacetic acid).

Example 353

Compound 353

Compound 353

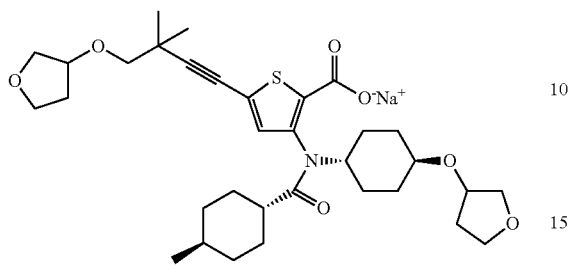

Compound 353 may be prepared in the same manner as in Example 314.

Example 354

Compound 354

Compound 354

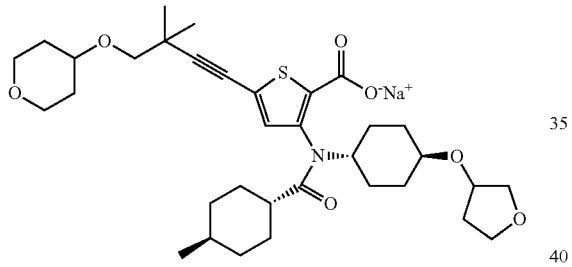

Compound 354 may be prepared in the same manner as in Example 314.

Example 355

Compound 355

Compound 355

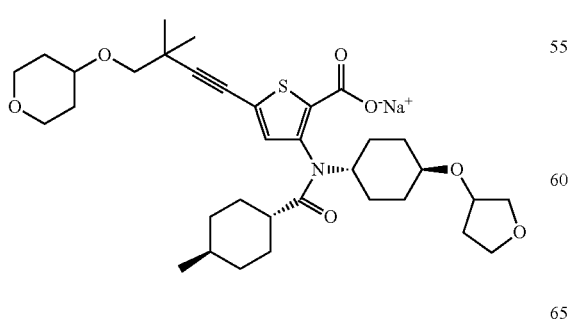

Compound 355 may be prepared in the same manner as in Example 314.

Example 356

Compound 356

Compound 356

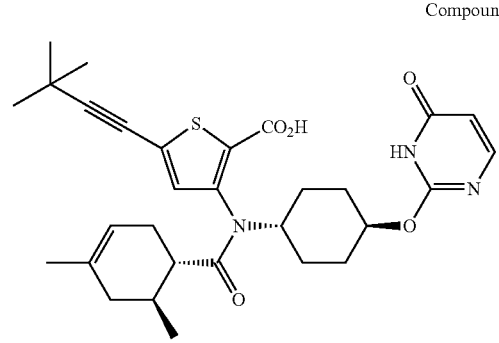

Compound 356 may be prepared in the same manner as Example 349 using 3,6-dichloropyridazine in place of 2-chloropyrimidine.

Example 357

Compound 357

Compound 357

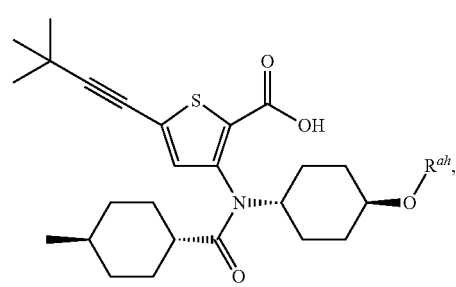

Compound 357 may be prepared in the same manner as Example 349 using 2-chloro-4-(2-(trimethylsilyl)ethoxy)pyrimidine in place of 2-chloropyrimidine.

Additional Prophetic Examples

The following prophetic examples may be synthesized using analogous techniques.

Aromatic Heterocycle Variants where R$^{ah}$ is
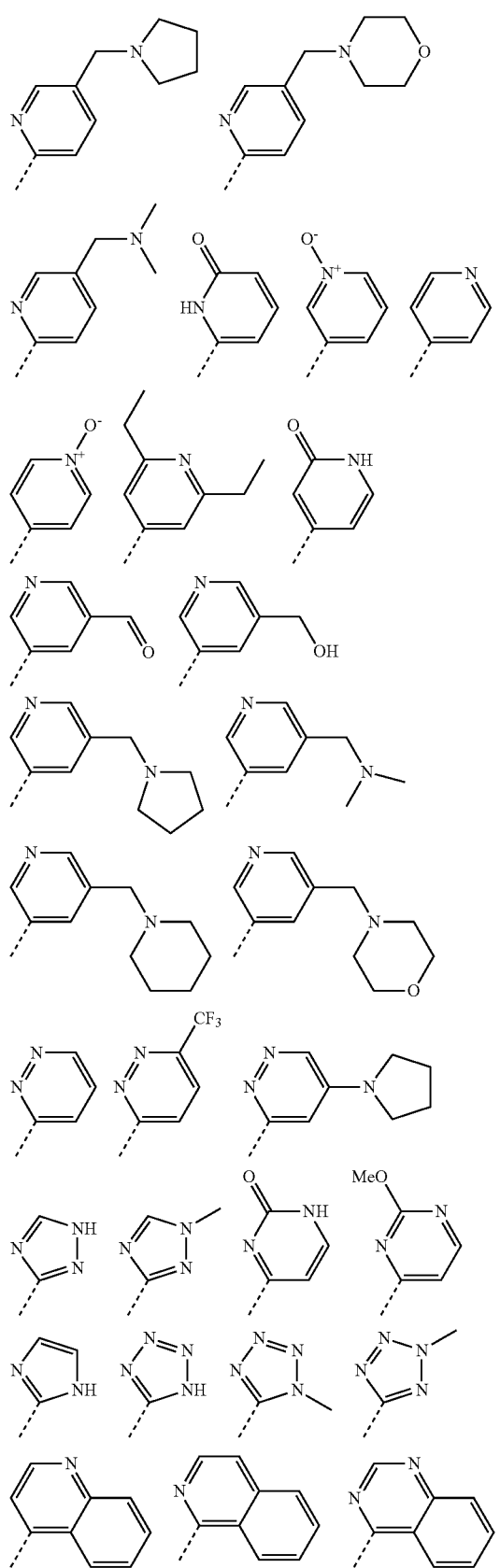
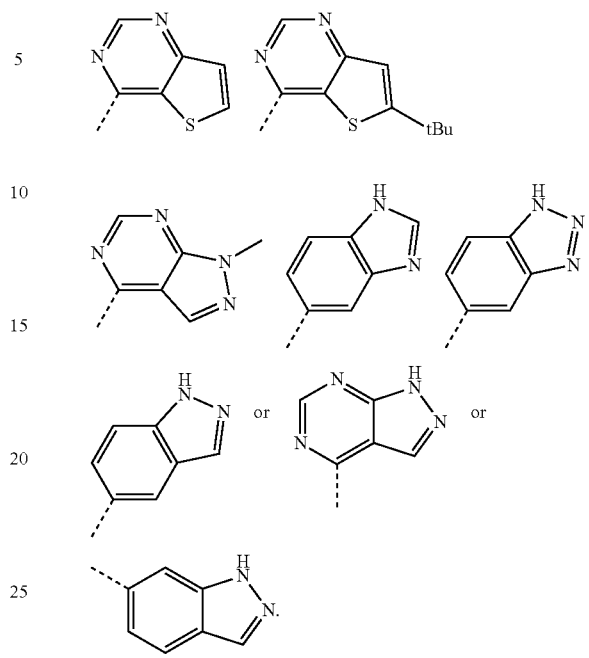
Saturated Heterocycle Variants
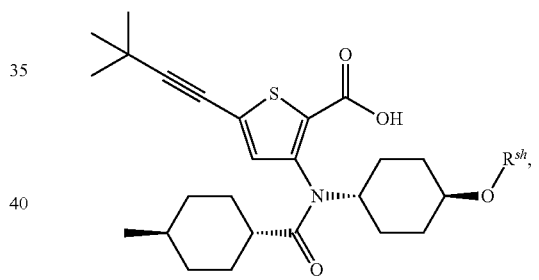
where R$^{sh}$ is
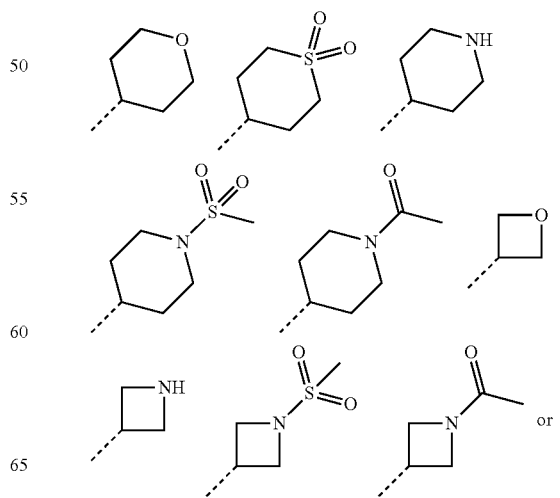

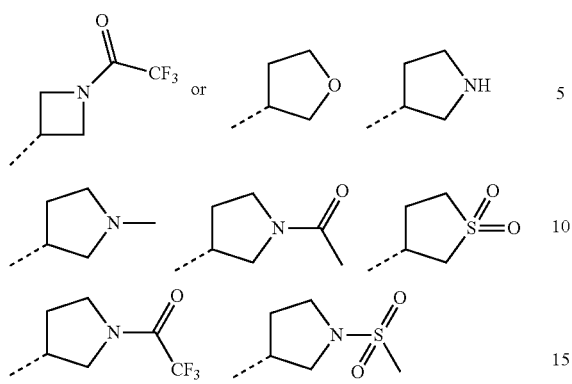
Cyclic and Acyclic R³ Variants
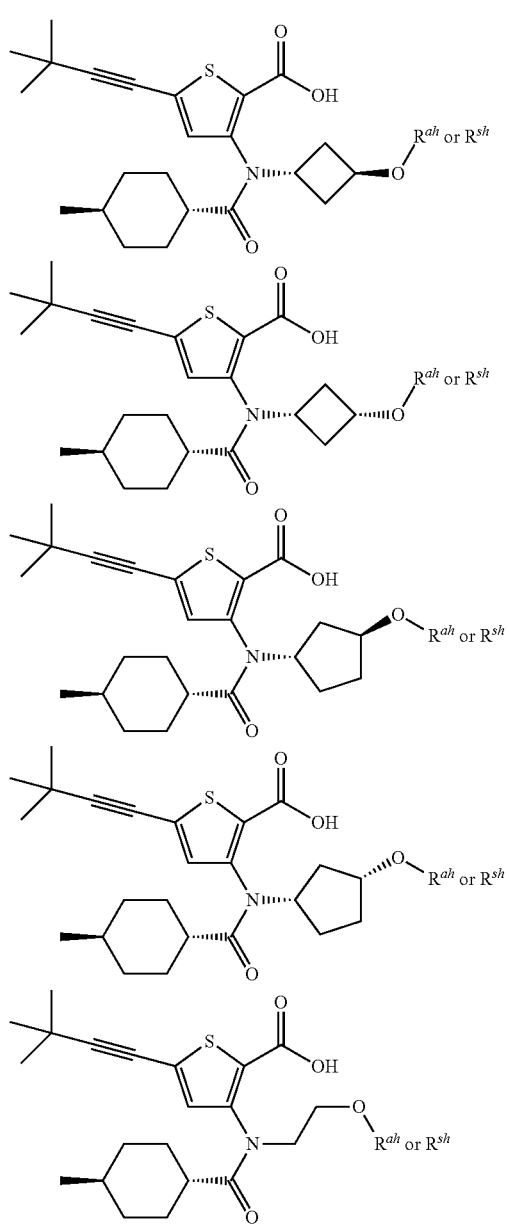
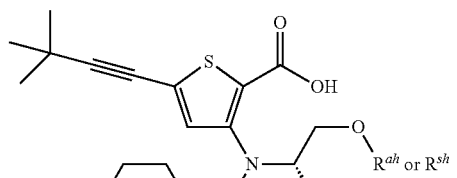
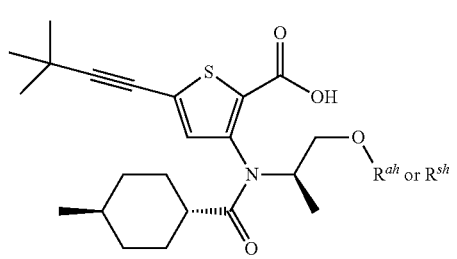
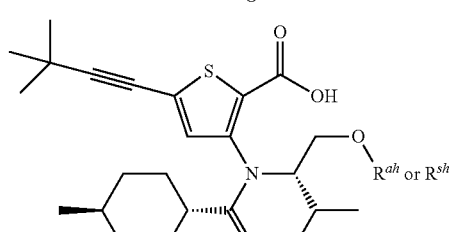
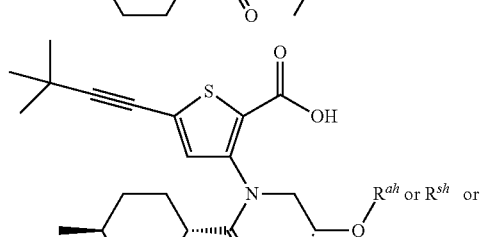
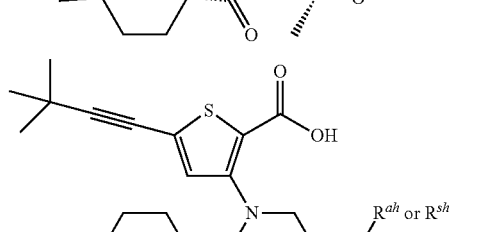
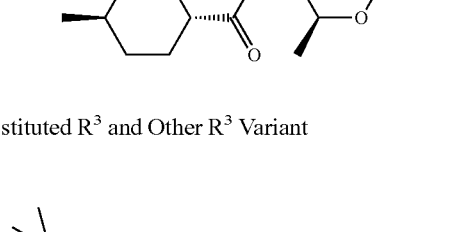
Substituted R³ and Other R³ Variant
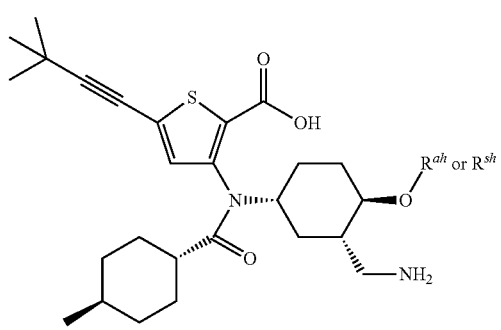

237
-continued
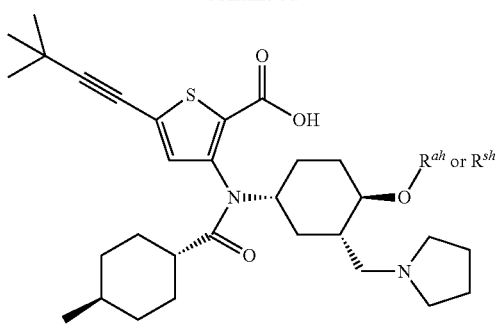
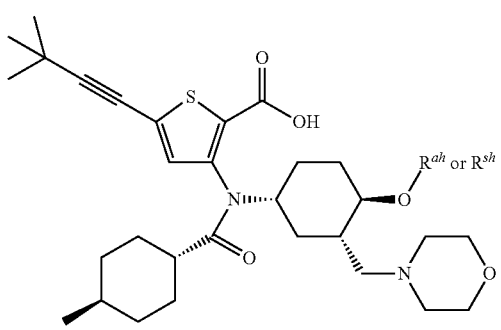
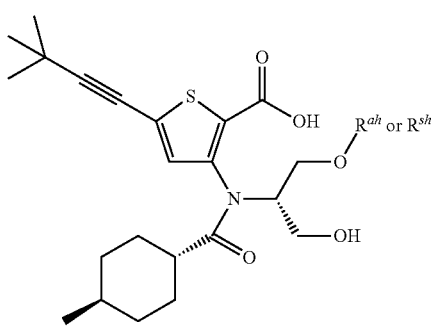
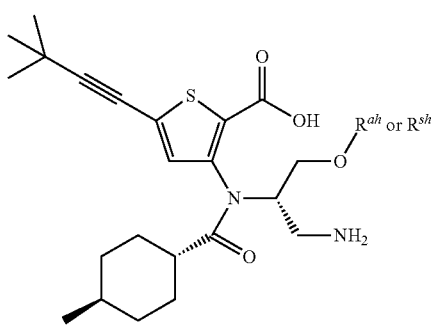
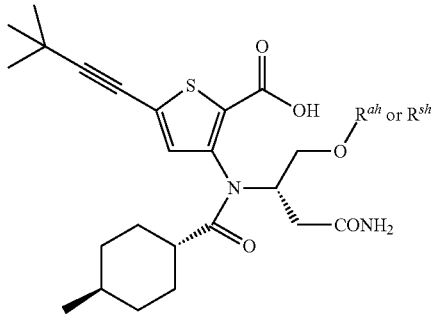
238
-continued
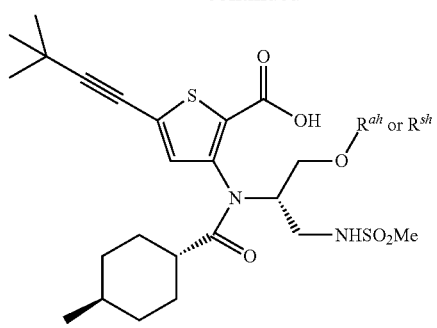
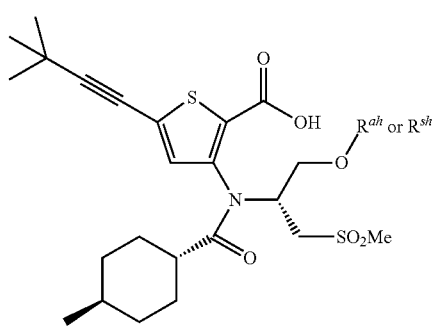
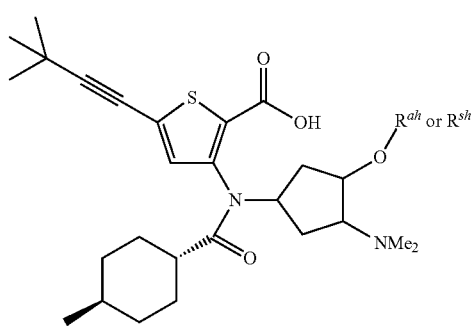
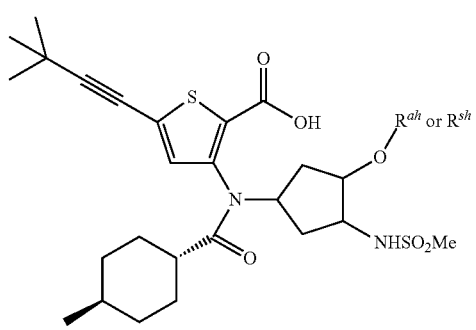
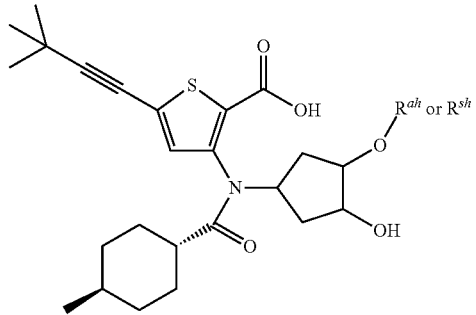

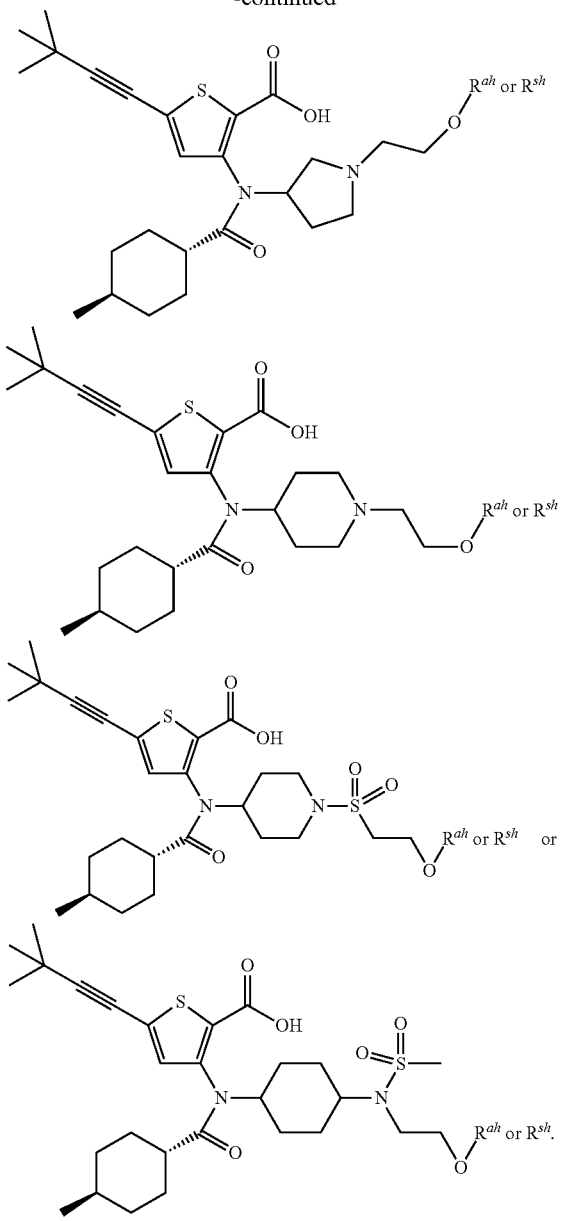

BIOLOGICAL EXAMPLES

Antiviral Activity

Another aspect of the invention relates to methods of inhibiting viral infections, comprising the step of treating a sample or subject suspected of needing such inhibition with a composition of the invention.

Within the context of the invention samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and man made materials such as cell cultures.

If desired, the anti-virus activity of a compound of the invention after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

The antiviral activity of a compound of the invention can be measured using standard screening protocols that are known. For example, the antiviral activity of a compound can be measured using the following general protocols.

Cell-Based Flavivirus Immunodetection Assay

BHK21 or A549 cells are trypsinized, counted and diluted to $2\times10^5$ cells/mL in Hams F-12 media (A549 cells) or RPMI-1640 media (BHK21 cells) supplemented with 2% fetal bovine serum (FBS) and 1% penicillin/streptomycin. $2\times10^4$ cells are dispensed in a clear 96-well tissue culture plates per well and placed at 37° C., 5% $CO_2$ overnight. On the next day, the cells are infected with viruses at multiplicity of infection (MOI) of 0.3 in the presence of varied concentrations of test compounds for 1 hour at 37° C. and 5% $CO_2$ for another 48 hours. The cells are washed once with PBS and fixed with cold methanol for 10 min. After washing twice with PBS, the fixed cells are blocked with PBS containing 1% FBS and 0.05% Tween-20 for 1 hour at room temperature. The primary antibody solution (4G2) is then added at a concentration of 1:20 to 1:100 in PBS containing 1% FBS and 0.05% Tween-20 for 3 hours. The cells are then washed three times with PBS followed by one hour incubation with horseradish peroxidase (HRP)-conjugated anti-mouse IgG (Sigma, 1:2000 dilution). After washing three times with PBS, 50 microliters of 3,3',5,5'-tetramethylbenzidine (TMB) substrate solution (Sigma) is added to each well for two minutes. The reaction is stopped by addition of 0.5 M sulfuric acid. The plates are read at 450 nm absorbance for viral load quantification. After measurement, the cells are washed three times with PBS followed by incubation with propidium iodide for 5 min. The plate is read in a Tecan Safire™ reader (excitation 537 nm, emission 617 nm) for cell number quantification. Dose response curves are plotted from the mean absorbance versus the log of the concentration of test compounds. The $EC_{50}$ is calculated by non-linear regression analysis. A positive control such as N-nonyl-deoxynojirimycin may be used.

Cell-Based Flavivirus Cytopathic Effect Assay

For testing against West Nile virus or Japanese encephalitis virus, BHK21 cells are trypsinized and diluted to a concentration of $4\times10^5$ cells/mL in RPMI-1640 media supplemented with 2% FBS and 1% penicillin/streptomycin. For testing against dengue virus, Huh7 cells are trypsinized and diluted to a concentration of $4\times10^5$ cells/mL in DMEM media supplemented with 5% FBS and 1% penicillin/streptomycin. A 50 microliter of cell suspension ($2\times10^4$ cells) is dispensed per well in a 96-well optical bottom PIT polymer-based plates (Nunc). Cells are grown overnight in culture medium at 37° C., 5% $CO_2$, and then infected with West Nile virus (e.g. B956 strain) or Japanese encephalitis virus (e.g. Nakayama strain) at MOI=0.3, or with dengue virus (e.g. DEN-2 NGC strain) at MOI=1, in the presence of different concentrations of test compounds. The plates containing the virus and the compounds are further incubated at 37° C., 5% $CO_2$ for 72 hours. At the end of incubation, 100 microliters of Celliter-Glo™ reagent is added into each well. Contents are mixed for 2 minutes on an orbital shaker to induce cell lysis. The plates are incubated at room temperature for 10 minutes to stabilize luminescent signal. Luminescence reading is recorded using a plate reader. A positive control such as N-nonyl-deoxynojirimycin may be used.

Antiviral Activity in a Mouse Model of Dengue Infection.

Compounds are tested in vivo in a mouse model of dengue virus infection (Schul et al., J. Infectious Dis. 2007; 195:665-74). Six to ten week old AG129 mice (B&K Universal Ltd, HII, UK) are housed in individually ventilated cages. Mice are injected intraperitoneally with 0.4 mL TSV01 dengue virus 2 suspension. Blood samples are taken by retro orbital puncture under isoflurane anaesthesia. Blood samples are collected in tubes containing sodium citrate to a final concentration of 0.4%, and immediately centrifuged for 3 minutes at 6000 g to obtain plasma. Plasma (20 microliters) is diluted in 780 microliters RPMI-1640 medium and snap frozen in liquid nitrogen for plaque assay analysis. The remaining plasma is reserved for cytokine and NS1 protein level determination. Mice develop dengue viremia rising over several days, peaking on day 3 post-infection.

For testing of antiviral activity, a compound of the invention is dissolved in vehicle fluid, e.g. 10% ethanol, 30% PEG 300 and 60% D5W (5% dextrose in water; or 6N HCl (1.5 eq): 1N NaOH (pH adjusted to 3.5): 100 mM citrate buffer pH 3.5 (0.9% v/v:2.5% v/v:96.6% v/v). Thirty six 6-10 week old AG129 mice are divided into six groups of six mice each. All mice are infected with dengue virus as described above (day 0). Group 1 is dosed by oral gavage of 200 mL/mouse with 0.2 mg/kg of a compound of the invention twice a day (once early in the morning and once late in the afternoon) for three consecutive days starting on day 0 (first dose just before dengue infection). Groups 2, 3 and 4 are dosed the same way with 1 mg/kg, 5 mg/kg and 25 mg/kg of the compound, respectively. A positive control may be used, such as (2R,3R,4R,5R)-2-(2-amino-6-hydroxy-purin-9-yl)-5-hydroxymethyl-3-methyl-tetrahydro-furan-3,4-diol, dosed by oral gavage of 200 microliters/mouse the same way as the previous groups. A further group is treated with only vehicle fluid.

On day 3 post-infection approximately 100 microliter blood samples (anti-coagulated with sodium citrate) are taken from the mice by retro-orbital puncture under isoflurane anaesthesia. Plasma is obtained from each blood sample by centrifugation and snap frozen in liquid nitrogen for plague assay analysis. The collected plasma samples are analyzed by plague assay as described in Schul et al. Cytokines are also analysed as as described by Schul. NS1 protein levels are analysed using a Platelia™ kit (BioRad Laboratories). An anti-viral effect is indicated by a reduction in cytokine levels and/or NS1 protein levels.

Typically, reductions in viremia of about 5-100 fold, more typically 10-60 fold, most typically 20-30 fold, are obtained with 5-50 mg/kg bid dosages of the compounds of the invention.

HCV Assay Protocol

The anti-HCV activity of the compounds of this invention was tested in a human hepatoma Huh-7 cell line harboring a HCV replicon. The assay comprised the following steps:

Step 1: Compound Preparation and Serial Dilution.

Serial dilution was performed in 100% DMSO in a 384-well plate. A solution containing a compound at 225-fold concentration of the starting final serial dilution concentration was prepared in 100% DMSO and 15 µL added to the pre-specified wells in column 3 or 13 of a polypropylene 384-well plate. The rest of the 384-well plate was filled with 10 µL 100% DMSO except for columns 23 and 24, where 10 µL of 500 µM a HCV protease inhibitor (ITMN-191) in 100% DMSO was added. The HCV protease inhibitor was used a control of 100% inhibition of HCV replication. The plate was then placed on a Biomek FX Workstation to start the serial dilution. The serial dilution was performed for ten cycles of 3-fold dilution from column 3 to 12 or from column 13 to 22.

Step 2: Cell Culture Plate Preparation and Compound Addition

To each well of a black polypropylene 384-well plate, 90 µL of cell media containing 1600 suspended Huh-7 HCV replicon cells was added with a Biotek uFlow Workstation. A volume of 0.4 µL of the compound solution was transferred from the serial dilution plate to the cell culture plate on a Biomek FX Workstation. The DMSO concentration in the final assay condition was 0.44%. The plates were incubated for 3 days at 37° C. with 5% $CO_2$ and 85% humidity.

Step 3: Detection of Cytotoxicity and Inhibition of Viral Replication a) Assessment of cytotoxicity: The media in the 384-well cell culture plate was aspirated with a Biotek EL405 plate-washer. A volume of 50 µL of a solution containing 400 nM Calcein AM in 100% PBS was added to each well of the plate with a Biotek uFlow Workstation. The plate was incubated for 30 minutes at room temperature before the fluorescence signal (emission 490 nm, exitation 520 nm) was measured with a Perkin Elmer Envision Plate Reader.

b) Assessment of inhibition of viral replication: The calcein-PBS solution in the 384-well cell culture plate was aspirated with a Biotek EL405 plate-washer. A volume of 20 µL of Dual-Glo luciferase buffer (Promega, Dual-Glo Luciferase Assay Reagent, cat. #E298B) was added to each well of the plate with a Biotek uFlow Workstation. The plate was incubated for 10 minutes at room temperature. A volume of 20 µL of a solution containing 1:100 mixture of Dual-Glo Stop & Glo substrate (Promega, Dual-Glo Luciferase Assay Reagent, cat. #E313B) and Dual-Glo Stop & Glo buffer (Promega, Dual-Glo Luciferase Assay Reagent, cat. #E314B) was then added to each well of the plate with a Biotek uFlow Workstation. The plate was incubated at room temperature for 10 minutes before the luminescence signal was measured with a Perkin Elmer Envision Plate Reader.

Step 4: Calculation

The percent cytotoxicity was determined by calcein AM conversion to fluorescent product. The average fluorescent signal from the DMSO control wells was defined as 100% nontoxic. The individual fluorescent signal from testing compound treated well was divided by the average signal from DMSO control wells and then multiplied by 100% to get the percent viability. The percent anti-HCV replication activity was determined by the luminescence signal from the testing well compared to DMSO control wells. The background signal was determined by the average luminescence signal from the HCV protease inhibitor treated wells and was subtracted from the signal from the testing wells as well as the DMSO control wells. Following 3-fold serial dilutions, the $EC_{50}$ and $CC_{50}$ values were calculated by fitting % inhibition at each concentration to the following equation:

$$\% \text{ inhibition} = 100\%/[EC_{50}/[I])^b + 1]$$

Where b is Hill's coefficient. See, for reference, Hill, A. V., *The Possible Effects of the Aggregation of the Molecules of Hæmoglobin on its Dissociation Curves*, J. Physiol. 40: iv-vii. (1910).

% inhibition values at a specific concentration, for example 2 µM, can also be derived from the formula above.

When tested, certain compounds of this invention were found to inhibit viral replication as listed in Table 1:

TABLE 1

| Compound | % inhibition at 2μM |
| --- | --- |
| 1 | 99.8 |
| 2 | 99.6 |
| 3 | 100 |
| 4 | 99.9 |
| 5 | 99.8 |
| 6 | 99.9 |
| 7 | 99.8 |
| 8 | 96.7 |
| 9 | 99.3 |
| 10 | 56.2 |
| 11 | 99.9 |
| 12 | 99.7 |
| 13 | 99.3 |
| 14 | 100.0 |
| 15 | 99.6 |
| 16 | 75.1 |
| 17 | 67.6 |
| 20 | 99.8 |
| 21 | 98.8 |
| 22 | 96.2 |
| 23 | 99.5 |
| 24 | 99.9 |
| 25 | 99.3 |
| 26 | 99.8 |
| 27 | 100 |
| 28 | 99.7 |
| 29 | 100 |
| 30 | 70.7 |
| 58 | 99.9 |
| 59 | 99.9 |
| 60 | 97.5 |
| 61 | 99.9 |
| 62 | 100 |
| 63 | 100 |
| 84 | 99.9 |
| 85 | 99.6 |
| 86 | 100 |
| 87 | 99.5 |
| 88 | 98.5 |
| 89 | 99.4 |
| 90 | 100 |
| 91 | 99.8 |
| 92 | 100 |
| 93 | 98.1 |
| 94 | 99.9 |
| 95 | 99.9 |
| 96 | 99.9 |
| 97 | 99.9 |
| 98 | 100 |
| 99 | 97.7 |
| 100 | 99.9 |
| 101 | 100 |
| 102 | 99.9 |
| 103 | 98.3 |
| 104 | 98.7 |
| 105 | 99.9 |
| 106 | 99.9 |
| 107 | 98.9 |
| 108 | 99.3 |
| 109 | 99.9 |
| 110 | 100 |
| 111 | 99.8 |
| 138 | 99.7 |
| 139 | 96.4 |
| 143 | 100 |
| 144 | 95.4 |
| 145 | 99.5 |
| 146 | 99.2 |
| 147 | 99.9 |
| 148 | 96.6 |
| 149 | 99.0 |
| 150 | 99.6 |
| 151 | 99.4 |
| 152 | 73.7 |
| 153 | 100 |
| 154 | 99.7 |
| 155 | 100 |
| 156 | 100 |
| 157 | 99.9 |
| 158 | 99.9 |
| 159 | 99.8 |
| 160 | 99.9 |
| 161 | 99.9 |
| 162 | 99.9 |
| 163 | 100 |
| 166 | 99.9 |
| 167 | 99.9 |
| 168 | 99.9 |
| 169 | 100 |
| 170 | 99.9 |
| 171 | 99.7 |
| 173 | 100 |
| 174 | 100 |
| 175 | 100 |
| 176 | 99.8 |
| 177 | 99.6 |
| 178 | 100 |
| 179 | 99.5 |
| 180 | 99.6 |
| 181 | 98.3 |
| 182 | 99.0 |
| 183 | 100 |
| 184 | 97.8 |
| 185 | 84.7 |
| 187 | 100 |
| 188 | 100 |
| 189 | 99.9 |
| 190 | 100 |
| 191 | 100 |
| 192 | 100 |
| 193 | 100 |
| 194 | 99.9 |
| 195 | 99.7 |
| 196 | 100 |
| 197 | 99.9 |
| 198 | 99.9 |
| 199 | 99.9 |
| 200 | 100 |
| 201 | 100 |
| 202 | 96.4 |
| 203 | 99.8 |
| 204 | 99.1 |
| 205 | 99.9 |
| 206 | 100 |
| 207 | 99.8 |
| 208 | 63.8 |
| 209 | 100 |
| 210 | 100 |
| 211 | 99.7 |
| 212 | 99.3 |
| 213 | 99.9 |
| 214 | 69.9 |
| 215 | 100 |
| 216 | 100 |
| 219 | 100 |
| 220 | 100 |
| 221 | 100 |
| 222 | 97.7 |
| 223 | 100 |
| 224 | 99.9 |
| 225 | 98.4 |
| 226 | 99.9 |
| 227 | 100 |
| 228 | 99.9 |
| 229 | 82.6 |
| 230 | 98.4 |
| 231 | 99.9 |
| 301 | 99.82 |
| 302 | 99.99 |
| 303 | 99.87 |
| 304 | 99.99 |
| 305 | 99.99 |
| 306 | 99.99 |
| 307 | 99.99 |
| 308 | 99.99 |
| 309 | 99.99 |

TABLE 1-continued

| Compound | % inhibition at 2μM |
|---|---|
| 310 | 99.99 |
| 311 | 95.25 |
| 314 | 99.89 |
| 317 | 99.98 |
| 318 | 99.66 |
| 321 | 99.91 |
| 322 | 99.96 |
| 325 | 99.99 |
| 326 | 99.93 |
| 331 | 99.95 |
| 332 | 99.92 |
| 333 | 99.97 |
| 334 | 99.87 |
| 335 | 99.93 |
| 336 | 100.0 |
| 337 | 99.99 |
| 338 | 99.94 |
| 339 | 99.93 |
| 340 | 99.97 |
| 341 | 99.97 |
| 342 | 99.96 |
| 343 | 99.96 |
| 344 | 99.85 |
| 345 | 99.95 |
| 346 | 99.54 |
| 347 | 99.97 |

Non-limiting preferred compounds of Table 1 include Compounds 3, 14, 24, 27, 29, 85, 96, 101, 104, 110, 143, 147, 155, 156, 158, 162, 169, 178, 179, 180, 183, 185, 187, 190, 191, 192, 193, 196, 197, 198, 199, 200, 209, 210, 220, 221, and 224.

The specific pharmacological and biochemical responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:
1. A compound of Formula I:

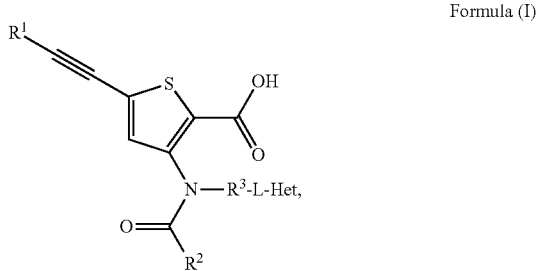

Formula (I)

or a pharmaceutically acceptable salt or ester thereof, wherein:
R$^1$ is selected from the group consisting of optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, optionally substituted 3-18 membered heterocyclylalkyl and optionally substituted C$_{6-18}$ arylalkyl, wherein, each substituted R$^1$ is substituted with one or more Q$^1$;

each Q$^1$ is independently selected from the group consisting of halogen, oxo, oxide, —NO$_2$, —N(=O), —SR$^{10}$, —S(O)R$^{10}$, —S(O)$_2$R$^{10}$, —S(O)$_2$NR$^{10}$R$^{11}$, —NR$^{10}$C(O)R$^{11}$, —NR$^{10}$C(O)NR$^{11}$R$^{12}$, —NR$^{10}$S(O)R$^{11}$, —NR$^{10}$S(O)$_2$R$^{11}$, —OP(O)R$^{11}$R$^{12}$, —P(O)R$^{11}$R$^{12}$, —P(O)OR$^{11}$R$^{12}$, —P(O)(OR$^{11}$)OR$^{12}$, —C(O)NR$^{11}$R$^{12}$, optionally substituted C$_{1-6}$ alkyl, optionally substituted C$_{2-6}$ alkenyl, optionally substituted C$_{2-6}$ alkynyl, optionally substituted C$_{3-6}$ cycloalkyl, optionally substituted C$_{6-12}$ arylalkyl, optionally substituted C$_{6-12}$ aryl, optionally substituted 3-14 membered heteroaryl, optionally substituted C$_{1-6}$ alkyloxy, optionally substituted C$_{2-6}$ alkenyloxy, optionally substituted C$_{2-6}$ alkynyloxy, optionally substituted C$_{3-6}$ cycloalkyloxy, optionally substituted C$_{6-12}$ aryloxy, optionally substituted 3-14 membered heteroaryloxy, optionally substituted 4-12 membered heterocyclyloxy, optionally substituted —C(O)C$_{1-6}$ alkyl, optionally substituted —C(O)C$_{2-6}$ alkenyl, optionally substituted —C(O)C$_{2-6}$ alkynyl, optionally substituted —C(O)C$_{3-6}$ cycloalkyl, optionally substituted —C(O)C$_{6-12}$ aryl, optionally substituted —C(O)-3-14 membered heteroaryl, optionally substituted —C(O)C$_{6-12}$ arylalkyl, optionally substituted -3-10 membered heterocyclyl, —OH, —NR$^{11}$R$^{12}$, —C(O)OR$^{10}$, —CN, —N$_3$, —C(=NR$^{13}$)NR$^{11}$R$^{12}$, —C(=NR$^{13}$)OR$^{10}$, —NR$^{10}$C(=NR$^{13}$)NR$^{11}$R$^{12}$, —NR$^{11}$C(O)OR$^{10}$, and —OC(O)NR$^{11}$R$^{12}$;

each R$^{10}$, R$^{11}$, and R$^{12}$, independently, is selected from the group consisting of H, optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, and optionally substituted C$_{6-18}$ arylalkyl;

or R$^{11}$ and R$^{12}$ taken together with the atoms to which they are attached form a 3 to 10 membered heterocyclyl;

each R$^{13}$, independently, is selected from the group consisting of H, optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, optionally substituted C$_{6-18}$ arylalkyl, —CN, —C(O)R$^{14}$, —CHO and —S(O)$_2$R$^{14}$;

each R$^{14}$, independently, is optionally substituted C$_{1-12}$ alkyl;

wherein, each substituted Q$^1$, substituted R$^{10}$, substituted R$^{11}$, substituted R$^{12}$, substituted R$^{13}$, or substituted R$^{14}$ is independently substituted with one or more Q$^6$;

R$^2$ is selected from the group consisting of optionally substituted C$_{1-12}$ alkyl, optionally substituted C$_{2-12}$ alkenyl, optionally substituted C$_{2-12}$ alkynyl, optionally substituted C$_{3-12}$ cycloalkyl, optionally substituted C$_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

wherein, each substituted $R^2$ is substituted with one or more $Q^2$;

each $Q^2$, independently, is selected from the group consisting of halogen, oxo, oxide, $-NO_2$, $-N(=O)$, $-SR^{20}$, $-S(O)R^{20}$, $-S(O)_2R^{20}$, $-S(O)_2NR^{20}R^{21}$, $-NR^{20}C(O)R^{21}$, $-NR^{20}C(O)NR^{21}R^{22}$, $-NR^{20}S(O)R^{21}$, $-NR^{20}S(O)_2R^{21}$, $-OP(O)R^{21}R^{22}$, $-P(O)R^{21}R^{22}$, $-P(O)OR^{21}R^{22}$, $-P(O)(OR^{21})OR^{22}$, $-C(O)NR^{21}R^{22}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted $-C(O)C_{1-6}$ alkyl, optionally substituted $-C(O)C_{2-6}$ alkenyl, optionally substituted $-C(O)C_{2-6}$ alkynyl, optionally substituted $-C(O)C_{3-6}$ cycloalkyl, optionally substituted $-C(O)C_{6-12}$ aryl, optionally substituted $-C(O)$-3-14 membered heteroaryl, optionally substituted $-C(O)C_{6-12}$ arylalkyl, optionally substituted 3-10 membered heterocyclyl, $-OH$, $-NR^{21}R^{22}$, $-C(O)OR^{20}$, $-CN$, $-N_3$, $-C(=NR^{23})NR^{21}R^{22}$, $-C(=NR^{23})OR^{20}$, $-NR^{20}C(=NR^{23})NR^{21}R^{22}$, $-NR^{21}C(O)OR^{20}$, and $-OC(O)NR^{21}R^{22}$;

each $R^{20}$, $R^{21}$, and $R^{22}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

or $R^{21}$ and $R^{22}$ taken together with the atoms to which they are attached form a 3 to 10 membered heterocyclyl;

each $R^{23}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, $-CN$, $-C(O)R^{24}$, $-CHO$ and $-S(O)_2R^{24}$;

each $R^{24}$ individually is optionally substituted $C_{1-12}$ alkyl;

wherein, each substituted $Q^2$, substituted $R^{20}$, substituted $R^{21}$, substituted $R^{22}$, substituted $R^{23}$, or substituted $R^{24}$ is independently substituted with one or more $Q^6$;

$R^3$ is selected from the group consisting of optionally substituted $C_{1-12}$ alkylene, $C_{2-12}$ alkenylene, substituted $C_{2-12}$ alkenylene, $C_{2-12}$ alkynylene, substituted $C_{2-12}$ alkynylene, $C_{3-12}$ cycloalkylene, substituted $C_{3-12}$ cycloalkylene, optionally substituted $C_{6-14}$ arylene, optionally substituted 3-14 membered heteroarylene, optionally substituted 3-12 membered heterocyclylene, optionally substituted 3-18 membered heteroarylalkylene, and optionally substituted $C_{6-18}$ arylalkylene;

wherein each substituted $R^3$ is substituted with one or more $Q^3$;

each $Q^3$, independently, is selected from the group consisting of halogen, oxo, oxide, $-NO_2$, $-N(=O)$, $-SR^{30}$, $-S(O)R^{30}$, $-S(O)_2R^{30}$, $-S(O)_2NR^{30}R^{31}$, $-NR^{30}C(O)R^{31}$, $-NR^{30}C(O)NR^{31}R^{32}$, $-NR^{30}S(O)R^{31}$, $-NR^{30}S(O)_2R^{31}$, $-OP(O)R^{31}R^{32}$, $-P(O)R^{31}R^{32}$, $-P(O)OR^{31}R^{32}$, $-P(O)(OR^{31})OR^{32}$, $-C(O)NR^{31}R^{32}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted $-C(O)C_{1-6}$ alkyl, optionally substituted $-C(O)C_{2-6}$ alkenyl, optionally substituted $-C(O)C_{2-6}$ alkynyl, optionally substituted $-C(O)C_{3-6}$ cycloalkyl, optionally substituted $-C(O)C_{6-12}$ aryl, optionally substituted $-C(O)$-3-14 membered heteroaryl, optionally substituted $-C(O)C_{6-12}$ arylalkyl, optionally substituted 3-10 membered heterocyclyl, $-OH$, $-NR^{31}R^{32}$, $-C(O)OR^{30}$, $-CN$, $-N_3$, $-C(=NR^{33})NR^{31}R^{32}$, $-C(=NR^{33})OR^{30}$, $-NR^{30}C(=NR^{33})NR^{31}R^{32}$, $-NR^{31}C(O)OR^{30}$, and $-OC(O)NR^{31}R^{32}$;

each $R^{30}$, $R^{31}$, and $R^{32}$, independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

or $R^{31}$ and $R^{32}$ taken together with the atoms to which they are attached form a 3 to 10 membered heterocyclyl;

each $R^{33}$ independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, $-CN$, $-C(O)R^{34}$, $-CHO$ and $-S(O)_2R^{34}$;

each $R^{34}$ individually is optionally substituted $C_{1-12}$ alkyl;

wherein, each substituted $Q^3$, substituted $R^{30}$, substituted $R^{31}$, substituted $R^{32}$, substituted $R^{33}$, or substituted $R^{34}$ is independently substituted with one or more $Q^6$;

L is selected from the group consisting of $-O-$, $-S-$, $-S(O)-$, and $-S(O)_2-$;

Het is an optionally substituted 3-12 membered heterocyclyl or optionally substituted 3-14 membered heteroaryl;

wherein, each substituted Het is substituted with one or more $Q^4$;

each $Q^4$, independently, is selected from the group consisting of halogen, oxo, oxide, $-NO_2$, $-SR^{40}$, $-S(O)R^{40}$, $-S(O)_2R^{40}$, $-S(O)_2NR^{40}R^{41}$, $-NR^{40}C(O)R^{41}$, $-NR^{40}C(O)NR^{41}R^{42}$, $-NR^{40}S(O)R^{41}$, $-NR^{40}S(O)_2R^{41}$, $-OP(O)R^{41}R^{42}$, $-P(O)OR^{41}R^{42}$, $-P(O)(OR^{41})OR^{42}$, $-C(O)NR^{41}R^{42}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)$C_{1-6}$ alkyl, optionally substituted —C(O)$C_{2-6}$ alkenyl, optionally substituted —C(O)$C_{2-6}$ alkynyl, optionally substituted —C(O)$C_{3-6}$ cycloalkyl, optionally substituted —C(O)$C_{6-12}$ aryl, optionally substituted —C(O)-3-14 membered heteroaryl, optionally substituted —C(O)$C_{6-12}$ arylalkyl, optionally substituted 3-10 membered heterocyclyl, —OH, —NR$^{41}$R$^{42}$, —C(O)OR$^{40}$, —CN, —N$_3$, —C(=NR$^{43}$)NR$^{41}$R$^{42}$, —C(=NR$^{43}$)OR$^{40}$, —NR$^{40}$C(=NR$^{43}$)NR$^{41}$R$^{42}$, —NR$^{41}$C(O)OR$^{40}$, and —OC(O)NR$^{41}$R$^{42}$;

each R$^{40}$, R$^{41}$, and R$^{42}$, independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

or R$^{41}$ and R$^{42}$ taken together with the atoms to which they are attached form a 3 to 10 membered heterocyclyl;

each R$^{43}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, —CN, —C(O)R$^{44}$, —CHO and —S(O)$_2$R$^{44}$;

each R$^{44}$ individually is optionally substituted $C_{1-12}$ alkyl;

wherein, each substituted Q$^4$, substituted R$^{40}$, substituted R$^{41}$, substituted R$^{42}$, substituted R$^{43}$, or substituted R$^{44}$ is independently substituted with one or more Q$^5$;

each Q$^5$, individually, is selected from the group consisting of halogen, oxo, oxide, —NO$_2$, —N(=O), —SR$^{50}$, —S(O)R$^{50}$, —S(O)$_2$R$^{50}$, —S(O)$_2$NR$^{50}$R$^{51}$, —NR$^{50}$C(O)R$^{51}$, —NR$^{50}$C(O)NR$^{51}$R$^{52}$, —NR$^{50}$S(O)R$^{51}$, —NR$^{50}$S(O)$_2$R$^{51}$, —OP(O)R$^{51}$R$^{52}$, —P(O)R$^{51}$R$^{52}$, —P(O)OR$^{51}$R$^{52}$, —P(O)(OR$^{51}$)OR$^{52}$, —C(O)NR$^{51}$R$^{52}$, optionally substituted $C_{1-6}$ alkyl, optionally substituted $C_{2-6}$ alkenyl, optionally substituted $C_{2-6}$ alkynyl, optionally substituted $C_{3-6}$ cycloalkyl, optionally substituted $C_{6-12}$ arylalkyl, optionally substituted $C_{6-12}$ aryl, optionally substituted 3-14 membered heteroaryl, optionally substituted $C_{1-6}$ alkyloxy, optionally substituted $C_{2-6}$ alkenyloxy, optionally substituted $C_{2-6}$ alkynyloxy, optionally substituted $C_{3-6}$ cycloalkyloxy, optionally substituted $C_{6-12}$ aryloxy, optionally substituted 3-14 membered heteroaryloxy, optionally substituted 4-12 membered heterocyclyloxy, optionally substituted —C(O)$C_{1-6}$ alkyl, optionally substituted —C(O)$C_{2-6}$ alkenyl, optionally substituted —C(O)$C_{2-6}$ alkynyl, optionally substituted —C(O)$C_{3-6}$ cycloalkyl, optionally substituted —C(O)$C_{6-12}$ aryl, optionally substituted —C(O)-3-14 membered heteroaryl, optionally substituted —C(O)$C_{6-12}$ arylalkyl, optionally substituted 3-10 membered heterocyclyl, —OH, —NR$^{51}$R$^{52}$, —C(O)OR$^{50}$, —CN, —N$_3$, —C(=NR$^{53}$)NR$^{51}$R$^{52}$, —C(=NR$^{53}$)OR$^{50}$, —NR$^{50}$C(=NR$^{53}$)NR$^{51}$R$^{52}$, —NR$^{51}$C(O)OR$^{50}$, and —OC(O)NR$^{51}$R$^{52}$;

each R$^{50}$, R$^{51}$, and R$^{52}$, independently is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, and optionally substituted $C_{6-18}$ arylalkyl;

or R$^{51}$ and R$^{52}$ taken together with the atoms to which they are attached form a 3 to 10 membered heterocyclyl;

each R$^{53}$, independently, is selected from the group consisting of H, optionally substituted $C_{1-12}$ alkyl, optionally substituted $C_{2-12}$ alkenyl, optionally substituted $C_{2-12}$ alkynyl, optionally substituted $C_{3-12}$ cycloalkyl, optionally substituted $C_{6-14}$ aryl, optionally substituted 3-14 membered heteroaryl, optionally substituted 3-12 membered heterocyclyl, optionally substituted 3-18 membered heteroarylalkyl, optionally substituted $C_{6-18}$ arylalkyl, —CN, —C(O)R$^{54}$, —CHO and —S(O)$_2$R$^{54}$;

each R$^{54}$, independently, is optionally substituted $C_{1-12}$ alkyl;

wherein, each substituted Q$^5$, substituted R$^{50}$, substituted R$^{51}$, substituted R$^{52}$, substituted R$^{53}$, or substituted R$^{54}$ is independently substituted with one or more Q$^6$;

each Q$^6$, independently, is selected from the group consisting of halogen, oxo, oxide, —NO$_2$, —N(=O), —SR$^{60}$, —S(O)R$^{60}$, —S(O)$_2$R$^{60}$, —S(O)$_2$NR$^{60}$R$^{61}$, —NR$^{60}$C(O)R$^{61}$, —NR$^{60}$C(O)NR$^{61}$R$^{62}$, —NR$^{60}$S(O)R$^{61}$, —NR$^{60}$S(O)$_2$R$^{61}$, —OP(O)R$^{61}$R$^{62}$, —P(O)R$^{61}$R$^{62}$, —P(O)OR$^{61}$R$^{62}$, —P(O)(OR$^{61}$)OR$^{62}$, —C(O)NR$^{61}$R$^{62}$, $C_{1-6}$ alkyl, $C_{2-6}$ alkenyl, $C_{2-6}$ alkynyl, $C_{3-6}$ cycloalkyl, $C_{6-12}$ arylalkyl, $C_{6-12}$ aryl, 3-14 membered heteroaryl, $C_{1-6}$ alkyloxy, $C_{2-6}$ alkenyloxy, $C_{2-6}$ alkynyloxy, $C_{3-6}$ cycloalkyloxy, $C_{6-12}$ aryloxy, 3-14 membered heteroaryloxy, 4-12 membered heterocyclyloxy, —C(O)$C_{1-6}$ alkyl, —C(O)$C_{2-6}$ alkenyl, —C(O)$C_{2-6}$ alkynyl, —C(O)$C_{3-6}$ cycloalkyl, —C(O)$C_{1-6}$ haloalkyl, —C(O)$C_{6-12}$ aryl, —C(O)-3-14 membered heteroaryl, —C(O)$C_{6-12}$ arylalkyl, 3-10 membered heterocyclyl, —OH, —NR$^{61}$R$^{62}$, —C(O)OR$^{60}$, —CN, —N$_3$, —C(=NR$^{63}$)NR$^{61}$R$^{62}$, —C(=NR$^{63}$)OR$^{60}$, —NR$^{60}$C(=NR$^{63}$)NR$^{61}$R$^{62}$, —NR$^{61}$C(O)OR$^{60}$, and —OC(O)NR$^{61}$R$^{62}$;

each R$^{60}$, R$^{61}$, and R$^{62}$, independently is selected from the group consisting of H, $C_{1-12}$ alkyl, $C_{2-12}$ alkenyl, $C_{2-12}$ alkynyl, $C_{3-12}$ cycloalkyl, $C_{1-12}$ haloalkyl, $C_{6-14}$ aryl, 3-14 membered heteroaryl, 3-12 membered heterocyclyl, 3-18 membered heteroarylalkyl, and $C_{6-18}$ arylalkyl;

or R$^{61}$ and R$^{62}$ taken together with the atoms to which they are attached form a 3 to 10 membered heterocyclyl;

each R$^{63}$ independently is selected from the group consisting of H, $C_{1-12}$ alkyl, $C_{2-12}$ alkenyl, $C_{2-12}$ alkynyl, $C_{3-12}$ cycloalkyl, $C_{6-14}$ aryl, 3-14 membered heteroaryl, 3-12 membered heterocyclyl, 3-18 membered heteroarylalkyl, $C_{6-18}$ arylalkyl, —CN, —C(O)R$^{64}$, —CHO and —S(O)$_2$R$^{64}$; and each R$^{64}$ individually is $C_{1-12}$ alkyl.

2. The compound of claim 1, wherein R$^1$ is optionally substituted $C_{1-12}$ alkyl or optionally substituted $C_{3-12}$ cycloalkyl.

3. The compound of claim 2, wherein R$^1$ is optionally substituted $C_3$-$C_7$ secondary or tertiary alkyl or optionally substituted $C_3$-$C_5$ cycloalkyl.

4. The compound of claim 2, wherein R$^2$ is optionally substituted methylcyclohexyl or optionally substituted methylcyclohexenyl.

5. The compound of claim 4, wherein $R^2$ is

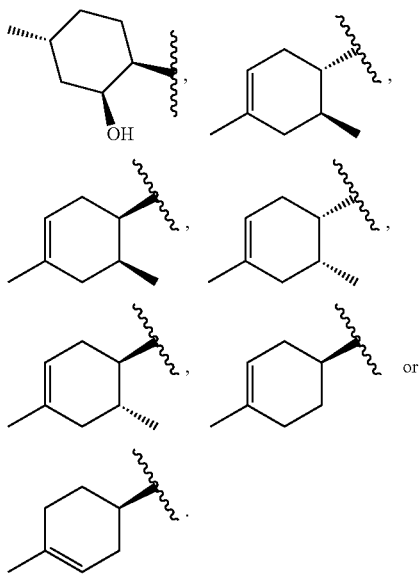

6. The compound of claim 4, wherein $R^2$ is

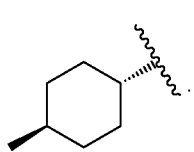 [SMILES: *[C@H]1CC[C@H](C)CC1]

7. The compound of claim 2, wherein $R^3$ is optionally substituted $C_{1-12}$ alkylene, $C_{3-12}$ cycloalkylene, substituted $C_{3-12}$ cycloalkylene, optionally substituted $C_{6-14}$ arylene or optionally substituted 3-12 membered heterocyclylene.

8. The compound of claim 2, wherein Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N.

9. The compound of claim 8, wherein Het is optionally substituted pyridinyl, optionally substituted pyridazinyl, optionally substituted tetrahydro-2H-pyranyl, optionally substituted piperidinyl, optionally substituted pyrrolidinyl, optionally substituted tetrahydrothiophenyl, optionally substituted pyrazinyl, optionally substituted 1H-tetrazolyl, optionally substituted azetidinyl, optionally substituted tetrahydrofuranyl, optionally substituted tetrahydro-2H-furo[2,3-b]furanyl, optionally substituted thiazoyl, optionally substituted 1H-imidazolyl, optionally substituted 4H-1,2,4-triazolyl, optionally substituted 1H-pyrazolyl, optionally substituted 1,3,4-thiadiazolyl, optionally substituted quinolinyl, optionally substituted [1,2,4]triazolo[4,3-a]pyridinyl, optionally substituted thiophenyl, optionally substituted 1,2,4-thiadiazolyl, optionally substituted pyrimidinyl, optionally substituted 1H-1,2,3-triazolyl, optionally substituted 1,3,4-oxadiazolyl or optionally substituted imidazo[1,2-b]pyridazinyl.

10. The compound of claim 3 represented by Formula II:

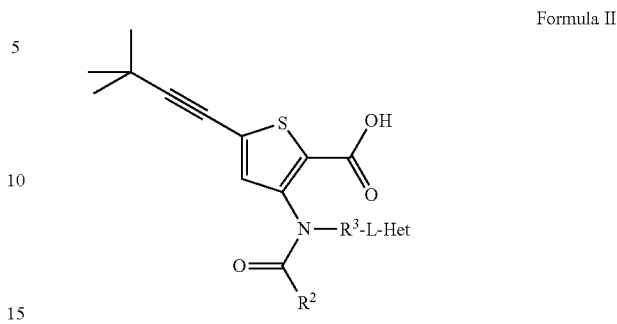

Formula II or a pharmaceutically acceptable salt or ester thereof, wherein:
$R^2$ is optionally substituted 4-methylcyclohexyl or optionally substituted methylcyclohexenyl.

11. The compound of claim 10, wherein $R^2$ is

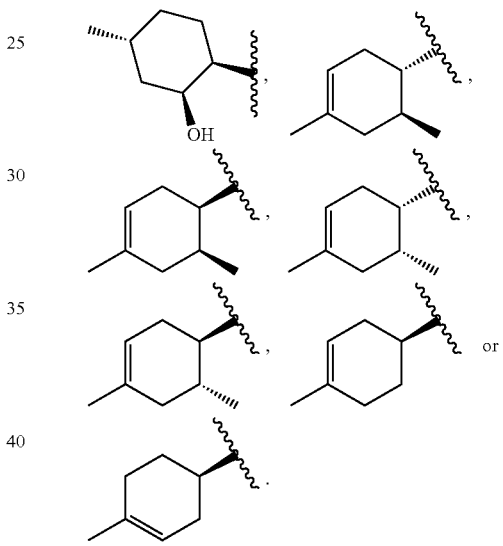

12. The compound of claim 10, wherein $R^2$ is

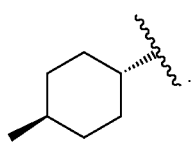

13. The compound of claim 10, wherein $R^3$ is optionally substituted $C_{1-12}$ alkylene, $C_{3-12}$ cycloalkylene, substituted $C_{3-12}$ cycloalkylene, optionally substituted $C_{6-14}$ arylene or optionally substituted 3-12 membered heterocyclylene.

14. The compound of claim 13, wherein $R^3$ is optionally substituted cyclohexylene.

15. The compound of claim 10, wherein Het is an optionally substituted 3-12 membered heterocyclyl or optionally substituted 3-14 membered heteroaryl wherein said optionally substituted 3-12 membered heterocyclyl or optionally substituted 3-14 membered heteroaryl comprises one to four heteroatoms selected from O, S, or N.

16. The compound of claim 10, wherein Het is optionally substituted pyridinyl, optionally substituted pyridazinyl, optionally substituted tetrahydro-2H-pyranyl, optionally substituted piperidinyl, optionally substituted pyrrolidinyl, optionally substituted tetrahydrothiophenyl, optionally substituted pyrazinyl, optionally substituted 1H-tetrazolyl, optionally substituted azetidinyl, optionally substituted tetrahydrofuranyl, optionally substituted tetrahydro-2H-furo[2,3-b]furanyl, optionally substituted thiazoyl, optionally substituted 1H-imidazolyl, optionally substituted 4H-1,2,4-triazolyl, optionally substituted 1H-pyrazolyl, optionally substituted 1,3,4-thiadiazolyl, optionally substituted quinolinyl, optionally substituted [1,2,4]triazolo[4,3-a]pyridinyl, optionally substituted thiophenyl, optionally substituted 1,2,4-thiadiazolyl, optionally substituted pyrimidinyl, optionally substituted 1H-1,2,3-triazolyl, optionally substituted 1,3,4-oxadiazolyl or optionally substituted imidazo[1,2-b]pyridazinyl.

17. The compound of claim 15, wherein Het is optionally substituted tetrahydrofuran-3-yl or optionally substituted pyridin-2-yl.

18. The compound of claim 1 that is

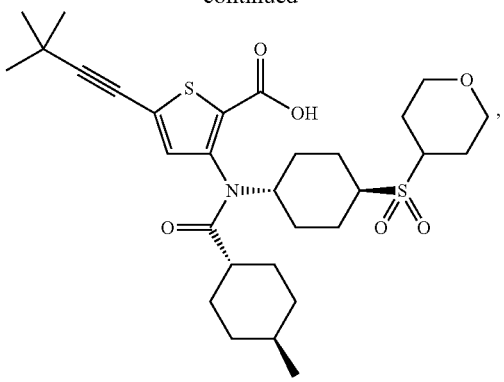

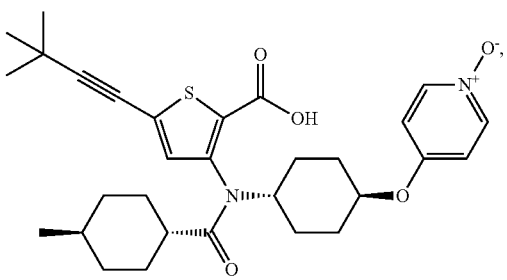

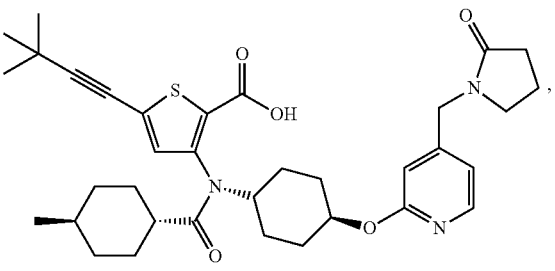

-continued

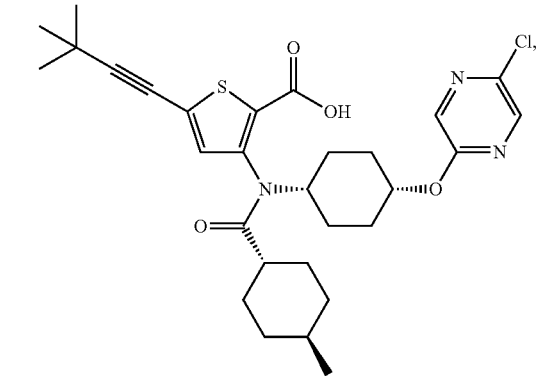

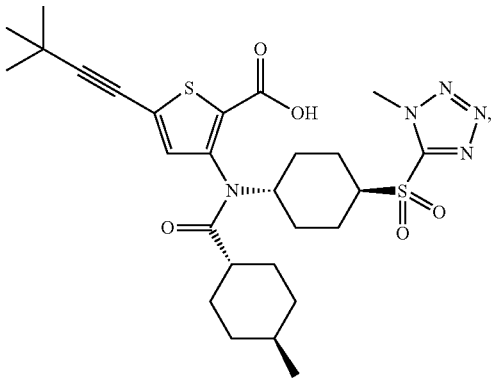

255
-continued
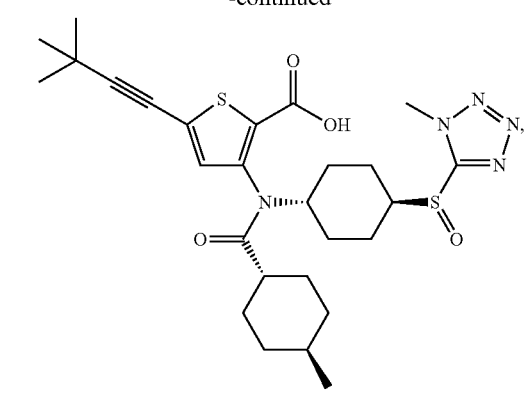
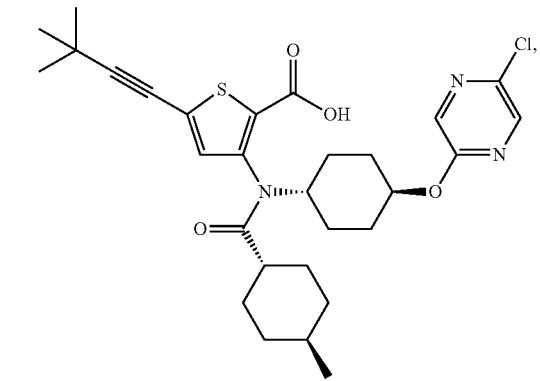
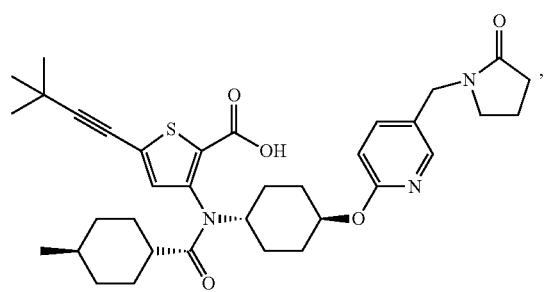
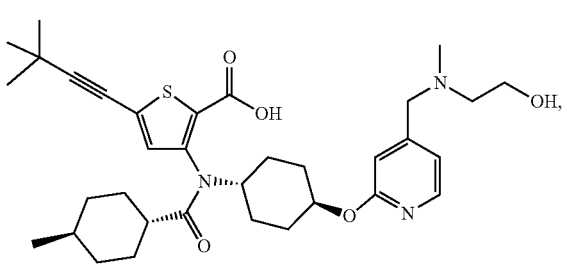
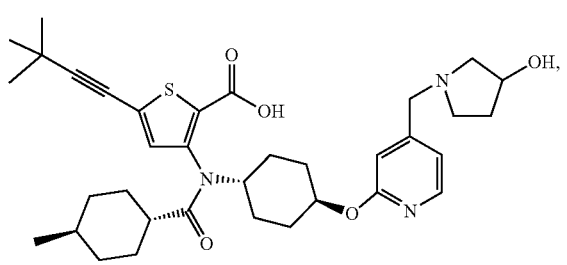
256
-continued
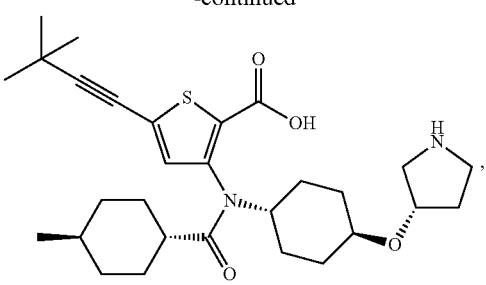
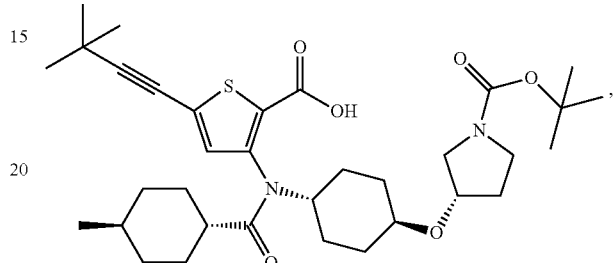
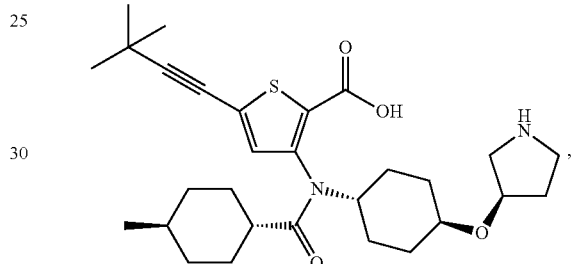
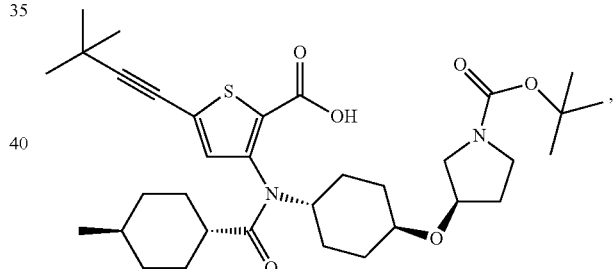
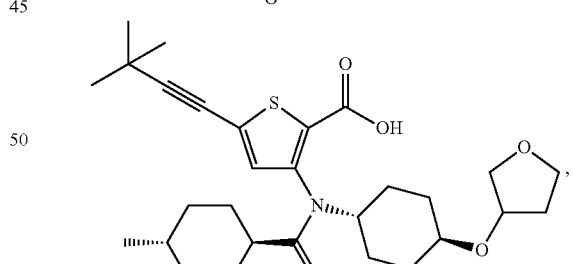
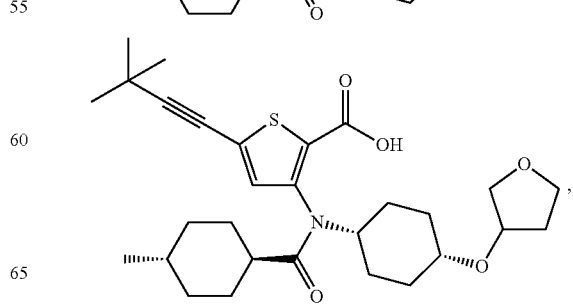

257
-continued
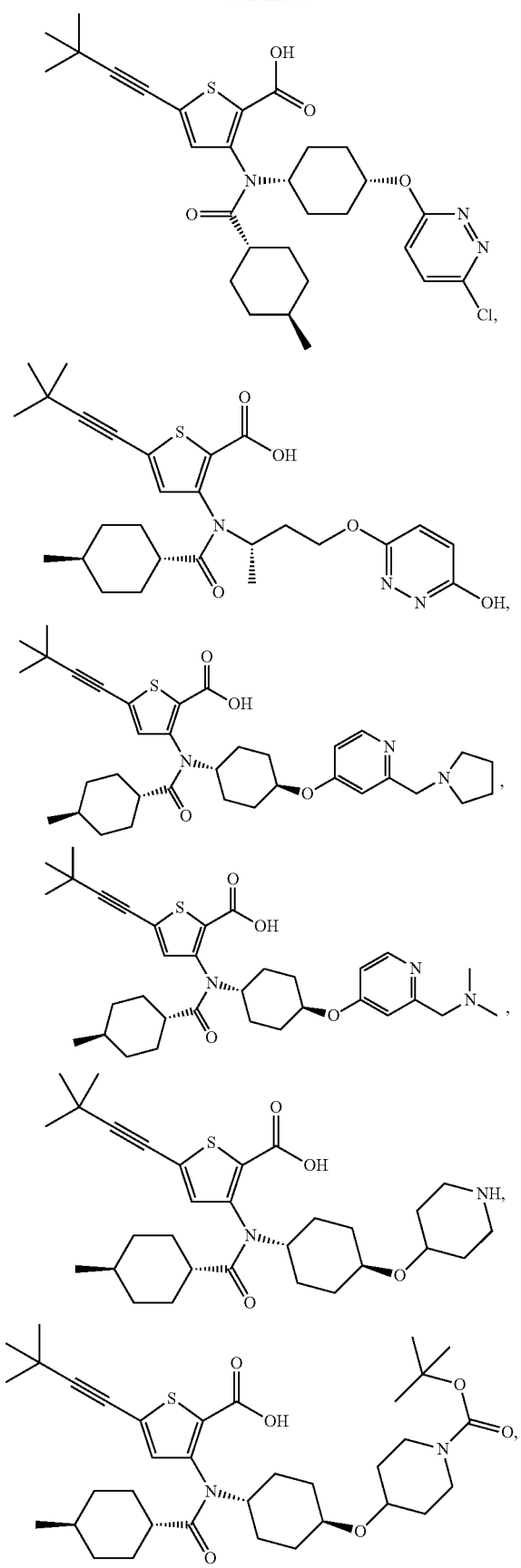
258
-continued
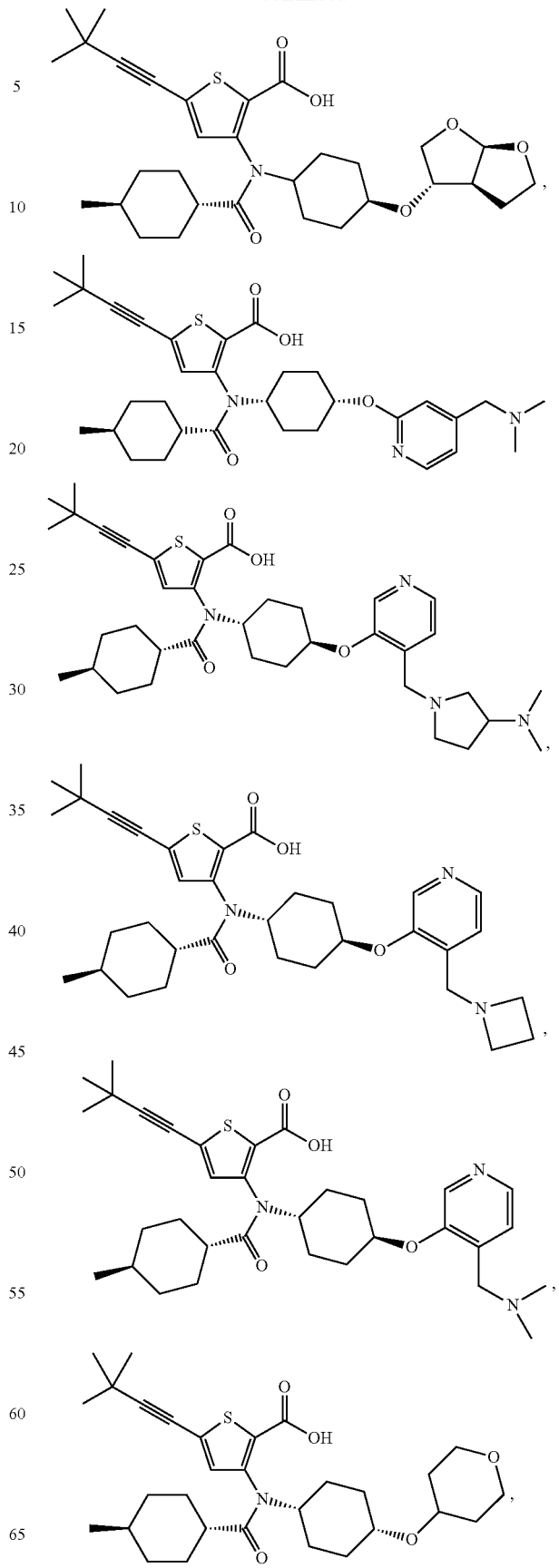

259
-continued
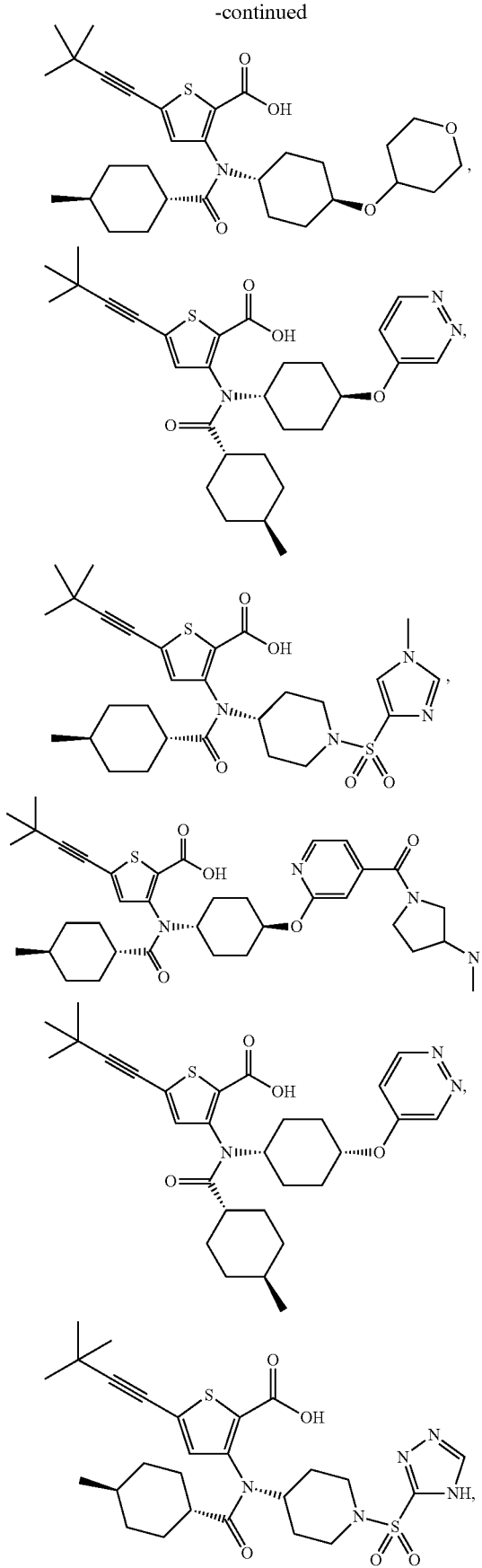
260
-continued
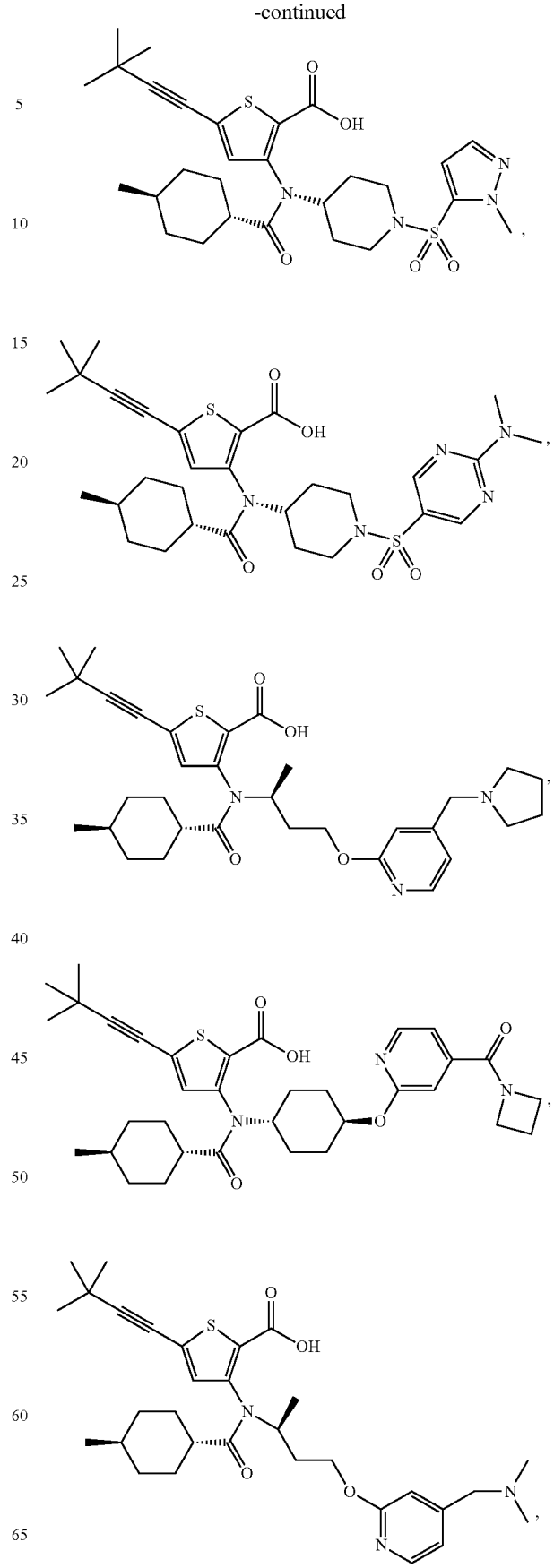

261
-continued
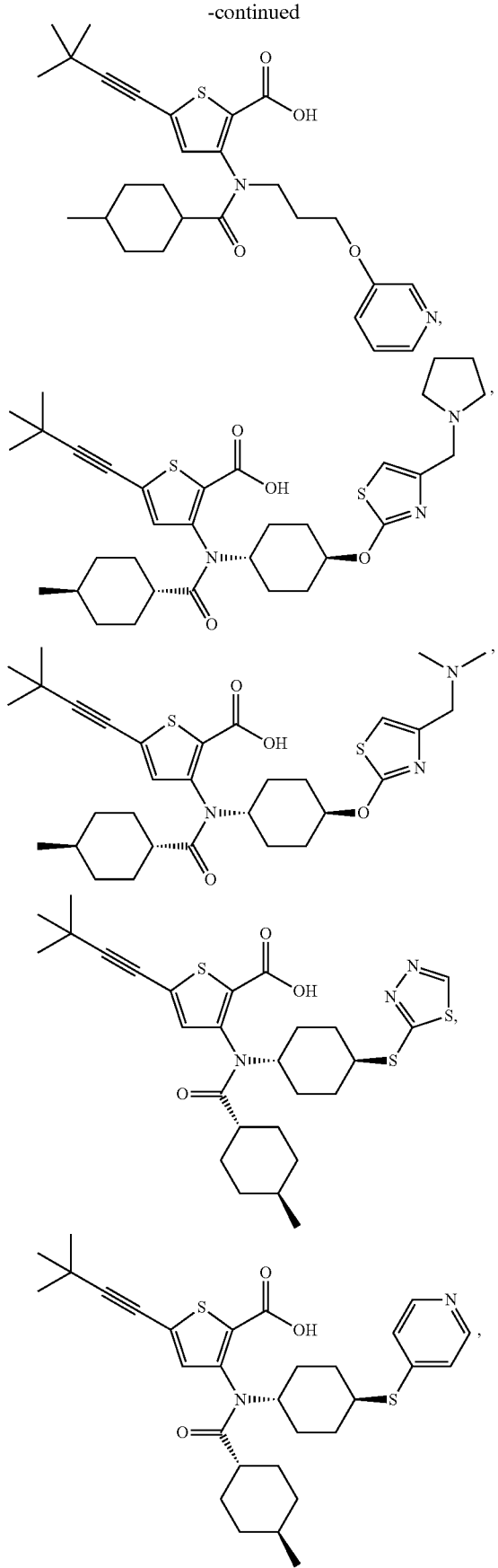
262
-continued
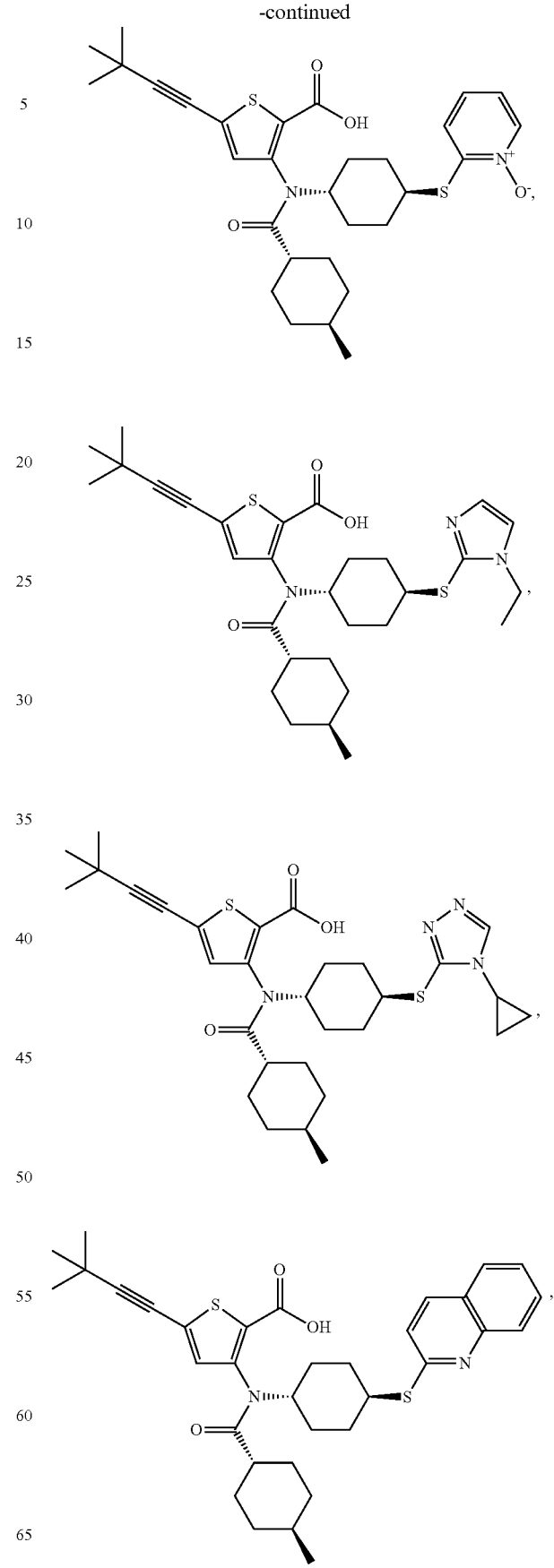

263
-continued
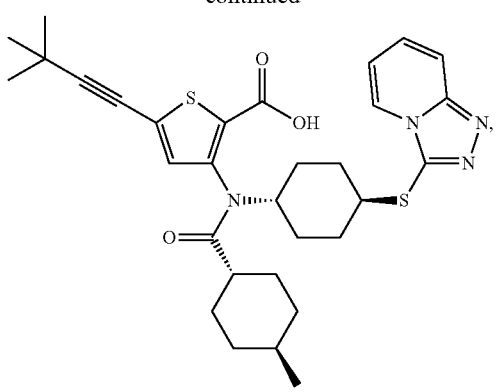
264
-continued
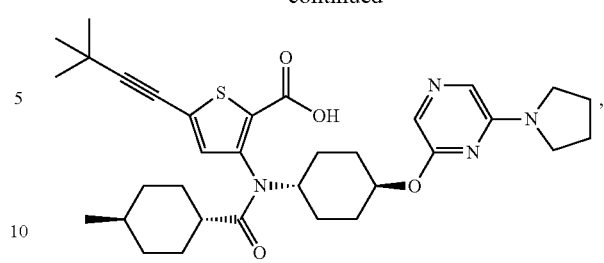
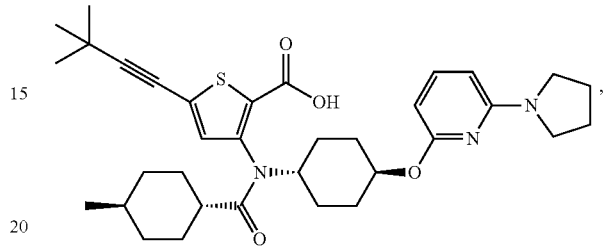
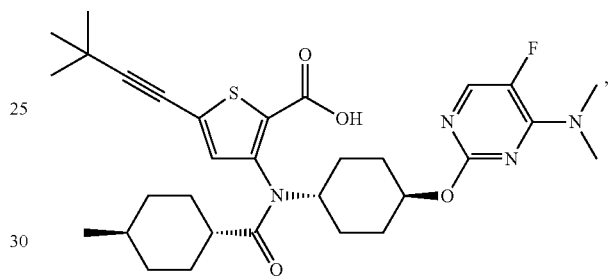
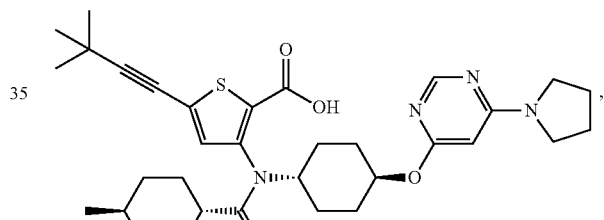
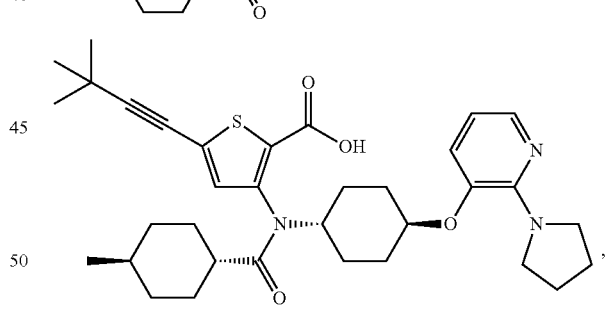
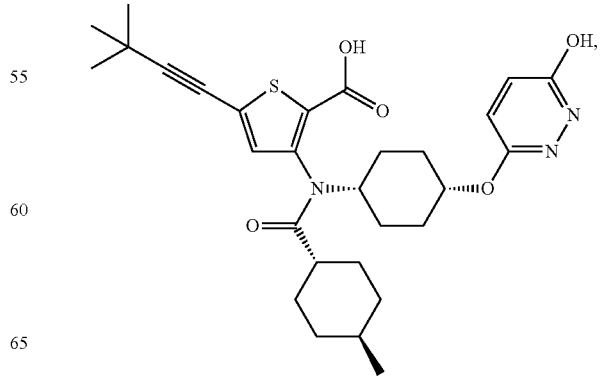

265
-continued
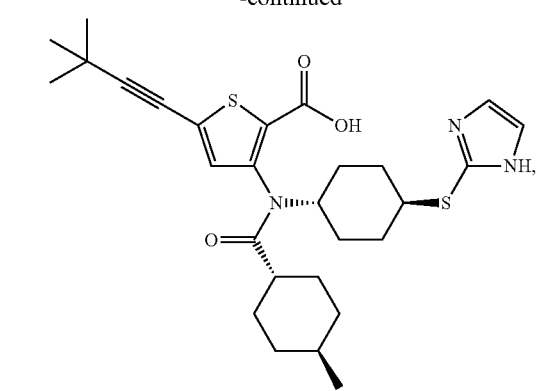
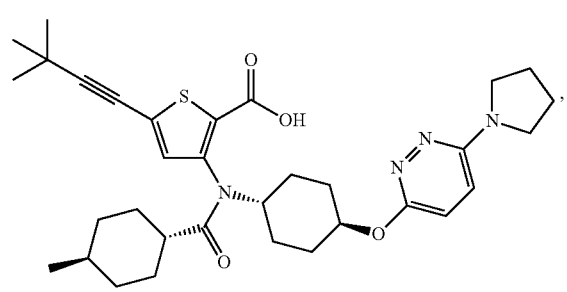
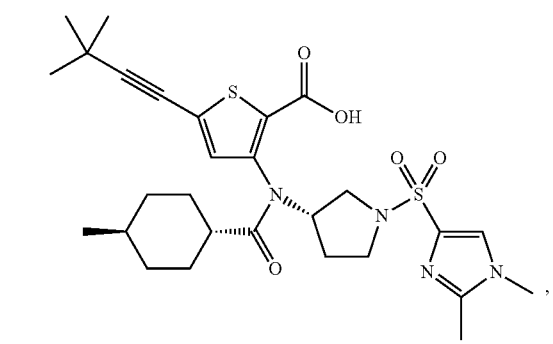
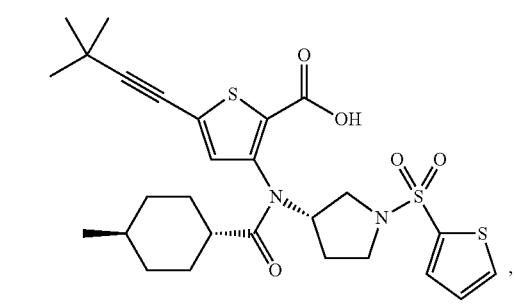
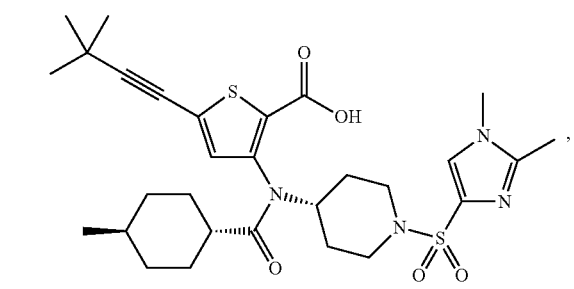
266
-continued
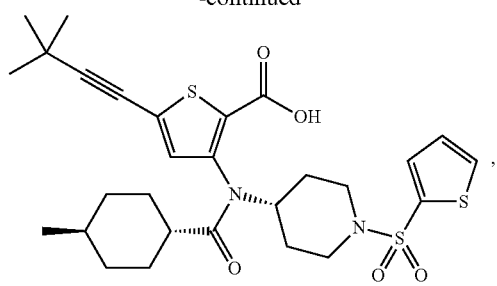
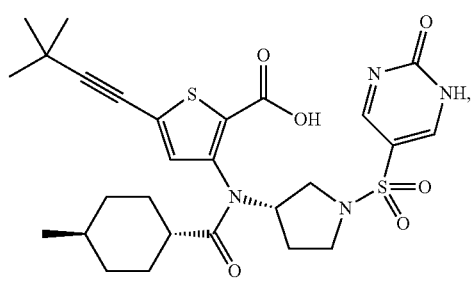
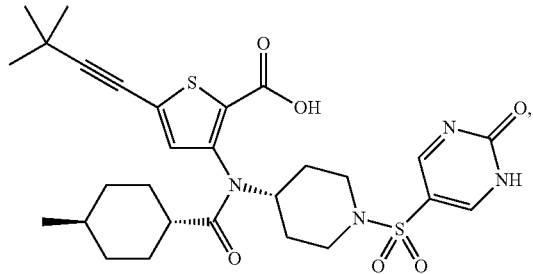
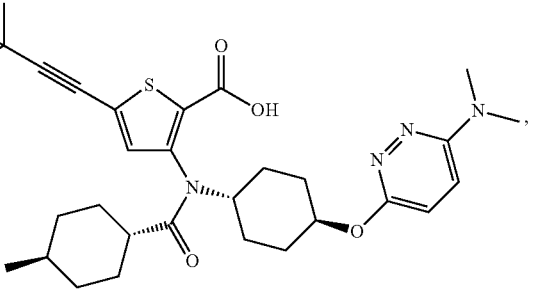
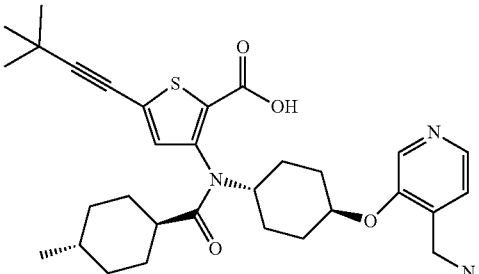
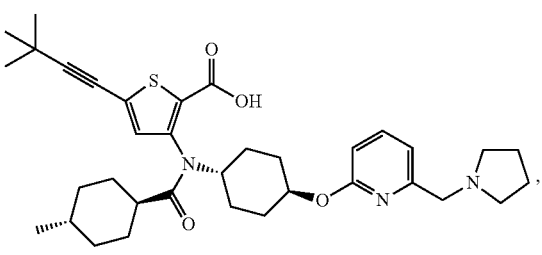

267
-continued
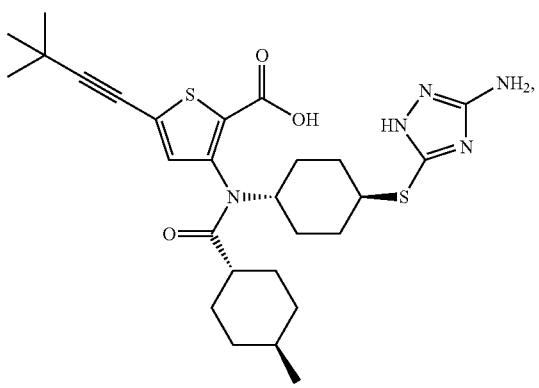
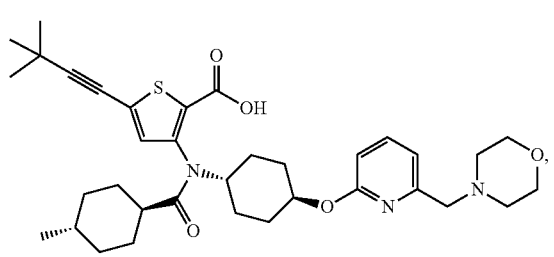
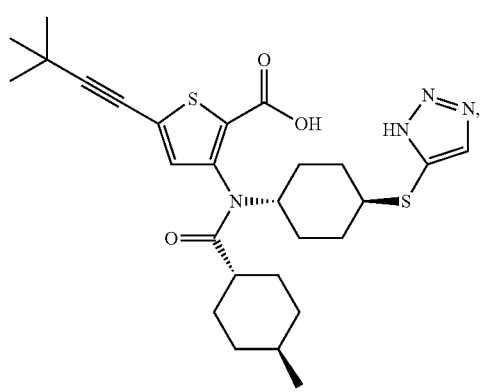
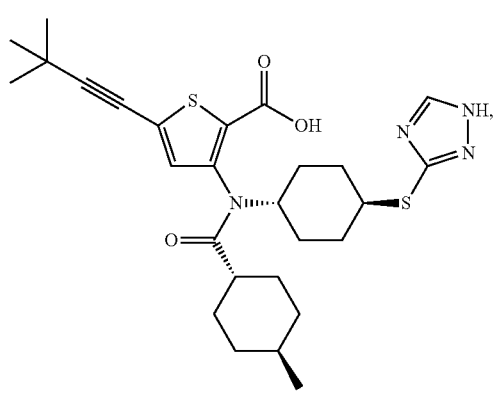
268
-continued
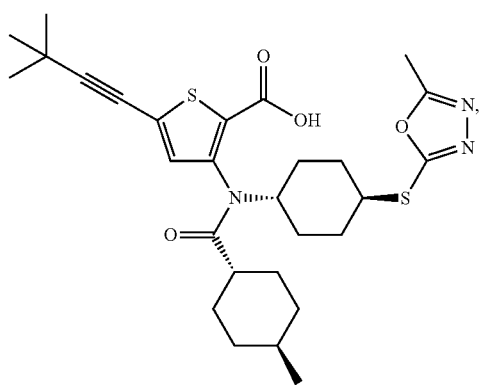
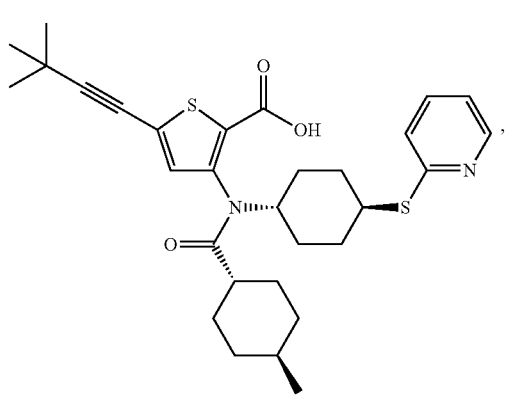
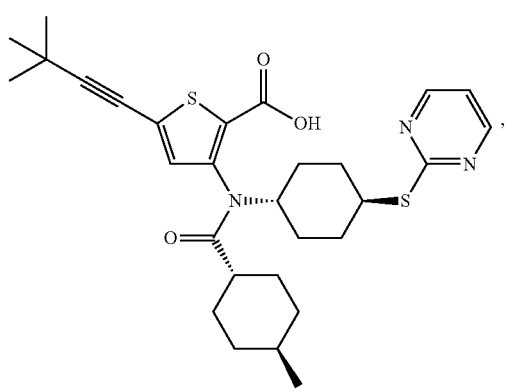
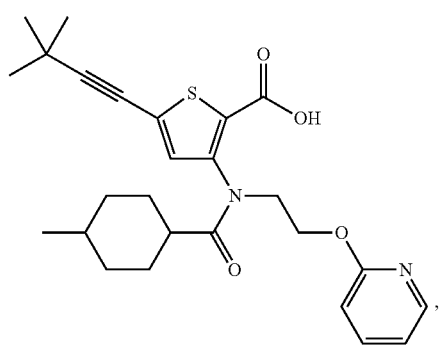

269
-continued
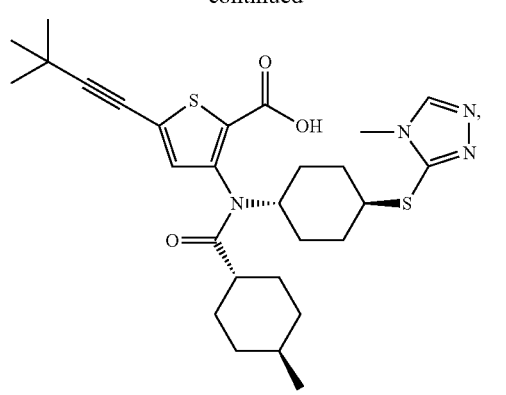
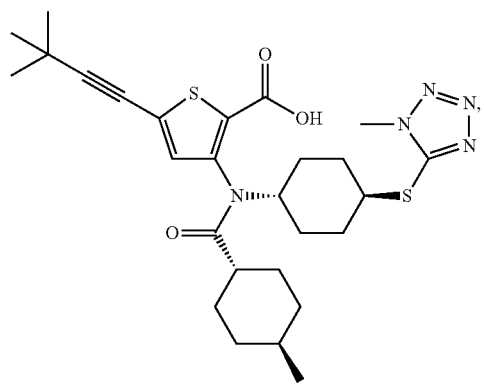
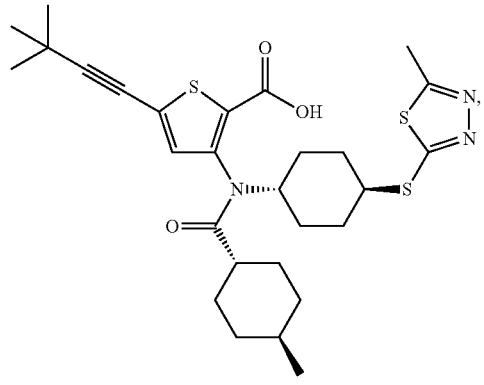
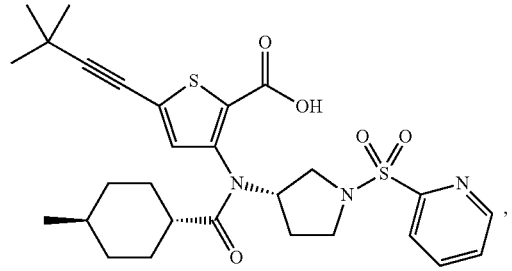
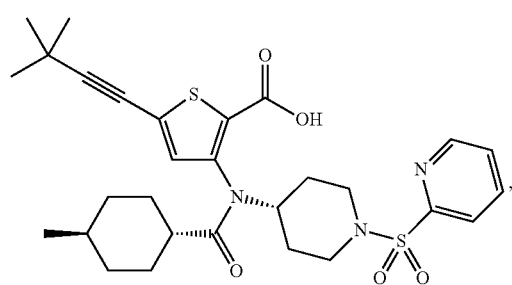
270
-continued
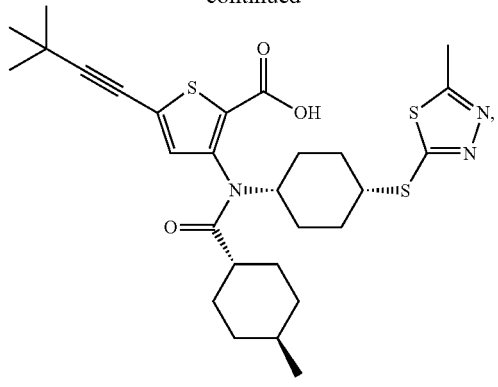
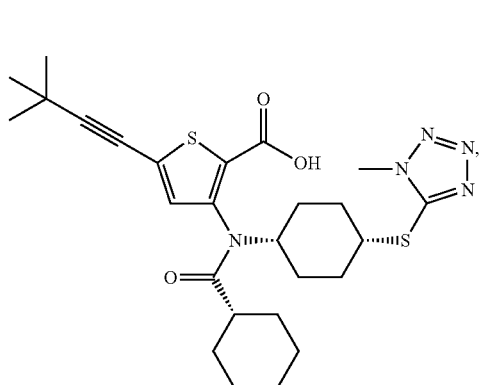
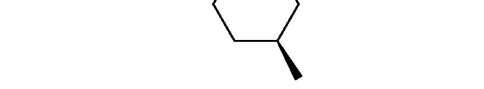
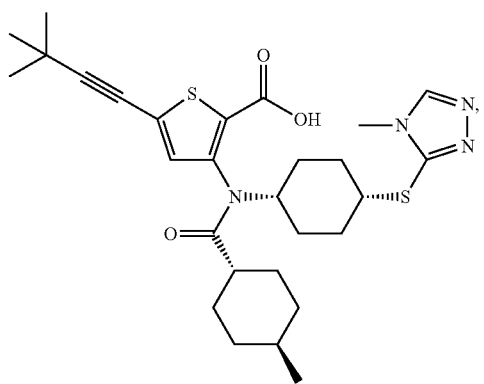
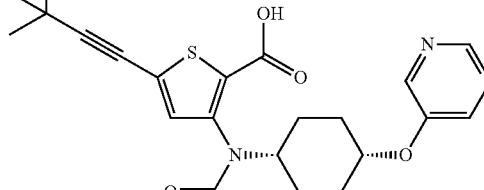
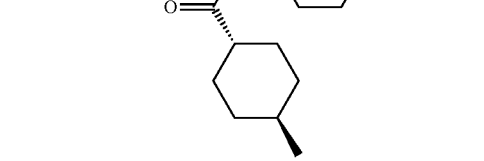

271
-continued
272
-continued
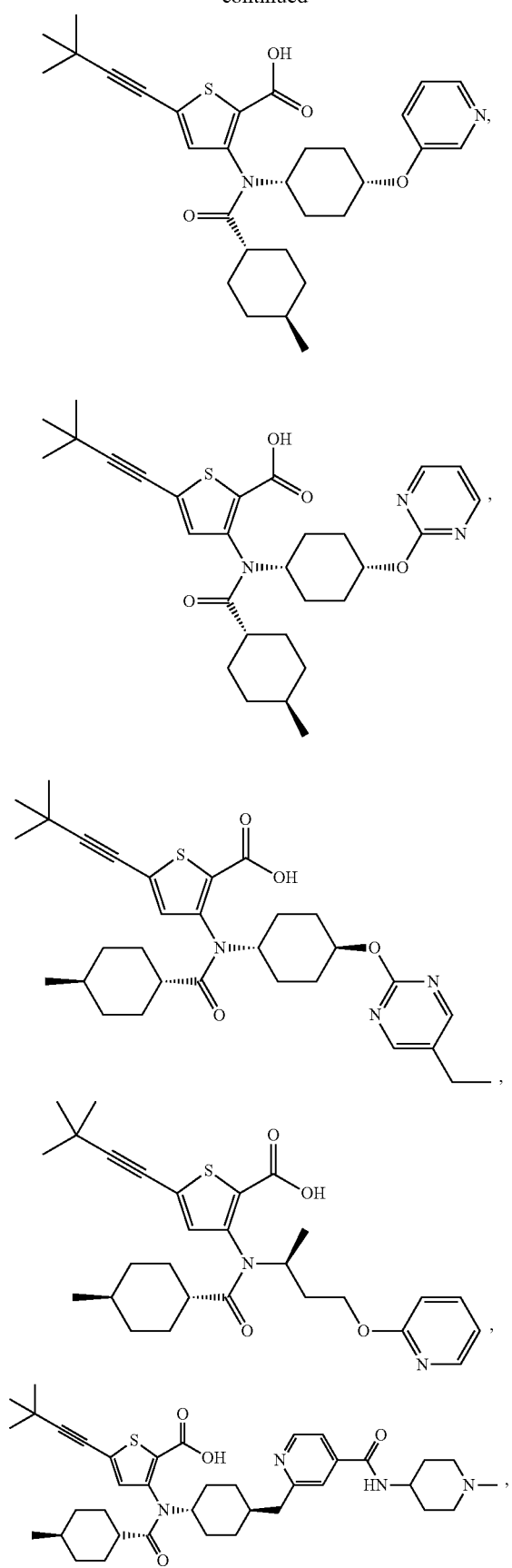
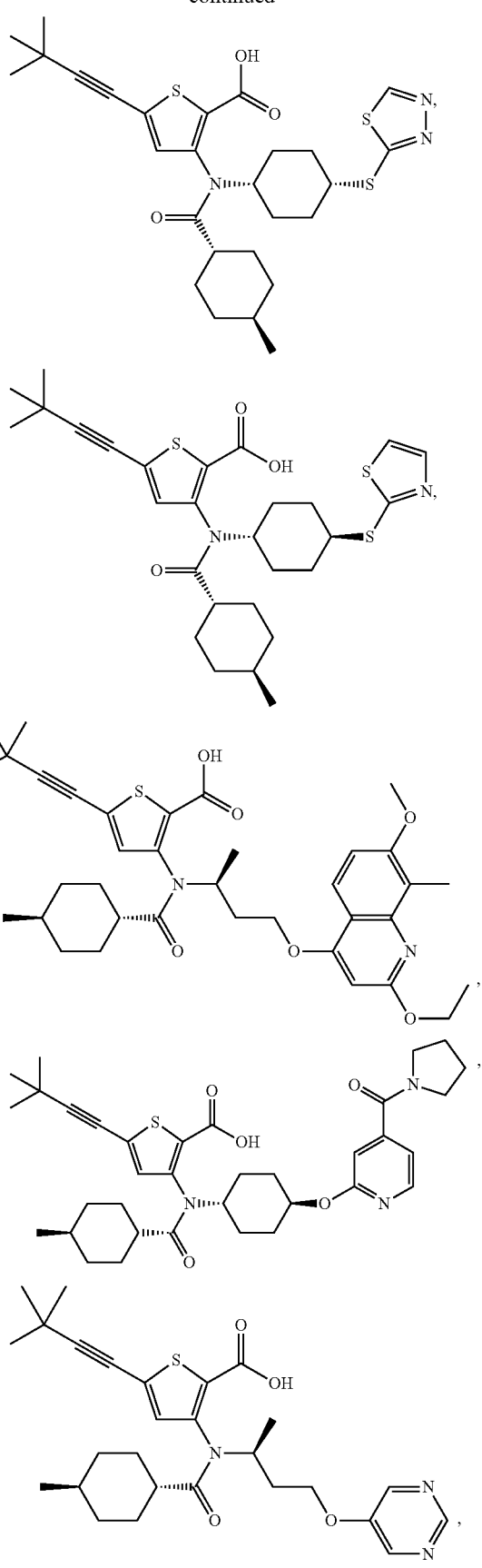

273
-continued
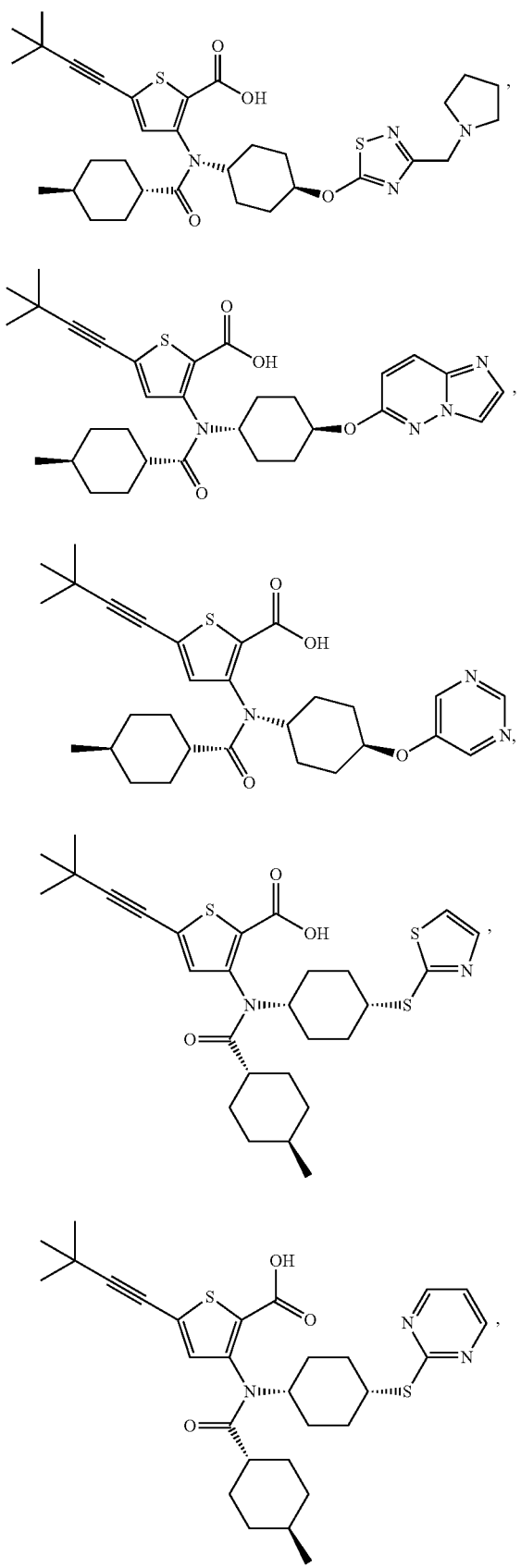
274
-continued
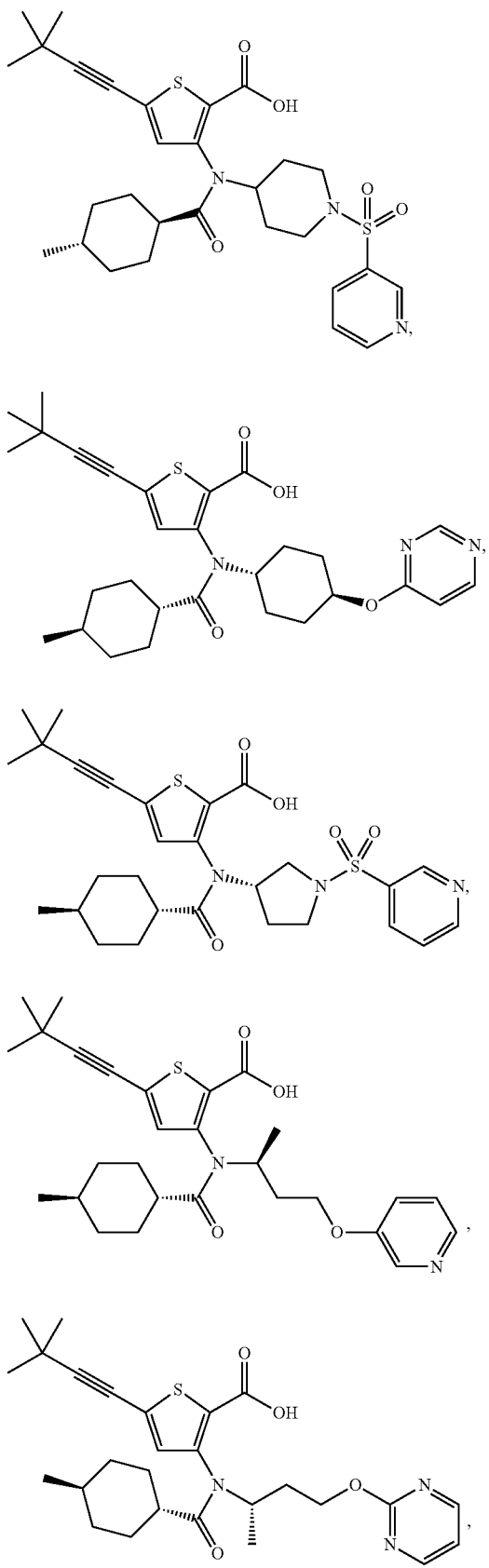

275
-continued
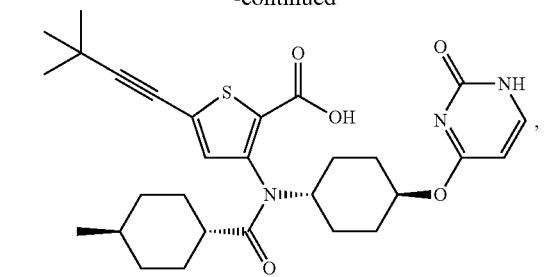
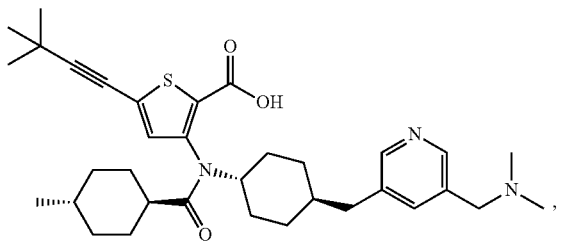
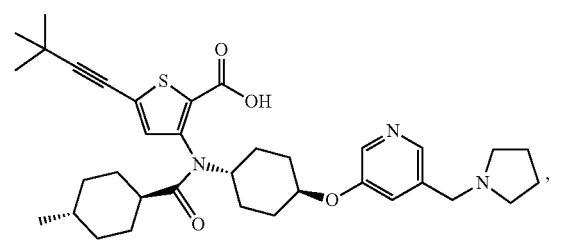
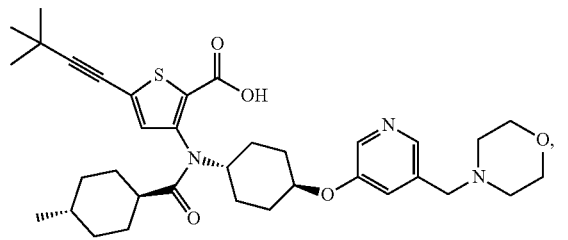
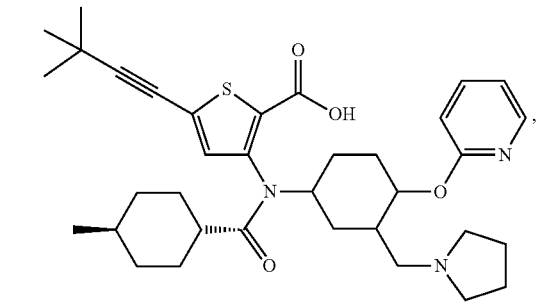
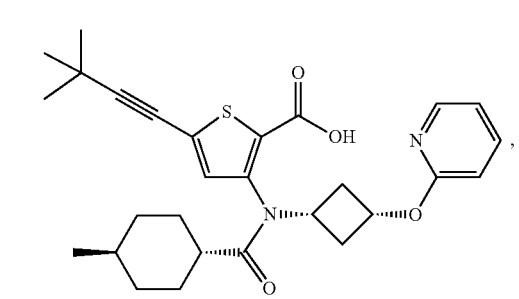
276
-continued
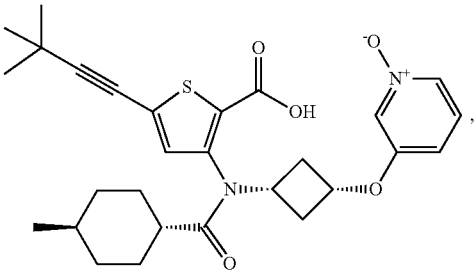
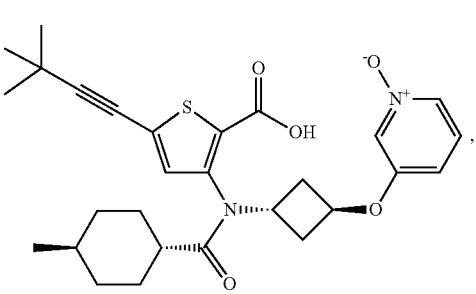
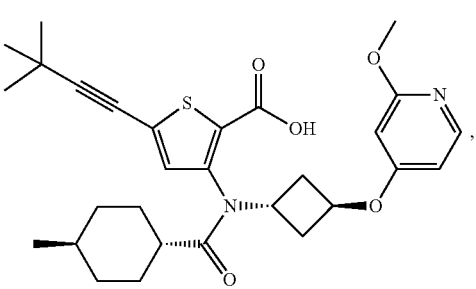
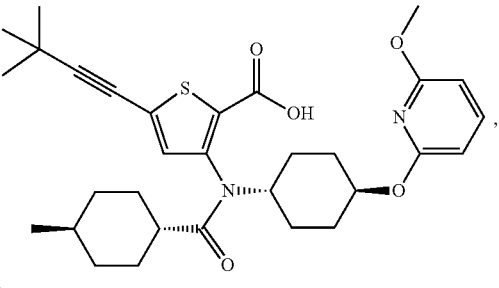
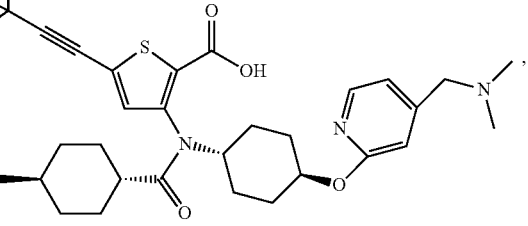
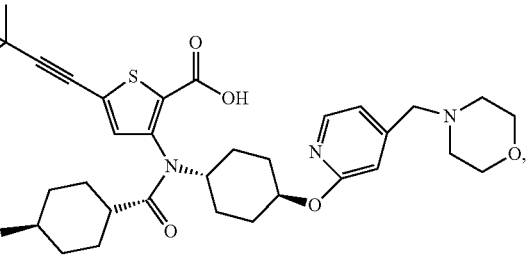

277
-continued
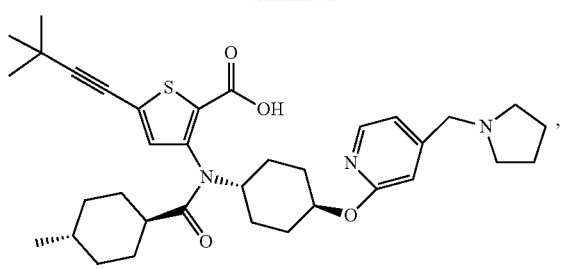
,
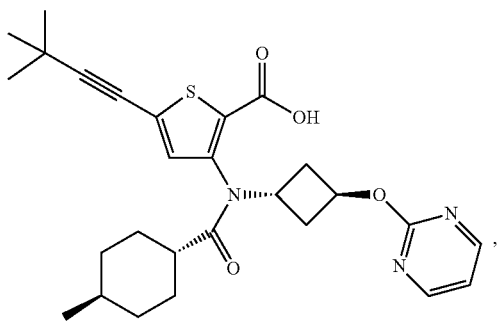
,
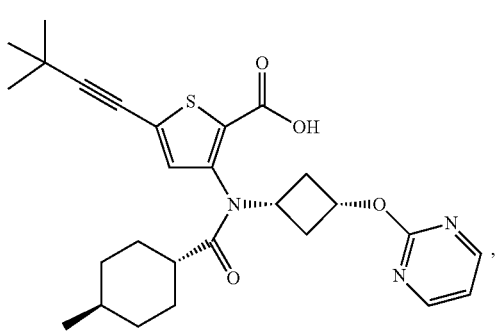
,
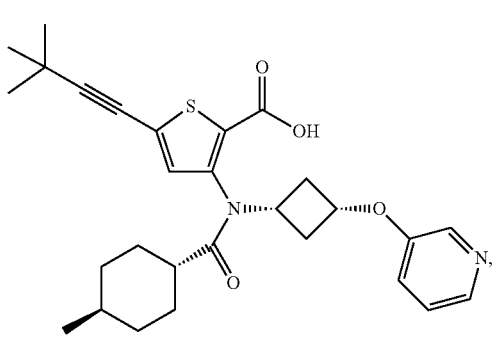
,
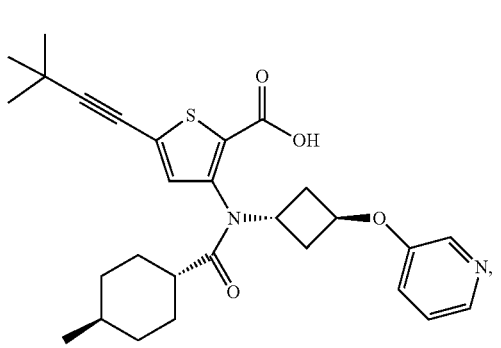
,
278
-continued
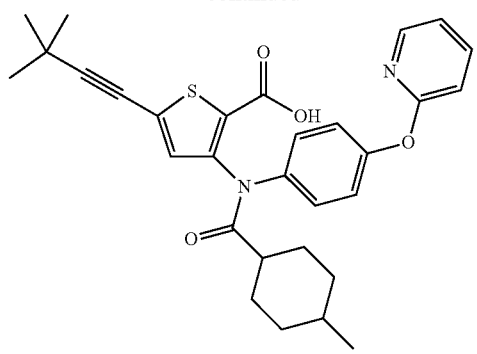
,
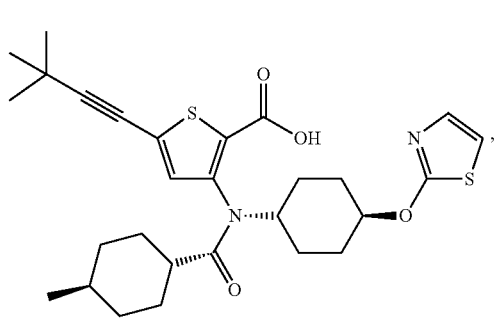
,
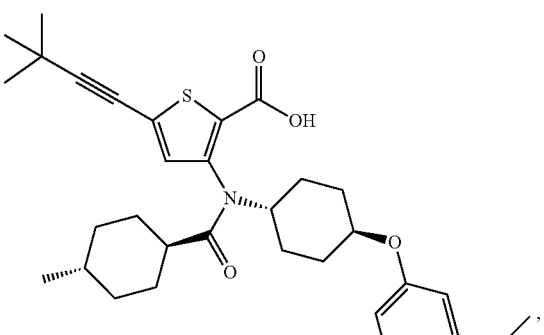
,
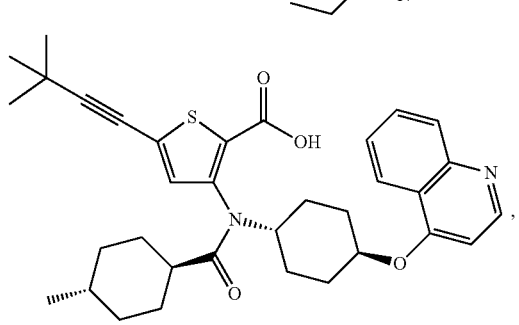
,
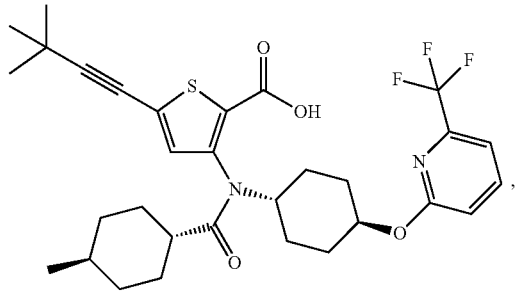
,

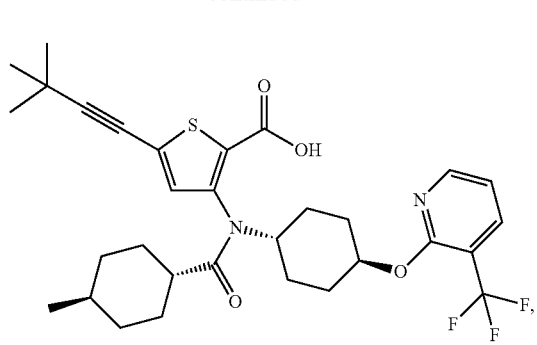
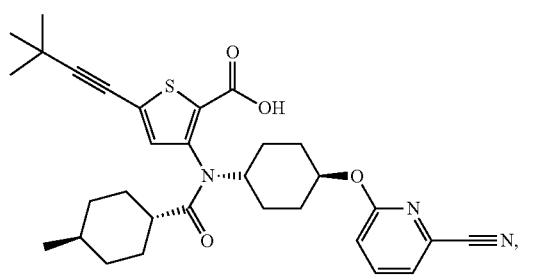
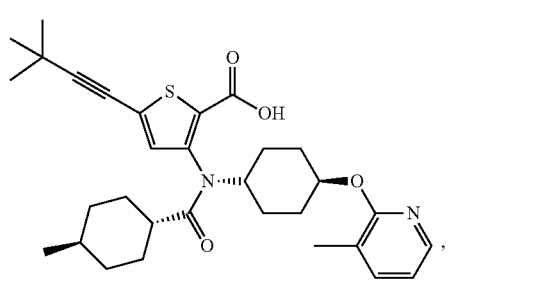
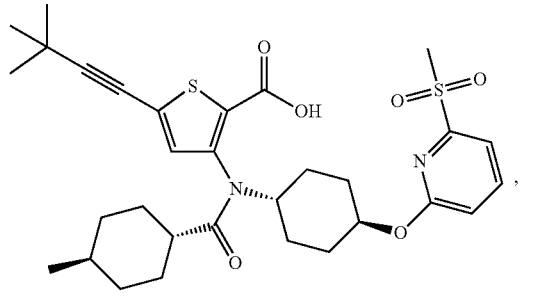
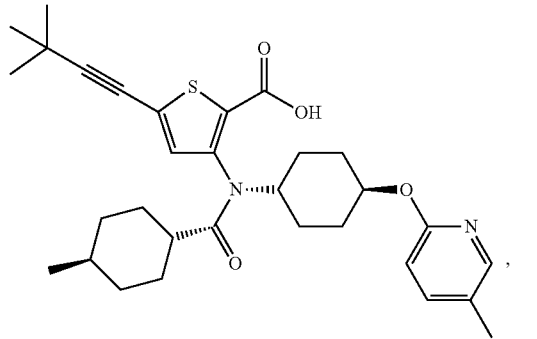
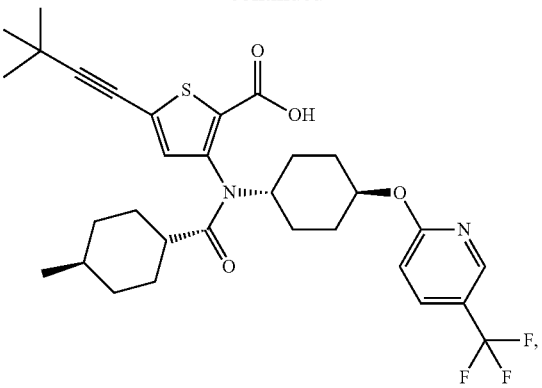
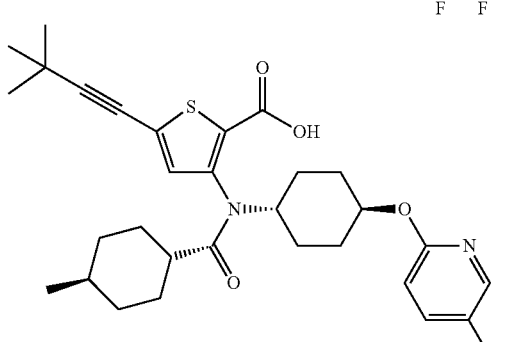
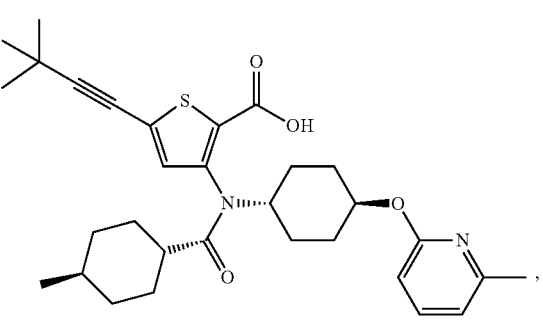
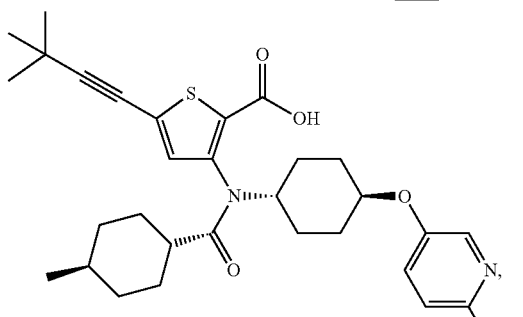
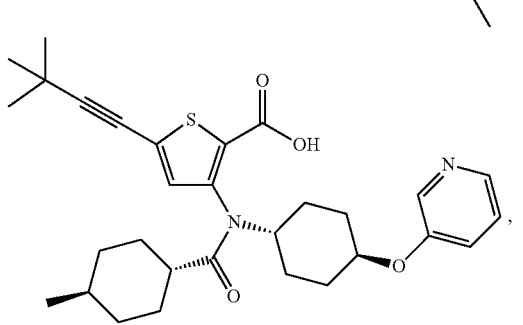

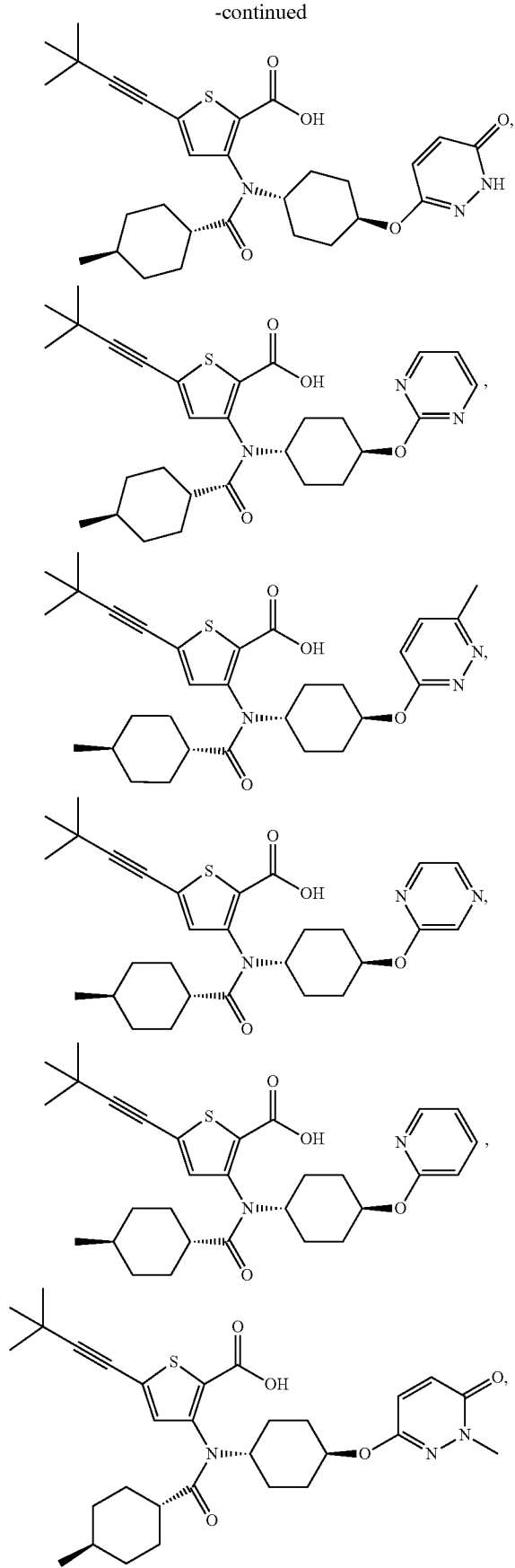
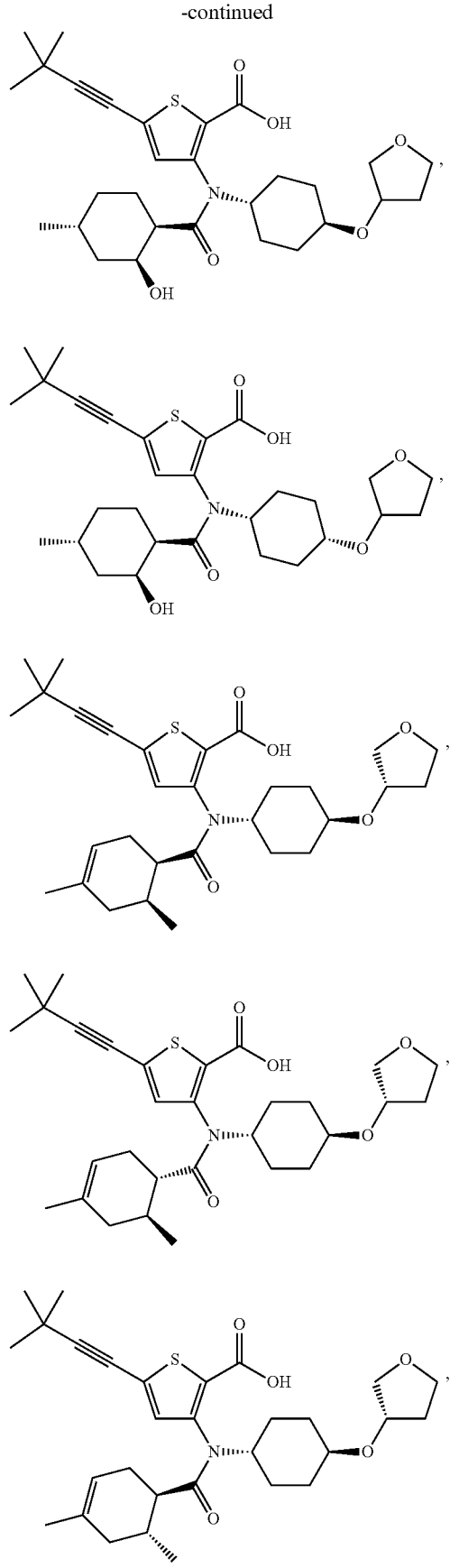

283
-continued
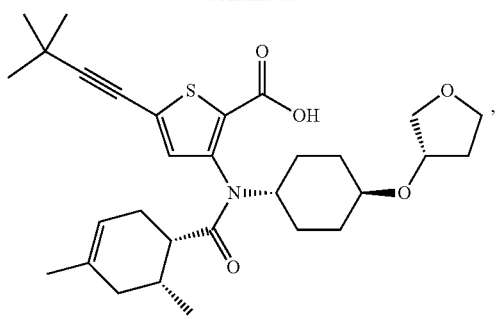
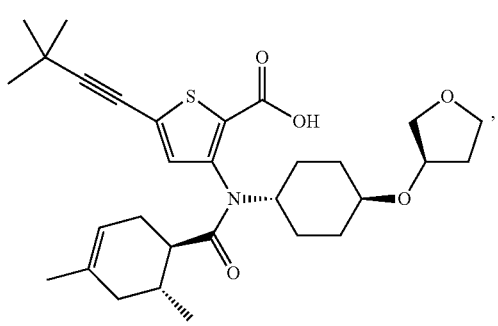
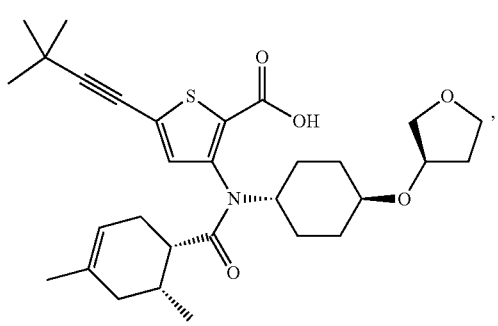
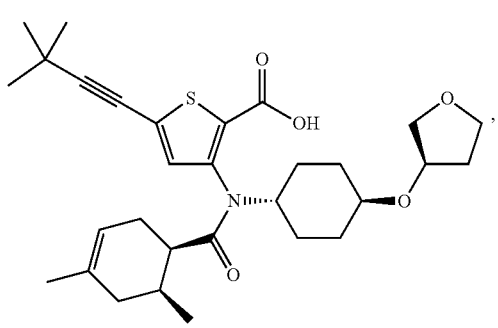
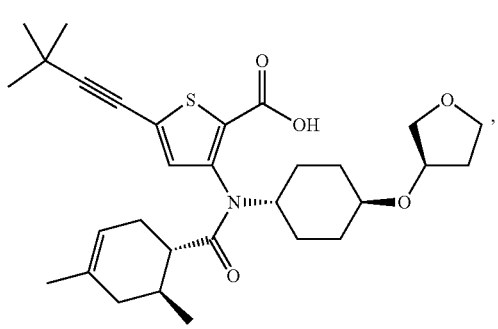
284
-continued
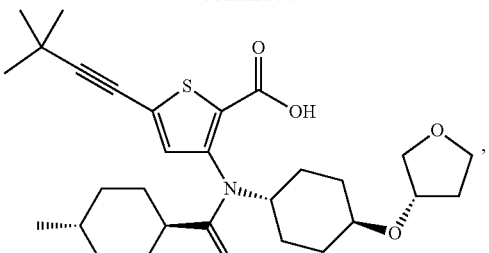
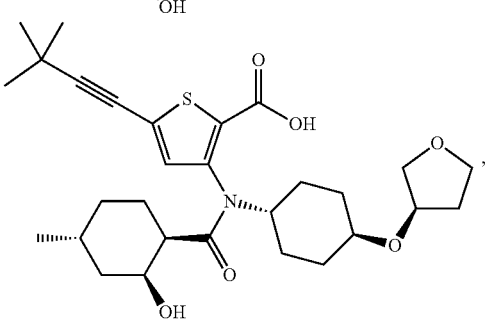
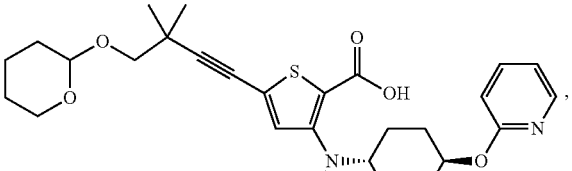
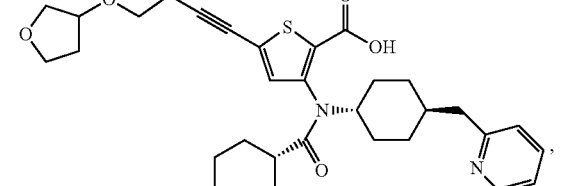
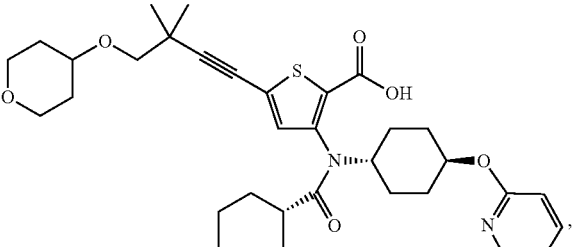

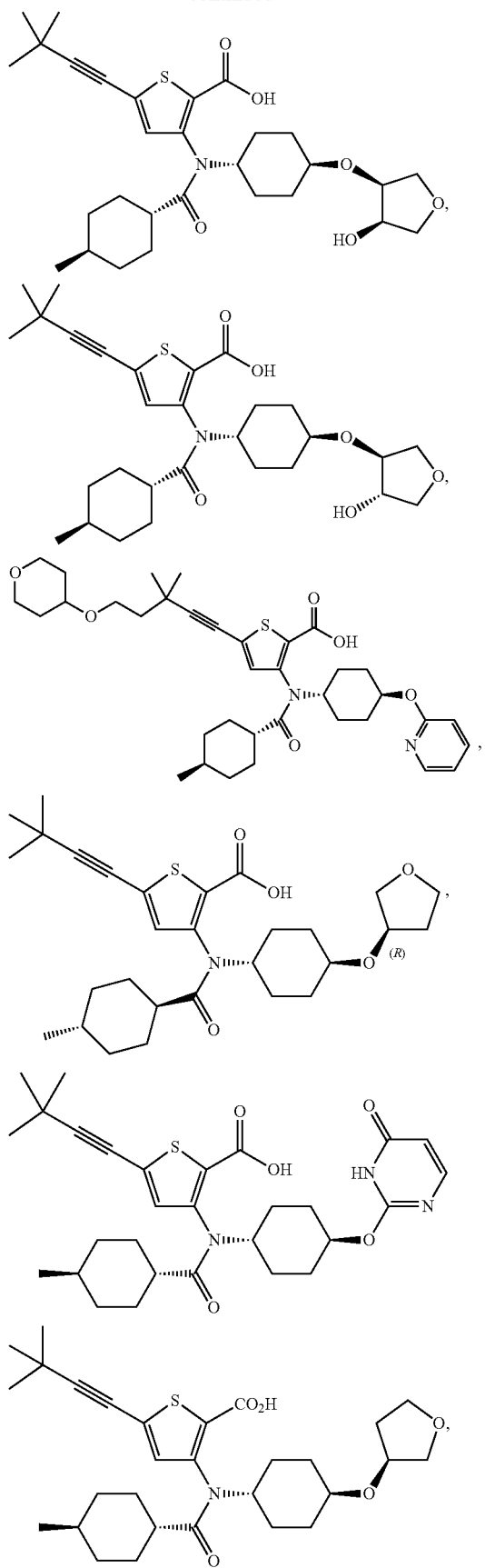
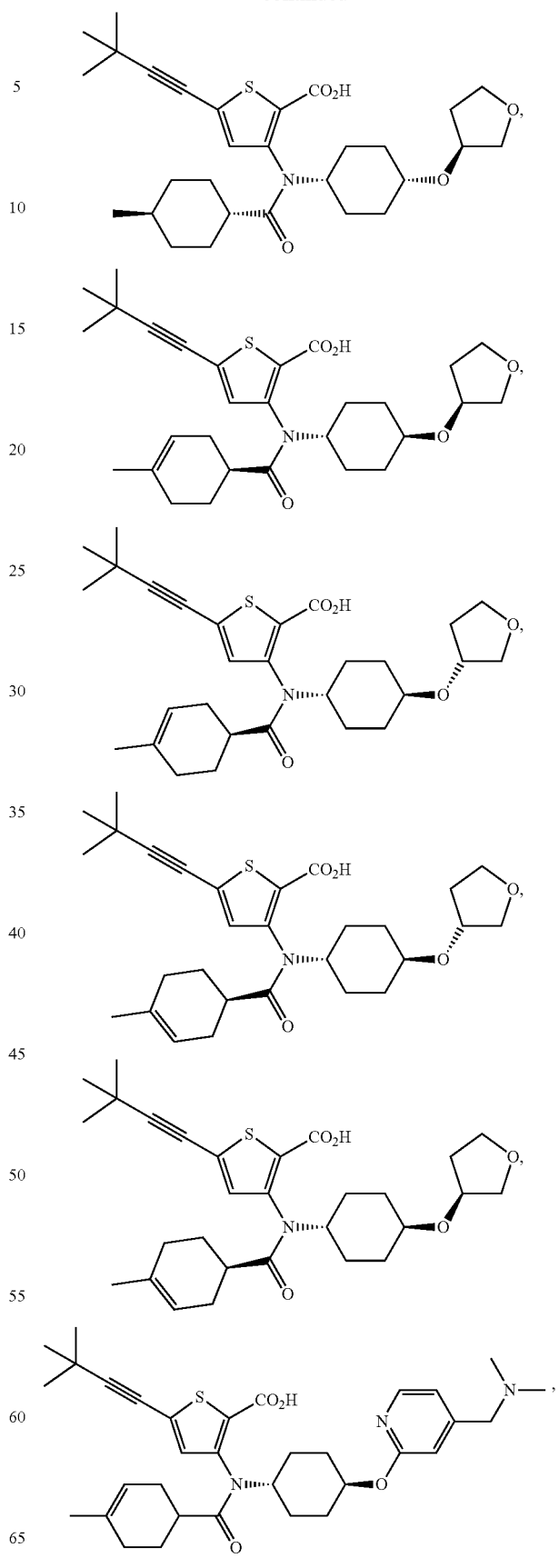

287
-continued
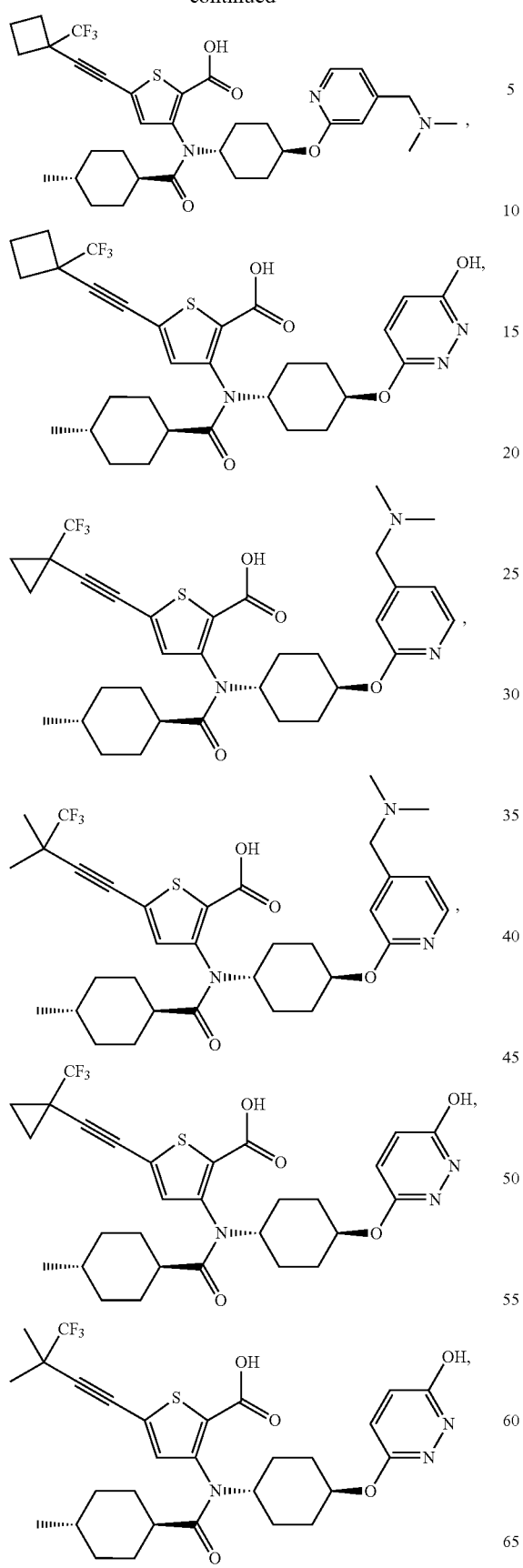
288
-continued
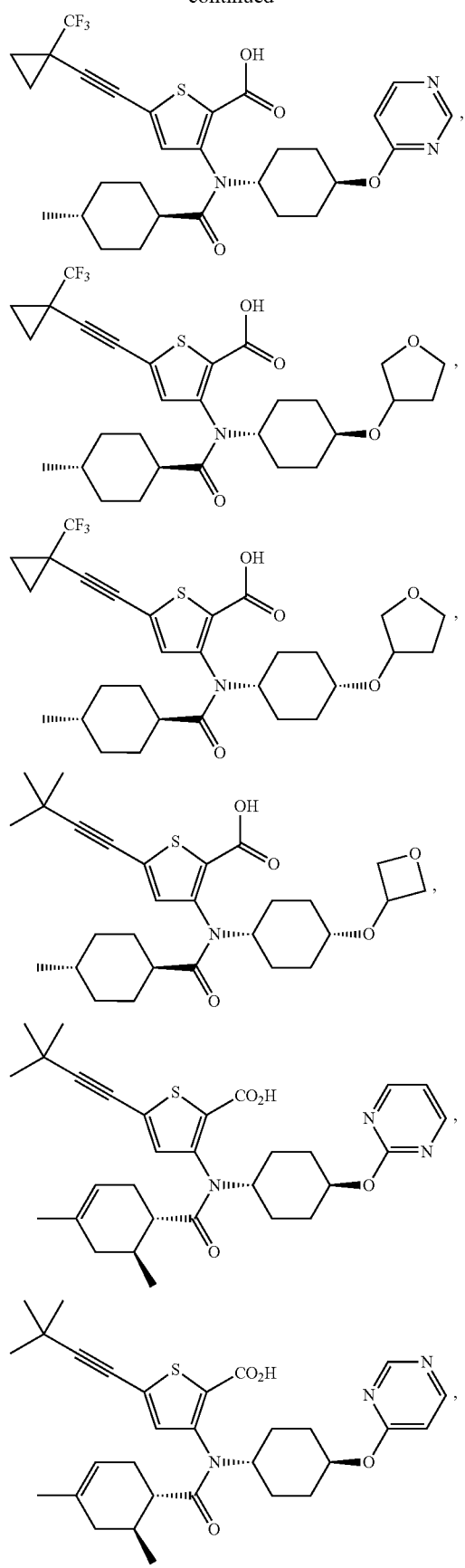

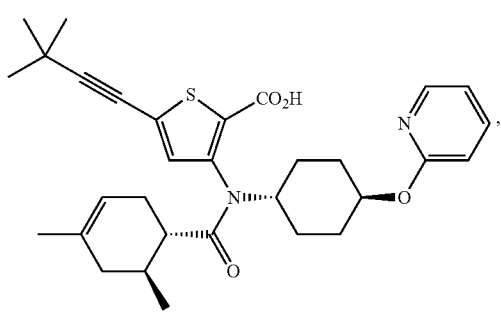

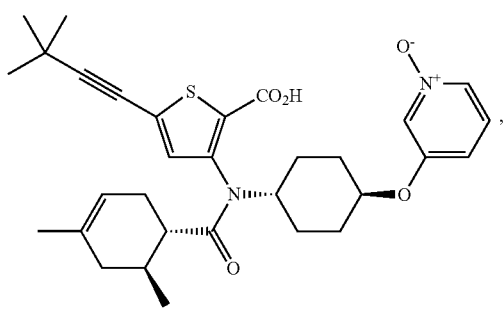

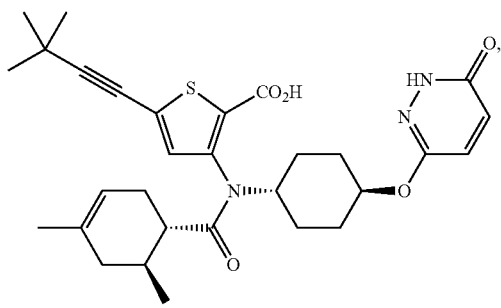

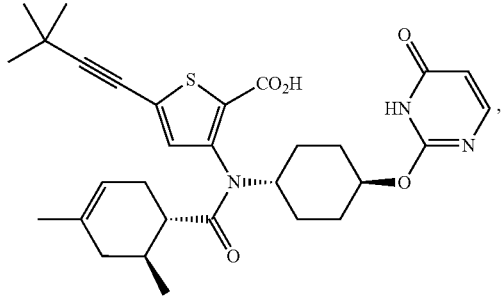

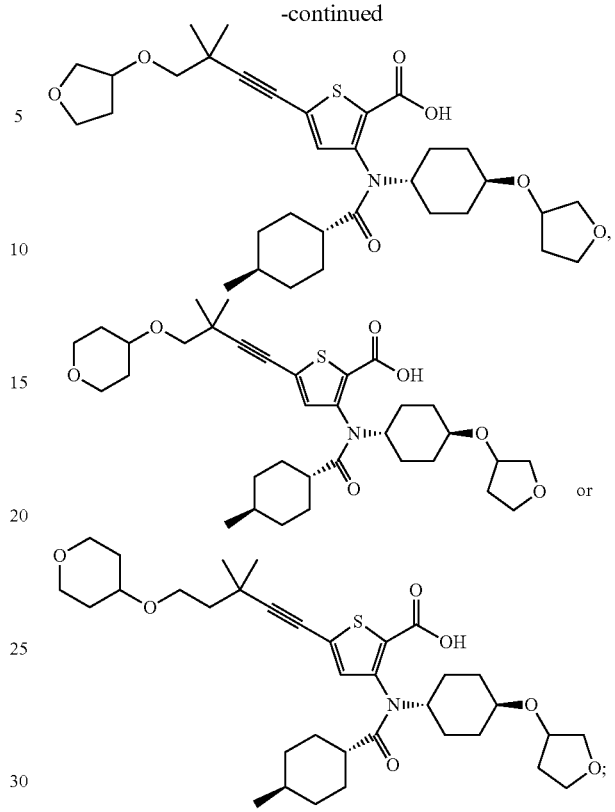

or a pharmaceutically acceptable salt or ester thereof.

19. A pharmaceutical composition comprising a therapeutically effective amount of a compound of claim 1 and a pharmaceutically acceptable carrier or excipient.

20. The pharmaceutical composition of claim 19 further comprising at least one therapeutic agent selected from the group consisting of an interferon, ribavirin or an analog thereof, an HCV NS3 protease inhibitor, an NS5a inhibitor, an alpha-glucosidase 1 inhibitor, a hepatoprotectant, a mevalonate decarboxylase antagonist, an antagonist of the renin-angiotensin system, an endothelin antagonist, other anti-fibrotic agents, a nucleoside or nucleotide inhibitor of HCV NS5B polymerase, a non-nucleoside inhibitor of HCV NS5B polymerase, an HCV NS5A inhibitor, a TLR-7 agonist, a cyclophillin inhibitor, an HCV IRES inhibitor, a pharmacokinetic enhancer and other drugs for treating HCV; or a mixture thereof.

* * * * *

UNITED STATES PATENT AND TRADEMARK OFFICE
CERTIFICATE OF CORRECTION

PATENT NO. : 8,569,302 B2  
APPLICATION NO. : 12/838684  
DATED : October 29, 2013  
INVENTOR(S) : Canales et al.

Page 1 of 5

It is certified that error appears in the above-identified patent and that said Letters Patent is hereby corrected as shown below:

In the specification:

In column 121, lines 25-35, please delete the compound below:

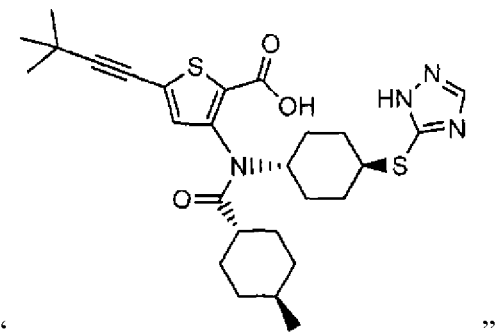

"                                      "

and replace it with the following compound:

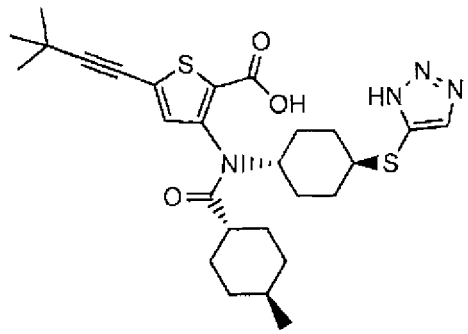

Signed and Sealed this  
First Day of July, 2014

Michelle K. Lee  
*Deputy Director of the United States Patent and Trademark Office*

CERTIFICATE OF CORRECTION (continued)
U.S. Pat. No. 8,569,302 B2

Page 2 of 5

In the specification:

In column 156, lines 15-25, please delete the compound below:

"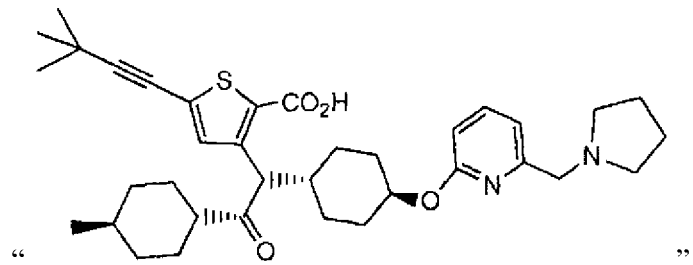"

and replace it with the following compound:

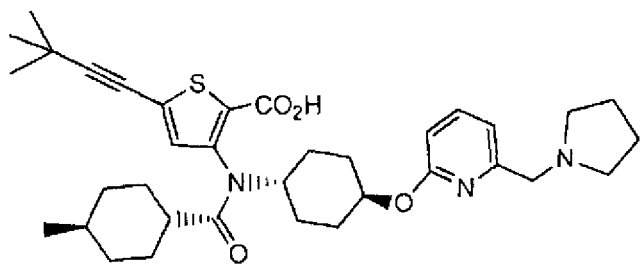

In column 190, lines 5-15, please delete the following compound below:

"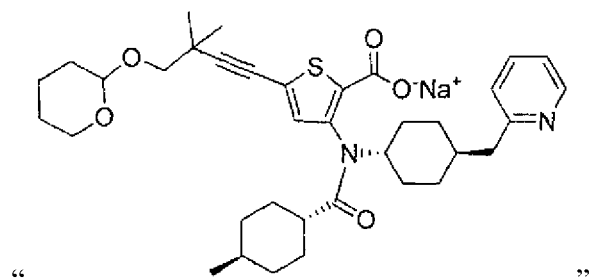"

and replace it with the following compound:

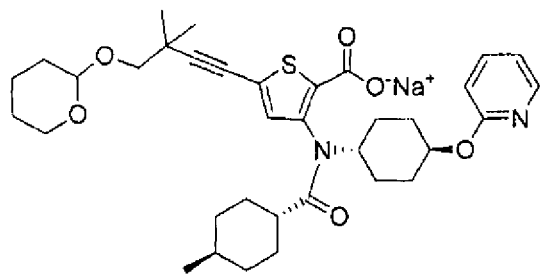

CERTIFICATE OF CORRECTION (continued)
U.S. Pat. No. 8,569,302 B2

In the specification:

In column 231, lines 55-65, please delete the following compound below:

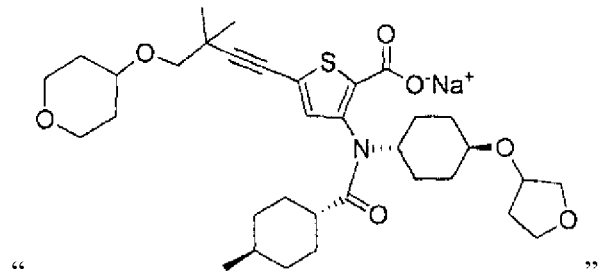

" "

and replace it with the following compound:

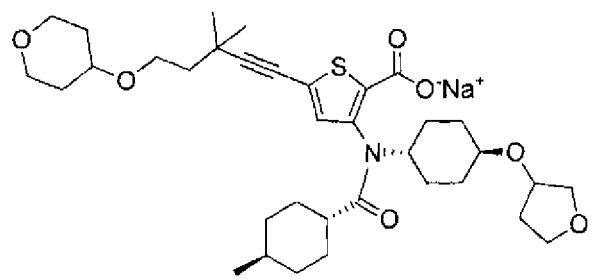

In the claims:

In column 261, claim 18, lines 5-15, please delete the compound below:

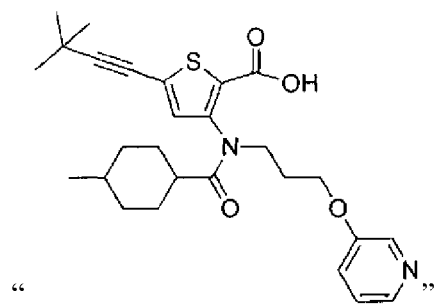

" "

and replace it with the following compound:

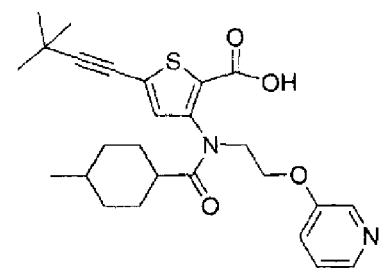

CERTIFICATE OF CORRECTION (continued)
U.S. Pat. No. 8,569,302 B2

In the claims:

In column 275, claim 18, lines 15-20, please delete the compound below:

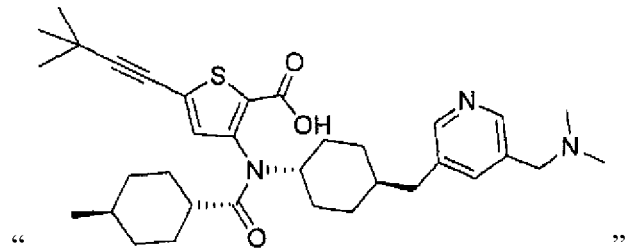

" "

and replace it with the following compound:

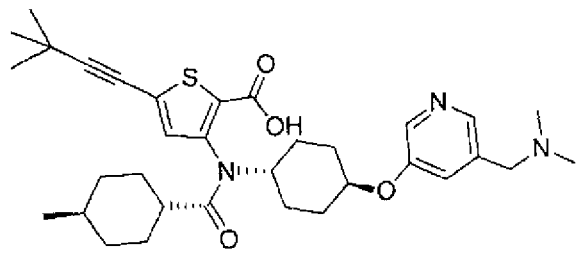

In column 276, claim 18, line 25-35, please delete the compound below:

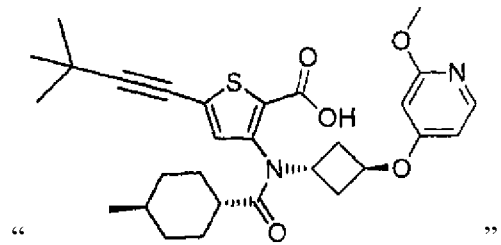

" "

and replace it with the following compound:

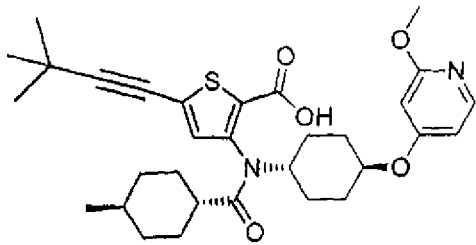

CERTIFICATE OF CORRECTION (continued)
U.S. Pat. No. 8,569,302 B2

In the claims:

In column 284, claim 18, lines 35-45, please delete the compound below:

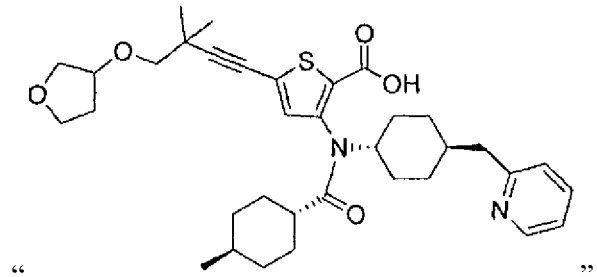

"                                              "

and replace it with the following compound:

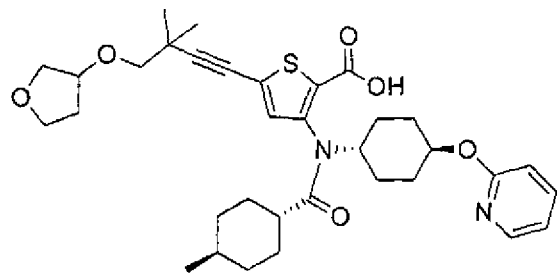

.